(12) United States Patent
Tamarkin et al.

(10) Patent No.: US 10,946,101 B2
(45) Date of Patent: *Mar. 16, 2021

(54) SURFACTANT-FREE WATER-FREE FOAMABLE COMPOSITIONS, BREAKABLE FOAMS AND GELS AND THEIR USES

(71) Applicant: Vyne Pharmaceuticals Ltd., Rehovot (IL)

(72) Inventors: Dov Tamarkin, Maccabim (IL); Elana Gazal, Rehovot (IL); Irakliy Papiashvili, Ashkelon (IL); Yohan Hazot, Rehovot (IL); David Schuz, Gimzu (IL); Rita Keynan, Rehovot (IL)

(73) Assignee: Vyne Therapeutics Inc., Bridgewater, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/235,986

(22) Filed: Dec. 28, 2018

(65) Prior Publication Data

US 2019/0134204 A1 May 9, 2019

Related U.S. Application Data

(63) Continuation of application No. 14/850,655, filed on Sep. 10, 2015, now Pat. No. 10,238,746, which is a
(Continued)

(51) Int. Cl.
| | |
|---|---|
| *A61K 8/31* | (2006.01) |
| *A61K 8/34* | (2006.01) |
| *A61K 8/36* | (2006.01) |
| *A61K 9/00* | (2006.01) |
| *A61K 9/12* | (2006.01) |
| *A61K 31/137* | (2006.01) |
| *A61K 31/192* | (2006.01) |
| *A61K 31/4164* | (2006.01) |
| *A61K 31/57* | (2006.01) |
| *A61K 31/573* | (2006.01) |
| *A61K 31/593* | (2006.01) |

(Continued)

(52) U.S. Cl.
CPC .............. *A61K 47/44* (2013.01); *A61K 8/31* (2013.01); *A61K 8/342* (2013.01); *A61K 8/361* (2013.01); *A61K 9/0014* (2013.01); *A61K 9/0048* (2013.01); *A61K 9/12* (2013.01); *A61K 9/122* (2013.01); *A61K 9/124* (2013.01); *A61K 31/137* (2013.01); *A61K 31/192* (2013.01); *A61K 31/4164* (2013.01); *A61K 31/57* (2013.01); *A61K 31/573* (2013.01); *A61K 31/593* (2013.01); *A61K 31/65* (2013.01); *A61K 45/06* (2013.01); *A61K 47/02* (2013.01); *A61K 47/06* (2013.01); *A61K 47/10* (2013.01); *A61K 47/12* (2013.01); *A61K 47/24* (2013.01); *A61Q 17/04* (2013.01); *A61Q 19/00* (2013.01); *A61Q 19/10* (2013.01); *A61K 2800/31* (2013.01); *A61K 2800/33* (2013.01)

(58) Field of Classification Search
CPC ........ A61K 9/124; A61K 9/12; A61K 9/0014; A61K 9/122; A61K 47/44; A61K 31/65; A61K 2800/31; A61K 2800/33; A61K 8/31; A61K 8/342; A61K 8/361; A61K 9/0048; A61K 31/137; A61K 31/192; A61K 31/4164; A61K 31/57; A61K 31/573; A61K 31/593; A61K 45/06; A61K 47/02; A61K 47/06; A61K 47/10; A61K 47/12; A61K 47/24; A61Q 19/00; A61Q 17/04; A61Q 19/10; A61P 1/00; A61P 5/00; A61P 7/10; A61P 9/00; A61P 9/08; A61P 11/00; A61P 15/00; A61P 15/02; A61P 17/00; A61P 17/02; A61P 17/04; A61P 17/06; A61P 17/08; A61P 17/10; A61P 17/12; A61P 17/14; A61P 17/16; A61P 19/02; A61P 23/00; A61P 25/00; A61P 25/20; A61P 25/24
USPC .......................................................... 424/43
See application file for complete search history.

(56) References Cited

U.S. PATENT DOCUMENTS

| 1,159,250 A | 11/1915 | Moulton |
|---|---|---|
| 1,666,684 A | 4/1928 | Carstens |

(Continued)

FOREIGN PATENT DOCUMENTS

| AU | 198780257 A | 9/1986 |
|---|---|---|
| AU | 782515 B2 | 12/2005 |

(Continued)

OTHER PUBLICATIONS

"Everything but the Olive." The Olive Oil Source 1998-2016 [online]. Retrieved from the Internet: http://www.oliveoilsource.com/pageA chemical-characteristics.

(Continued)

*Primary Examiner* — Trevor Love
(74) *Attorney, Agent, or Firm* — Finnegan, Henderson, Farabow, Garrett & Dunner, LLP

(57) ABSTRACT

A substantially surface active agent free composition which includes a hydrophobic solvent, and/or a petrolatum, a paraffin wax and/or a fatty alcohol, a fatty acid and/or a wax and/or shea butter, with and without a propellant. A substantially surface active agent free composition, further comprising, a tetracycline antibiotic, or a vitamin D derivative, or one or more other active agents. A method of treatment using a substantially surface active agent free composition.

24 Claims, No Drawings

Related U.S. Application Data continuation of application No. 14/577,659, filed on Dec. 19, 2014, now abandoned, which is a continuation of application No. 13/499,501, filed as application No. PCT/IB2010/002612 on Oct. 1, 2010, now Pat. No. 8,945,516.

(60) Provisional application No. 61/388,884, filed on Oct. 1, 2010, provisional application No. 61/385,385, filed on Sep. 22, 2010, provisional application No. 61/380,568, filed on Sep. 7, 2010, provisional application No. 61/349,911, filed on May 31, 2010, provisional application No. 61/331,126, filed on May 4, 2010, provisional application No. 61/322,148, filed on Apr. 8, 2010, provisional application No. 61/248,144, filed on Oct. 2, 2009.

(51) Int. Cl.
  *A61K 31/65* (2006.01)
  *A61K 45/06* (2006.01)
  *A61K 47/02* (2006.01)
  *A61K 47/06* (2006.01)
  *A61K 47/10* (2017.01)
  *A61K 47/12* (2006.01)
  *A61K 47/24* (2006.01)
  *A61K 47/44* (2017.01)
  *A61Q 17/04* (2006.01)
  *A61Q 19/00* (2006.01)
  *A61Q 19/10* (2006.01)

(56) References Cited

U.S. PATENT DOCUMENTS

| | | |
|---|---|---|
| 1,924,972 A | 8/1933 | Beckert |
| 2,085,733 A | 7/1937 | Bird |
| 2,390,921 A | 12/1945 | Clark |
| 2,524,590 A | 10/1950 | Boe |
| 2,586,287 A | 2/1952 | Apperson |
| 2,617,754 A | 11/1952 | Neely |
| 2,767,712 A | 10/1956 | Waterman |
| 2,968,628 A | 1/1961 | Reed |
| 3,004,894 A | 10/1961 | Johnson et al. |
| 3,062,715 A | 11/1962 | Reese et al. |
| 3,067,784 A | 12/1962 | Gorman |
| 3,092,255 A | 6/1963 | Hohman |
| 3,092,555 A | 6/1963 | Horn |
| 3,141,821 A | 7/1964 | Compeau |
| 3,142,420 A | 7/1964 | Gawthrop |
| 3,144,386 A | 8/1964 | Brightenback |
| 3,149,543 A | 9/1964 | Naab |
| 3,154,075 A | 10/1964 | Weckesser |
| 3,178,352 A | 4/1965 | Erickson |
| 3,236,457 A | 2/1966 | Kennedy et al. |
| 3,244,589 A | 4/1966 | Sunnen |
| 3,252,859 A | 5/1966 | Silver |
| 3,261,695 A | 7/1966 | Sienkiewicz |
| 3,263,867 A | 8/1966 | Lehmann |
| 3,263,869 A | 8/1966 | Corsette |
| 3,298,919 A | 1/1967 | Bishop et al. |
| 3,301,444 A | 1/1967 | Wittke |
| 3,303,970 A | 2/1967 | Breslau et al. |
| 3,330,730 A | 7/1967 | Hernandez |
| 3,333,333 A | 8/1967 | Noack |
| 3,334,147 A | 8/1967 | Brunelle et al. |
| 3,342,845 A | 9/1967 | Sayigh et al. |
| 3,346,451 A | 10/1967 | Collins et al. |
| 3,366,494 A | 1/1968 | Bower et al. |
| 3,369,034 A | 2/1968 | Chalmers |
| 3,377,004 A | 4/1968 | Wittke |
| 3,383,280 A | 5/1968 | Kuehns |
| 3,384,541 A | 5/1968 | Clark et al. |
| 3,395,214 A | 7/1968 | Mummert |
| 3,395,215 A | 7/1968 | Schubert |
| 3,401,849 A | 9/1968 | Weber, III |
| 3,419,658 A | 12/1968 | Sanders |
| 3,456,052 A | 7/1969 | Gordon |
| 3,527,559 A | 9/1970 | Sliwinski |
| 3,540,448 A | 11/1970 | Sunnen |
| 3,559,890 A | 2/1971 | Brooks et al. |
| 3,561,262 A | 2/1971 | Borucki |
| 3,563,098 A | 2/1971 | Weber, III |
| 3,574,821 A | 4/1971 | Pfirrmann |
| 3,577,518 A | 5/1971 | Shepherd |
| 3,667,461 A | 6/1972 | Zamarra |
| 3,751,562 A | 8/1973 | Nichols |
| 3,770,648 A | 11/1973 | Mackles |
| 3,787,566 A | 1/1974 | Gauvreau |
| 3,819,524 A | 6/1974 | Schubert et al. |
| 3,824,303 A | 7/1974 | Lanzet et al. |
| 3,841,525 A | 10/1974 | Siegel |
| 3,849,569 A | 11/1974 | Mead |
| 3,849,580 A | 11/1974 | Weinstein et al. |
| 3,865,275 A | 2/1975 | De Nunzio |
| 3,866,800 A | 2/1975 | Schmitt |
| 3,878,118 A | 4/1975 | Watson |
| 3,882,228 A | 5/1975 | Boncey et al. |
| 3,886,084 A | 5/1975 | Vassiliades |
| 3,890,305 A | 6/1975 | Weber et al. |
| 3,912,665 A | 10/1975 | Spitzer et al. |
| 3,912,667 A | 10/1975 | Spitzer et al. |
| 3,923,970 A | 12/1975 | Breuer |
| 3,929,985 A | 12/1975 | Webb, Jr. |
| 3,952,916 A | 4/1976 | Phillips |
| 3,953,591 A | 4/1976 | Snyder |
| 3,959,160 A | 5/1976 | Horsier et al. |
| 3,962,150 A | 6/1976 | Viola |
| 3,963,833 A | 6/1976 | DeSalva et al. |
| 3,966,090 A | 6/1976 | Prussin et al. |
| 3,966,632 A | 6/1976 | Colliopoulos et al. |
| 3,970,219 A | 7/1976 | Spitzer et al. |
| 3,970,584 A | 7/1976 | Hart et al. |
| 3,993,224 A | 11/1976 | Harrison |
| 3,997,467 A | 12/1976 | Jederstrom |
| 4,001,391 A | 1/1977 | Feinstone et al. |
| 4,001,442 A | 1/1977 | Stahlberger et al. |
| 4,018,396 A | 4/1977 | Showmaker et al. |
| 4,019,657 A | 4/1977 | Spitzer et al. |
| 4,052,513 A | 10/1977 | Kaplan |
| 4,083,974 A | 4/1978 | Turi |
| 4,102,995 A | 7/1978 | Hebborn |
| 4,110,426 A | 8/1978 | Barnhurst et al. |
| 4,124,149 A | 11/1978 | Spitzer et al. |
| 4,145,411 A | 3/1979 | Mende |
| 4,151,272 A | 4/1979 | Geary et al. |
| 4,160,827 A | 7/1979 | Cho et al. |
| 4,178,373 A | 12/1979 | Klein et al. |
| 4,213,979 A | 7/1980 | Levine |
| 4,214,000 A | 7/1980 | Papa |
| 4,226,344 A | 10/1980 | Booth et al. |
| 4,229,432 A | 10/1980 | Geria |
| 4,230,701 A | 10/1980 | Holick et al. |
| 4,241,048 A | 12/1980 | Durbak et al. |
| 4,241,149 A | 12/1980 | Labes et al. |
| 4,252,787 A | 2/1981 | Sherman et al. |
| 4,254,104 A | 3/1981 | Suzuki et al. |
| 4,268,499 A | 5/1981 | Keil |
| 4,271,149 A | 6/1981 | Winicov et al. |
| 4,278,206 A | 7/1981 | Prussin |
| 4,292,250 A | 9/1981 | DeLuca et al. |
| 4,292,326 A | 9/1981 | Nazzaro-Porro et al. |
| 4,299,826 A | 11/1981 | Luedders |
| 4,305,936 A | 12/1981 | Klein |
| 4,309,995 A | 1/1982 | Sacco |
| 4,310,510 A | 1/1982 | Sherman et al. |
| 4,323,582 A | 4/1982 | Siegel et al. |
| 4,323,694 A | 4/1982 | Scala, Jr. |
| 4,325,939 A | 4/1982 | Shah |
| 4,329,990 A | 5/1982 | Sneider |
| 4,335,120 A | 6/1982 | Holick et al. |
| 4,338,211 A | 7/1982 | Stiros |
| 4,352,808 A | 10/1982 | Rane et al. |

(56) References Cited

U.S. PATENT DOCUMENTS

| | | |
|---|---|---|
| 4,363,806 A | 12/1982 | Bergström et al. |
| 4,385,161 A | 5/1983 | Caunt et al. |
| 4,386,104 A | 5/1983 | Nazzaro-Porro |
| 4,393,066 A | 7/1983 | Garrett et al. |
| 4,427,670 A | 1/1984 | Ofuchi et al. |
| 4,439,416 A | 3/1984 | Cordon et al. |
| 4,439,441 A | 3/1984 | Hallesy et al. |
| 4,440,320 A | 4/1984 | Wernicke |
| 4,447,486 A | 5/1984 | Hoppe et al. |
| 4,469,674 A | 9/1984 | Shah et al. |
| 4,508,705 A | 4/1985 | Chaudhuri et al. |
| 4,522,948 A | 6/1985 | Walker |
| 4,529,601 A | 7/1985 | Broberg et al. |
| 4,529,605 A | 7/1985 | Lynch et al. |
| 4,552,872 A | 11/1985 | Cooper et al. |
| 4,574,052 A | 3/1986 | Gupte et al. |
| 4,576,961 A | 3/1986 | Lorck et al. |
| 4,595,526 A | 6/1986 | Lai |
| 4,603,812 A | 8/1986 | Stoesser et al. |
| 4,607,101 A | 8/1986 | Bernstein |
| 4,612,193 A | 9/1986 | Gordon et al. |
| 4,627,973 A | 12/1986 | Moran et al. |
| 4,628,063 A | 12/1986 | Haines et al. |
| 4,661,340 A | 4/1987 | Nagy née Kricsfalussy et al. |
| 4,661,524 A | 4/1987 | Thomson et al. |
| 4,672,078 A | 6/1987 | Sakai et al. |
| 4,673,569 A | 6/1987 | Shernov et al. |
| 4,678,463 A | 7/1987 | Millar |
| 4,701,320 A | 10/1987 | Hasegawa et al. |
| 4,725,609 A | 2/1988 | Kull, Jr. et al. |
| 4,738,396 A | 4/1988 | Doi et al. |
| 4,741,855 A | 5/1988 | Grote et al. |
| 4,752,465 A | 6/1988 | Mackles |
| 4,770,634 A | 9/1988 | Pellico |
| 4,772,427 A | 9/1988 | Dawson |
| 4,780,309 A | 10/1988 | Geria et al. |
| 4,784,842 A | 11/1988 | London et al. |
| 4,792,062 A | 12/1988 | Goncalves |
| 4,798,682 A | 1/1989 | Ansmann |
| 4,804,674 A | 2/1989 | Curtis-Prior et al. |
| 4,806,262 A | 2/1989 | Snyder |
| 4,808,388 A | 2/1989 | Beutler et al. |
| 4,822,613 A | 4/1989 | Rodero |
| 4,822,614 A | 4/1989 | Rodero |
| 4,826,048 A | 5/1989 | Skorka et al. |
| 4,827,378 A | 5/1989 | Gillan et al. |
| 4,828,837 A | 5/1989 | Uster et al. |
| 4,836,217 A | 6/1989 | Fischer et al. |
| 4,837,019 A | 6/1989 | Georgalas et al. |
| 4,837,378 A | 6/1989 | Borgman |
| 4,844,902 A | 7/1989 | Grohe |
| 4,847,068 A | 7/1989 | Dole et al. |
| 4,849,117 A | 7/1989 | Bronner et al. |
| 4,849,211 A | 7/1989 | Schrauzer |
| 4,851,154 A | 7/1989 | Grollier et al. |
| 4,855,294 A | 8/1989 | Patel et al. |
| 4,863,900 A | 9/1989 | Pollock et al. |
| 4,867,967 A | 9/1989 | Crutcher |
| 4,873,078 A | 10/1989 | Edmundson et al. |
| 4,874,794 A | 10/1989 | Katz |
| 4,876,083 A | 10/1989 | Grollier et al. |
| 4,877,805 A | 10/1989 | Kligman |
| 4,885,282 A | 12/1989 | Thornfeldt |
| 4,897,262 A | 1/1990 | Nandagiri et al. |
| 4,902,281 A | 2/1990 | Avoy |
| 4,906,453 A | 3/1990 | Tsoucalas |
| 4,913,893 A | 4/1990 | Varco et al. |
| 4,919,934 A | 4/1990 | Deckner et al. |
| 4,933,330 A | 6/1990 | Jorgensen et al. |
| 4,950,420 A | 8/1990 | Svarz |
| 4,954,487 A | 9/1990 | Cooper et al. |
| 4,956,049 A | 9/1990 | Bernheim et al. |
| 4,957,732 A | 9/1990 | Grollier et al. |
| 4,963,351 A | 10/1990 | Weston |
| 4,965,063 A | 10/1990 | Casey et al. |
| 4,966,779 A | 10/1990 | Kirk |
| 4,970,067 A | 11/1990 | Panandiker et al. |
| 4,975,466 A | 12/1990 | Bottcher et al. |
| 4,981,367 A | 1/1991 | Brazelton |
| 4,981,677 A | 1/1991 | Thau |
| 4,981,679 A | 1/1991 | Briggs et al. |
| 4,981,845 A | 1/1991 | Pereira et al. |
| 4,985,459 A | 1/1991 | Sunshine et al. |
| 4,992,478 A | 2/1991 | Geria |
| 4,993,496 A | 2/1991 | Riedle et al. |
| 4,996,193 A | 2/1991 | Hewitt et al. |
| 5,002,540 A | 3/1991 | Brodman et al. |
| 5,002,680 A | 3/1991 | Schmidt et al. |
| 5,007,556 A | 4/1991 | Lover |
| 5,013,297 A | 5/1991 | Cattanach |
| 5,015,471 A | 5/1991 | Birtwistle et al. |
| 5,019,375 A | 5/1991 | Tanner et al. |
| 5,034,220 A | 7/1991 | Helioff et al. |
| 5,035,895 A | 7/1991 | Shibusawa et al. |
| 5,053,228 A | 10/1991 | Mori et al. |
| 5,071,648 A | 12/1991 | Rosenblatt |
| 5,071,881 A | 12/1991 | Parfondry et al. |
| 5,073,371 A | 12/1991 | Turner et al. |
| 5,082,651 A | 1/1992 | Healey et al. |
| 5,087,618 A | 2/1992 | Bodor |
| 5,089,252 A | 2/1992 | Grollier et al. |
| 5,091,111 A | 2/1992 | Neumiller |
| 5,094,853 A | 3/1992 | Hagarty |
| 5,100,917 A | 3/1992 | Flynn et al. |
| 5,104,645 A | 4/1992 | Cardin et al. |
| 5,112,359 A | 5/1992 | Murphy et al. |
| 5,114,718 A | 5/1992 | Damani |
| 5,122,519 A | 6/1992 | Ritter |
| 5,130,121 A | 7/1992 | Kopolow et al. |
| 5,133,972 A | 7/1992 | Ferrini et al. |
| 5,135,915 A | 8/1992 | Czarniecki et al. |
| 5,137,714 A | 8/1992 | Scott |
| 5,143,717 A | 9/1992 | Davis |
| 5,156,765 A | 10/1992 | Smrt |
| 5,160,665 A | 11/1992 | Owada et al. |
| 5,164,357 A | 11/1992 | Bartman et al. |
| 5,164,367 A | 11/1992 | Pickart |
| 5,167,950 A | 12/1992 | Lins |
| 5,171,577 A | 12/1992 | Griat et al. |
| 5,196,405 A | 3/1993 | Packman |
| 5,204,090 A | 4/1993 | Han |
| 5,204,093 A | 4/1993 | Victor |
| 5,208,031 A | 5/1993 | Kelly |
| 5,217,707 A | 6/1993 | Szabo et al. |
| 5,219,877 A | 6/1993 | Shah et al. |
| 5,221,530 A | 6/1993 | Janchitraponvej et al. |
| 5,221,534 A | 6/1993 | DesLauriers et al. |
| 5,221,696 A | 6/1993 | Ke et al. |
| 5,230,897 A | 7/1993 | Griffin et al. |
| 5,236,707 A | 8/1993 | Stewart, II |
| 5,252,246 A | 10/1993 | Ding et al. |
| 5,254,334 A | 10/1993 | Ramirez et al. |
| 5,262,407 A | 11/1993 | Leveque et al. |
| 5,266,592 A | 11/1993 | Grub et al. |
| 5,279,819 A | 1/1994 | Hayes |
| 5,286,475 A | 2/1994 | Louvet et al. |
| 5,294,365 A | 3/1994 | Welch et al. |
| 5,300,286 A | 4/1994 | Gee |
| 5,301,841 A | 4/1994 | Fuchs |
| 5,308,643 A | 5/1994 | Osipow et al. |
| 5,314,904 A | 5/1994 | Egidio et al. |
| 5,318,774 A | 6/1994 | Alban et al. |
| 5,322,683 A | 6/1994 | Mackles et al. |
| 5,326,557 A | 7/1994 | Glover et al. |
| 5,344,051 A | 9/1994 | Brown |
| 5,346,135 A | 9/1994 | Vincent |
| 5,352,437 A | 10/1994 | Nakagawa et al. |
| 5,369,131 A | 11/1994 | Poli et al. |
| 5,378,451 A | 1/1995 | Gorman et al. |
| 5,378,730 A | 1/1995 | Lee et al. |
| 5,380,761 A | 1/1995 | Szabo et al. |
| 5,384,308 A | 1/1995 | Henkin |
| 5,385,943 A | 1/1995 | Nazzaro-Porro |
| 5,389,305 A | 2/1995 | Repinec et al. |

(56) References Cited

U.S. PATENT DOCUMENTS

| | | |
|---|---|---|
| 5,389,676 A | 2/1995 | Michaels |
| 5,397,312 A | 3/1995 | Rademaker et al. |
| 5,398,846 A | 3/1995 | Corba et al. |
| 5,399,205 A | 3/1995 | Shinohara et al. |
| 5,411,992 A | 5/1995 | Eini et al. |
| 5,422,361 A | 6/1995 | Munayyer et al. |
| 5,429,815 A | 7/1995 | Faryniarz et al. |
| 5,435,996 A | 7/1995 | Glover et al. |
| 5,439,670 A | 8/1995 | Purewal et al. |
| 5,439,682 A | 8/1995 | Wivell et al. |
| 5,447,725 A | 9/1995 | Damani et al. |
| 5,449,520 A | 9/1995 | Frigerio et al. |
| 5,451,404 A | 9/1995 | Furman |
| 5,482,965 A | 1/1996 | Rajadhyaksha |
| 5,491,245 A | 2/1996 | Gruning et al. |
| 5,500,211 A | 3/1996 | George et al. |
| 5,508,033 A | 4/1996 | Briand et al. |
| 5,512,555 A | 4/1996 | Waldstreicher |
| 5,514,367 A | 5/1996 | Lentini et al. |
| 5,514,369 A | 5/1996 | Salka et al. |
| 5,520,918 A | 5/1996 | Smith |
| 5,523,078 A | 6/1996 | Baylin |
| 5,527,534 A | 6/1996 | Myhling |
| 5,527,822 A | 6/1996 | Scheiner |
| 5,529,770 A | 6/1996 | McKinzie et al. |
| 5,531,703 A | 7/1996 | Skwarek et al. |
| 5,534,261 A | 7/1996 | Rodgers et al. |
| 5,536,743 A | 7/1996 | Borgman |
| 5,540,853 A | 7/1996 | Trinh et al. |
| 5,545,401 A | 8/1996 | Shanbrom |
| 5,547,989 A | 8/1996 | Chamness |
| 5,558,872 A | 9/1996 | Jones et al. |
| 5,560,859 A | 10/1996 | Hartmann et al. |
| 5,567,420 A | 10/1996 | McEleney et al. |
| 5,576,016 A | 11/1996 | Amselem et al. |
| 5,578,315 A | 11/1996 | Chien et al. |
| 5,585,104 A | 12/1996 | Ha et al. |
| 5,589,157 A | 12/1996 | Hatfield |
| 5,589,515 A | 12/1996 | Suzuki et al. |
| 5,597,560 A | 1/1997 | Bergamini et al. |
| 5,603,940 A | 2/1997 | Candau et al. |
| 5,605,679 A | 2/1997 | Hansenne et al. |
| 5,608,119 A | 3/1997 | Amano et al. |
| 5,611,463 A | 3/1997 | Favre |
| 5,612,056 A | 3/1997 | Jenner et al. |
| 5,613,583 A | 3/1997 | Kono et al. |
| 5,613,623 A | 3/1997 | Hildebrandt |
| 5,614,171 A | 3/1997 | Clavenna et al. |
| 5,614,178 A | 3/1997 | Bloom et al. |
| 5,618,516 A | 4/1997 | Clavenna et al. |
| 5,635,469 A | 6/1997 | Fowler et al. |
| 5,641,480 A | 6/1997 | Vermeer |
| 5,643,600 A | 7/1997 | Mathur |
| 5,645,842 A | 7/1997 | Gruning et al. |
| 5,648,380 A | 7/1997 | Martin |
| 5,650,554 A | 7/1997 | Moloney |
| 5,658,575 A | 8/1997 | Ribier et al. |
| 5,658,749 A | 8/1997 | Thornton |
| 5,658,956 A | 8/1997 | Martin et al. |
| 5,663,208 A | 9/1997 | Martin |
| 5,672,634 A | 9/1997 | Tseng et al. |
| 5,679,324 A | 10/1997 | Lisboa et al. |
| 5,683,710 A | 11/1997 | Akemi et al. |
| 5,686,088 A | 11/1997 | Mitra et al. |
| 5,693,258 A | 12/1997 | Tonomura et al. |
| 5,695,551 A | 12/1997 | Buckingham et al. |
| 5,695,747 A | 12/1997 | Forestier et al. |
| 5,700,396 A | 12/1997 | Suzuki et al. |
| 5,705,472 A | 1/1998 | Hayes et al. |
| 5,716,611 A | 2/1998 | Oshlack et al. |
| 5,716,621 A | 2/1998 | Bello |
| 5,719,122 A | 2/1998 | Chiodini et al. |
| 5,719,197 A | 2/1998 | Kanios et al. |
| 5,725,872 A | 3/1998 | Stamm et al. |
| 5,725,874 A | 3/1998 | Oda |
| 5,730,964 A | 3/1998 | Waldstreicher |
| 5,733,558 A | 3/1998 | Breton et al. |
| 5,733,572 A | 3/1998 | Unger et al. |
| 5,741,509 A | 4/1998 | Kushner |
| 5,747,049 A | 5/1998 | Tominaga |
| 5,753,241 A | 5/1998 | Ribier et al. |
| 5,753,245 A | 5/1998 | Fowler et al. |
| 5,753,270 A | 5/1998 | Beauchamp et al. |
| 5,759,520 A | 6/1998 | Sachetto |
| 5,759,579 A | 6/1998 | Singh et al. |
| 5,767,104 A | 6/1998 | Bar-Shalom et al. |
| 5,773,410 A | 6/1998 | Yamamoto |
| 5,783,202 A | 7/1998 | Tomlinson et al. |
| 5,788,664 A | 8/1998 | Scalise |
| 5,792,448 A | 8/1998 | Dubief et al. |
| 5,792,922 A | 8/1998 | Moloney et al. |
| 5,797,955 A | 8/1998 | Walters |
| 5,804,546 A | 9/1998 | Hall et al. |
| 5,807,571 A | 9/1998 | List |
| 5,817,322 A | 10/1998 | Xu et al. |
| 5,824,650 A | 10/1998 | De Lacharriere et al. |
| 5,833,960 A | 11/1998 | Gers-Barlag et al. |
| 5,833,961 A | 11/1998 | Siegfried et al. |
| 5,837,270 A | 11/1998 | Burgess |
| 5,840,744 A | 11/1998 | Borgman |
| 5,840,771 A | 11/1998 | Oldham et al. |
| 5,843,411 A | 12/1998 | Hernandez et al. |
| 5,846,983 A | 12/1998 | Sandborn et al. |
| 5,849,042 A | 12/1998 | Lim et al. |
| 5,854,246 A | 12/1998 | Francois et al. |
| 5,856,452 A | 1/1999 | Moloney et al. |
| 5,858,371 A | 1/1999 | Singh et al. |
| 5,865,347 A | 2/1999 | Welschoff |
| 5,866,040 A | 2/1999 | Nakama et al. |
| 5,869,529 A | 2/1999 | Sintov et al. |
| 5,871,720 A | 2/1999 | Gutierrez et al. |
| 5,877,216 A | 3/1999 | Place et al. |
| 5,879,469 A | 3/1999 | Avram et al. |
| 5,881,493 A | 3/1999 | Restive |
| 5,885,581 A | 3/1999 | Massand |
| 5,889,028 A | 3/1999 | Sandborn et al. |
| 5,889,054 A | 3/1999 | Yu et al. |
| 5,891,458 A | 4/1999 | Britton et al. |
| 5,902,574 A | 5/1999 | Stoner et al. |
| 5,902,789 A | 5/1999 | Stoltz |
| 5,905,092 A | 5/1999 | Osborne et al. |
| 5,910,382 A | 6/1999 | Goodenough et al. |
| 5,911,981 A | 6/1999 | Dahms et al. |
| 5,912,007 A | 6/1999 | Pan et al. |
| 5,914,122 A | 6/1999 | Otterbeck et al. |
| 5,914,310 A | 6/1999 | Li et al. |
| 5,919,830 A | 7/1999 | Gopalkrishnan et al. |
| 5,922,331 A | 7/1999 | Mausner |
| 5,925,669 A | 7/1999 | Katz et al. |
| 5,939,376 A | 8/1999 | Durbut et al. |
| 5,948,682 A | 9/1999 | Moloney |
| 5,951,544 A | 9/1999 | Konwitz |
| 5,951,989 A | 9/1999 | Heymann |
| 5,951,993 A | 9/1999 | Scholz et al. |
| 5,952,373 A | 9/1999 | Lanzendorfer et al. |
| 5,952,392 A | 9/1999 | Katz et al. |
| 5,955,414 A | 9/1999 | Brown et al. |
| 5,959,161 A | 9/1999 | Kenmochi et al. |
| 5,961,957 A | 10/1999 | McAnalley |
| 5,961,998 A | 10/1999 | Arnaud et al. |
| 5,972,310 A | 10/1999 | Sachetto |
| 5,976,555 A | 11/1999 | Liu et al. |
| 5,980,904 A | 11/1999 | Leverett et al. |
| 5,990,100 A | 11/1999 | Rosenberg et al. |
| 5,993,846 A | 11/1999 | Friedman et al. |
| 6,001,341 A | 12/1999 | Genova et al. |
| 6,006,948 A | 12/1999 | Auer |
| 6,017,912 A | 1/2000 | Bussell |
| 6,019,967 A | 2/2000 | Breton et al. |
| 6,024,942 A | 2/2000 | Tanner et al. |
| 6,030,630 A | 2/2000 | Fleury et al. |
| 6,033,647 A | 3/2000 | Touzan et al. |
| 6,039,936 A | 3/2000 | Restle et al. |
| 6,042,848 A | 3/2000 | Lawyer et al. |

(56) References Cited

U.S. PATENT DOCUMENTS

| | | | |
|---|---|---|---|
| 6,045,779 | A | 4/2000 | Mueller et al. |
| 6,060,041 | A | 5/2000 | Candau et al. |
| 6,071,536 | A | 6/2000 | Suzuki et al. |
| 6,071,541 | A | 6/2000 | Murad |
| 6,075,056 | A | 6/2000 | Quigley, Jr. et al. |
| 6,080,394 | A | 6/2000 | Lin et al. |
| 6,087,310 | A | 7/2000 | Heinkel |
| 6,087,317 | A | 7/2000 | Gee |
| 6,090,772 | A | 7/2000 | Kaiser et al. |
| 6,093,408 | A | 7/2000 | Hasenoehrl et al. |
| 6,096,756 | A | 8/2000 | Crain et al. |
| 6,110,477 | A | 8/2000 | Hernandez et al. |
| 6,110,966 | A | 8/2000 | Pollock |
| 6,113,888 | A | 9/2000 | Castro et al. |
| 6,116,466 | A | 9/2000 | Gueret |
| 6,121,210 | A | 9/2000 | Taylor |
| 6,126,920 | A | 10/2000 | Jones et al. |
| 6,133,327 | A | 10/2000 | Kimura et al. |
| 6,140,355 | A | 10/2000 | Egidio et al. |
| 6,146,645 | A | 11/2000 | Deckers et al. |
| 6,146,664 | A | 11/2000 | Siddiqui |
| 6,162,834 | A | 12/2000 | Sebillotte-Arnaud et al. |
| 6,165,455 | A | 12/2000 | Torgerson et al. |
| 6,168,576 | B1 | 1/2001 | Reynolds |
| 6,171,347 | B1 | 1/2001 | Kunz et al. |
| 6,180,662 | B1 | 1/2001 | Lanzendörfer et al. |
| 6,180,669 | B1 | 1/2001 | Tamarkin |
| 6,183,762 | B1 | 2/2001 | Deckers et al. |
| 6,186,367 | B1 | 2/2001 | Harrold |
| 6,187,290 | B1 | 2/2001 | Gilchrist et al. |
| 6,189,810 | B1 | 2/2001 | Nerushai et al. |
| 6,190,365 | B1 | 2/2001 | Abbott et al. |
| 6,204,285 | B1 | 3/2001 | Fabiano et al. |
| 6,210,656 | B1 | 4/2001 | Touzan et al. |
| 6,210,742 | B1 | 4/2001 | Deckers et al. |
| 6,214,318 | B1 | 4/2001 | Osipow et al. |
| 6,214,788 | B1 | 4/2001 | Velazco et al. |
| 6,217,887 | B1 | 4/2001 | Beerse et al. |
| 6,221,381 | B1 | 4/2001 | Shelford et al. |
| 6,221,823 | B1 | 4/2001 | Crisanti et al. |
| 6,224,888 | B1 | 5/2001 | Vatter et al. |
| 6,231,837 | B1 | 5/2001 | Stroud et al. |
| 6,232,315 | B1 | 5/2001 | Shafer et al. |
| 6,241,971 | B1 | 6/2001 | Fox et al. |
| 6,251,369 | B1 | 6/2001 | Stoltz |
| 6,258,374 | B1 | 7/2001 | Friess et al. |
| 6,261,544 | B1 | 7/2001 | Coury et al. |
| 6,264,964 | B1 | 7/2001 | Mohammadi |
| 6,270,781 | B1 | 8/2001 | Gehlsen |
| 6,271,295 | B1 | 8/2001 | Powell et al. |
| 6,274,150 | B1 | 8/2001 | Simonnet et al. |
| 6,283,336 | B1 | 9/2001 | Dwyer et al. |
| 6,284,802 | B1 | 9/2001 | Bissett et al. |
| 6,287,546 | B1 | 9/2001 | Reich et al. |
| 6,294,550 | B1 | 9/2001 | Place et al. |
| 6,299,023 | B1 | 10/2001 | Arnone |
| 6,299,032 | B1 | 10/2001 | Hamilton |
| 6,299,900 | B1 | 10/2001 | Reed et al. |
| 6,305,578 | B1 | 10/2001 | Hildebrandt et al. |
| 6,306,841 | B1 | 10/2001 | Place et al. |
| 6,308,863 | B1 | 10/2001 | Harman |
| 6,319,913 | B1 | 11/2001 | Mak et al. |
| 6,328,950 | B1 | 12/2001 | Franzke et al. |
| 6,328,982 | B1 | 12/2001 | Shiroyama et al. |
| 6,333,362 | B1 | 12/2001 | Lorant |
| 6,335,022 | B1 | 1/2002 | Simonnet et al. |
| 6,341,717 | B2 | 1/2002 | Auer |
| 6,344,218 | B1 | 2/2002 | Dodd et al. |
| 6,348,229 | B1 | 2/2002 | Eini et al. |
| 6,352,727 | B1 | 3/2002 | Takahashi |
| 6,355,230 | B2 | 3/2002 | Gers-Barlag et al. |
| 6,358,541 | B1 | 3/2002 | Goodman |
| 6,358,924 | B1 | 3/2002 | Hoffmann |
| 6,364,854 | B1 | 4/2002 | Ferrer et al. |
| 6,372,234 | B1 | 4/2002 | Deckers et al. |
| 6,375,936 | B1 | 4/2002 | Allard et al. |
| 6,375,960 | B1 | 4/2002 | Simonnet et al. |
| 6,383,471 | B1 | 5/2002 | Chen et al. |
| 6,395,258 | B1 | 5/2002 | Steer |
| 6,395,300 | B1 | 5/2002 | Straub et al. |
| 6,403,061 | B1 | 6/2002 | Candau et al. |
| 6,403,069 | B1 | 6/2002 | Chopra et al. |
| 6,410,036 | B1 | 6/2002 | De Rosa et al. |
| 6,423,323 | B2 | 7/2002 | Neubourg |
| 6,423,329 | B1 | 7/2002 | Sine et al. |
| 6,428,772 | B1 | 8/2002 | Singh et al. |
| 6,433,003 | B1 | 8/2002 | Bobrove et al. |
| 6,433,024 | B1 | 8/2002 | Popp et al. |
| 6,433,033 | B1 | 8/2002 | Isobe et al. |
| 6,433,068 | B1 | 8/2002 | Morrison et al. |
| 6,437,006 | B1 | 8/2002 | Yoon et al. |
| 6,440,429 | B1 | 8/2002 | Torizuka et al. |
| 6,447,801 | B1 | 9/2002 | Salafsky et al. |
| 6,451,777 | B1 | 9/2002 | Bradbury et al. |
| 6,455,076 | B1 | 9/2002 | Hahn et al. |
| 6,468,989 | B1 | 10/2002 | Chang et al. |
| 6,479,058 | B1 | 11/2002 | McCadden |
| 6,479,060 | B1 | 11/2002 | Jones et al. |
| 6,479,532 | B1 | 11/2002 | Kamimura et al. |
| 6,482,810 | B1 | 11/2002 | Brem et al. |
| 6,486,168 | B1 | 11/2002 | Skwierczynski et al. |
| 6,488,947 | B1 | 12/2002 | Bekele |
| 6,511,655 | B1 | 1/2003 | Muller et al. |
| 6,514,487 | B1 | 2/2003 | Barr |
| 6,524,594 | B1 | 2/2003 | Santora et al. |
| 6,531,118 | B1 | 3/2003 | Gonzalez et al. |
| 6,534,455 | B1 | 3/2003 | Maurin et al. |
| 6,536,629 | B2 | 3/2003 | van der Heijden |
| 6,544,530 | B1 | 4/2003 | Friedman |
| 6,544,562 | B2 | 4/2003 | Singh et al. |
| 6,547,063 | B1 | 4/2003 | Zaveri et al. |
| 6,548,074 | B1 | 4/2003 | Mohammadi |
| 6,551,604 | B1 | 4/2003 | Beck et al. |
| 6,562,355 | B1 | 5/2003 | Renault |
| 6,566,350 | B2 | 5/2003 | Ono et al. |
| 6,582,679 | B2 | 6/2003 | Stein et al. |
| 6,582,710 | B2 | 6/2003 | Deckers et al. |
| 6,589,509 | B2 | 7/2003 | Keller et al. |
| 6,596,287 | B2 | 7/2003 | Deckers et al. |
| 6,599,513 | B2 | 7/2003 | Deckers et al. |
| 6,607,716 | B1 | 8/2003 | Smith et al. |
| 6,610,315 | B2 | 8/2003 | Scholz et al. |
| 6,620,773 | B1 | 9/2003 | Stork et al. |
| 6,638,981 | B2 | 10/2003 | Williams et al. |
| 6,649,571 | B1 | 11/2003 | Morgan |
| 6,649,574 | B2 | 11/2003 | Cardis et al. |
| 6,672,483 | B1 | 1/2004 | Roy |
| 6,682,726 | B2 | 1/2004 | Marchesi et al. |
| 6,682,750 | B2 | 1/2004 | Loeffler et al. |
| 6,691,898 | B2 | 2/2004 | Hurray et al. |
| 6,706,290 | B1 | 3/2004 | Kajander et al. |
| 6,709,663 | B2 | 3/2004 | Espinoza |
| 6,723,309 | B1 | 4/2004 | Deane |
| 6,730,288 | B1 | 5/2004 | Abram |
| 6,736,860 | B2 | 5/2004 | Patel et al. |
| 6,753,000 | B2 | 6/2004 | Breton et al. |
| 6,753,013 | B1 | 6/2004 | Didriksen et al. |
| 6,753,167 | B2 | 6/2004 | Moloney et al. |
| 6,762,158 | B2 | 7/2004 | Lukenbach et al. |
| 6,765,001 | B2 | 7/2004 | Gans et al. |
| 6,774,114 | B2 | 8/2004 | Castiel et al. |
| 6,777,591 | B2 | 8/2004 | Chaudhary et al. |
| 6,790,435 | B1 | 9/2004 | Ma et al. |
| 6,796,973 | B1 | 9/2004 | Contente et al. |
| RE38,623 | E | 10/2004 | Hernandez et al. |
| 6,811,767 | B1 | 11/2004 | Bosch et al. |
| 6,834,778 | B2 | 12/2004 | Jinbo et al. |
| 6,841,547 | B2 | 1/2005 | Brown et al. |
| 6,843,390 | B1 | 1/2005 | Bristor |
| 6,875,438 | B2 | 4/2005 | Kraemer et al. |
| 6,881,271 | B2 | 4/2005 | Ochiai |
| 6,890,567 | B2 | 5/2005 | Nakatsu et al. |
| 6,897,195 | B2 | 5/2005 | Su et al. |
| 6,902,737 | B2 | 6/2005 | Quemin et al. |

(56) References Cited

U.S. PATENT DOCUMENTS

| | | |
|---|---|---|
| 6,911,211 B2 | 6/2005 | Eini et al. |
| 6,914,057 B1 | 7/2005 | Ryan et al. |
| 6,946,120 B2 | 9/2005 | Wai-Chiu So et al. |
| 6,946,139 B2 | 9/2005 | Henning |
| 6,951,654 B2 | 10/2005 | Malcolm et al. |
| 6,955,816 B2 | 10/2005 | Klysz |
| 6,956,062 B2 | 10/2005 | Beilfuss et al. |
| 6,958,154 B2 | 10/2005 | Andolino Brandt et al. |
| 6,967,023 B1 | 11/2005 | Eini et al. |
| 6,968,982 B1 | 11/2005 | Burns |
| 6,969,521 B1 | 11/2005 | Gonzalez et al. |
| RE38,964 E | 1/2006 | Shillington |
| 6,986,883 B2 | 1/2006 | Pellico |
| 6,994,863 B2 | 2/2006 | Eini et al. |
| 7,002,486 B2 | 2/2006 | Lawrence |
| 7,014,844 B2 | 3/2006 | Mahalingam et al. |
| 7,021,499 B2 | 4/2006 | Hansen et al. |
| 7,029,659 B2 | 4/2006 | Abram |
| 7,060,253 B1 | 6/2006 | Mundschenk |
| 7,078,058 B2 | 7/2006 | Jones et al. |
| 7,083,799 B1 | 8/2006 | Giacomoni |
| 7,137,536 B2 | 11/2006 | Walters et al. |
| 7,195,135 B1 | 3/2007 | Garcia |
| 7,222,802 B2 | 5/2007 | Sweeton |
| 7,225,518 B2 | 6/2007 | Eidenschink et al. |
| 7,226,230 B2 | 6/2007 | Liberatore |
| 7,235,251 B2 | 6/2007 | Hamer et al. |
| 7,252,816 B1 | 8/2007 | Angel et al. |
| 7,270,828 B2 | 9/2007 | Masuda et al. |
| 7,455,195 B2 | 11/2008 | Meketa |
| 7,497,354 B2 | 3/2009 | Decottignies et al. |
| 7,575,739 B2 | 8/2009 | Tamarkin et al. |
| 7,645,803 B2 | 1/2010 | Tamarkin et al. |
| 7,654,415 B2 | 2/2010 | van der Heijden |
| 7,682,623 B2 | 3/2010 | Eini et al. |
| 7,700,076 B2 | 4/2010 | Tamarkin et al. |
| 7,704,518 B2 | 4/2010 | Tamarkin et al. |
| 7,758,888 B2 | 7/2010 | Lapidot et al. |
| 7,793,807 B2 | 9/2010 | Goujon et al. |
| 7,820,145 B2 | 10/2010 | Tamarkin et al. |
| 7,842,791 B2 | 11/2010 | Britten et al. |
| 7,960,416 B2 | 6/2011 | Sato et al. |
| 8,114,385 B2 | 2/2012 | Tamarkin et al. |
| 8,119,106 B2 | 2/2012 | Tamarkin et al. |
| 8,119,109 B2 | 2/2012 | Tamarkin et al. |
| 8,119,150 B2 | 2/2012 | Tamarkin et al. |
| 8,158,109 B2 | 4/2012 | Abram et al. |
| 8,192,749 B2 | 6/2012 | Ashley |
| 8,211,874 B2 | 7/2012 | Theobald et al. |
| 8,343,945 B2 | 1/2013 | Tamarkin et al. |
| 8,362,091 B2 | 1/2013 | Tamarkin et al. |
| 8,435,498 B2 | 5/2013 | Tamarkin et al. |
| 8,486,374 B2 | 7/2013 | Tamarkin et al. |
| 8,486,375 B2 | 7/2013 | Tamarkin et al. |
| 8,486,376 B2 | 7/2013 | Friedman et al. |
| 8,512,718 B2 | 8/2013 | Eini et al. |
| 8,518,376 B2 | 8/2013 | Tamarkin et al. |
| 8,518,378 B2 | 8/2013 | Tamarkin et al. |
| 8,592,380 B2 | 11/2013 | Trumbore et al. |
| 8,617,100 B2 | 12/2013 | Eini et al. |
| 8,618,081 B2 | 12/2013 | Tamarkin et al. |
| 8,623,330 B2 | 1/2014 | Gurge et al. |
| 8,636,982 B2 | 1/2014 | Tamarkin et al. |
| 8,652,443 B2 | 2/2014 | Varanasi et al. |
| 8,703,105 B2 | 4/2014 | Tamarkin et al. |
| 8,709,385 B2 | 4/2014 | Tamarkin et al. |
| 8,722,021 B2 | 5/2014 | Friedman et al. |
| 8,735,377 B1 | 5/2014 | Sipos |
| 8,741,265 B2 | 6/2014 | Tamarkin et al. |
| 8,778,365 B1 | 7/2014 | Hardas et al. |
| 8,784,780 B2 | 7/2014 | Gurge et al. |
| 8,795,635 B2 | 8/2014 | Tamarkin et al. |
| 8,795,693 B2 | 8/2014 | Tamarkin et al. |
| 8,840,869 B2 | 9/2014 | Friedman et al. |
| 8,846,039 B2 | 9/2014 | Chung et al. |
| 8,859,618 B2 | 10/2014 | Palefsky et al. |
| 8,865,139 B1 | 10/2014 | Tamarkin et al. |
| 8,871,184 B2 | 10/2014 | Tamarkin et al. |
| 8,895,536 B2 | 11/2014 | Bannister et al. |
| 8,900,553 B2 | 12/2014 | Tamarkin et al. |
| 8,900,554 B2 | 12/2014 | Tamarkin et al. |
| 8,945,516 B2 | 2/2015 | Tamarkin et al. |
| 8,992,896 B2 | 3/2015 | Tamarkin et al. |
| 9,050,253 B2 | 6/2015 | Tamarkin et al. |
| 9,072,667 B2 | 7/2015 | Tamarkin et al. |
| 9,101,662 B2 | 8/2015 | Tamarkin et al. |
| 9,161,916 B2 | 10/2015 | Tamarkin et al. |
| 9,167,813 B2 | 10/2015 | Tamarkin et al. |
| 9,192,558 B2 | 11/2015 | Chen et al. |
| 9,211,259 B2 | 12/2015 | Friedman et al. |
| 9,265,725 B2 | 2/2016 | Tamarkin et al. |
| 9,265,740 B2 | 2/2016 | Johnston et al. |
| 9,271,930 B2 | 3/2016 | At |
| 9,320,705 B2 | 4/2016 | Tamarkin et al. |
| 9,439,857 B2 | 9/2016 | Tamarkin et al. |
| 9,474,720 B2 | 10/2016 | Yamamoto |
| 9,492,412 B2 | 11/2016 | Tamarkin et al. |
| 9,539,208 B2 | 1/2017 | Tamarkin et al. |
| 9,539,266 B2 | 1/2017 | Mansouri |
| 9,549,898 B2 | 1/2017 | Tamarkin et al. |
| 9,572,775 B2 | 2/2017 | Tamarkin et al. |
| 9,592,246 B2 | 3/2017 | Salman et al. |
| 9,622,947 B2 | 4/2017 | Tamarkin et al. |
| 9,636,405 B2 | 5/2017 | Tamarkin et al. |
| 9,662,298 B2 | 5/2017 | Tamarkin et al. |
| 9,668,972 B2 | 6/2017 | Tamarkin et al. |
| 9,675,700 B2 | 6/2017 | Tamarkin et al. |
| 9,682,021 B2 | 6/2017 | Tamarkin et al. |
| 9,713,643 B2 | 7/2017 | Friedman et al. |
| 9,795,564 B2 | 10/2017 | Tamarkin et al. |
| 9,841,142 B2 | 12/2017 | Nair |
| 9,849,142 B2 | 12/2017 | Tamarkin et al. |
| 9,884,017 B2 | 2/2018 | Tamarkin et al. |
| 9,931,328 B2 | 4/2018 | Kandavilli et al. |
| 10,029,013 B2 | 7/2018 | Tamarkin et al. |
| 10,086,080 B2 | 10/2018 | Tamarkin et al. |
| 10,092,588 B2 | 10/2018 | Tamarkin et al. |
| 10,117,812 B2 | 11/2018 | Tamarkin et al. |
| 10,137,200 B2 | 11/2018 | Tamarkin et al. |
| 10,213,384 B2 | 2/2019 | Tamarkin et al. |
| 10,213,512 B2 | 2/2019 | Tamarkin et al. |
| 10,238,746 B2 | 3/2019 | Tamarkin et al. |
| 10,265,404 B2 | 4/2019 | Tamarkin et al. |
| 10,322,085 B2 | 6/2019 | Tamarkin et al. |
| 10,322,186 B2 | 6/2019 | Tamarkin et al. |
| 10,350,166 B2 | 7/2019 | Tamarkin et al. |
| 10,363,216 B2 | 7/2019 | Tamarkin et al. |
| 10,369,102 B2 | 8/2019 | Tamarkin et al. |
| 10,398,641 B2 | 9/2019 | Tamarkin et al. |
| 10,463,742 B2 | 11/2019 | Tamarkin et al. |
| 10,517,882 B2 | 12/2019 | Tamarkin et al. |
| 10,588,858 B2 | 3/2020 | Tamarkin et al. |
| 2002/0183399 A1* | 12/2002 | Kang ............ A61K 31/07 514/725 |
| 2012/0093876 A1 | 4/2012 | Ouster, III |
| 2013/0064777 A1 | 3/2013 | Tamarkin et al. |
| 2019/0076339 A1 | 3/2019 | Tamarkin et al. |
| 2019/0076356 A1 | 3/2019 | Tamarkin et al. |
| 2019/0076451 A1 | 3/2019 | Friedman et al. |
| 2019/0091149 A1 | 3/2019 | Tamarkin et al. |
| 2019/0134203 A1 | 5/2019 | Tamarkin et al. |
| 2019/0134204 A1 | 5/2019 | Tamarkin et al. |

FOREIGN PATENT DOCUMENTS

| | | |
|---|---|---|
| CA | 2114537 A1 | 2/1993 |
| CA | 2154438 A1 | 1/1996 |
| CA | 2422244 A1 | 9/2003 |
| CA | 2502986 A1 | 5/2004 |
| CA | 2534372 A1 | 10/2005 |
| CH | 639913 A5 | 12/1983 |
| DE | 1 882 100 U | 11/1963 |
| DE | 1926796 A1 | 3/1970 |
| DE | 2 608 226 A1 | 9/1977 |

(56) References Cited

FOREIGN PATENT DOCUMENTS

| | | |
|---|---|---|
| DE | 4140474 A1 | 6/1993 |
| DE | 10009233 A1 | 8/2000 |
| DE | 10138495 A1 | 2/2003 |
| DE | 102004016710 A1 | 10/2005 |
| EP | 0 052 404 A2 | 5/1982 |
| EP | 0 156 507 A1 | 10/1985 |
| EP | 0 186 453 A2 | 7/1986 |
| EP | 0 213 827 A2 | 3/1987 |
| EP | 0 214 865 A2 | 3/1987 |
| EP | 0 270 316 A2 | 6/1988 |
| EP | 0 297 436 A2 | 1/1989 |
| EP | 0 336 812 A2 | 10/1989 |
| EP | 0 414 920 A1 | 3/1991 |
| EP | 0 211 550 B1 | 4/1991 |
| EP | 0 216 856 B1 | 7/1991 |
| EP | 0 454 102 A2 | 10/1991 |
| EP | 0 326 196 B2 | 3/1992 |
| EP | 0 484 530 A1 | 5/1992 |
| EP | 0 485 299 A1 | 5/1992 |
| EP | 0 488 089 A1 | 6/1992 |
| EP | 0 528 190 A1 | 2/1993 |
| EP | 0 552 612 A2 | 7/1993 |
| EP | 0 569 773 A2 | 11/1993 |
| EP | 0 404 376 B1 | 3/1994 |
| EP | 0 598 412 A2 | 5/1994 |
| EP | 0 391 124 B1 | 6/1995 |
| EP | 0 662 431 A2 | 7/1995 |
| EP | 0 535 327 B1 | 10/1996 |
| EP | 0 738 516 A1 | 10/1996 |
| EP | 0 757 959 A1 | 2/1997 |
| EP | 0 824 911 A2 | 2/1998 |
| EP | 0 829 259 A1 | 3/1998 |
| EP | 0 676 198 B1 | 10/1998 |
| EP | 0 979 654 A1 | 2/2000 |
| EP | 0 993 827 A1 | 4/2000 |
| EP | 1 025 836 A1 | 8/2000 |
| EP | 1 055 425 A2 | 11/2000 |
| EP | 0 506 197 B2 | 7/2001 |
| EP | 1 215 258 A2 | 6/2002 |
| EP | 1 287 813 A1 | 3/2003 |
| EP | 1 308 169 A1 | 5/2003 |
| EP | 1 375 386 A1 | 1/2004 |
| EP | 0 504 301 B1 | 3/2004 |
| EP | 1 428 521 A2 | 6/2004 |
| EP | 1 438 946 A1 | 7/2004 |
| EP | 1 189 579 B1 | 9/2004 |
| EP | 1 475 381 A1 | 11/2004 |
| EP | 1 500 385 A1 | 1/2005 |
| EP | 1 537 916 A1 | 6/2005 |
| EP | 1 600 185 A1 | 11/2005 |
| EP | 0 928 608 B1 | 3/2006 |
| EP | 1 653 932 A1 | 5/2006 |
| EP | 1 734 927 A1 | 12/2006 |
| EP | 1 758 547 A1 | 3/2007 |
| EP | 1 483 001 B1 | 11/2007 |
| EP | 1 584 324 B1 | 11/2007 |
| EP | 1 889 609 A2 | 2/2008 |
| EP | 1 902 706 A1 | 3/2008 |
| EP | 2 129 383 A1 | 12/2009 |
| EP | 2 422 768 A2 | 2/2012 |
| EP | 2 494 959 A1 | 9/2012 |
| FR | 2 456 522 A1 | 12/1980 |
| FR | 2 591 331 A1 | 6/1987 |
| FR | 2 640 942 A2 | 6/1990 |
| FR | 2 736 824 A1 | 1/1997 |
| FR | 2 774 595 A1 | 8/1999 |
| FR | 2 789 371 A1 | 8/2000 |
| FR | 2 793 479 A1 | 11/2000 |
| FR | 2 814 959 A1 | 4/2002 |
| FR | 2 833 246 A1 | 6/2003 |
| FR | 2 840 903 A1 | 12/2003 |
| FR | 2 843 373 A1 | 2/2004 |
| FR | 2 845 672 A1 | 4/2004 |
| FR | 2 848 998 A1 | 6/2004 |
| FR | 2 860 976 | 4/2005 |
| FR | 2 915 891 A1 | 11/2008 |
| GB | 808 104 A | 1/1959 |
| GB | 808 105 A | 1/1959 |
| GB | 922 930 A | 4/1963 |
| GB | 933 486 A | 8/1963 |
| GB | 998 490 A | 7/1965 |
| GB | 1 026 831 A | 4/1966 |
| GB | 1 033 299 A | 6/1966 |
| GB | 1 081 949 A | 9/1967 |
| GB | 1 121 358 A | 7/1968 |
| GB | 1 162 684 A | 8/1969 |
| GB | 1 170 152 A | 11/1969 |
| GB | 1 201 918 A | 8/1970 |
| GB | 1 347 950 A | 2/1974 |
| GB | 1 351 761 A | 5/1974 |
| GB | 1 351 762 A | 5/1974 |
| GB | 1 353 381 A | 5/1974 |
| GB | 1 376 649 A | 12/1974 |
| GB | 1 397 285 A | 6/1975 |
| GB | 1 408 036 A | 10/1975 |
| GB | 1 457 671 A | 12/1976 |
| GB | 1 489 672 A | 10/1977 |
| GB | 2 004 746 A | 4/1979 |
| GB | 1 561 423 A | 2/1980 |
| GB | 2 114 580 A | 8/1983 |
| GB | 2 166 651 A | 5/1986 |
| GB | 2 153 686 B | 7/1987 |
| GB | 2 172 298 B | 11/1988 |
| GB | 2 206 099 A | 12/1988 |
| GB | 2 337 461 A | 11/1999 |
| GB | 2 367 809 A | 4/2002 |
| GB | 2 406 330 A | 3/2005 |
| GB | 2 406 791 B | 2/2008 |
| GB | 2 474 930 A | 5/2011 |
| IL | 49491 A | 9/1979 |
| IL | 152 486 A | 5/2003 |
| JP | 55-069682 A | 5/1980 |
| JP | 56-039815 A | 4/1981 |
| JP | 57-044429 A | 3/1982 |
| JP | 60-001113 A | 1/1985 |
| JP | 61-275395 A | 12/1986 |
| JP | 62-241701 A | 10/1987 |
| JP | 63-119420 A | 5/1988 |
| JP | 01-100111 A | 4/1989 |
| JP | 01-156906 A | 6/1989 |
| JP | 02-184614 A | 7/1990 |
| JP | 02-255890 A | 10/1990 |
| JP | 03-050289 A | 3/1991 |
| JP | 04-51958 A | 2/1992 |
| JP | 04-282311 A | 10/1992 |
| JP | 04-312521 A | 11/1992 |
| JP | 05-070340 A | 3/1993 |
| JP | 05-213734 A | 8/1993 |
| JP | 06-100414 A | 4/1994 |
| JP | 06-263630 A | 9/1994 |
| JP | 06-329532 A | 11/1994 |
| JP | 07-215835 A | 8/1995 |
| JP | 08-040899 A | 2/1996 |
| JP | 08-501529 A | 2/1996 |
| JP | 08-119831 A | 5/1996 |
| JP | 08-165218 A | 6/1996 |
| JP | 08-277209 A | 10/1996 |
| JP | 09-84855 A | 3/1997 |
| JP | 09-099553 A | 4/1997 |
| JP | 09-110636 A | 4/1997 |
| JP | 10-114619 A | 5/1998 |
| JP | 10-332456 A | 12/1998 |
| JP | 11-501045 A | 1/1999 |
| JP | 11-250543 A | 9/1999 |
| JP | 2000-017174 A | 1/2000 |
| JP | 2000-080017 A | 3/2000 |
| JP | 2000-128734 A | 5/2000 |
| JP | 2000-191429 A | 7/2000 |
| JP | 2000-239140 A | 9/2000 |
| JP | 2000-351726 A | 12/2000 |
| JP | 2000-354623 A | 12/2000 |
| JP | 2001-002526 A | 1/2001 |
| JP | 2001-019606 A | 1/2001 |
| JP | 2001-072963 A | 3/2001 |

(56) References Cited

FOREIGN PATENT DOCUMENTS

| | | |
|---|---|---|
| JP | 2002-012513 A | 1/2002 |
| JP | 2002-047136 A | 2/2002 |
| JP | 2002-524490 A | 8/2002 |
| JP | 2002-302419 A | 10/2002 |
| JP | 2003-012511 A | 1/2003 |
| JP | 2003-055146 A | 2/2003 |
| JP | 2004-047136 A | 2/2004 |
| JP | 2004-250435 A | 9/2004 |
| JP | 2004-348277 A | 12/2004 |
| JP | 2005-314323 A | 11/2005 |
| JP | 2005-350378 A | 12/2005 |
| JP | 2006-008574 A | 1/2006 |
| JP | 2006-036317 A | 2/2006 |
| JP | 2006-103799 A | 4/2006 |
| JP | 2006-525145 A | 11/2006 |
| JP | 2007-131539 A2 | 5/2007 |
| JP | 2007-155667 A | 6/2007 |
| JP | 2007-326996 A | 12/2007 |
| KR | 0143232 A | 7/1998 |
| KR | 2001-003063 A | 1/2001 |
| NZ | 520014 A | 5/2005 |
| NZ | 540166 A | 6/2007 |
| RU | 2277501 C2 | 6/2006 |
| UA | 66796 C2 | 7/2001 |
| WO | WO 82/001821 A1 | 6/1982 |
| WO | WO 86/05389 A1 | 9/1986 |
| WO | WO 88/01502 A1 | 3/1988 |
| WO | WO 88/01863 A1 | 3/1988 |
| WO | WO 88/08316 A1 | 11/1988 |
| WO | WO 89/06537 A1 | 7/1989 |
| WO | WO 90/05774 A1 | 5/1990 |
| WO | WO 91/11991 A1 | 8/1991 |
| WO | WO 92/00077 A1 | 1/1992 |
| WO | WO 92/005142 A1 | 4/1992 |
| WO | WO 92/05763 A1 | 4/1992 |
| WO | WO 92/11839 A1 | 7/1992 |
| WO | WO 92/13602 A1 | 8/1992 |
| WO | WO 93/025189 A1 | 12/1993 |
| WO | WO 94/006440 A1 | 3/1994 |
| WO | WO 96/03115 A1 | 2/1996 |
| WO | WO 96/19921 A1 | 7/1996 |
| WO | WO 96/24325 A1 | 8/1996 |
| WO | WO 96/26711 A1 | 9/1996 |
| WO | WO 96/27376 A1 | 9/1996 |
| WO | WO 96/39119 A1 | 12/1996 |
| WO | WO 97/03638 A1 | 2/1997 |
| WO | WO 97/39745 A1 | 10/1997 |
| WO | WO 98/17282 A1 | 4/1998 |
| WO | WO 98/18472 A1 | 5/1998 |
| WO | WO 98/19654 A1 | 5/1998 |
| WO | WO 98/21955 A1 | 5/1998 |
| WO | WO 98/23291 A1 | 6/1998 |
| WO | WO 98/31339 A1 | 7/1998 |
| WO | WO 98/36733 A2 | 8/1998 |
| WO | WO 98/52536 A1 | 11/1998 |
| WO | WO 99/08649 A2 | 2/1999 |
| WO | WO 99/20250 A1 | 4/1999 |
| WO | WO 99/37282 A2 | 7/1999 |
| WO | WO 99/53923 A1 | 10/1999 |
| WO | WO 2000/09082 A1 | 2/2000 |
| WO | WO 2000/15193 A1 | 3/2000 |
| WO | WO 2000/23051 A1 | 4/2000 |
| WO | WO 2000/33825 A2 | 6/2000 |
| WO | WO 2000/38731 A1 | 7/2000 |
| WO | WO 2000/61076 A1 | 10/2000 |
| WO | WO 2000/62776 A1 | 10/2000 |
| WO | WO 2000/72805 A1 | 12/2000 |
| WO | WO 2000/76461 A2 | 12/2000 |
| WO | WO 2001/01949 A1 | 1/2001 |
| WO | WO 2001/05366 A1 | 1/2001 |
| WO | WO 2001/08681 A1 | 2/2001 |
| WO | WO 2001/10961 A1 | 2/2001 |
| WO | WO 2001/53198 A1 | 7/2001 |
| WO | WO 2001/54212 A1 | 7/2001 |
| WO | WO 2001/54679 A2 | 8/2001 |
| WO | WO 2001/62209 A2 | 8/2001 |
| WO | WO 2001/70242 A2 | 9/2001 |
| WO | WO 2001/76579 A1 | 10/2001 |
| WO | WO 2001/82880 A3 | 11/2001 |
| WO | WO 2001/82890 A1 | 11/2001 |
| WO | WO 2001/85102 A2 | 11/2001 |
| WO | WO 2001/85128 A2 | 11/2001 |
| WO | WO 2001/95728 A1 | 12/2001 |
| WO | WO 2002/00820 A1 | 1/2002 |
| WO | WO 2002/07685 A2 | 1/2002 |
| WO | WO 2002/15860 A1 | 2/2002 |
| WO | WO 2002/15873 A2 | 2/2002 |
| WO | WO 2002/24161 A1 | 3/2002 |
| WO | WO 2002/28435 A1 | 4/2002 |
| WO | WO 2002/41847 A1 | 5/2002 |
| WO | WO 2002/43490 A1 | 6/2002 |
| WO | WO 2002/062324 A2 | 8/2002 |
| WO | WO 2002/078667 A1 | 10/2002 |
| WO | WO 2002/087519 A2 | 11/2002 |
| WO | WO 2003/000223 A1 | 1/2003 |
| WO | WO 2003/002082 A1 | 1/2003 |
| WO | WO 2003/005985 A1 | 1/2003 |
| WO | WO 2003/013984 A1 | 2/2003 |
| WO | WO 2003/015699 A2 | 2/2003 |
| WO | WO 2003/051294 A2 | 6/2003 |
| WO | WO 2003/053292 A1 | 7/2003 |
| WO | WO 2003/055445 A2 | 7/2003 |
| WO | WO 2003/055454 A1 | 7/2003 |
| WO | WO 2003/070301 A1 | 8/2003 |
| WO | WO 2003/071995 A1 | 9/2003 |
| WO | WO 2003/075851 A2 | 9/2003 |
| WO | WO 2003/092641 A1 | 11/2003 |
| WO | WO 2003/094873 A1 | 11/2003 |
| WO | WO 2003/097002 A1 | 11/2003 |
| WO | WO 2004/017962 A2 | 3/2004 |
| WO | WO 2004/037197 A2 | 5/2004 |
| WO | WO 2004/037225 A2 | 5/2004 |
| WO | WO 2004/003284 A1 | 8/2004 |
| WO | WO 2004/064769 A2 | 8/2004 |
| WO | WO 2004/064833 A1 | 8/2004 |
| WO | WO 2004/071479 A1 | 8/2004 |
| WO | WO 2004/078158 A2 | 9/2004 |
| WO | WO 2004/078896 A1 | 9/2004 |
| WO | WO 2004/093895 A1 | 11/2004 |
| WO | WO 2004/112780 A1 | 12/2004 |
| WO | WO 2005/009416 A1 | 2/2005 |
| WO | WO 2005/011567 A2 | 2/2005 |
| WO | WO 2005/018530 A2 | 3/2005 |
| WO | WO 2005/032522 A1 | 4/2005 |
| WO | WO 2005/044219 A1 | 5/2005 |
| WO | WO 2005/063224 A1 | 7/2005 |
| WO | WO 2005/065652 A1 | 7/2005 |
| WO | WO 2005/076697 A2 | 8/2005 |
| WO | WO 2005/097068 A1 | 10/2005 |
| WO | WO 2005/102282 A1 | 11/2005 |
| WO | WO 2005/102539 A1 | 11/2005 |
| WO | WO 2005/117813 A1 | 12/2005 |
| WO | WO 2006/003481 A2 | 1/2006 |
| WO | WO 2006/010589 A2 | 2/2006 |
| WO | WO 2006/011046 A1 | 2/2006 |
| WO | WO 2006/020682 A1 | 2/2006 |
| WO | WO 2006/028339 A1 | 3/2006 |
| WO | WO 2006/031271 A2 | 3/2006 |
| WO | WO 2006/045170 A2 | 5/2006 |
| WO | WO 2006/079632 A1 | 8/2006 |
| WO | WO 2006/081327 A2 | 8/2006 |
| WO | WO 2006/091229 A2 | 8/2006 |
| WO | WO 2006/100485 A1 | 9/2006 |
| WO | WO 2006/120682 A2 | 11/2006 |
| WO | WO 2006/121610 A2 | 11/2006 |
| WO | WO 2006/122158 A2 | 11/2006 |
| WO | WO 2006/129161 A2 | 12/2006 |
| WO | WO 2006/131784 A1 | 12/2006 |
| WO | WO 2007/007208 A2 | 1/2007 |
| WO | WO 2007/010494 A1 | 1/2007 |
| WO | WO 2007/012977 A2 | 2/2007 |
| WO | WO 2007/023396 A2 | 3/2007 |
| WO | WO 2007/031621 A2 | 3/2007 |
| WO | WO 2007/039825 A2 | 4/2007 |

(56) References Cited

FOREIGN PATENT DOCUMENTS

| | | |
|---|---|---|
| WO | WO 2007/050543 A2 | 5/2007 |
| WO | WO 2007/054818 A2 | 5/2007 |
| WO | WO 2007/072216 A2 | 6/2007 |
| WO | WO 2007/082698 A1 | 7/2007 |
| WO | WO 2007/085902 A2 | 8/2007 |
| WO | WO 2007/099396 A2 | 9/2007 |
| WO | WO 2007/111962 A2 | 10/2007 |
| WO | WO 2008/008397 A2 | 1/2008 |
| WO | WO 2008/010963 A2 | 1/2008 |
| WO | WO 2008/038147 A2 | 4/2008 |
| WO | WO 2008/041045 A1 | 4/2008 |
| WO | WO 2008/075207 A2 | 6/2008 |
| WO | WO 2008/087148 A2 | 7/2008 |
| WO | WO 2008/104734 A1 | 9/2008 |
| WO | WO 2008/110872 A2 | 9/2008 |
| WO | WO 2008/152444 A2 | 12/2008 |
| WO | WO 2009/007785 A2 | 1/2009 |
| WO | WO 2009/069006 A2 | 6/2009 |
| WO | WO 2009/072007 A2 | 6/2009 |
| WO | WO 2009/087578 A2 | 7/2009 |
| WO | WO 2009/090495 A2 | 7/2009 |
| WO | WO 2009/090558 A2 | 7/2009 |
| WO | WO 2009/098595 A2 | 8/2009 |
| WO | WO 2011/006026 A1 | 1/2011 |
| WO | WO 2011/013008 A2 | 2/2011 |
| WO | WO 2011/013009 A2 | 2/2011 |
| WO | WO 2011/026094 A2 | 3/2011 |
| WO | WO 2011/039637 A2 | 4/2011 |
| WO | WO 2011/039638 A2 | 4/2011 |
| WO | WO 2011/064631 A1 | 6/2011 |
| WO | WO 2011/106026 A1 | 9/2011 |
| WO | WO 2011/138678 A2 | 11/2011 |
| WO | WO 2012/100097 A2 | 7/2012 |
| WO | WO 2012/100097 A3 | 7/2012 |
| WO | WO 2013/136192 A2 | 9/2013 |
| WO | WO 2014/134394 A1 | 9/2014 |
| WO | WO 2014/134427 A1 | 9/2014 |
| WO | WO 2014/151347 A1 | 9/2014 |
| WO | WO 2014/201541 A1 | 12/2014 |
| WO | WO 2015/075640 A1 | 5/2015 |
| WO | WO 2015/114320 A1 | 8/2015 |
| WO | WO 2015/153864 A2 | 10/2015 |
| WO | WO 2017/029647 A1 | 2/2017 |
| WO | WO 2017/030555 A1 | 2/2017 |
| WO | WO 2017/089809 A1 | 6/2017 |

OTHER PUBLICATIONS

"Suppositories?" CareCure Community, SCI Forum [online]. http://sci.rutgers.edu/forum/showthread.php?4176-Suppositories. Published: Apr. 16, 2002, 3 pages.
1058. Benzalkonium Chloride; 2350. Citric Acid; 6143. Methyl Salicylate. The Merck Index: An Encyclopedia of Chemicals, Drugs, and Biologicals. 13th Edition, 2001, pp. 181, 405-406, 1090-1091, 1556.
242. Allantoin, The Merck Index: An Encyclopedia of Chemicals, Drugs, and Biologicals. 10th edition, Merck & Co., Inc., 1983, p. 39.
Abdullah, G.Z. et al. (Jan. 2013) "Carbopol 934, 940 and Ultrez 10 as viscosity modifiers of palm olein esters based nano-scaled emulsion containing ibuprofen" Pak J Pharm Sci, 26(1):75-83.
Abrams et al., "Ciclopirox gel treatment of scalp seborrheic dermatitis," in: Shuster, S. (ed.) Hydroxy-Piridones as Antifungal Agents with Special Emphasis on Onychomycosis. Springer, Berlin, Heidelberg; 1999, Chapter 8, pp. 45-50.
Adachi, "Storage and Oxidative Stability of O/W/ Nano-emulsions," Foods Food Ingredients J. Jpn., 2004, 209(11), 1 page (Abstract).
Adisen et al., "Topical tetracycline in the treatment of acne vulgaris," J Drugs Dermatol., Oct. 2008, 7(10):953-955.
Alcohol SDA 40B, 200 Proof. Material Safety Data Sheets [online]. Retrieved from the Internet: http://www.pharmco-prod.com/pages/MSDS/SDA.sub.--40B.sub.--200.pdf, on Dec. 9, 2008. MSDS 044, Revision 2.1, Revision Date Dec. 2005, 2 pages.
Alcohol, Wikipedia, the free encyclopedia [online]. Last modified on Apr. 23, 2014. Retrieved on May 17, 2014, http://en.wikipedia.org/wiki/Alcohol, 17 pages.
Aldara™ (imiquimod) Cream. Highlights of Prescribing Information, Graceway Pharmaceuticals, LLC, Mar. 2007, 29 pages.
Allantoin, Römpp Online, retrieved on Sep. 23, 2015, https:roempp.thieme.de/roempp4.0/do/data/RD-O 1-01552, 5 pages.
Al-Mughrabi et al., "Effectiveness of Essential Oils and Their Combinations with Aluminum Starch Octenylsuccinate on Potato Storage Pathogens," TEOP, 2013, 16(1):23-31.
Ambrose et al., "In Vitro Studies of Water Activity and Bacterial Growth Inhibition of Sucrose-Polyethylene Glycol 400-Hydrogen Peroxide and Xylose-Polyethylene Glycol 400-Hydrogen Peroxide Pastes Used to Treat Infected Wounds," Antimicrobial Agents and Chemotherapy, Sep. 1991, 35(9):1799-1803.
Aminobenzoic Acid, Knovel, 2006, retrieved on Apr. 18, 2012, http://www.knovel.com/web/portal/knovel_content?p_p_id=EXT_KNOVEL_CONTENT . . . , 2 pages.
Anton et al., "Water-in-oil nano-emulsion formation by the phase inversion temperature method: a novel and general concept, a new template for nanoencapsulation," Proceedings of the 33rd Annual Meeting and Exposition of the Controlled Release Society, Jul. 2006, Vienna, Austria, 2 pages.
Arct et al., "Common cosmetic hydrophilic ingredients as penetration modifiers of flavonoids," International Journal of Cosmetic Science, Dec. 2002, 24(6):357-366 (Abstract Only).
Arisan, Kozmetic ve Kisisel Bakim Urunleri Grubu, retrieved on Dec. 10, 2008, http://www.arisankimya.com/kozmetik.htm, 8 pages.
Arquad HTL8-MS, AkzoNobel Functional Applications, retrieved on Mar. 18, 2013, Retrieved from the Internet: <URL: http://sc.akzonobel.com/en/fa/Pages/product-detail.aspx?prodID=8764>, 1 page.
Aslam et al. (2015) "Emerging drugs for the treatment of acne" Expert Opin Emerging Drugs, 20:91-101.
Atopic Dermatitis/Eczema, ibabydoc.com, Copyright 2000, retrieved on Jan. 30, 2010, http://www.ibabydoc.com/online/diseaseeczema.asp 6 pages.
Ausburger and Shangraw, "Bubble size analysis of high consistency aerosol foams and its relationship to foam rheology; Effects fo Container Emptying, Propellent Type, and Time," J. Pharma Sci, Apr. 1968, 57(4):624-631.
Austria, et al., "Stability of vitamin C derivatives in solution and topical formulations", Journal of Pharmaceutical and Biomedical Analysis, 1997, 15:795-801.
Barry and Badal, "Stability of minocycline, doxycycline, and tetracycline stored in agar plates and microdilution trays," Current Microbiology, 1978, 1:33-36.
Barry and Woodford, "Comparative bio-availability and activity of proprietary topical corticosteroid preparations: vasoconstrictor assays on thirty-one ointments," British J. Dermatology, 1975, 93:563-571.
Baskaran et al., "Poloxamer-188 improves capillary blood flow and tissue viability in a cutaneous burn wound," J. Surg. Res., 2001, 101(1):56-61.
Beauty Banter, "Interesting list of comedogenic ingredients!!!!!!!!!!!" QVC blog, Interesting list of comedogenic ingredients, 2014, 1-14.
Bell-Syer et al., "A systematic review of oral treatments for fungal infections of the skin of the feet," J. Dermatology. Treat., 2001, 12:69-74.
Ben-Et and Tatarsky "Application of NMR for the Determination of HLB Values of Nonionic Surfactants," Journal of the American Oil Chemists Society, Mar. 20, 1972, 49:499-500.
Bernstein and Harrison, "Effects of the Immunomodulating Agent R837 on Acute and Latent Herpes Simplex Virus Type 2 Infections," Antimicrobial Agents and Chemotherapy, Sep. 1989, 33(9):1511-1515.
Beuchat (Feb. 1983) "Influence of Water Activity on Growth, Metabolic Activities and Survival of Yeasts and Molds" J Food Prot, 46(2):135-141.
Blaney and Cook, "Topical use of tetracycline in the treatment of acne," Arch Dermatol, Jul. 1976, 112:971-973.

(56) References Cited

OTHER PUBLICATIONS

Blute et al., "Phase behaviour of alkyl glycerol ether surfactants", Physikalische Chemie/Physical Chemistry Tenside Surf. Det., 1998, 35(3):207-212.
Boehm et al., "Synthesis of high specific activity [.sup.3 H]-9-cis-retinoic acid and its application for identifying retinoids with unusual binding properties," J. Med. Chem., 1994, 37:408-414.
Brenes, et al., "Stability of Copigmented Anthocyanins and Ascorbic Acid in a Grape Juice Model System", J. Agric Food Chem, 2005, 53(1):49-56 (Abstract Only).
Brisaert, M. et al. (1996) "Investigation on the chemical stability of erythromycin in solutions using an optimization system" Pharm World Sci, 18(5):182-186.
Bronopol, 2-Bromo-2-Nuro-1,3-Propanediol, Chemical land, Jul. 17, 2006, retrieved on Jun. 4, 2011, http://chemicalland21.com/specialtychem/perchem/BRONOPOL.html, 4 pages.
Brown et al., "Structural dependence of flavonoid interactions with Cu2+ ions: implications for their antioxidant properties," Biochem. J., 1998, 330:1173-1178.
Buck and Guth, "Treatment of Vaginal Intraepithelial Neoplasia (Primarily Low Grade) with Imiquimod 5% Cream", Journal of Lower Genital Tract Disease, 2003, 7(3):290-293.
Bucks et al., "Bioavailability of Topically Administered Steroids: A "Mass Balance" Technique," J. Investigative Dermatology, 1988, 91(1):29-33.
Bunker and Dowd, "Alterations in Scalp Blood Flow after the Epicutaneous Application of 3% Minoxidil and 0.1% Hexyl Nicotinate in Alopecia," British Society for Investigative Dermatology, Sep. 1986, 117(5):668-669.
Burn Patients Need Vitamin D Supplements, NUTRAingredients.com, Jan. 23, 2004, retrieved on May 5, 2010, http://www.nutraingredients.com/Research/Burn-patients-need-vitamin-D-supplements, 1 page.
Burton and Marshall, "Hypertrichosis due to minoxidil," British J. Dermatology, 1979, 101:593-595.
C12-15 Alkyl Benzoate, Paula's Choice Skincare, retrieved on Oct. 24, 2010, http://ww.cosmeticscop.com/cosmetic-ingredient-dictionary/definition/259/c12-15-alkyl-benzoate.aspx, 1 page.
Campos and Silva, "Ascorbic Acid and Its Derivatives in Cosmetic Formulations", Cosmetics and Toiletries, 2000, 115(6):59-62 (Abstract Only.
Can Tuberous Sclerosis be Prevented?, Sharecare, 2002, retrieved on Aug. 29, 2013, <URL: http://www.sharecare.com/health/autosomal-dominant-genetic-disorders/can-tuberous-sclerosis-be-prevented;jsessionid=850579B60520A907DE75930E061E60E6>, 2 pages.
Canavan et al. (2016) "Optimizing Non-Antibiotic Treatments for Patients with Acne: A Review" Dermatol Ther, 6:555-578.
Carapeti et al., "Topical diltiazem and bethanechol decrease anal sphincter pressure and heal anal fissures without side effects," Dis Colon Rectum, 2000, 43(10):1359-1362.
Carbowax 1000MSDS, Material Safety Data Sheet for Polyethylene glycol 1000 MSDS, last updated Nov. 6, 2008, retrieved on Dec. 13, 2008, http://www.sciencelab.com/xMSDS-Polyethylene.sub.-glycol.sub.-1000-9926-622, 6 pages.
Carelli et al., "Effect of Vehicles on Yohimbine Permeation Across Excised Hairless Mouse Skin", Pharm Acta Helv, Aug. 1978, 73(3):127-134 (Abstract Only).
Causes of Psoriasis, retrieved on Sep. 9, 2010, http://www.quickcare.org/skin/causes-of0psoriasis.html, 3 pages.
Cetearyl Alcohol, Natural Wellbeing, Copyright 2001-2012, retrieved on Apr. 10, 2014, http://www.naturalwellbeing.com/learning-center/Cetearyl_Alcohol, 3 pages.
Chebil et al., "Solubility of Flavonoids in Organic Solvents," J. Chem. Eng. Data, 2007, 52(5):1552-1556 (Abstract Only).
Chemical Characteristics, The Olive Oil Source, © 1998-2015, retrieved on Jun. 12, 2015, http://www.oliveoilsource.com/page/chemical-characteristics, 10 pages.
Cheshire and Freeman, "Disorders of Sweating," Semin Neurol, 2003, 23(4):399-406.
Chevrant-Breton et al., "Etude du Traitement Capillaire «Bioscalin» dans les Alopecies Diffuses de la Femme", Gazette Medicale, 1986, 93(17):75-79 (English Abstract).
Chiang et al., "Bioavailability Assessment of Topical Delivery Systems: In Vitro Delivery of Minoxidil from Prototypical Semi-Solid Formulations", Int. J. Pharm, 1989, 49(2):109-114 (Abstract Only).
Chinnian et al., "Photostability Profiles of Minoxidil Solutions", PDA J. Pharm Sci Technol., Mar.-Apr. 1996, 50(2):94-98 (English Abstract).
Chollet et al., "Development of a Topically Active Imiquimod Formulation", Pharmaceutical Development and Technology, 1999, 4(1):35-43.
Chollet et al., "The Effect of Temperatures on the Solubility of Imiquimod in Isostearic Acid", Abstract 3031, Pharmaceutical Research, Nov. 1997, 14(11 Supplemental):S475.
Chrysos et al., "Effect of nifedipine on rectoanal motility," Dis Colon Rectum, Feb. 1996, 39(2):212-216.
Clobetasol Propionate Cream and Ointment, Apr. 2006, retrieved Jul. 3, 2014, http://dailymed.nlm.nih.gov/dailymed/archives/fdaDrugInfo.cfm?archiveid=994, 7 pages.
Cloez-Tayarani et al., "Differential effect of serotonin on cytokine production in lipopolysaccharide-stimulated human peripheral blood mononuclear cells: involvement of 5-hydroxytryptamine2A receptors," Int. Immunol., 2003, 15:233-240.
Coal Tars and Coal-Tar Pitches, Report on Carcinogens, Twelfth Edition, 2011, 3 pages.
Coatzee et al., "Acceptability and feasibility of Micralax® applicators and of methyl cellulose gel placebo for large-scale clinical trials of vaginal microbicides," AIDS, 2001, 15:1837-1842.
Coconut Oil, Wikipedia, the free encyclopedia, retrieved on Jul. 3, 2015, https://en.wikipedia.org/wiki/Coconut_oil, 8 pages.
Codex Standard for Olive Oils and Olive Pomace Oils Codex Stan 33/1981, Adopted in 1981, recently amended 2013, 8 pages.
Cole and Gazewood, "Diagnosis and Treatment of Impetigo," American Family Physical Website, 2007, http://www.aafp.org/afp, 6 pages.
Colloidal Silica, W.R. Grace & Co. Enriching Lives, Everywhere™, 2011, retrieved on Jun. 4, 2011, http://www.grace.com/engineeredmaterials/materialsciences/colloidalsilica/default.aspx, 4 pages.
Communication of a Notice of Opposition in European Application No. 03772600.7, dated Jan. 13, 2015, 36 pages.
Cook and Mortenson, "Nifedipine for treatment of anal fissures," Dis Colon Rectum, 2000, 43(3):430-431.
Craig, D.Q.M. et al. (Jul. 1994) "An investigation into the structure and properties of Carbopol 934 gels using dielectric spectroscopy and oscillatory rheometry" J Controlled Rel, 30(3):213-223 (Abstract).
Cremophor A Grades, BASF The Chemical Company, Jan. 2008, 6 pages.
Croda Crop Care, Arlacel 165, 2011, retrieved on Aug. 3, 2015, http://www.crodapersonalcare.com/home.aspx?view=dtl&d=content&s=157&r=401&p=2578&productName=&inciname=&application=&subapplication=&productfunction=&consumerbenefit=&prodID=1926, 2 pages.
Croda Product Care Europe, Cetomacrogol 1000, 2011, retrieved on Aug. 3, 2015, http://www.crodapersonalcare.com/home.aspx?view=dtl&d=content&s=157&r=273&p=1859&productName=&inciname=&chemicaltype=&application=&subapplication=&productfunction=&consumerbenefit=&prodID=27, 1 page.
Crohn's Disease, Merck Manual Home Edition, retrieved on Jan. 16, 2013, <http://www.merckmanuals.com/home/digestive_disorders/inflammatory_bowel_diseases_ibd/crohn_disease.html?qt=crohn's disease&alt=sh>, 3 pages.
Cunha, "Minocycline versus Doxycycline in the treatment of Lyme Neuroborreliosis," Clin. Infect. Diseases, 2000, 30: 237-238.
Dacarbazine, Chemical Book, 2010, retrieved on Oct. 18, 2013, <URL: http://www.chemicalbook.com/ChemicalProductProperty_EN_CB7710656.htm>, 2 pages.
Dalby et al., "Determination of Drug Solubility in Aerosol Propellants," Pharmaceutical Research, 1991, 8(9):1206-1209.

(56) References Cited

OTHER PUBLICATIONS

Dawber and Rundegren, "Hypertrichosis in Females Applying Minoxidil Topical Solution and in Normal Controls", JEADV, 2003, 17:271-275.
Denatonium Benzoate, retrieved Dec. 9, 2008, http://www.newdruginfo.com/pharmaceopeia/usp28/v28230/usp28nf23s0_m-22790.htm, 2 pages.
Dentinger, et al., "Stability of Nifedipine in an Extemporaneously Compounded Oral Solution", American Journal of Health-System Pharmacy, 2003, 60(10):1019-1022 (English Abstract).
Derivative, Merriam Webster Online Dictionary, retrieved on Jul. 5, 2008, http://www.merriam-webster.com/cgi-bin/dictionary?book=dictionary&va=derivative, 1 page.
Devos and Miller, "Antisense Oligonucleotides: Treating neurodegeneration at the Level of RNA," Neurotherapeutics, 2013, 10:486-497.
Diethyltoluamide, Wikipedia, the free encyclopedia, retrieved on Sep. 11, 2015, https://de.wikipedia.org/wiki/Diethyltoluamid, 12 pages.
Dimethylphthalate, Wikipedia, the free encyclopedia, retrieved on Sep. 11, 2015, http://de.wikipedia.org/wiki/Dimethylphthalat, 8 pages.
Disorder, American Heritage Dictionary of the English Language, 2007, retrieved on Oct. 9, 2010, http://www.credoreference.com/entry/hmdictenglang/disorder, 1 page.
Draelos, "Antiperspirants and the Hyperhidrosis Patients," Dermatologic Therapy, 2001, 14:220-224.
Drug Index—Dacarbazine, BC Cancer Agency, Jun. 2004, retrieved on Oct. 18, 2013, <URL:http://www.bccancer.bc.ca/HPI/DrugDatabase/DrugIndexPro/Dacarbazine.htm>, 6 pages.
Drugfuture, Chemical Index Database, "Sorbitan Esters" Monograph [online]. Retrieved from: http://www.drugfuture.com/chemdata/sorbitan-esters.html, on Jul. 1, 2016, 2 pages.
Durian et al., "Scaling behavior in shaving cream," The American Physical Society, Dec. 1991, 44(12):R7902-7905.
Durmortier et al., "A review of poloxamer 407 pharmaceutical and pharmacological characteristics," Pharmaceutical Res., Dec. 2006, 23(12):2709-2728.
E7023 Ethanol 200 Proof (Absolute), Sigma-Aldrich Co., © 2008, retrieved on Dec. 9, 2008, http://www.sigmaaldrich.com/catalog/ProductDetail.do?N4=E7023SIAL&N5=SEAR-CH.sub.--CONCAT.sub.--PNOBRAND.sub.--KEY&F=SPEC, 2 pages.
Ebadi et al., "Healing effect of topical nifedipine on skin wounds of diabetic rats," DARU, 2003, 11(1):19-22.
Edens et al., "Storage Stability and Safety of Active Vitamin C in a New Dual-Chamber Dispenser", Journal of Applied Cosmetology, 1999, 17(4):136-143 (English Abstract).
Edirisinghe et al., "Effect of fatty acids on endothelium-dependent relaxation in the rabbit aorta", Clin Sci, Aug. 2006, 111(2): 145-51.
Edwards, "Imiquimod in Clinical Practice," J. Am Acad Dermatol., Jul. 2000 43(1, Pt 2):S12-S17 (English Abstract).
Effendy and Maibach "Surfactants and Experimental Irritant Contact Dermatitis." Contact Dermatol., 1995, 33:217-225.
Elias and Ghadially, "The aged epidermal permeability barrier," Clinical Geriatric Medicine, Feb. 2002, 103-120.
Ellis et al., "The Treatment of Psoriasis with Liquor Carbonis Detergens," J. Invest Dermatology, 1948, 10:455-459.
Emulsifiers With HLB Values, The Herbarie, retrieved on Aug. 5, 2009, http://www.theherbarie.com/files/resources-center/formulating/Emulsifiers-.sub.--HLB.sub.--Values.pdf, 3 pages.
Esposito et al., "Nanosystems for Skin Hydration: A Comparative Study," International Journal of Cosmetic Science, 2007, 29: 39-47.
Established ("Approved") Excipients, Encyclopedia of Pharmaceutical Technology, Second Edition, © 2002, vol. 3, 2146-2147.
Ethylene Oxide Derivatives: An Essence of Every Industry, retrieved on Jul. 12, 2011, http://www.emulsifiers.in/ethylene_oxide_derivatives2.htm, 3 pages.
European Patent Application No. 03772600.7 (Patent No. 1556009): Communication of a Notice of Opposition, dated Sep. 23, 2015, 42 pages.
European Patent Application No. 03772600.7 (Patent No. 1556009): Communication of a Notice of Opposition. dated Sep. 24, 2015, 30 pages.
European Patent Application No. 03772600.7 (Patent No. 1556009): Reply of the Patent Proprietor to the Notices of Opposition, dated May 9, 2016, 134 pages.
European Patent Application No. 03772600.7 (Patent No. 1556009): Summons to Attend Oral Proceedings, dated Jun. 30, 2016, 19 pages.
European Patent Application No. 03772600.7 (Patent No. 1556009): Interlocutory Decision in Opposition Proceedings, dated Feb. 3, 2017, 54 pages.
European Patent Application No. 03772600.7 (Patent No. 1556009): Minutes of Oral Proceedings, dated Feb. 3, 2017, 6 pages.
Excessive Sweating, Merck Manual Home Edition, Oct. 2007, retrieved on Apr. 14, 2011, www.merckmanuals.com/home/print/sec18/ch206/ch206c.html, 2 pages.
Fantin et al., "Critical influence of resistance to streptogramin B-type antibiotics on activity of RP 59500 (Quinupristin-dalfopristin) in experimental endocarditis due to *Staphylococcus aureus*," Antimicrob Agents and Chemothery, Feb. 1995, 39:400-405.
Farahmand et al., "Formulation and Evaluation of a Vitamin C Multiple Emulsion", Pharmaceutical Development and Technology, May 2006, 11(2):255-261 (English Abstract).
Flick, Cosmetic and Toiletry Formulations, 2nd Edition, Copyright 1996, vol. 5, 251-309.
Floyd, "Silicone Surfactants: Applicants in the Personal Care Industry," Silicone Surfactants, 1999, Chapter 7, 181-207.
Fluhr et al., "Glycerol accelerates recovery of barrier function in vivo," Acta Derm. Venereol, 1999, 79:418-421.
Foamix Pharmaceuticals Ltd. (May 1, 2017) "Foamix Pharmaceuticals Announces Plans for Additional Phase 3 Trial for FMX101 in Moderate to Severe Acne," Press Release [online]. Retrieved from: http://www.foamix.co.il/news.asp?nodeID=564&itemID=204, on Jun. 12, 2017, 5 pages.
Foamix Pharmaceuticals, Statement: Use of Luviquat FC 370, Approved by Yohan Hazot, May 3, 2016, 3 pages.
Fontana, "Water Activity: Why It is Important for Food Safety," International Conference on Food Safety, Nov. 16-18, 1998, 177-185.
Fontana (Apr. 1999) "Pharmaceutical Applications for Water Activity" Pharmaceutical Online [online]. Retrieved from https://www.pharmaceuticalonline.com/doc/pharmaceutical-applications-for-water-activit- . . . , on Jan. 17, 2018 (4 pages).
Frankel, A.J. et al. (2010) "Coal Tar 2% Foam in Combination with a Superpotent Corticosteroid Foam for Plaque Psoriasis. Case Report and Clinical Implications" J Clin Aesthet Dermatol, 3(10):42-45.
Fully-Refined Paraffin Wax (FRP Wax), Industrial Raw Materials LLC, Feb. 21, 2008, retrieved on Aug. 22, 2013, <http://irmwax.com/Wax/Paraffin/fully_refined.asp> 1 page.
Gallarate et al., "On the Stability of Ascorbic Acid in Emulsified Systems for Topical and Cosmetic Use", International Journal of Pharmaceutics, 1999, 188:233-241.
Galligan et al., "Adhesive Polyurethane Liners for Anterior Restorations," J. Dent. Res., Jul.-Aug. 1968, 629-632.
Garti et al. "Sucrose Esters microemulsions," J. Molec. Liquids, 1999, 80:253-296.
Gas Gangrene, Merck Manual Home Edition, 2008, retrieved on Jan. 16, 2013, <http://www.merckmanuals.com/home/infections/bacterial_infections/gas_gangrene.html?qt=gasgangrene&alt=sh>1 page.
Gelbard et al. "Primary Pediatric Hyperhidrosis: A Review of Current Treatment Options," Pediatric Dermatology, 2008, 25(6):591-598.
Gels, UNC: The Pharmaceutics and Compounding Laboratory, retrieved on Aug. 25, 2014, http://pharmlabs.unc.edu/labs/gels/agents/htm, 4 pages.
Ghica, M.V. et al. (2011) "Design and optimization of some collagen-minocycline based hydrogels potentially applicable for the treatment of cutaneous wound infections" Pharmazie, 66:853-861.
Gill et al., "Adverse Drug Reactions in a Paediatric Intensive Care Unit," Acta Paediatric, 1995, 84:438-441.
Gladkikh, "Ascorbic Acid and Methods of Increasing its Stability in Drugs", Translated from Khimiko-Farmatsevticheskii Zhurnal, 1970, 4(12):37-42.

(56) References Cited

OTHER PUBLICATIONS

Glaser and Ballard, "Hyperhidrosis: A Comprehensive and Practical Approach to Patient Management," Expert Rev. Dermatol., Oct. 2006, 1(6):773-775.
Google Search Strategy for Minocycline Solubility, retrieved on Aug. 15, 2013, <http://www.googl.com/search?rls=com.microsoft%3Aen-us%3AIE-SearchBox&q-melocycline+solubility>, 1 page.
Graves et al., "Structure of Concentrated Nanoemulsions," The Journal of Chemical Physics, Apr. 1, 2005, 122:134703, 6 pages.
Griffin, "Calculation of HLB Values of Non-Ionic Surfactants," Journal of the Society of Cosmetic Chemists, May 14, 1954, 249-256.
Groveman et al., "Lack of Efficacy of Polysorbate 60 in the Treatment of Male Pattern Baldness", Arch Intern Med, 1985, 145:1454-1458.
Gschnait et al., "Topical Indomethacin Protects from UVB and UVA Irradiation," Arch. Dermatol. Res., 1984, 276:131-132.
Hakan et al., "The protective effect of fish oil enema in acetic acid and ethanol induced colitis," The Turkish Journal of Gastroenterology, 2000, 11(2):155-161.
Hall, "Diaper Area Hemangiomas: A Unique Set of Concerns," retrieved on Dec. 1, 2008, http://members.tripod.com/.about.Michelle.sub.--G/diaper.html, 8 pages.
Hallstar® GMS SE/AS, retrieved on Jun. 4, 2011, http://www.hallstar.com/pis.php?product=1H022, 1 page.
Hammer et al., "Anti-Microbial Activity of Essential Oils and other Plant extracts," J. Applied Microbiology, 1999, 86:985-990.
Hargreaves, "Chemical Formulation, An Overview of Surfactant-Based Preparations Used in Everyday Life", The Royal Society of Chemistry, 2003, 114-115.
Harrison et al., "Effects of cytokines and R-837, a cytokine inducer, on UV-irradiation augmented recurrent genital herpes in guinea pigs", Antiviral Res., 1991, 15(4):315-322.
Harrison et al., "Modification of Immunological Responses and Clinical Disease During Topical R-837 Treatment of Genital HSV-2 Infection," Antiviral Research, 1988, 10:209-224.
Harrison et al., "Pharmacokinetics and Safety of Imiquimod 5% Cream in the Treatment of Actinic Keratoses of the Face, Scalp, or Hands and Arms", Arch. Dermatol. Res., Jun. 2004, 296(1):6-11 (English Abstract).
Harrison et al., "Posttherapy Suppression of Genital Herpes Simplex Virus (HSV) Recurrences and Enhancement of HSV-Specific T-Cell Memory by Imiquimod in Guinea Pigs", Antimicrobial Agents and Chemotherapy, Sep. 1994, 38(9):2059-2064.
Harry, "Skin Penetration," The British Journal of Dermatology and Syphilis, 1941, 53:65-82.
Hashim et al., "Tinea versicolor and visceral leishmaniasis," Int J Dermatol., Apr. 1994; 33(4):258-259 (Abstract).
Haute.De, "Substance (INCI-Designation): Triethanolamine" [online]. Retrieved on Sep. 14, 2015, http://www.haut.de/service/inci/anzeige&id=16384&query=Triethanolamine&funktio . . . ; German with English translation, 3 pages.
Haw, "The HLB System: A Time Saving Guide to Surfactant Selection," Presentation to the Midwest Chapter of the Society of Cosmetic Chemists, Mar. 9, 2004, 39 pages.
Healy, "Gelled Emollient Systems for Controlled Fragrance Release and Enhanced Product Performance," Cosmetics and toiletries, 2002, 117(2): 47-54.
Heart Failure, The Merck Manual, 2008, retrieved Oct. 9, 2010, http://www.merck.com/mmhe/sec03/ch025/ch025a.html, 12 pages.
Helmenstine, "Surfactant Definition—Chemistry Glossary Definition of Surfactant," About.com Chemistry, retrieved on Mar. 5, 2012, http://chemistry.about.com/od/chemistryglossary/g/surfactant.htm, 1 page.
Hepburn, "Cutaneous leishmaniasis," Clin Exp Dermatol, Jul. 2000, 25(5):363-370 (Abstract).
HLB Systems, Pharmcal.tripod.com, retrieved on Sep. 17, 2010, http://pharmcal.tripod.com/ch17.htm, 3 pages.

HLB-Numbers, Sigma Aldrich, 2009, retrieved on Feb. 2, 2009, http://www.sigmaaldrich.com/materials-science/micro-and-nanoelectronics/l-ithography-nanopatterning/hlb-numbers.html, 3 pages.
How to Have a Healthy Libido in Mid-Life and Beyond, GreenWillowTree.com, Jan. 2001, retrieved on Jul. 28, 2012, http://www.greenwillowtree.com/Page.bok?file=libido.html, 5 pages.
Hubbe, Colloidal Silica, Mini-Encyclopedia of Papermaking Wet-End Chemistry: Additives and Ingredients, their Composition, Functions, Strategies for Use, Feb. 1, 2001, retrieved on Jun. 4, 2011, http://www4.ncsu.edu/~hubbe/CSIL.htm, 2 pages.
Human Immunodeficiency Virus Infection, Merck Manual Home Edition, 2008, retrieved on Jan. 16, 2013, <http://www.merckmanuals.com/home/infections/human_immunodeficiency_virus_hiv_infection/human_immunodeficiency_virus_infection.html?qt=human immunodeficiency virus infection&alt=sh >, 11 pages.
Hwang et al., "Isolation and identification of mosquito repellents in Artemisia vulgaris," J. Chem. Ecol., 1985, 11: 1297-1306.
ICI Americas Inc., "Meaning of HLB Advantages and Limitations" Chapter 1 in the HLB System. A Time-Saving Guide to Emulsifier Selection. Wilmington, Delaware: 1980; pp. 1-4.
Ikuta et al., "Scanning Electron Microscopic Observation of Oil/Wax/Water/Surfactant System", Journal of SCCJ, 2004, 34(4):280-291 (English Abstract).
Indomethacin, Aug. 15, 2009, retrived on Jun. 3, 2011, http://it03.net/com/oxymatrine/down/1249534834.pdf, 3 pages.
Innocenzi et al., "An Open-Label Tolerability and Effacy Study of an Aluminum Sesquichlorhydrate Topical Foam in Axillary and Palmar Primary Hyperhidrosis," Dermatologic Therapy, 2008, 21:S27-S30.
Izquierdo et al. "Formation and Stability of Nano-Emulsions Prepared Using the Phase Inversion Temperature Method," Langmuir, 2002, 18(1):26-30 (Abstract).
Jan, "Troubled Times: Detergent Foam," retrieved on Feb. 9, 2012, http://zetatalk.com/health/theal17c.htm, 2 pages.
Joseph, "Understanding foams & foaming," University of Minnesota, May 1997, http://www.aem.umn.edu/people/faculty/joseph/archive/docs/understandingfoams.pdf, 8 pages.
Kalkan et al., "The Measurement of Sweat Intensity Using a New Technique," Tr. J. of Medical Sciences, 1998, 28:515-517.
Kanamoto et al., "Pharmacokinetics of two rectal dosage forms of ketoprofen in patients after anal surgery," J Pharmacobiodyn., Mar. 1988, 11(3):141-145.
Kang et al., "Enhancement of the Stability and Skin Penetration of Vitamin C by Polyphenol", Immune Netw., Dec. 2004, 4(4):250-254 (English Abstract).
Kanicky, J.R. and D.O. Shah (2002) "Effect of Degree, Type, and Position of Unsaturation on the pKa of Long-Chain Fatty Acids" J Colloid and Interface Science, 256:201-207.
Karasu et al., "Practice Guideline for the Treatment of Patients with Major Depressive Disorder," Second Edition, Apr. 2000, 78 pages.
Kathon™ CG, Rohm and Haas Personal Care, Jun. 2006, 9 pages.
Kaur et al., "Formulation Development of Self Nanoemulsifying Drug Delivery System (SNEDDS) of Celecoxib for Improvement of Oral Bioavailability," Pharmacophore, 2013, 4(4):120-133.
Kim, "Stability of Minoxidil in Aqueous Solution", Yakhak Hoechi, 1986, 30(5):228-231 (English Abstract).
Kinnunen and Hannuksela, "Skin reactions to hexylene glycol," Contact Dermatitis, Sep. 1989, 21(3):154-158.
Kircik, L.H. and S. Kumar (Aug. 2010) "Scalp Psoriasis" J Drugs Dermatol, 9(8 Suppl):s101-s137.
Kleber et al., "Practice Guideline for the Treatment of Patients with Substance Use Disorders," Aug. 2006, 276 pages.
Klucel Hydroxypropylcellulose; Chemical and Physical Properties, Hercules Limited, copyright 1986, retrieved on Aug. 25, 2014, http://legacy.library.ucsf.edu/tid/cnf81a99/pdf, 35 pages.
Knight et al., "Topical diltiazem ointment in the treatment of chronic anal fissure," Br. J. Surg., 2001, 88(4):553-556.
Koerber, "Humectants and Water Activity," Water Activity News, 2000, 8 pages.
Kolb, "Emulsifiers, emollients and solubilizers for personal care", pp. 1-9, accessed Jun. 20, 2018.

(56) References Cited

OTHER PUBLICATIONS

Kreuter, "Nanoparticles and microparticles for drug and vaccine delivery," J. Anat., 1996, 189:503-505.
Kucharekova et al., "Effect of a lipid-rich emollient containing ceramide 3 in experimentally induced skin barrier dysfunction," Contact Dermatitis, Jun. 2002, 46:331-338.
Kumar et al., "Application of Broad Spectrum Antiseptic Povidone Iodine as Powerful Action: A Review," Journal of Pharmaceutical Science and Technology, 2009, 1(2):48-58.
Kwak et al. "Study of Complete Transparent Nano-Emulsions which Contain Oils." IFSCC Conference, Seoul Korea, Sep. 2003, 3 pages.
Laboratory 6-Characteristics of Surfactants and Emulsions, retrieved on Jan. 29, 2010, http://web.archive.org/web/20000106225413/http://pharmacy.wilkes.edu/kibbeweb/lab7.html, 5 pages.
Lautenschlager, "A Closer Look on Natural Agents: Facts and Future Aspects," Kosmetic Konzept Kosmetische Praxis, 2006, 5:8-10.
Le Vine et al., "Components of the Goeckerman Regimen," Journal of Investigative Dermatology, 1979, 73:170-173.
Lebwohl and Ali, "Treatment of psoriasis. Part 1. Topical therapy and phototherapy," J. Am Acad Dermatol, Oct. 2001, 487-498.
Lebwohl et al., "A randomized, double-blind, placebo-controlled study of clobestasol propionate 0.05% foam in the treatment of nonscalp psoriasis," International Journal of Dermatology, 2002, 41(5): 269-274.
Lee et al., "Historical review of melanoma treatment and outcomes," Clinics in Dermatology, 2013, 31: 141-147.
Lee et al., "The Stabilization of L-Ascorbic Acid in Aqueous Solution and Water-in-Oil-in-Water Double Emulsion by Controlling pH and Electrolyte Concentration," J. Cosmet. Sci., Jan./Feb. 2004, 55:1-12.
Leive et al., "Tetracyclines of various hydrophobicities as a probe for permeability of *Escherichia coli* outer membrane," Antimicrobial Agents and Chemotherapy, 1984, 25:539-544.
Leunapon-F, Leuna-Tenside, Screenshot, retrieved on Sep. 18, 2015, http://www.leuna-tenside.de/2006_7_14_3143/2006_8_7 5750/2006_8_7 241/cas-68439-49-6, 1 page.
Leung and Robinson, "Bioadhesive Drug Delivery," American Chemical Society, 1991, Chapter 23, 350-366.
Li et al., "Solubility Behavior of Imiquimod in Alkanoic Acids", Pharmaceutical Research, Abstract 3029, Nov. 1997,14(11):S475, 2 pages.
Licking Vaginal Dryness Without a Prescription, retrieved on Dec. 14, 2008, http://www.estronaut.com/a/vag.sub.--dryness.htm, 3 pages.
Lin et al., "Ferulic acid stabilizes a solution of vitamins c and e and doubles its photoprotection of skin," J Invest Dermatol, 2005, 125:826-832.
Lippacher et al., "Liquid and Semisolid SLN Dispersions for Topical Application: Rheological Characterization," European Journal of Pharmaceutics and Biopharmaceutics, 2004, 58:561-567.
Livingstone and Hubel, "Segregation of form, color, movement, and depth: Anatomy, physiology, and perception," Science, May 1988, 240:740-749.
Lupke and Kemper, "The HET-CAM Test: An Alternative to the Draize Eye Test," FD Chem. Toxic., 1986, 24:495-196.
Lupo, "Antioxidants and Vitamins in Cosmetics", Clinics in Dermatology, 2001, 19:467-473.
Luviquat Polymer Grades, BASF The Chemical Company, May 2012, 32 pages.
Mailer, "Chemistry and quality of olive oil," NSW Dept. of Primary Industries, Aug. 2006, Primefact 227, 1-4.
Martindale: The Complete Drug Reference, 33rd Edition, Jun. 2002, Pharmaceutical Press, pp. 1073 and 1473.
Martindale: The Complete Drug Reference, Thirty-third edition, Bath Press, London, 2002, 1073 and 1473.
Martindale: The Extra Pharmacopoeia, Twenty-eighth edition, The Pharmaceutical Press, London, 1982, 862-864.
Material Safety Data Sheet, Luvitol EHO, Caelo, Nov. 28, 2013, 4 pages.
Material Safety Data Sheet, Butane, Gas Innovations, Sep. 7, 2007, 3 pages.
Material Safety Data Sheet, Carbon Dioxide, Airgas, Feb. 11, 2016, 11 pages.
Material Safety Data Sheet, Dimethyl Ether, Airgas, May 14, 2015, 12 pages.
Material Safety Data Sheet, Hydroxyethyl Cellulose, Sigma-Aldrich, Jan. 14, 2004, http://terpconnect.umd.edu/-choi/MSDS/Sigma-Aldrich/HYDROXYETHYL%20CELLULOSE, 5 pages.
Material Safety Data Sheet, Hydroxyethyl Cellulose, Sigma-Aldrich, Jan. 2004, 5 pages.
Material Safety Data Sheet, Liquor carbonis detergens, Caelo, Nov. 28, 2013, 5 pages.
Material Safety Data Sheet, Mineral Oil, Macron Fine Chemicals, Oct. 24, 2011, 6 pages.
Material Safety Data Sheet, N-Butane, Airgas, May 7, 2015, 13 pages.
Material Safety Data Sheet, Nitrous Oxide, Airgas, Feb. 11, 2016, 11 pages.
Material Safety Data Sheet, Propane, Airgas, Oct. 20, 2015, 12 pages.
Material Safety Data Sheet, Science Lab.com, Polyethylene Glycol 200, MSDS, Nov. 6, 2008, 6 pages.
Material Safety Data Sheet, USP, Progesterone, Apr. 26, 2006, 5 pages.
Mead, "Electrostatic Mechanisms Underlie Neomycin Block of the Cardiac Ryanodine Receptor Channel (RyR2)," Biophysical Journal, 2004, (87): 3814-3825.
Messenger et al., "Minoxidil: Mechanisms of Action on Hair Growth", British Journal of Dermatology, 2004, 150:186-194.
Metronidazole (Veterinary—Systemic), The United States Pharmacopeial Convention, 2007, retrieved on Sep. 10, 2009, www.usp.org/pdf/EN/veterinary/metronidazole.pdf, 4 pages.
Metz et al., "A Phase I Study of Topical Tempol for the Prevention of Alopecia Induced by Whole Brain Radiotherapy," Clinical Cancer Research, Oct. 2004, 10:6411-6417.
Meucci et al., "Ascorbic Acid Stability in Aqueous Solutions", Acta Vitaminol Enzymol, 1985, 7(3-4):147-153 (English Abstact).
Milton, D.T. et al. (2006) "A Phase I/II Study of Weekly High-Dose Erlotinib in Previously Treated Patients With Nonsmall Cell Lung Cancer" Cancer, 107:1034-1041.
Mineral Oil USP, U.S. Department of Health & Human Services, Chemical Abstracts Service Registry No. 8012-95-1, 2011, 7 pages.
Minocycline (DB01017), Drug Bank, Feb. 8, 2013, retrieved on Aug. 15, 2013, <http://www.drugbank.ca/drugs/DB01017>, 10 pages.
Minocycline, Wikipedia, the free encyclopedia, retrieved on Oct. 21, 2011, http://en.wikipedia.org/wiki/Minocycline, 7 pages.
MMP Inc., International Development and Manufacturing, "Formulating specialties," retrieved on Feb. 2, 2010, http://mmpinc.com, 3 pages.
Molan, "World Wide Wounds: Honey as a topical antibacterial agent for treatment of infected wounds," Dec. 2001, retrieved May 7, 2008, http://www.worldwidewounds.com/2001/november/Molan/honey-as-topical-agent.html, 13 pages.
*Molins PLC v. Textron Inc.*, 48 F.3d 1172, 33 USPQ2d 1823 (Fed. Cir. 1995), 19 pages.
Morgan et al., "Enhanced Skin Permeation of Sex Hormones with Novel Topical Spray Vehicles," Journal of Pharmaceutical Sciences, Oct. 1998, 87(10):1213-1218.
Mousse, Merriam-Webster Online Dictionary, retrieved on Dec. 8, 2008, http://www.merriam-webster.com/dictionary/mousse, 2 pages.
Musial, W. and A. Kubis (2004) "Carbopols as factors buffering triethanolamine interacting with artificial skin sebum" Polim Med, 34(4):17-30 (Abstract).
Natural Skincare Authority, "Disodium EDTA: Cosmetic Toxin Data," 2011, retrieved on Nov. 17, 2013, http://www.natural-skincare-authority.com/DISODIUM-EDTA.html, 4 pages.
Neutrogena Clinical SPF 30 Facial Lifting Wrinkle Treatment, Apr. 28, 2010, retrieved on Sep. 11, 2010, http://www.cosmetoscope.com/2010/04/neutrogea-clinical-with-johnson-johnsons-cytomimic-techology/, 5 pages.
Neves et al., "Rheological Properties of Vaginal Hydrophilic Polymer Gels," Current Drug Delivery, 2009, 6:83-92.

(56) References Cited

OTHER PUBLICATIONS

New Nanomaterials to Deliver Anticancer Drugs to Cells Developed, Science Daily, Jun. 2007, retrieved on Oct. 14, 2013, <URL: http://www.sciencedaily.com/releases/2007/06/070607112931.htm>, 3 pages.
Nietz, "Molecular orientation at surfaces of solids," J. Phys. Chem., 1928, 32(2): 255-269.
Niram Chemicals, Chemical products—Cetostearyl Alcohol, Cetyl Alcohol, Stearyl Alcohol and Polyethylene Glycol Importer & Supplier, retrieved on Jul. 17, 2012, http://www.indiamart.com/niramchemicals/chemicals.html, 7 pages.
Novartis "Lamisil®" Product Information, T2001-29 [online]. Retrieved from: http://www.fda.gov/downloads/Drugs/DrugSafety/PostmarketDrugSafetyInformationforPatientsandProviders/ucm052213.pdf; Published: Apr. 2001, 8 pages.
Oh et al., "Antimicrobial activity of ethanol, glycerol monolaurate or lactic acid against Listeria moncylogenes," Int. J. Food Microbiology, 1993, 20:239-246.
Olsen et al., "A Multicenter, Randomized, Placebo-Controlled, Double-Blind Clinical Trial of a Novel Formulation of 5% Minoxidil Topical Foam Versus Placebo in the Treatment of Androgenetic Alopecia in Men", J. Am. Acad Dermatol, Nov. 2007, 57:767-774.
Om-Cinnamate, MakingCosmetics.com, retrieved on Sep. 26, 2009, http://www.makingcosmetics.com/sunscreens/OM-Cinnamate-p102.html, 1 page.
Omega-9 Fatty Acids (Oleic Acid), Orthomolecular.org, Dec. 2004, retrieved on Aug. 15, 2014, http://orthomolecular.org/nutrients/omega9.html, 1 page.
Optimization of Nano-Emulsions Production by Microfluidization, European Food Research and Technology. Sep. 2007, 22:5-6 (English Abstract).
Oranje et al., "Topical retapamulin ointment, 1%, versus sodium fusidate ointment, 2%, for impetigo: a randomized, observer-blinded, noninferiority study," Dermatology, 2007, 215(4):331-340.
Osborne and Henke, "Skin Penetration Enhancers Cited in the Technical Literature," Pharm. Technology, Nov. 1997, 21(11):58-86.
Padhi et al., "Phospho-olivines as positive-electrode materials for rechargeable lithium batteries," J. Electrochemical Soc., Apr. 1997, 144(4): 1188-1194.
Padi and Kulkarni, "Minocycline prevents the development of neuropathic pain, but not acute pain: possible anti-inflammatory and antioxidant mechanisms," Eur J. Pharmacol, 2008, 601:79-87.
Pakpayat et al., "Formulation of Ascorbic Acid Microemulsions with Alkyl Polyglycosides", European Journal of Pharmaceutics and Biopharmaceutics, 2009, 72:444-452.
Palamaras and Kyriakis, "Calcium antagonists in dermatology: a review of the evidence and research-based studies," Derm. Online Journal, 2005, 11(2):8.
Passi et al., "Lipophilic antioxidants in human sebum and aging," Free Radical Research, 2002,36(4):471-477.
Pharmaceutical Benefits Advisory Committee (PBAC) of Australia. PBAC Public Summary Document—Nov. 2014 Meeting (5 pages).
Pendergrass et al., "The shape and dimension of the human vagina as seen in three-dimensional vinyl polysiloxane casts," Gynecol Obstet. Invest., 1996, 42(3):178-82 (Abstract).
Penreco, "Intelligent Gel Technology Product Specifications," Rev. Jun. 2016 (2 pages).
Permethrin (Insecticide), Wildpro, retrieved on Jun. 4, 2015, http://wildpro.twycrosszoo.org/S/00Chem/ChComplex/perm.htm, 5 pages.
Perotti et al., "Topical Nifedipine With Lidocaine Ointment vs. Active Control for Treatment of Chronic Anal Fissure," Dis Colon Rectum, 2002, 45(11):1468-1475.
Polystyrene, Wikipedia the free encyclopedia, retrieved Apr. 21, 2014, http://web.archive.org/web/20060312210423/http://en.wikipedia.org/wiki/Polystyrene, 4 pages.
PPG-40-PEG-60 Lanolin Oil, Environmental Working Group, 2010, retrieved on May 19, 2010, http://www.cosmeticsdatabase.com/ingredient/722972/PPG-40-PEG-60_Lanolin_Oil/?ingred06=722972., 3 pages.

Prevent, The American Heritage Dictionary of the English Language, 2007, retrieved on Oct. 9, 2010, http://www.credoreference.com/entry/hmdictenglang/prevent, 1 page.
Product Data Sheet for Meclocycline, bioaustralis fine chemicals, Jun. 28, 2013, 1 page.
Promius™ Pharma LLC (2012) Scytera™ (coal tar) Foam, 2%. Product Information Sheet, 1 page.
Prud'Homme et al., Foams: theory, measurements and applications, Marcel Dekker, Inc., 1996, 327-328.
Purcell, "Natural Jojoba Oil Versus Dryness and Free Radicals," Cosmetics and Toiletries Manufacture Worldwide, 1988, 4 pages.
Purdy et al., "Transfusion-transmitted malaria: unpreventable by current donor exclusion guidelines?" Transfusion, Mar. 2004, 44:464.
Raschke et al., "Topical Activity of Ascorbic Acid: From In Vitro Optimization to In Vivo Efficacy", Skin Pharmacology and Physiology, Jul./Aug. 2004, 17(4):200-206 (Abstract).
Ravet et al., "Electroactivity of natural and synthetic triphylite," J. Power Sources, 2001, 97-98: 503-507.
Raymond, "Iodine as an Aerial Disinfectant," J. Hygiene, May 1946, 44(5):359-361.
Reaction Rate, Wikipedia, the free encyclopedia, retrieved on Dec. 18, 2011, en.wikipedia.org/wiki/Reaction_rate, 6 pages.
Receptacle, Merriam Webster, retrieved on Jul. 12, 2011, http://www.merriam-webster.com/dictionary/receptacle, 1 page.
Refina, "Viscosity Guide for Paints, Petroleum & Food Products," accessed Mar. 4, 2015, http://www.refina.co.uk/webpdfs/info_docs/Viscosity_guide_chart.pdf, 2 pages.
Regulation (EC) No. 2003/2003 of the European Parliament and of the Council, Official Journal of the European Union, Oct. 13, 2003, 2 pages.
Repa et al. "All-trans-retinol is a ligand for the retinoic acid receptors," Proc. Natl. Acad Sci, USA, Aug. 1993, 90: 7293-7297.
Reregistration Eligibility Decision for Pyrethrins, EPA, Jun. 7, 2006, 108 pages.
Richwald, "Imiquimod", Drugs Today, 1999, 35(7):497 (Abstract).
Rieger and Rhien, "Emulsifier Selection/HLB," Surfactants in Cosmetics, 129, 1997.
Rohstoffinformationen, Hoffmann Mineral, 2008, 8 pages (with English translation).
Rosacea, Clinuvel Pharmaceuticals, 2010, retrieved on Sep. 9, 2010, http://clinuvel.com/skin-conditions/common-skin-conditions/rosacea#h0-6-prevention, 5 pages.
Rowe et al., "Glyceryl Monooleate," Handbook of Pharmaceutical Excipients, 2011, 10 pages, retrieved on Dec. 19, 2011, http://www.medicinescomplete.com/mc/excipients/current/1001938996.htm?q=glyceryl%20monooleate&t=search&ss=text&p=1# hit.
Rowe et al., "Octyldodecanol," Handbook of Pharmaceutical Excipients, 2011, 9 pages, retrieved on Dec. 19, 2011, URL:http://www.medicinescomplete.com/mc/excipients/current/1001942450.htm?q=octyldodecanol&t=search&ss=text&p=1# hit.
Rowe et al., "Sucrose Palmitate," Handbook of Pharmaceutical Excipients, 2011, 11 pages, retrieved on Dec. 19, 2011, URL:http://www.medicinescomplete.com/mc/excipients/current/EXP-TD-c46-mn0001.htm?q=sucrose%20stearate&t=search&ss=text&p=1# hit.
Rowe et al., "Sucrose Stearate," Handbook of Pharmaceutical Excipients, 2011, 11 pages, retrieved on Dec. 19, 2011, URL:http://www.medicinescomplete.com/mc/excipients/current/EXP-TD-cll-mnOOOl-mnOOOl.htm?q=sucrose%20stearate&t=search&ss=text&p=3# hit.
Rses (Oil in Refrigerator Systems, Service Application Manual, 2009).
Rutledge, "Some corrections to the record on insect repellents and attractants," J. Am. Mosquito Control Assoc, Dec. 1988, 4(4): 414-425.
Sakai et al., "Characterization of the physical properties of the stratum corneum by a new tactile sensor," Skin Research and Technology, Aug. 2000, 6:128-134.
Sanders et al., "Stabilization of Aerosol Emulsions and Foams," J. Soc. Cosmet. Chem., 1970, 21:377-391.
Sarpotdar, P.P. et al. (Jan. 1986) "Effect of Polyethylene Glycol 400 on the Penetration of Drugs Through Human Cadaver Skin In Vitro" J Pharma Sci, 75(1):26-28.

(56) References Cited

OTHER PUBLICATIONS

Savin et al., "Tinea versicolor treated with terbinafine 1% solution," Int J. Dermatol, Nov. 1999; 38(11): 863-865.
Schaefer, "Silicone Surfactants," Tenside Surf. Det., 1990, 27(3): 154-158.
Schmidt, "*Malassezia furfur*: a fungus belonging to the physiological skin flora and its relevance in skin disorders," Cutis, Jan. 1997, 59(1):21-24 (Abstract).
Schmolka, "A review of block polymer surfactants," Journal of the American Oil Chemists Society, Mar. 1977, 54: 110-116.
Schott, "Rheology," Remington's Pharmaceutical Sciences, 17th Edition, 1985, 330-345.
Schutze, "Iodine and Sodium Hypochlorite as Wound Disinfectants," The British Medical Journal, 1915, 921-922.
Sciarra, "Aerosol Technology," Kirk-Othmer Encyclopedia of Chemical Technology, Jul. 2012, 20 pages.
Scientific Discussion for the Approval of Aldara, EMEA, 2005, 10 pages.
Scott, "A Practical Guide to Equipment Selection and Operating Techniques," Pharmaceutical Dosage Forms: Disperse Systems, vol. 3, Copyright 1998, 291-362.
Scully et al., "Cancers of the oral mucosa treatment and management," Medscape Drugs, Diseases and Procedures, Apr. 20, 2012, retrieved on Oct. 12, 2013, <http://emedicine.medscape.com/article/1075729-treatment>, 10 pages.
Seborrheic Dermatitis, retrieved on Sep. 9, 2010, http://www.cumc.columbia.edu/student/health/pdf/R-S/Seborrhea%20Dermatitis.pdf, 2 pages.
Security Datasheet, Luvitol EHO, Cetearyloctanoat, Nov. 27, 2013, 10 pages.
Sehgal, "Ciclopirox: a new topical pyrodonium antimycotic agent: A double-blind study in superficial dermatomycoses," British Journal of Dermatology, 1976, 95:83-88.
Sharp, "Oil," Dictionary of Chemistry, Copyright 1990, 286.
Shear et al., "Pharmacoeconomic analysis of topical treatments for tinea infections," Pharmacoeconomics, Mar. 1995, 7(3):251-267.
Shear, Vocabulary.com, retrieved on Aug. 23, 2013, <URL: https://www.vocabulary.com/dictionary/shear>, 3 pages.
Sheer, Vocabulary.com, retrieved on Aug. 23, 2013, https://www.vocabulary.com/dictionary/sheer, 3 pages.
Shemer, A. et al. (2016) "Topical minocycline foam for moderate to severe acne vulgaris: Phase 2 randomized double-blind, vehicle-controlled study results" J Am Acad Dermatol, 74(6):1251-1252.
Sheu et al., "Effect of Tocopheryl Polyethylene Glycol Succinate on the Percutaneous Penetration of Minoxidil from Water/Ethanol/Polyethylene Glycol 400 Solutions," Drug Dev. Ind. Pharm., Jun. 2006, 32(5):595-607 (Abstract).
Shim et al., "Transdermal Delivery of Mixnoxidil with Block Copolymer Nanoparticles," J. Control Release, Jul. 2004, 97(3):477-484 (Abstract).
Shrestha et al., "Forming properties of monoglycerol fatty acid esters in nonpolar oil systems," Langmuir, 2006, 22: 8337-8345.
Sigma-Aldrich. http://www.sigmaaldrich.com/catalog/product/sial/p1754?lang=en® ion=. Published:Mar. 5, 2014.
Sigma Aldrich, "Surfactants Classified by HLB Numbers" 2017 [online]. Retrieved from the Internet: www.sigmaaldrich.com/materials-science/material-science-products.html?TablePage=22686648, on Jul. 8, 2017 (3 pages).
Silicone, Oxford Dictionaries Online, retrieved on Apr. 19, 2011, http://www.oxforddictionaries.com/definition/silicone?view=uk, 1 page.
Simoni et al., "Retinoic acid and analogs as potent inducers of differentiation and apoptosis. New promising chemopreventive and chemotherapeutic agents in oncology," Pure Appl Chem., 2001, 73(9):1437-1444.
Simovic et al., "The influence of Processing Variables on Performance of O/W Emulsion Gels Based on Polymeric Emulsifier (Pemulen® TR-2NF)," International Journal of Cosmetic Science, Dec. 2001, 21(2)119-125 (Abstract).
Smith, "Hydroxy acids and skin again," Soap Cosmetics Chemical Specialties, Sep. 1993, 69(9):54-59.
Smith, "Sore Nipples," Breastfeeding Mom's Sore Nipples / Breastfeeding Basics, retrieved on Feb. 8, 2012, http://breastfeedingbasics.com/articles/sore-nipples, 9 pages.
Softemul-165: Product Data Sheet, Mohini Organics PVT LTD, retrieved Apr. 10, 2014, http://www.mohiniorganics.com/Softemul165.html#, 1 page.
Solans et al., "Overview of basic aspects of microemulsions," Industrial Applications of Microemulsions, New York, 1997, 1-17.
Solodyn® (Minocycline HCI, USP) Prescribing Information; revised Jun. 2016, 2 pages.
Sonneville-Aubrun et al., "Nanoemulsions: A New Vehicle for Skincare Products," Advances in Colloid and Interface Science, 2004, 108-109:145-149.
Spa Collections, Ag & Co. Essential oil workshop, retrieved on Jan. 31, 2010, http://www.agworkshop.com/p3.asp, 1 page.
Squillante et al., "Codiffusion of propylene glycol and dimethyl isosorbide in hairless mouse skin," European J. Pharm. Biopharm., 1998, 46:265-271.
Squire and Goode, "A randomized, single-blind, single-centre clinical trial to evaluate comparative clinical efficacy of shampoos containing ciclopirox olamine (1.5%) and salicylic acid (3%), or ketoconazole (2%, Nizoral) for the treatment of dandruff/seborrhoeic dermatitis," Dermatolog Treat., Jun. 2002, 13(2):51-60 (Abstract).
Sreenivasa et al., "Preparation and Evaluation of Minoxidil Gels for Topical Application in Alopecia," Indian Journal of Pharmaceutical Sciences, 2006, 68(4):432-436.
Sreenivasan, B. et al. (1956)"Studies on Castor Oil. I. Fatty Acid Composition of Castor Oil" J Am Oil Chem Soc, 33:61-66.
Stehle et al., "Uptake of minoxidil from a new foam formulation devoid of propylene glycol to hamster ear hair follicles," J. Invest. Dermatol., 2005, 124(4): A101 (Abstract).
Sugisaka et al., "The Physicochemical Properties of Imiquimod, The First Imidazoquinoline Immune Response Modifier", Pharmaceutical Research, Nov. 1997, 14(11):S475, Abstract 3030.
*Sun Pharmaceutical Industries Ltd.* v. *Eli Lilly and Co.*, 611 F.3d 1381, 95 USPQ2d 1797 (Fed. Cir. 2010),7 pages.
Sung, J.H. et al. (2010) "Gel characterisation and in vivo evaluation of minocycline-loaded wound dressing with enhanced wound healing using polyvinyl alcohol and chitosan" Intl J Pharmaceut, 392:232-240.
Surfactant, Wikipedia, the free encyclopedia, retrieved on Oct. 24, 2010, http://en.wikipedia.org/wiki/Surfactant, 7 pages.
Tadros, "Surfactants in Nano-Emulsions." Applied Surfactants: Principles and Applications, 2005, 285-308.
Tamarkin, D. (2013) "Foam: A Unique Delivery Vehicle for Topically Applied Formulations" in: Formulating Topical Applications—a Practical Guide. Dayan N, Ed., Carol Stream, IL: CT Books, Chapter 9, pp. 233-260.
Tan et al., "Effect of Carbopol and PolyvinYlpyrrolidone on the Mechanical, Rheological, and Release Properties of Bioadhesive Polyethylene Glycol Gels," AAPS PharmSciTech, 2000; 1(3) Article 24, 10 pages.
Tanhehco, "Potassium Channel Modulators as Anti-Inflammatory Agents", Expert Opinion on Therapeutic Patents, Jul. 2001, 11(7):1137-1145 (Abstract).
Tarumoto et al., "Studies on toxicity of hydrocortisone 17-butyrate 21-propionate-1. Acute toxicity of hydrocortisone 17-butyrate 21-propionate and its analogues in mice, rats and dogs (author's transl)," J Toxicol Sci., Jul. 1981, 6:1-16 (Abstract).
Tata et al., "Penetration of Minoxidil from Ethanol Propylene Glycol Solutions: Effect of Application Volume on Occlusion," Journal of Pharmaceutical Sciences, Jun. 1995, 84(6):688-691.
Tata et al., "Relative Influence of Ethanol and Propylene Glycol Cosolvents on Deposition of Minoxidil into the Skin," Journal of Pharmaceutical Sciences, Jul. 1994, 83(10):1508-1510.
Tavss et al., "Anionic detergent-induced skin irritation and anionic detergent-induced pH rise of bovine serum albumin," J. Soc. Cosmet. Chem., Jul./Aug. 1988, 39:267-272.
TCI America, Safety Data Sheet; Product Name: Squalane. Product Code: H0096 [online]. Retrieved from: https://www.spectrumchemical.com/MSDS/TCI-H0096.pdf. Revised: Oct. 6, 2014, 5 pages.

(56) References Cited

OTHER PUBLICATIONS

Tea Tree Oil, LookChem, Chemical Abstract No. 68647-73-4, 2012, 2 pages.

The HLB System—A Time-Saving Guide to Emulsifier Selection, ICI Americas Inc., Mar. 1980, 1-22.

The United States Pharmacopeia: The National Formulary, USP23/NF18, US Pharmacopoeia, Jan. 1995, p. 10-14.

Third Party Submission in Published Patent Application, U.S. Appl. No. 12/014,088, Feb. 4, 2009, 4 pages.

Thorgeirsdottir et al., "Antimicrobial activity of monocaprin: a monoglyceride with potential use as a denture disinfectant," Acta Odontologica Scandinavica, Feb. 2006, 64:21-26 (Abstract only).

Tirumala et al., "Abstract: D28.00011: Enhanced order in thinfilms of Pluronic (A-B-A) and Brij (A-B) Block copolymers blended with poly (acrylic acid)," Session D28: Block Copolymer Thin Films, Mar. 13, 2006, 1 page, Abstract.

Tjulandin, S. et al. (2013) "Phase I, dose-finding study of AZD8931, an inhibitor of EGFR (erbB1), HER2 (erbB2) and HER3 (erbB3) signaling, in patients with advanced solid tumors" Invest New Drugs, 32(1):145-153.

Todd et al., "Volatile Silicone Fluids for Cosmetic Formulations," Cosmetics and Toiletries, Jan. 1976, 91:27-32.

Torma et al., "Biologic activities of retinoic acid and 3,4-Didehydroretinoic acid in human keratinocytes are similar and correlate with receptor affinities and transactivation properties," J. Invest. Dermatology, 1994, 102: 49-54.

Torres-Rodriguez, "New topical antifungal drugs," Arch Med Res., Winter 1993, 24(4): 371-375 (Abstract).

Toxicology and Carcinogenesis Studies of T-Butyl Alcohol (CAS No. 75-65-0) in F344/N Rats and B6C3F1 Mice (Drinking Water Studies), May 1995, retrieved on Dec. 9, 2008, http://ntp.niehs.nih.gob/?objectid-=0709F73D-A849-80CA-5FB784E866B576D1, 4 pages.

Trofatter, "Imiqimod in clinical practice", European Journal of Dermatology, Oct./Nov. 1998, 8(7 Supp.):17-19 (Abstract).

Tsai et al., "Drug and Vehicle Deposition from Topical Applications: Use of In Vitro Mass Balance Technique with Minoxidil Solutions", J. Pharm. Sci., Aug. 1992, 81(8):736-743 (Abstract).

Tsai et al., "Effect of Minoxidil Concentration on the Deposition of Drug and Vehicle into the Skin," International Journal of Pharmaceutics, 1993, 96(1-3):111-117 (Abstract).

Tsai et al., "Influence of Application Time and Formulation Reapplication on the Delivery of Minoxidil through Hairless Mouse Skin as Measured in Franz Diffusion Cells," Skin Pharmacol., 1994, 7:270-277.

Tyring, "Immune-Response Modifiers: A New Paradigm in the Treatment of Human Papillomavirus," Current Therapeutic Research, Sep. 2000, 61(9):584-596 (Abstract).

Tzen et al. "Surface Structure and Properties of Plant Seed Oil Bodies," Department of Botany and Plant Sciences, University of California, Riverside, California 92521, Apr. 15, 1992, 9 pages.

Tzen et al., "Lipids, proteins and structure of seed oil bodies from diverse species," Plant Physiol., 1993, 101:267-276.

U.S. Final Office Action for U.S. Appl. No. 11/430,437, Tamarkin et al., dated Dec. 16, 2008, 24 pages.

U.S. Office Action for U.S. Appl. No. 11/430,437, Tamarkin et al., dated May 9, 2008, 27 pages.

U.S. Office Action from U.S. Appl. No. 11/430,599, dated Jul. 28, 2008, 59 pages.

Uner et al., "Skin Moisturizing Effect and Skin Penetration of Ascorbyl Palmitate Entrapped in Solid Lipid Nanoparticles (SLN) and Nanostructured Lipid Carriers (NLC) Incorporated into Hydrogel," Pharmazie, 2005, 60:751-755.

United States Standards for Grades of Olive Oil and Olive-Pomace Oil, United States Dept. of Agriculture, Oct. 25, 2010, 21 pages.

Valenta, "Effects of Penetration Enhancers on the In-vitro Percutaneous Absorption of Progesterone," J. Pharm. Pharmacol., 1997, 49: 955-959.

Van Cutsem et al., "The anti-inflammatory effects of ketoconazole," J. Am. Acad. Dermatol., Aug. 1991, 25(2):257-261.

Van Slyke, "On the measurement of buffer values and on the relationship of buffer value to the dissociation constant of the buffer and the concentration and reaction of the buffer solution," J. Biol. Chem., 1922, 52:525-570.

Vera et al., "Scattering optics of Foam," Applied Optics, Aug. 20, 2001, 40(24):4210-4214.

Veron et al., "Stability of Minoxidil Topical Formulations", Ciencia Pharmaceutica, 1992, 2(6):411-414 (Abstract).

Versagel® M Series, Mineral Oil Moisturizing Gels. Product Bulletin, retrieved from https://archive.org/web/, as archived Oct. 15, 2006, 3 pages.

View of NCT01171326 on Dec. 7, 2010, ClinicalTrials.gov archive, Dec. 7, 2010, retrieved on Sep. 9, 2013, http://clinicaltrials.gov/archive/NCT01171326/2010_12_07, 4 pages.

View of NCT01362010 on Jun. 9, 2011, ClinicalTrials.gov archive, Jun. 9, 2011, retrieved on Sep. 9, 2013, < http://clinicaltrials.gov/archive/NCT01362010/2011_06_09>, 3 pages.

Wang and Chen, "Preparation and surface active properties of biodegradable dextrin derivative surfactants," Colloids and Surfaces A: Physicochemical and Engineering Aspects, 2006, 281(1-3):190-193.

Water Jel Technologies, "Material Safety Data Sheet for Neomycin Antibiotic Ointment," Dec. 1, 2004, 7 pages.

WebMD (2014) "Psoriasis Health Center" [online]. Retrieved Apr. 13, 2015; retrieved from the Internet: http://www.webmd.com/skin-problems-and-treatments/psoriasis/psoriasis-symptoms, 3 pages.

WebMD (2014) "Understanding Rosacea—the Basics" [online]. Retrieved Apr. 13, 2015; retrieved from the Internet: http://www.webmd.com/skin-problems-and-treatments/understanding-rosacea-basics (5 pages).

WebMD (2017) "User Reviews & Ratings—Scytera topical" [online]. Retrieved Mar. 1, 2017; retrieved from the Internet: http://www.webmd.com/drugs/drugreview-151502-Scytera+topical.aspx?drugid=151502&drugname=Scytera+topical&sortby=3 (2 pages).

Weindl et al., "Hyaluronic acid in the treatment and prevention of skin diseases: molecular biological, pharmaceutical and clinical aspects," Skin Pharmacology and Physiology, 2004, 17: 207-213.

Wenninger et al., "International Cosmetic Ingredient Dictionary and Handbook," The Cosmetic, Toiletry, and Fragrance Association, Washington, DC., 1997, vol. 1, 4 pages.

Wermuth, "Similarity in drugs: reflections on analogue design," Drug Discovery Today, Apr. 2006, 11(7/8):348-354.

What is CP Serum, Skin Biology, retrieved on Dec. 1, 2008, http://web.archive.org/web/20030810230608/http://www.skinbio.com/cpserum.-html, 21 pages.

What is TSC?, Tuberous Sclerosis Alliance, Jan. 1, 2005, retrieved on Feb. 6, 2014, http://www.tsalliance.org.pages.aspx?content=2, 3 pages.

Williams et al., "Acne vulgaris," Lancet, 2012, 379:361-372.

Williams et al., "Scale up of an olive/water cream containing 40% diethylene glycol monoethyl ether," Dev. Ind. Pharm., 2000, 26(1):71-77.

Williams et al., "Urea analogues in propylene glycol as penetration enhancers in human skin," International Journal of Pharmaceutics, 1989, 36, 43-50.

Wormser et al., "Protective effect of povidone-iodine ointment against skin lesions induced by sulphur and nitrogen mustards and by non-mustard vesicants," Arch. Toxicol., 1997, 71, 165-170.

Wormser, "Early topical treatment with providone-iodine ointment reduces, and sometimes prevents, skin damage following heat stimulus," Letter to the Editor, Burns, 1998, 24:383.

Wrightson, W.R. et al. (1998) "Analysis of minocycline by high-performance liquid chromatography in tissue and serum" J Chromatography B, 706:358-361.

Wu et al., "Interaction of Fatty Acid Monolayers with Cobalt Nanoparticles," Nano Letters, 2004, 4(2): 383-386.

Yamada et al., "Candesartan, an angiotensin II receptor antagonist, suppresses pancreatic inflammation and fibrosis in rats," J. Pharmacol. Exp. Ther., 2003, 307(1):17-23.

Zeichner, J.A. (2010) "Use of Topical Coal Tar Foam for the Treatment of Psoriasis in Difficult-to-treat Areas" J Clin Aesthet Dermatol, 3(9):37-40.

(56) References Cited

OTHER PUBLICATIONS

Zinc Oxide, Knovel, 2006, retrieved on Apr. 18, 2012, http://www.knovel.com/web/portal/knovel_content?p_p_id=EXT_KNOVEL_CONTENT . . . , 2 pages.
Ziolkowsky, "Moderne Aerosolschaume in der Kosmetik (Modern Aerosol Foams in Chemical and Marketing Aspects)" Seifen-Ole-Fette-Wachse, Aug. 1986, 112(13): 427-429 (with English translation).
Allen, The Art, Science, and Technology of Pharmaceutical Compounding, pp. 173-185 (1998).
Allen, The Art, Science, and Technology of Pharmaceutical Compounding, 2nd edition, pp. 250, 251, 263, 267-269, 287, 288, 301-305, tables 16-1 and 16-2 (2002).
Ansel et al., Pharmaceutical Dosage Forms and Drug Delivery Systems, 7th ed., pp. 87-92, 250, 378-380, table 3.3 (1999).
Attwood et al., Surfactant Systems: Their chemistry, pharmacy and biology, pp. 1-8 (1993).
Bowles et al., "Protection against Minocycline Pigment Formation by Ascorbic Acid (Vitamin C)", Journal of Esthetic Dentistry, vol. 10/No. 4, pp. 182-186 (1998).
Brewer, "Gramicidin", 8 Profiles of Drug Substances, Excipients and Related Methodology, 43 pages (1979).
Calvert, "Foam in Motion", Foams: Physics, Chemistry and Structure, pp. 27-37 (1989).
Declaration Pursuant to 37 C.F.R. §1.132 of Dr. Mohammad Salman, dated Dec. 28, 2015, filed in U.S. Appl. No. 14/074,868.
Declaration Pursuant to 37 C.F.R. §1.132 of Dr. Mohammad Salman, dated May 19, 2016, filed in U.S. Appl. No. 14/074,868.
Declaration Pursuant to 37 C.F.R. §1.132 of Dr. Mohammad Salman, dated Jul. 19, 2016, filed in U.S. Appl. No. 14/074,868.
Donnelly et al., Novel Delivery Systems for Transdermal and Intradermal Drug Delivery, p. 103.
Hanasono et al., "The Effect of Silicone Gel on Basic Fibroblast Growth Factor Levels in Fibroblast Cell Culture", Arch Facial Plast Surg, vol. 6, pp. 88-23 (2004).
Handbook of Pharmaceutical Excipients 79, 85, 215, 336, 386, 443, 568, 599 (Arthur H. Kibbe ed., 2000).
Healy et al., "Acne vulgaris", Br. Med. J., 308: 831-833, 831 (1994).
Johns Hopkins on Acne https://www.hopkinsmedicine.org/health/conditions-and-diseases/acne, 6 pages, 2019.
Kanwar et al., "Treatment of Melasma with Potent Topical Corticosteroids", Dermatology, 188(2):170 (1994). 188(2):170.
Kircik et al., "Formulation and Profile of FMX101 4% Minocycline Topical Foam for the Treatment of Acne Vulgaris," J. Clin. Aesthet. Dermatol., 13(4): 14-21 (2020).
Mah et al., "Irrational Use of Skin-Bleaching Products Can Delay the Diagnosis of Leprosy", International Journal of Leprosy and Other Mycobacterial Diseases, vol. 70, No. 2, pp. 119-121 (2002).
McKetta, Encyclopedia of Chemical Processing and Design: vol. 2—Additives to Alpha, 1st Ed., pp. 214-238 (1977).
The Merck Index: An Encyclopedia of Chemicals, Drugs, and Biologicals 1299-1300, 1638 (13th ed., 2001).
O'Neil, The Merck Index an Encyclopedia of Chemicals, Drugs, and Biologicals, p. 153 (2006).
Olux Prescribing Information (2013).
Pantaris et al., "The lauric (coconut and palmkernal) oils", Vegetable Oils in Food Technology, Chemistry and Technology of Oils and Fats, pp. 157-202 (2002).
Sarkar et al., "A Comparative Study of 20% Azelaic Acid Cream Monotherapy versus a Sequential Therapy in the Treatment of Melasma in Dark-Skinned Patients", Dermatology, 205(3): 249-54 (2002).
Sciarra et al., "Aerosols", Remington: The Science and Practice of Pharmacy, pp. 963-966 (2000).
Tenjarla, "Microemulsions: An Overview and Pharmaceutical Applications", Crit. Rev. Ther. Drug Carrier Sys., 16(5): 461-521 (1999).
Walstra, "Principles of Foam Formation and Stability", Foams: Physics, Chemistry and Structure, pp. 1-15 (1989).

\* cited by examiner

SURFACTANT-FREE WATER-FREE FOAMABLE COMPOSITIONS, BREAKABLE FOAMS AND GELS AND THEIR USES

CROSS REFERENCE TO RELATED APPLICATIONS

This application is a continuation of U.S. application Ser. No. 14/850,655, filed Sep. 10, 2015, which is a continuation of U.S. application Ser. No. 14/577,659, filed Dec. 19, 2014, which is a continuation of U.S. application Ser. No. 13/499,501, which is a U.S. National Stage entry under 35 U.S.C. § 371 of International Application No. PCT/IB2010/002612, filed Oct. 1, 2010, which claims the benefit of priority under 35 U.S.C. § 119(e) to U.S. Provision al Application No. 61/248,144 filed Oct. 2, 2009 and entitled "Surfactant-Free Water-Free Foamable Compositions, Breakable Foams and Their Uses"; U.S. Provisional Application No. 61/322,148 filed Apr. 8, 2010 and entitled "Surfactant-Free Water-Free Foamable Compositions, Breakable Foams and Their Uses"; U.S. Provisional Application No. 61/349,911 filed May 31, 2010 and entitled "Surfactant-Free Water-Free Foamable Compositions, Breakable foams and Their Uses"; U.S. Provisional Application No. 61/385,385 filed Sep. 22, 2010 and entitled "'Surfactant-Free Water-Free Foamable Compositions, Breakable Foams and Gels and Their Uses"; U.S. Provisional Application No. 61/331,126 filed May 4, 2010 and entitled "Compositions, Gels and Foams with Rheology Modulators and Uses Thereof"; and U.S. Provisional Application No. 61/380,568 filed Sep. 7, 2010 and entitled "Surfactant-Free Water-Free Foamable Compositions and Breakable Foams and Their Uses"; all of which are herein incorporated in their entirety by reference.

BACKGROUND

Foam compositions with high amounts of hydrophobic solvents are little known in the art.

Foams and, in particular, oleaginous single-phase foams are complicated systems which do not form under all circumstances. Slight shifts in foam composition, such as by the addition of active ingredients or the removal of any of the essential ingredients, may destabilize the foam.

The prior art teaches oleaginous foam compositions require significant amounts of surface active agents to form, a foam. These compositions require various standard surfactants, as essential components.

Surfactants are known as essential ingredients in foam, compositions because of their amphiphilic properties and because they are considered essential in forming a foam. However, many surfactants are known to be irritating when left on the skin, as they can extract lipids from the skin, thereby damaging skin barrier and exposing the skin to contact with pro-inflammatory factors. (See for example: Effendy, I. and Maibach, H. I. "*Surfactants and Experimental Irritant Contact Dermatitis.*" Contact Dermatol., 33 (1995), 217-225). Many surfactants can also react with unstable active agents and lead to their rapid degradation.

Briefly, the term surfactant has been often loosely used in the art to include substances which do not function effectively as stand alone surfactants to reduce surface tension between two substances or phases. Reduction of surface tension can be significant in foam technology in relation to the ability to create small stable bubbles. In the context herein, the term "standard surfactant" or "customary surfactant" refers to customary non-ionic, anionic, cationic, zwitterionic, amphoteric and amphiphilic surfactants. Many standard surfactants are derivatives of fatty alcohols or fatty acids, such as ethers or esters formed from such fatty alcohols or fatty acids with hydrophilic moieties, such as polyethyleneglycol (PEG). However, a native (non derivatized) fatty alcohol or fatty acid, as well as waxes are not regarded as a standard surfactant.

In the context herein the term "foam adjuvant" includes only native fatty alcohols and fatty acids. These are amphiphatic, and essentially hydrophobic with a minor hydrophilic region. For the purposes of forming an emulsion these foam adjuvants, unlike "standard" or "customary surfactants", are not effective as stand-alone surfactants in foamable emulsion compositions, because of their very weak emulsifying capacity on their own. Fatty alcohols and fatty acids have been loosely described as co-surfactants in foamable emulsion compositions, because they assist customary surfactants to boost foam quality, help evolve the foaming properties and because they stabilize the foam in part because of their property as thickeners.

SUMMARY

The present application relates to oleaginous foamable formulations and foams and their uses comprising hydrophobic solvents. In addition, it relates to formulations with an active agent. Surprisingly, the application also relates to foamable formulations and foam without surfactants; and/or without surfactants and polymeric agents. In one or more embodiments the hydrophobic solvents are provided as part of a drug carrier. For example certain drugs require hydrophobic solvents in order to solubilize them. In one or more other embodiments, the hydrophobic solvents are provided to facilitate or enhance the transdermal penetration or delivery of a drug. In one or more additional cases, the hydrophobic sol vents are provided to have an occlusive effect at the target site, for example where the site of treatment is a damaged skin and the occlusive effect of hydrophobic solvents is desirable. The application further describes semi solid gel compositions that liquefy oil application of mild shear force such as gentle rubbing.

It is known in the art that foams can easily be formulated based on high amounts of water, in combination with surface active agents, foam adjuvants and polymeric agents. As described in the literature, hydrophobic solvents can have a de-foaming effect which makes the formulation of foams based on hydrophobic solvents challenging, especially in compositions that do not contain water. To overcome this challenge, the prior art requires the use of substantial levels of surfactants that act as foaming agents. Surface active agents are known to be irritating, especially ionic surface active agents and repeated use can cause dry skin and so it is desirable to reduce their use in pharmaceutical compositions intended to treat skin or mucosa. The prior art further teaches the incorporation of foam adjuvants, such as fatty alcohols and fatty acids, as foam stabilizing agents and also the incorporation of polymeric agents (e.g. gelling agents) as foam stabilizers, which can prolong the collapse time of a foam. Waxes may also be introduced into these surfactant-based formulations but as will be appreciated, waxes, which are solids at ambient temperature, can easily precipitate.

The technical problems to be overcome in formulating carriers and pharmaceutical compositions with hydrophobic solvent (a) without surfactants; and/or (b) without polymeric agents and/or (c) without water and/or (e) without short chain alcohols and/or (f) without polyols; are multifold and include finding a suitable substitute for surfactant which provides foam generating properties; finding a suitable replacement that preferably does not need to have a foam adjuvant present with the surfactant (substitute), which if present would inter alia help to boost the foam and as an aid to the surfactant and preferably does not need to have a polymeric agent present with the surfactant (substitute), which if present would inter alia help prolong stability of the foam.

It was surprisingly discovered in the present invention, that surface active agents can be advantageously eliminated and replaced by foam adjuvants and waxes in the context of hydrophobic solvent based-foams. Waxes possess several advantages over other foaming agents such as excellent skin compatibility, almost no chemical reactivity which ensures active ingredients stability and efficient skin occlusion which helps reducing skin water loss and can enhance skin penetration of active agents. Albeit waxes introduce their own additional problems into formulating foamable compositions and foams, including their tendency to solidify and precipitate out from a formulation and to block canister valves, against which the formulations need to be designed so that the formulations are not negatively disturbed upon adding an effective amount of propellant and that the formulations are shakable and are homogenous and can readily reform at least upon mild or reasonable shaking prior to use.

Incorporated in or added to the above is the aspect of how to provide formulations in which unstable active ingredients, such as tetracyclines, which readily degrade can nevertheless remain sufficiently chemically stable for prolonged periods of time such that allowing for a reasonable or acceptable amount of breakdown (for example as may be accepted by a regulatory drug authority) they remain capable of providing a therapeutic effect or prevention or remission of a disorder or disease (hereinafter "chemically stable"). A further challenge is providing and delivering a composition in which the active agent is homogenous. Additionally the formulations should avoid the use of substances, which can be irritating if applied to a sensitive target or can cause depletion or drying or soreness on repeated use.

Incorporated in or added to the above is the aspect of how to provide physically stable formulations which are at least short term stable upon release from the pressurized container and not break as a result of exposure to skin temperature. Foams which are structurally stable on the skin for at least one minute are termed "short term stable" carriers or foams. In another aspect of physically stability the foamable formulation including propellant remains homogenous and does not separate to any significant extent for at least one minute after being shaken (hereinafter "physically stable").

A feature of a product for cosmetic or medical use is long term stability. Propellants, which are a mixture of low molecular weight hydrocarbons, tend to impair the stability. The foamable compositions herein are surprisingly stable, even in the absence of customary surfactants. Following accelerated stability studies, they demonstrate desirable texture; they form fine bubble structures that do not break immediately upon contact with a surface, spread easily on the treated area and absorb quickly. In one or more embodiments the foam composition has an acceptable shelf-life of at least six months. In one or more embodiments the foam composition has an acceptable shelf-life of at least one year. In one or more embodiments the foam composition has an acceptable shelf-life of at least 15 months, or at least 18 months or at least 21 months or at least two years at ambient temperature.

In one or more embodiments there is provided a composition which is a single phase.

In one or more embodiments there is provided a composition which prevents the degradation of the active ingredient upon application on the target site of treatment.

Thanks to the absence of surfactants in the compositions, the oleaginous formulations and foams of the present invention, containing different concentrations of minocycline hydrochloride, demonstrated no signs of irritation as demonstrated using an in vitro irritation HET-CAM test. In one or more embodiments the drug carrier is formulated for use on sensitive targets such as the eye. In one or more embodiments the active pharmaceutical ingredients are formulated for use on sensitive target areas such as sensitive or damaged skin areas, wounds, burns, mucosal membranes, and body cavities. Hydrophobic solvents that are suitable, for example, for eye treatment or for use in wounds or burns. In one or more embodiments the drug carrier and the respective pharmaceutical composition with an active agent are both formulated for use on sensitive targets such as the eye. In one or more embodiments the composition is intended for use in treatment or prevention of eye infections.

Unexpectedly, it has been discovered that quality oleaginous formulations and foams can be achieved without the presence of significant amounts of standard surfactants. Thus, in one or more embodiments, there is provided a substantially surfactant free oleaginous formulation or foam. In one or more embodiments, there is provided an essentially surfactant free oleaginous formulation or foam. In one or more preferred embodiments the oleaginous formulations and foams are free of surfactants. Further, unexpectedly, it has been discovered that quality oleaginous formulations and foams can be achieved without the presence of significant amounts of standard polymeric agents (e.g. gelling agents). Thus, in one or more embodiments, there is provided a substantially surfactant-free and substantially polymeric agent-free oleaginous formulation or foam. In one or more preferred embodiments the oleaginous formulations and foams are free of standard surfactants and polymers. Moreover, it has been further discovered that these formulations and foams can be achieved over a large range of hydrophobic solvent content. There is thus provided easy to use, chemically and physically stable and non-irritating topical foam formulations, and pharmaceutical compositions thereof, containing a stable or stabilized active pharmaceutical or cosmetic agent having a therapeutic or beneficial effect, intended for treatment of dermal and mucosal tissues free or substantially free of standard surfactants and/or polymeric agents.

In one or more embodiments there is provided a safe and effective foamable carrier composition and foam comprising a hydrophobic solvent, an oleaginous foamer complex (also termed "foamer complex"), comprising a first member, comprising about 0.1% to about 20% by weight of a fatty alcohol; and a second member, comprising about 0.1% to about 20% by weight of (i) a fatty acid; and/or (ii) a wax; and a liquefied or compressed gas propellant. In one or more embodiments the foamer agent comprises a paraffin wax alone or in combination with the first member and/or the second member. In certain embodiments, the concentration of the propellant is about 3% to about 30% by weight of the total composition.

In other certain embodiments, the concentration of the propellant is about 1% to about 3% by weight of the total composition; or about 3% to about 25%; or about 7% to about 17%; or about 10% to about 14%. Where a bag in can or can in can system is used where part of the propellant is in the formulation and part separate from the formulation, the amount in the formulation may be as little as about 1% by weight of the total composition. In additional embodiments there is provided a safe and effective foamable pharmaceutical or cosmetic composition and foam comprising at least one active agent. In additional embodiments there is provided a safe and effective foamable pharmaceutical or cosmetic composition and foam comprising an effective amount of a pharmaceutical or cosmetic active agent, a hydrophobic solvent, a foamer complex and a liquefied or compressed gas propellant.

The percent by weight Is based on weight foamable composition; where the ratio of composition other than propellant to propellant is from about 100:1 to about 100:30; or from about 100:3 to about 100:30; or from about 100:4 to about 100:25; or from about 100:7 to about 100:17; or from, about 100:10 to about 100:14 or from any one of the lower ratios to any one of the higher ratios.

In one or more embodiments there is provided a composition comprising a propellant having a vapor pressure between about 10 psi and about 130 psi. In one or more embodiments there is provided a composition comprising a propellant which is hydrocarbon propellant or a hydrofluorocarbon or another environmentally acceptable propellant.

The composition does not contain a surfactant; and the foaming effect is achieved by the addition of the foamer complex, as specified herein. The hydrophobic solvent is present in a substantial amount. In one or more embodiments the hydrophobic solvent is at a concentration between about 60% to about 95% by weight, or about 70% to about 90% by weight. In alternative embodiments the formulation, is formulated, without propellant and delivered as a gel, ointment or rub. In one or more embodiments the composition comprises a concentration between about 1% to about 80% by weight petrolatum and about 15% to about 94% by weight hydrophobic solvent, wherein the total amount of hydrophobic solvent and petrolatum is at least about 60% by weight. In one or more alternative embodiments the formulation comprises 0% to about 80% by weight petrolatum, and about 15% to about 95% by weight hydrophobic solvent, provided that if present the combined amount of hydrophobic solvent and petrolatum is at least about 60% by weight.

In one or more alternative embodiments the formulation comprises 0% to about 91% petrolatum and about 4% to about 95% hydrophobic solvent, provided that if present the combined amount of hydrophobic solvent and petrolatum is at least about 60% by weight. In one or more alternative embodiments the formulation comprises 0% to about 95% petrolatum and about 0% to about 95% hydrophobic solvent, provided that if present the combined amount of hydrophobic solvent and petrolatum is at least about 60% by weight.

In certain embodiments the petrolatum is about 1% to about 20% and the hydrophobic solvent is about 75% to about 94% provided that the combined amount of hydrophobic solvent and petrolatum is at least about 60% by weight. In certain embodiments the petrolatum is about 21% to about 40% and the hydrophobic solvent is about 55% to about 74% provided that the combined amount of hydrophobic solvent and petrolatum is at least about 60% by weight. In certain embodiments the petrolatum is about 41% to about 60% and the hydrophobic solvent is about 35% to about 54% provided that the combined amount of hydrophobic solvent and petrolatum is at least about 60% by weight. In certain embodiments the petrolatum is about 61% to about 70% and the hydrophobic solvent is about 25% to about 34% provided that the combined amount of hydrophobic solvent and petrolatum is at least about 60% by weight. In certain embodiments the petrolatum is about 61% to about 80% and the hydrophobic solvent is about 15% to about 34% provided that the combined amount of hydrophobic solvent and petrolatum is at least about 60% by weight.

In certain embodiments the petrolatum is about 81% to about 95% and the hydrophobic solvent is about 0.1% to about 14%, provided that the combined amount of hydrophobic solvent and petrolatum is at least about 60% by weight. According to additional embodiments where a petrolatum is present the formulation comprises about 1% to about 80% petrolatum and about 15% to about 94% hydrophobic solvent, provided that the combined amount of hydrophobic solvent and petrolatum is at least about 60% by weight. In further embodiments petrolatum may be in excess of about 80% (see for example formulation A8 in Table 9, which produced foam of excellent quality. In one or more embodiments, there is provided a foamable formulation comprising petrolatum in excess of about 80%, optionally a liquid oil, a fatty alcohol, and a wax, wherein the formulation generates quality breakable foam. In one or more embodiments, there is provided a foamable formulation comprising petrolatum in excess of about 80%, optionally a liquid oil, a fatty alcohol and/or a fatty acid, and/or a wax, wherein the formulation generates quality breakable foam. In one or more other embodiments, there is provided a foamable formulation comprising petrolatum in cxccss of about 80%, a liquid oil, and at least one of a fatty alcohol and/or a fatty acid, and/or a wax, wherein the formulation generates quality breakable foam.

As will be appreciated from the above illustrative examples as the amount of petrolatum is increased the amount of hydrophobic solvent is reduced. Accordingly, different amounts of petrolatum other than the amounts specified can be contemplated with a parallel increase or decrease in solvent as appropriate. In one or more embodiments when mineral oil is combined with different oils, high amounts of petrolatum and shea butter quality foam can be obtained with fatty alcohol(s) as the foamer complex. In one or more embodiments, there is provided a foamable formulation comprising petrolatum, mineral oil, fatty alcohol(s) and optionally shea butter, wherein the formulation generates quality breakable foam.

Upon dispensing the foamable carrier composition forms a breakable foam that is stable, yet breaks easily upon application of shear force. In one or more embodiments the composition is used for intradermal delivery of the active agent into the skin with minimal or negligible transdermal delivery. In one or more alternative embodiments a formulation is provided to achieve intra mucosal delivery. In certain embodiments the composition provides for transdermal delivery. In one or more embodiments the composition can be used for prevention of a disease or disorder. The composition or foam is applied to a target surface or area in or on which prevention is sought. The composition or foam is applied to a target surface or area having a dermato logical or mucosal disorder in need of treatment. In other embodiments the composition or foam is used to treat or ameliorate a dermatological or mucosal disease or disorder. In still further embodiments it may be used to provide a period of remission from the dermatological or mucosal disease or disorder.

According to an embodiment the one or more active agents is selected from the group consisting of adipic acid, an acaricide, an active herbal extract, an age spot and keratose removing agent, an allergen, an alpha hydroxyl acid, an analgesic agent, an androgen, an anesthetic, an anti wrinkle agent, an antiacne agent, an antiaging agent, an antiallergic agent, an antiandrogen agent, an antiapoptotic agent, an antibacterial agent, an antibiotic, an antibiotic agent, an antiburn agent, an anticancer agent, an antidandruff agent, an antidepressant, an antidermatitis agent, an antiedemic agent, an antifungal agent, an antihelminth agent, an antihistamine, an anti-hyperkeratosis agent, an anti-infective agent, an antiinflammatory agent, an antiirritant, an antilipemic agent, an antimicrobial agent, an antimycotic agent, an antioxidant, an antiparasitic agent, an anti-photoaging agent, an anti-photodamaging agent, an antiproliferative agent, an antipruritic agent, an antipsoriatic agent, an antirosacea agent, an antiseborrheic agent, an antiseptic agent, an antiswelling agent, an antiviral agent, an anti-wart, agent, an anti-wrinkle agent, an anti-yeast agent, an astringent, azelaic acid, benzoyl chloride, benzoyl peroxide, a beta-hydroxy acid, calcitriol, calcium hypochlorite, carbon, a cardiovascular agent, a chemotherapeutic agent, a corticosteroid, a dicarboxylic acid, a dihydrotestosterone inhibitor, a disinfectant, doxycycline, an estrogen, a fungicide, fumaric acid, glycolic acid, a hair growth regulator, a haptene, a herbal extract (comprising an active substance), a hormonal agent, a hormone, a hydroxy acid, an immunogenic substance, an immunomodulator, an immunoregulating agent, an immunostimulant, an immunosuppressant, an immunosuppressive agent, an insect repellent, an insecticide, iron oxide, a keratolytic agent, lactic acid, a lactam, lidocaine, a local anesthetic agent, a lubricating agent, a masking agent, a metal, a metal oxide, minocycline, a mitocide, mometasone fuorate, a neuropeptide, a non-steroidal anti-inflammatory agent, an organo-beryllium compound, an organo-metallic compound, an oxidizing agent, and organo-boron compound, a pediculicide, a peptide, a pesticide, a photodynamic therapy agent, a progesterone, a prostaglandin, a protein, a radical scavenger, a refatting agent, a retinoid, a sadative agent, a scabicide, sebacic acid, a sedative, a sedative agent, a self tanning agent, silicone oxide, silver, a silver compound, a skin protective agent, a skin whitening agent, a steroid, a steroid hormone, a steroidal anti-inflammatory agent, talc, titanium dioxide, a tellurium compound, a testosterone inhibitor, a tetracycline antibiotic, urea, a urea derivative, a vasoactive agent, a vasoconstrictor, a vasodilator, a vitamin, a vitamin A, a vitamin A derivative, a vitamin B, a vitamin B derivative, a vitamin C, a vitamin C derivative, a vitamin D, a vitamin D analog, a vitamin D derivative, a vitamin E, a vitamin E derivative, a vitamin F, a vitamin F derivative, a vitamin K, a vitamin K derivative, a wart remover, a wound healing agent, zinc oxide, zirconium oxide.

In certain embodiments the active agent is a tetracycline antibiotic. In one or more embodiments the tetracycline is tetracycline, oxytetracycline, demeclocycline, doxycycline, lymecycline, meclocycline, methacycline, minocycline, rolitetracycline, chlorotetracycline or tigecycline. In certain embodiments the tetracycline is a mixture of two or more tetracyclines. In one or more embodiments the tetracycline is tetracycline, minocycline or doxycyline or a salt thereof. In one or more embodiments the tetracycline is a hydrophobic tetracyline, selected from minocycline and doxycycline. In one or more embodiments the tetracycline is present in a free base form, a hydrate form, a salt form or a complex form. In one or more embodiments the tetracycline is not soluble or is partially soluble and all or part thereof is suspended in the composition. In certain, embodiments the tetracycline is minocycline. In certain embodiments the tetracycline is doxycycline. In one or more embodiments the properties or uses discovered for minocycline can be applied to any tetracycline antibiotic. In certain embodiments the active agent is selected from a group consisting of mometasone furoate, calcitriol and calciptriol. In certain embodiments the active agent is a vitamin D derivative or analog. In certain embodiments the Vitamin D derivative is calcitriol or calcipotriol or the corticosteroid is mometasone furoate.

According to a further embodiment the active agent, is chemically stable for at least two months and where the active agent is compatible with the other ingredients. According to a further embodiment the active agent is chemically stable for at least three months and where the active agent is compatible with the other ingredients. According to a further embodiment the active agent is chemically stable for at least six months; or for at least nine months, or for at least twelve months; or for at least, fifteen months; or for at least, eighteen months; or for at least, twenty one months: or for at least twenty four months.

As is known to one skilled in the art, in some instances a specific active agent may have more than one activity, function or effect.

In certain embodiments, the inclusion of two or more therapeutic agents in the foamable pharmaceutical composition is desirable.

In an embodiment the fatty alcohol is a therapeutically active fatty alcohol. The fatty alcohol can be a straight chain fatty alcohol, a saturated fatty alcohol, an unsaturated fatty alcohol, a hydroxyl substituted fatty alcohol or a branched fatty alcohol. In one or more embodiments the fatty alcohol has a carbon chain length of 14 to 22 carbons.

In an embodiment, the foamable composition comprises a fatty acid. The fatty acid can be a straight chain fatty acid, a saturated fatty acid, an unsaturated fatty acid, a hydroxyl fatty acid or a branched fatty acid. In an embodiment the fatty acid is a therapeutically active fatty acid. In one or more embodiments the fatty acid is stearic acid.

In an embodiment, the foamable composition comprises a wax. The wax can be a liquid wax, a solid wax, an animal wax, a vegetable wax, a mineral wax, a natural wax or a synthetic wax. In an embodiment the fatty acid is a therapeutically active wax.

In an embodiment the wax is selected from a list comprising paraffin wax, beeswax, hydrogenated castor oil or mixtures thereof. In one or more embodiments there is provided a composition comprising a paraffin wax. In one or more embodiments the paraffin wax can have a melting point from about 37° C. In one or more embodiments the paraffin wax comprises of alkane chains of between about $C_{20}H_{42}$ to $C_{40}H_{82}$. In one or more embodiments the alkane chains are substantially straight chain. In some embodiments branched or unsaturated molecules can be present. Branched chains are sometimes referred to as isoparaffins. In one or more embodiments the paraffin wax can be selected from the group consisting of paraffin wax 58-62° C., paraffin wax 51-53° C., and paraffin wax 42-44° C. or mixtures thereof. In one or more other embodiments other melting point ranges can be selected such as 125° F. to 135° F.; 127° F. to 130° F.; 130° F. to 135° F.; 135° F. to 145° F.; 140° F. to 145° F.; 150° F. to 155° F.; 150° F. to 165° F.: 160° F. to 165° F.; or such as 43-46° C.; 46-53° C.; 48-50° C.; 52-54° C.; 53-55° C.; 54-57° C.; 54-58° C.; 58-60° C.; 59-61° C.; 60-62° C.; 62-66° C.; 65-68° C.; or any other similar or relative range(s) or mixtures thereof. In one or more embodiments the wax comprises a polyolefin. In an embodiment the wax is fully refined. In an embodiment it is suitable for cosmetic use. In an embodiment it is suitable for pharmaceutical use. In an embodiment the paraffin wax is soft. In one or more embodiments the wax is a mixture of two or more waxes. In certain embodiments the mixture of waxes comprises hydrogenated caster oil and beeswax. In certain embodiments the ratio of beeswax to hydrogenated castor oil is about or at least 1:1. In one or more embodiments the ratio is between about 1:1: to about 1:10, or between about 1:1 to about 1:6, or between about 1:1 to about 1:5.

In one or more embodiments the ratio of fatty alcohol to wax is between about 4:1 to about 1:4.

In an embodiment, the foamable composition is physically and chemically stable for at least two and preferably at least three months. In an embodiment, the foamable composition containing a vitamin D derivative or analog is physically and chemically stable for at least three months. In an embodiment, the foamable composition containing calcitriol is physically and chemically stable for at least three months. In an embodiment, the foamable composition containing a corticosteroid is physically and chemically stable for at least three months. In an embodiment, the foamable composition containing mometasone furoate is physically and chemically stable for at least three months. In an embodiment, the foamable composition containing a tetracycline is physically and chemically stable for at least three months. In an embodiment, the foamable composition containing minocyline is physically and chemically stable for at least six months.

In one or more embodiments the drug carrier is formulated substantially free of short chain alcohols, such as, ethanol, propanol or butanol. In one or more embodiments the drug carrier is formulated essentially free of short chain alcohols. In one or more specific embodiments the drug carrier is formulated essentially free of fatty alcohols. In one or more specific embodiments the drug carrier is formulated essentially free of derivatives of fatty alcohols or fatty acids. In one or more other specific embodiments the drug carrier is formulated essentially free of polyols. In one or more other specific embodiments the drug carrier is formulated substantially free of surfactants and/or short chain alcohols and/or polyols. In one or more other specific embodiments the drug carrier is formulated essentially free of surfactants and/or short chain alcohols and/or polyols. In one or more embodiments there is provided a composition which is essentially waterless. In one or more embodiments there is provided a surfactant free composition that is also free of short chain alcohols and/or polyol-free. In one or more embodiments there is provided a substantially polymer free composition. In other embodiments it is essentially polymer free. In still further embodiments the composition is free of polymeric agent. In one or more embodiments a polymeric agent has a Molecular weight of at least about 1000 Daltons.

In one or more embodiments the composition is essentially free of two or more of water; polymeric agent; surfactant; short chain alcohol; or polyol. In one or more embodiments the composition is essentially free of three or more of water; polymeric agent; surfactant; short chain alcohol; or polyol. In one or more embodiments the composition is essentially free of four or more of water; polymeric agent; surfactant; short chain alcohol; or polyol. In one or more embodiments the composition is essentially free of water; polymeric agent; surfactant; short chain alcohol; and polyol.

In one or more other specific embodiments the drug carrier is formulated substantially free of elastomers. In one or more other specific embodiments the drug carrier is formulated essentially free of elastomers. In one or more other specific embodiments the drug carrier is formulated substantially free of silicones. In one or more other specific embodiments the drug carrier is formulated essentially free of silicones. In one or more other specific embodiments the drug carrier is formulated with less than about 30% silicone, or less than about 25% silicone, or less than about 20% silicone, or less than about 15% silicone, or less than about 10% silicone, or less than about 7.5% silicone, or less than about 5% silicone or less than about 2% silicone; or less than about 1% silicone; or less than about 0.5% silicone.

According to additional embodiments there is provided a substantially surfactant free foamable composition comprising:
  a) about 60% to about 95% by weight of a hydrophobic solvent, or about 1% to about 80% by weight petrolatum and about 15% to about 94% by weight hydrophobic solvent, wherein if combined the total amount of hydrophobic solvent and petrolatum is at least about 60% by weight;
  b) an oleaginous foamer complex comprising:
    (1) about 0.1% to about 20% by weight of a fatty alcohol; and
    (2) about 0.1% to about 20% by weight of a fatty acid and/or a wax and/or shea butter;
  c) a liquefied or compressed gas propellant;
wherein the percent by weight is based on weight foamable composition; wherein the ratio of composition other than propellant to propellant is from about 100:3 to about 100:30; and wherein upon dispensing the foamable carrier composition forms a breakable foam that breaks easily upon application of shear force.

According to additional embodiments there is provided a substantially surfactant free composition comprising:
  a) about 60% to about 95% by weight of a hydrophobic solvent or about 1% to about 80% by weight petrolatum and about 15% to about 94% by weight hydrophobic solvent wherein if combined the total amount of hydrophobic solvent and petrolatum is at least about 60% by weight;
  b) an oleaginous foamer complex comprising:
    (1) about 0.1% to about 20% by weight of a fatty alcohol; and
    (2) about 0.1% to about 20% by weight of a fatty acid and/or a wax and/or shea butter; or
  c) an active agent,
wherein the active agent is compatible with and chemically stable in the composition.

In one or more embodiments the active agent is considered chemically stable when more than about 90% of the active agent does not break down after a period of two months in the formulation at room temperature. In one or more embodiments the period is six months. In one or more embodiments more than about 88% of the active agent does not break down. In one or more embodiments the active agent is chemically stable in the composition at 40° C.

According to additional embodiments there is provided a method of producing a foamable composition, including:
  1. providing a foamable therapeutic composition including a therapeutic agent at a therapeutically effective concentration, a hydrophobic solvent, for example, at a concentration of about 60% to about 95% by w eight, a foamer complex (including at least two of a fatty alcohol, a fatty acid and a wax);
  2. introducing the foamable composition in an aerosol packaging assembly, comprising of a container, suitable for containing a pressurized product and a valve, capable of extruding a foam; and
  3. introducing to the aerosol packaging assembly a liquefied or compressed gas propellant at a concentration sufficient to enable the composition to foam and/or to expel the composition from the canister.

According to further embodiments there is provided a method of preventing, treating ameliorating or eliminating a or alleviating a disease or a disorder by selecting and releasing on to a convenient surface having or anticipated to have a dermatological or mucosal disorder or disease in need of treatment a safe and effective pharmaceutical or cosmetic a substantially surfactant free foamable composition comprising an effective amount of a pharmaceutical or cosmetic agent, a hydrophobic solvent, a foamer complex and a liquefied or compressed gas propellant at a concentration of about 3% to about 30% by weight of the total composition; directing the released foam on to a target on a patient in need; applying a shear force to and spreading the foam over the target surface such that after a simple rub the foam is no longer visible to the naked eye as it is absorbed rapidly on to the target surface. In one or more embodiments the active agent is a placebo.

According to further embodiments there is provided a method of treating or alleviating or preventing a dermatological or mucosal disorder, comprising: applying a substantially surfactant free foamable composition comprising to a surface having a dermatological or mucosal disorder in need of treatment, said composition comprising:
 a) about 60% to about 95% by weight of a hydrophobic solvent or about 1% to about 80% by weight petrolatum and about 15% to about 94% by weight hydrophobic solvent wherein if combined the total amount of hydrophobic solvent and petrolatum is at least about 60% by weight;
 b) an oleaginous foamer complex comprising:
  (1) about 0.1% to about 20% by weight of a fatty alcohol; and
  (2) about 0.1% to about 20% by weight of a fatty acid and/or a wax and/or shea butter;
 c) at least one active agent
 d) liquefied or compressed gas propellant;
wherein the percent by weight is based on weight foamable composition; wherein the ratio of composition other than propellant to propellant is from about 100:3 to about 100:30; and wherein upon dispensing the foamable carrier composition forms a breakable foam that breaks easily upon application of shear force.

In one or more embodiments there is provided use of a substantially surfactant free foamable composition for preventing or treating or alleviating a dermatological or mucosal disorder wherein the disorder or disease is selected from the group(s) consisting of a bacterial infection, a benign tumor, a bullous disease, a burn, a chlamydia infection, a condition which respond to hormone therapy, a cut, a dermatitis, a dermatophyte infection, a dermatose, a disorder of a body cavity, a disorder of cornification, a disorder of the nose, a disorder of the penile urethra or ear canal, a disorder of the rectum, a disorder of the respiratory system, a disorder of the vagina, a disorder which responds to hormone replacement therapy, a disorder which responds to transdermal nicotine administration, a disorders of hair follicles, a disorders of sebaceous glands, a disorders of sweating, a fungal infection, a gonorrhea infection, a gynecological disorders that respond to hormonal therapy, a malignant tumor, a non-dermatological disorder which responds to topical or transdermal delivery of an active agent, a parasitic infection, a pelvic inflammation, a pigmentation disorder, a scaling papular diseases, a sexual dysfunction disorder, a sexually transmitted disease, a vaginal disorder, a viral infection, a vulvar disorder, a vulvovaginal infection, a wound, a yeast infection, abscess, acne, acne conglobata, acne fulminans, acne scars, acne vulgaris, actinic keratosis, acute and chronic salpingitis, acute febrile neutrophilic dermatosis, acute lymphangitis, acute pelvic inflammatory disease, acute soft tissue injury, albinism, allergic contact dermatitis, alopecia, alopecia areata, alopecia totalis, alopecia universalis, an allergy, an anal abscess or fistula, an anal and rectal disease, an anal disorder, an anal fissure, an anal wart, an ear disorder, an hormonal disorder, an inflammatory reaction, an intra-vaginal or rectal sexually-transmitted and non-sexually-transmitted infectious disease, anal cancer, anal excoriation, anal fissures, anal itch, anal pruritus, anal soreness, anal warts, angiomas, arthritis, athlete's foot, atopic dermatitis, back pain, bacterial skin infections, bacterial vaginosis, baldness, basal cell carcinoma, benign tumors, blisters, bromhidrosis, bullous diseases, bullous pemphigoid, burn, calluses, calluses candidiasis, cancer of the cervix, cancer of the vagina, cancer of the vulva, candidal vaginitis, candidiasis, carbuncles, cellulitis, cervical cancer, cervicitis, chancroid, chemical burns, chicken pox, chloasma, cholesteatoma, cholinergic urticaria, chronic dermatitis, chronic effects of sunlight, cold sores, cold urticaria, comedones, constipation, contact dermatitis, corns, creeping eruption, Crohn's disease, cutaneous abscess, cutaneous larva migrans, cutaneous myiasis, dark spots, delusional parasitosis, Dercum disease, dermatitis, dermatitis herpetiformis, dermatofibroma, dermatological inflammation, dermatological pain, dermatophytoses, dermographism, diaper rash, drug eruptions and reactions, drug-induced hyperpigmentation, dyshidrotic eczema, dysmenorrhea, dyspareunia, dysplastic nevi, ecthyma, ectodermal dysplasia, ectopic pregnancy, eczema, endometriosis, endometritis, epidermal necrolysis, epidermoid cyst, erysipelas, erythema multiforme, erythema nodosum, erythrasma, exfoliative dermatitis, fallopian tube cancer and gestational trophoblastic disease, fecal incontinence, female orgasmic disorder, folliculitis, fungal nail infections, fungal skin infections, furuncles, gangrene, generalized exfoliative dermatitis, genital cancer, genital herpes, genital ulcer, genital warts, granuloma annulare, granuloma inguinale, gynecological neoplasms including endometrial cancer, head lice, hemorrhoids, hepatitis B, herpes, herpes simplex, hidradenitis suppurativa, hirsutism, HIV/AIDS, hives, human papillomavirus (HPV), hyperhidrosis, hyperpigmentation melasma, hypertrichosis, hypohidrosis, hypopigmentation, ichthyosis, impetigo, inflammatory acne, inflammatory reactions, ingrown nails, intertrigo, irritant contact dermatitis, ischemic necrosis, itching, jock itch, joint pain, Kaposi's sarcoma, keloid, keratinous cyst, keratoacanthoma, keratosis pilaris, lichen planus, lichen sclerosus, lichen simplex chronicus, linear immunoglobulin A disease, lipomas, localized pain in general, lymphadenitis, lymphangitis, lymphogranloma venereum, male pattern baldness, malignant melanoma, malignant tumors, mastocytosis, measles, melanoma, midcycle pain, midcycle pain due to ovulation, miliaria, mittelschmerz, moles, molluscum contagiosum, MRSA, mucopurulent cervicitis (MPC), muscle pain, necrotizing fasciitis, necrotizing myositis, necrotizing subcutaneous infection, necrotizing subcutaneous infections, nodular papulopustular acne, nongonococcal urethritis (NGU), non-inflammatory acne, nummular dermatitis, oophoritis, oral herpes, osteoarthritis, osteoarthritis, ovarian cancer, ovarian cysts and masses, paget's disease of the nipples, panniculitis, papules, parapsoriasis paronychia, parasitic infections, parasitic skin infections, paronychial infection, pediculosis, pelvic congestion syndrome, pelvic inflammatory disease, pelvic pain, pemphigus, perianal pruritus, perianal thrush, perioral dermatitis, photo-allergy, photo-damage, photo-irritation, photosensitivity, pigmentation disorders, pimples, pityriasis Lichenoides, pityriasis rosea, pityriasis rubra pilaris, poison ivy, poison oak, polyps of the colon and rectum, postinflammatory hyperpigmentation, postinflammatory hypopigmentation, post-operative or post-surgical skin conditions, premenstrual syndrome, pressure sores, pressure ulcers, pressure urticaria, pruritis, pruritus ani, pseudofolliculitis barbae, psoriasis, PUPPP, purpura, pustules, pyogenic granuloma, rash, reactions to sunlight, rectal abscess, rectal fistula, rheumatic pain, ringworm, rosacea, roseola, rubella, salpingitis, scabies, scalded skin syndrome, scaling papular diseases, scarring, scleroderma, sebaceous cyst, seborrheic dermatitis, seborrheic keratoses, seborrheic keratosis, sexual arousal disorder, shingles, skin aging, skin cancer, skin neoplasia, skin neoplasms, skin rash, skin tags, skin ulcers, sports injuries, squamous cell carcinoma, staphylococcal scalded skin syndrome, stasis dermatitis, Stevens-Johnson syndrome, sun spots, sunburn, thermal burns, tinea corporis, tinea cruris, tinea pedis, tinea versicolor, toxic epidermal necrolysis, trauma or injury to the skin, *Trichomonas vaginalis*, trichomoniasis, vaginal cancer, vaginal dryness, vaginismus, varicella zoster virus, viral skin infections, vitamin D deficiency, vitiligo, vulvar cancer, vulvar disorders, vulvar dystrophy, vulvar intraepithelial neoplasia (VIN), vulvar pain, vulvodynia, warts, water hives, wrinkles, xerosis, yeast skin infections, zoster According to one or more further embodiments the foamable composition, for treatment of a disorder, is able to reduce skin photodamage or radiation damage and photoaging, and more generally to reduce oxidative stress and inflammation in skin pathologies which are known to be accompanied by apoptotic cell death. In one or more embodiments, there is provided a composition for use in preventing or ameliorating or treating photodamage or radiation damage or photoaging or reducing oxidative stress or inflammation in skin pathologies which are known to be accompanied by apoptic cell death or any two or more thereof.

According to one or more further embodiments the foamable composition comprising minocycline, for treatment of a disorder, has properties or activities selected from a list including regenerative, anti-apoptotic, anti-inflammatory, anti-photodamaging, anti-radiation damage and anti-photoaging. In one or more embodiments, there is provided a composition for use in preventing or ameliorating or treating a disorder, the minocycline composition having at least one property or activity selected from, a list including regenerative, anti-apoptotic, anti-inflammatory, anti-photodamaging anti-radiation damage and anti-photoaging.

According to one or more further embodiments the foamable composition comprising minocycline for treatment of a disorder, has protective and/or therapeutic properties or activities in the case of UVB-induced skin damage. In one or more embodiments, there is provided a composition comprising minocycline for use in preventing protecting from or ameliorating or treating UVB-induced skin damage.

According to one or more further embodiments the foamable composition for treatment of a disorder that results in apoptosis comprising minocycline which decreases apoptosis and/or increases cell viability. In one or more embodiments, there is provided a composition comprising minocycline for use in preventing, protecting from or ameliorating or treating a disorder with symptoms including increased apoptosis and/or decreased cell viability, where the formulation acts to decrease apoptosis and/or increase cell viability. In one or more embodiments there is provided a composition for use in decreasing apoptosis and/or increasing cell viability.

According to one or more further embodiments the disorder treated by the foamable composition comprising minocycline for use in reducing oxidative stress and inflammation in skin pathologies which are known to be accompanied by apoptotic cell death including rosacea and impetigo. In one or more embodiments, there is provided a composition for use in preventing or ameliorating or treating disorders by reducing oxidative stress and inflammation in skin pathologies which are known to be accompanied by apoptotic cell death including rosacea and impetigo.

According to one of more further embodiments the foamable composition comprising minocycline is non-irritant and suitable for ophthalmic use and/or other sensitive targets such as for use internal and/or external wounds or burns or in skin, body cavities and mucosal membrane. In one or more embodiments, there is provided a composition, comprising minocycline, which is non-irritant, for use in preventing or ameliorating or treating a disorder and is suitable for ophthalmic use and can be applied on other sensitive targets such as for use on internal and/or external wounds or burns or in skin, body cavities and mucosal membranes.

Thus in one or more embodiments there is provided a tetracycline composition having regenerative, or anti-apoptotic, or anti-inflammatory, or anti-photodamaging, or anti-photoaging activity, or protective and/or therapeutic properties in the case of UVB-induced skin damage, or which decreases apoptosis and/or increases cell viability, or in reducing oxidative stress and inflammation in skin pathologies accompanied by apoptotic cell death including rosacea and impetigo, or antibacterial activity, or any two or more thereof.

According to one or more farther embodiments the foamable composition comprising minocycline has antibacterial activity. In certain embodiments the activity is against enterobacteria and mycobacteria. In certain embodiments the minocycline has antibacterial activity for use against enterobacteria and mycobacteria.

According to certain further embodiments the foamable composition comprising minocycline has antibacterial activity against at least one of the species selected from the group consisting of *Staphylococcus aureus*, Streptococci, *Neisseria meningitidis, Streptococcus pyogenes, Pseudomonas aeruginosa, Staphylococcus aureus, Staphylococcus aureus* (MRSA,) *Propionbacterium acnes, Acinetobacter, Bacteroides, Haemophilus, Nocardia, M. leprae*. In certain embodiments the minocycline has antibacterial activity for use against at least one of the species selected from the group consisting of *Staphylococcus aureus, Streptococci*, Neisseria, meningitidis, *Streptococcus pyogenes, Pseudomonas aeruginosa, Staphylococcus aureus, Staphylococcus aureus* (MRSA,) *Propionbacterium acnes, Acinetobacter, Bacteroides, Haemophilus, Nocardia, M. leprae*.

In one or more embodiments there is provided a composition comprising a hydrophobic solvent which is a liquid oil, selected from the group consisting of a diglyceride, a PPG alkyl ether, a therapeutic oil, acetylated lanolin alcohol, alexandria laurel tree oil, alkyl benzoate, alkyl octanoate, almond oil, an essential oil, an unsaturated or polyunsaturated oil, apricot stone oil, arachidyl behenate, arachidyl propionate, avocado oil, barley oil, basil oil, beeswax, benzyl laurate, benzyl myristate, benzyl palmitate, bis (octyldodecyl stearoyl) dimer dilinoleate, borage seed oil, butyl myristate, butyl stearate, C12-C15 alkyl benzoate, C12-C15 alkyl octanoate, calendula oil, camphor oil, canelle nut tree oil, canola oil, capric/caprylic triglycerides, caprylic/capric triglyceride castor oil, caprylyl methicone, cardamom oil, carrot oil, castor oil, cetearyl ethylhexanoate, cetearyl isononanoate, cetearyl octanoate, cetyl acetate, cetyl dimethicone, cetyl ethylhexanoate, cetyl lactate, cetyl myristate, cetyl octanoate, cetyl palmitate, cetyl ricinoleate, citronella oil, clary sage oil, clove oil, cocoglycerides, coconut oil, cod-liver oil, corn oil, cotton oil, cottonseed oil, cyclohexasiloxane, cyclomethicone, Cyclomethicone 5-NF (cyclopentasiloxane), cyclotetrasiloxane, cypress oil, decyl oleate, diethyleneglycol diethylhexanoate, diethyleneglycol diisononanoate, diethyleneglycol dioctanoate, diethylhexanoate, diethylhexyl adipate, diethylhexyl malate, diethylhexyl succinate, diisopropyl adipate, diisopropyl dimerate, diisopropyl sebacate, diisosteary dimer dilinoleate, diisostearyl fumerate, dimethicone, dimethyl polysiloxane, dioctyl malate, dioctyl sebacate, disopropyl adipate, dodecyl oleate, Dow Corning 244 Fluid (cyclotetrasiloxane), Dow corning 246 Fluid (d6+d5) (cyclohexasiloxane & cyclopentasiloxane), epoxy-modified silicone oil, essential oils, ester derivatives of lanolic acid, ester oils, ethylhexyl cocoate, ethylhexyl ethylhexanoate, ethylhexyl hydroxystarate, ethylhexyl isononanoate, ethylhexyl palmitate, ethylhexyl palmytate, ethylhexyl pelargonate, ethylhexyl stearate, evening primrose oil, fatty acid-modified silicone oil, flaxseed oil, fluoro group-modified silicone oil, frankincense oil, gelled mineral oil, ginger oil, glycereth triacetate, glycerol triheptanoate, glyceryl oleate, glyceryl trioctanoate, glyceryl triundecanoate, grape seed oil, grapefruit oil, groundnut oil, hard fat, hazelnut oil, heavy mineral oil, hempseed oil, herring oil, hexadecyl stearate, hexyl laurate, hydrocarbon oils, hydrogenated castor oil, hyssop oil, isoamyl laurate, isocetearyl octanoate, isocetyl isocetyl behenate, isocetyl lanolate, isocetyl palmitate, isocetyl salicylate, isocetyl stearate, isocetyl stearoyl stearate, isodecyl ethylhexanoate, isodecyl isononanoate, isodecyl oleate, isododecane, isohexadecane isododecane, isohexadecanol, isohexyl decanoate, isononyl isononanoate, isononyl octanoate, isoparaffin, isopropyl isostearate, isopropyl lanolate, isopropyl laurate, isopropyl myristate, isopropyl palmitate, isopropyl stearate, isosteary citrate, isosteary salicylate, isosteary tartarate, isostearyl behenate, isostearyl erucate, isostearyl glycolate, isostearyl isononanoate, isostearyl isostearate, isostearyl lactate, isostearyl linoleate, isostearyl linolenate, isostearyl malate, isostearyl neopentanoate, isostearyl palmitate, isotridecyl isononanoate, jasmine oil, jojoba oil, lauryl lactate, lavender oil, lemon oil, light mineral oil, liquid paraffin, liquid triglycerides, lucerne oil, maize germ oil, maleated soybean oil, mandarin oil, manuka oil, marjoram oil, marrow oil, MCT oil, methylphenylpolysiloxane, millet oil, mineral oil, myristyl lactate, myristyl myristate, myristyl neopentanoate, myristyl propionate, myrrh oil, neopentylglycol dicaprate, neopentylglycol dicaprylate/dicaprate, neroli oil, nutmeg oil, octyl palmitate, octyl stearate, octyldodecanol, octyldodecyl behenate, octyldodecyl hydroxystearate, octyldodecyl myristate, octyldodecyl stearoyl stearate, oils from animal origin, oils of plant origin, oleyl erucate, oleyl lactate, oleyl oleate, olive oil, or dimethiconol, palm oil, passionflower oil, peanut oil, PEG/PPG 18/18 dimethicone, pentaerythrityl tetrastearate, petitgrain oil, petrolatum, phenyl trimethicone, phenyltrimethicone, poly(dimethylsiloxane)-(diphenyl-siloxane) copolymer, polyalkyl siloxane, polyalkylaryl siloxane, polyalphaolefin, polyaryl siloxane, polyaryl siloxanes, polyether group-modified silicone oil cyclomethicone, polyether siloxane copolymer, polyether siloxane copolymers, polyisobutylene, polyolefin, poppy oil, PPG alkyl ethers, PPG-10 cetyl ether, PPG-10 oleyl ether, PPG-11 stearyl ether, PPG-12 butyl ether, PPG-14 butyl ether, PPG-15 butyl ether, PPG-15 stearyl ether, PPG-16 butyl ether, PPG-17 butyl ether, PPG-18 butyl ether, PPG-2 butyl ether, PPG-2 methyl ether, PPG-20 butyl ether, PPG-20 oleyl ether, PPG-22 butyl ether, PPG-23 oleyl ether, PPG-24 butyl ether, PPG-26 butyl ether, PPG-28 cetyl ether, PPG-3 methyl ether, PPG-3 myristyl ether, PPG-30 butyl ether, PPG-30 cetyl ether, PPG-30 isocetyl ether, PPG-30 oleyl ether, PPG-33 butyl ether, PPG-37 oleyl ether, PPG-4 butyl ether, PPG-4 lauryl ether, PPG-4 myristyl ether, PPG-40 butyl ether, PPG-5 butyl ether, PPG-50 cetyl ether, PPG-50 oleyl ether, PPG-52 butyl ether, PPG-53 butyl ether, PPG-7 lauryl ether, PPG-9 butyl ether, PPG-9-13 butyl ether, propyl myristate, propylene glycol dicaprate, propylene glycol dicaprylate, propylene glycol myristyl ether acetate, propylene glycol ricinoleate, rapeseed oil, rosehip oil, rye oil, safflower oil, sage oil, salmon oil, sesame oil, shea butter, silicone oils, soya oil, soybean oil, stearyl caprate, stearyl dimethicone, stearyl heptanoate, stearyl propionate, sunflower oil, sweet almond oil, synthetic isoalkane, sysymbrium oil, syzigium aromaticum oil, tangerine oil, tea tree oil, therapeutic oils, tocopheryl acetate, tocopheryl linoleate, tridecyl ethylhexanoate, tridecyl isononanoate, triisocetyl citrate, unsaturated or polyunsaturated oils, vanilla oil, verbena oil, walnut oil, wheat germ glycerides, wheat germ oil, white petrolatum and mixtures thereof.

DETAILED DESCRIPTION

Foamable Composition and Foam Properties

In one or more embodiments, the composition is a gel that when packaged into an aerosol canister, equipped with a valve and pressurized with a liquid or pressurized gas propellant is capable of releasing a foam of quality that is breakable upon application of shear force but is not thermolabile at about or close to body temperature (about 36° C.).

The ability to achieve quality foam with a substantial concentration of hydrophobic solvent without a surfactant and/or without a polymer is surprising, because usually, such solvents are not prone to creating a foam. The challenge is not just to achieve a quality foam but also to attain a formulation that will satisfy a plurality of two, three, four, five, six or more of the following property specifications simultaneously.

Notably, the pressurized composition is flowable and releases a foam freely, even though it might be expected that such concentrations of a fatty alcohol and fatty acid would make the hydrophobic solvent 'gel' or 'semi-solid'.

1. Uniformity: The composition should be formulated so that it is and can remain uniform without phase separation or precipitation overtime. This property is of high importance when the product is intended to be a pharmaceutical product.
2. Flowability: The composition, when placed in an aerosol container and pressurized with a propellant should be flowable such that it can be expelled through the canister valve. It should preferably also be shakable inside the container. These requirements create a formulation challenge, because non-viscous flowable and shakable compositions are prone to undergo phase separation or precipitation.
3. Quality: Upon release from the can, the composition should generate a foam of good or excellent quality having low density and small bubble size.
4. Stability/Breakability: The fine balance between stability and breakability of the foam coming out of the container is very delicate: on one hand the foam should preferably not be "quick breaking", i.e., it should be at least short term stable upon release from the pressurized container and not break as a result of exposure to skin temperature; and on the other hand, it should be "breakable", i.e., it should spread easily, break down and absorb into the skin or membrane upon application of mild shear force.
5. Skin Feeling: To ensure patient, compliance the skin feeling after application should be pleasant, and greasy or waxy residues should be minimal.
6. Non-irritating: The above requirements should be achieved with the awareness that formulation excipients, especially surfactants, can be irritating, and should preferably be eliminated from the composition or reduced as much as possible.
7. Delivery: Finally, the composition should also be designed to ensure efficient delivery of a therapeutic agent into the target site of treatment.
8. Compatibility: The components of the composition should be compatible and not react with an active agent.

Based on extensive investigations and trial and error experiments, it has been found that such properties can be achieved for formulations as described below and which are further advantageous because of the ability of hydrophobic solvents to dissolve or suspend certain active agents while providing an environment for the active agent which assists in preventing their degradation. In one or more embodiments there is provided a composition which is adapted to prevent, the degradation of the active ingredient during storage in the canister and also upon application on the target site of treatment.

In one or more embodiments there is provided prior to adding propellant a solid or semi-solid composition or gel. In one or more embodiments the composition or gel is a liquid. Examples of a liquid gel include where a propellant is added to the formulation (which prior to adding the propellant is a gel) or where the gel is loose or such that when subjected to gravity will pour or become liquid. In one or more embodiments the composition is thixotropic.

Compositions

All % values are provided on a weight (w/w) basis.

In one or more embodiments where ever a phrase is used to refer to a concentration of above X % or below X % it can also include X % or of above about X % or below about X % it can also include about X %.

In one or more embodiments the term "about" has its usual meaning in the context of pharmaceutical and cosmetic formulations to allow for reasonable variations in amounts that can achieve the same effect. In one or more embodiments about can encompass a range of plus and minus 20%. In one or more embodiments abo ut can encompass a range of plus and minus 10%.

In one or more embodiments there is provided a foamable carrier composition including:
1. a hydrophobic solvent
2. a foamer complex comprising:
    i. a first member, comprising about 0.1% to about 20% by weight of a fatty alcohol; and
    ii. a second member, comprising about 0.1% to about 20% by weight of
        1. a fatty acid; and/or
        2. a wax; or
3. a liquefied or compressed gas propellant.

In one or more certain embodiments shea butter may replace the second member.

In one or more embodiments oily emollients are added to provide or improve a pleasant skin feeling, and/or lubricating effect with reduced friction. In one or more embodiments volatile silicones are added to reduce greasy feeling. In one or more embodiments waxes are added to improve rheology or stabilize foam structure. Surfactants play a role in foam formation and induce foam stability. In one or more embodiments the formulation is substantially or essentially free of surfactants. In one or more alternative embodiments a small amount of surfactant may be added preferably less than 1%. Scientific literature is not always accurate and may loosely or even inaccurately describe a substance as a surfactant. For example, fatty alcohols or fatty acids (in the absence of a base) when used in combination with classic surfactants have sometimes been referred to as surfactants, whereas at best they merely function as an aid to classic surfactant and may loosely be termed as a co-surfactant but they are not able to stabilize an emulsion and achieve a stable foam emulsion on their own without the presence of a true surfactant. (For more detail see "co-surfactant" below.) In the context of the present application such fatty acids and fatty alcohols are not surface active agents but are foam adjuvants. Similarly propoxylated lanolin oil derivatives have been loosely referred to as surfactants. In the context herein they are emollients not surfactants. In one or more embodiments the composition is essentially free of propoxylated lanolin oil derivatives. In one or more embodiments the composition is essentially free of ethoxylated lanolin oil derivatives. In further embodiments the compositions are free of such derivatives. In one or more certain embodiments the composition is free of PPG, lanolin oils, such as PPG 40 PEG 60 lanolin oil. In one or more embodiments foam adjuvants (e.g. fatty alcohols and fatty acids) and additives (such as SiO2 which acts as a thickener and can provide thixotropy) are added to Improve rheology or stabilize foam structure or as a protective agent. In one or more embodiments antioxidants can be used to prevent degradation/oxidation, for example, butylated hydroxytoluene, which is a fat soluble antioxidant.

In one or more embodiments the foamable composition is substantially surfactant free. In one or more other embodiments it is essentially free of any surfactants.

Upon release from an aerosol container, the foamable composition forms an expanded thermally stable breakable foam suitable for topical administration.

The foamable composition is suitable for administration to various body areas, including, but not limited to the skin, a body surface, a body cavity, a mucosal surface, e.g., the mucosa of the nose, mouth and eye, the ear, the respiratory system, the vagina or the rectum (severally and interchangeably termed herein "target site").

In one or more embodiments, the composition is waterless. By waterless is meant that the composition contains no or substantially no, free or unassociated or absorbed water. It will be understood by a person, of the art that to the extent the waterless solvents and substances miscible with them of the present disclosure are hydrophilic, they can contain water in an associated or unfree or absorbed form and may absorb water from the atmosphere.

According to one or more embodiments, the foamable composition further comprises one or more cosmetic active agents or a pharmaceutical active agents (severally and interchangeably termed herein "active agent").

In one or more embodiments the carrier comprises an active pharmaceutical or cosmetic agent which degrades in the presence of water, and in such cases the presence of water in the composition is clearly not desirable. Thus, in certain preferred embodiments, the composition is waterless. In other embodiments the active agent may tolerate the presence of a small amount of water and the waterless composition is substantially non-aqueous. The term "substantially non-aqueous" is intended to indicate that the waterless composition has water content preferably below about 2%, such as, below about 1.5%, below about 1%; or below about 0.5%. In one or more alternative embodiments, where for example, the formulation is for cosmetic purposes or where the active agent is not sensitive to water the formulation may contain low amounts of water of up to about 25%. In certain embodiments the amount of water is about or less than about 20%. In certain embodiments the amount of water is about or less than about 15%. In certain embodiments the amount of water is about or less than about 10%. In certain embodiments the amount of water is about or less than about 5%. Where water is present the formulation may be an emulsion or may form micelles or a colloid. In one or more embodiments the emulsion formulation, has some resistance to centrifugation. In one or more embodiments the emulsion formulation is substantially resistant to centrifugation at about 1000 rpm for a few minutes or for about up to 10 minutes.

In one or more embodiments there is provided a foamable therapeutic composition including:
1. an active agent;
2. a hydrophobic solvent
3. a foamer complex comprising:
   i. a first member, comprising about 0.1% to about 20% by weight of a fatty alcohol; and
   ii. a second member, comprising about 0.1% to about 20% by weight of
      1. a fatty acid; and/or
      2. a wax; or
4. a liquefied or compressed gas propellant.

In one or more embodiments, at least a portion of the therapeutic agent is suspended or dissolved evenly throughout the entire composition.

It has been discovered that formulations containing high amount of a hydrophobic solvents (such as mineral oil) are not prone to foaming. Surprisingly, it has been further discovered that the combination of a fatty alcohol and fatty acid and/or a wax has foam boosting properties and provides breakable foams of good quality in the absence of customary surfactants. It has been discovered that fatty alcohols or fatty acids with a saturated carbon chain of between 16 to 22 carbons combined have outstanding foam boosting properties. It has been further discovered that the combination of a fatty alcohol with a fatty acid and a wax has improved foaming properties. It has been discovered that different factors can influence foaming properties. Non limiting examples include: a) the ratio of fatty alcohol to fatty acid e.g. foams of excellent quality that did not collapse after 180 seconds at 36° C. were obtained with a ratio of fatty alcohol:fatty acid of 1:1 and a total concentration of fatty alcohol together with fatty acid ranging from about 7% to about 10%; b) the ratio of beeswax to hydrogenated castor oil; e.g. foams of good quality that did not collapse after 180 seconds at 36° C. were obtained with a ratio of beeswax to hydrogenated castor oil of 1:1 or more, c) ratio of fatty alcohol to wax e.g. foams of good quality that did not collapse after 180 seconds at 36° C. were obtained with a ratio of fatty alcohol to wax of 2:3 to 3:2. d) the type and concentration of propellant e.g. AP-70 and Tetrafluoroethane improved foam quality in comparison to A-46.

Furthermore, the oleaginous formulations of the present invention can provide foams of good quality in the presence of various active ingredients. It was found for example that compositions of the present invention comprising one or more of Doxycycline Hyclate, Betamethasone Valerate, Progesterone, Terbinafine, Metronidazole, Mometasone Furoate, Calcitriol, Calcipotriol and Naproxen can give rise to breakable foams of good to excellent quality which did not collapse for at least 2 minutes at 36° C.

In one or more embodiments, the active agent is a vitamin A or a derivative or analog thereof.

In one or more embodiments, the active agent is a vitamin E or a derivative or analog thereof.

In one or more embodiments, the active agent is a vitamin K or a derivative or analog thereof.

In one or more embodiments, the active agent is a vitamin F or a derivative or analog thereof.

In one or more embodiments, the active agent is vitamin D or a derivative or analog thereof.

In one or more embodiments, the active agent is calcipotriol.

In one or more embodiments, the active agent is calcitriol.

In one or more embodiments, the active agent is corticosteroid.

In one or more embodiments, the active agent is mometasone furoate.

In one or more embodiments, the active agent is doxycycline hyclate.

In one or more embodiments, the active agent is betamethasone valerate.

In one or more embodiments, the active agent is progesterone.

In one or more embodiments, the active agent is terbinafine.

In one or more embodiments, the active agent is metronidazole.

In one or more embodiments, the active agent is naproxen.

In one or more embodiments, the active agent is one or more of doxycycline hyclate, betamethasone valerate, progesterone, terbinafine, metronidazole, mometasone furcate, calcitriol, calcipotriol and naproxen.

In one or more embodiments, the composition is essentially free of polyols.

In one or more embodiments, composition is capable of providing intradermal delivery of the active agent into the skin with minimal or negligible transdermal delivery.

In one or more embodiments, the composition has some preservative efficacy.

In one or more embodiments, the composition is for use in eye infections.

In one or more embodiments, the composition is physically and chemically stable for at least two months and wherein the active agent is compatible with and chemically stable in the composition.

In one or more embodiments, the composition, is physically and chemically stable for at least three months and wherein the active agent is compatible with and chemically stable in the composition.

In one or more embodiments, the composition is physically and chemically stable for at least six months and wherein the active agent is compatible with and chemically stable in the composition.

It was further found that different waxes had a different influence pre foam formulation (PFF) homogeneity. For example beeswax resulted PFF separation (decrease in homogeneity), whereas hydrogenated castor oil increased homogeneity. Paraffin wax 51-53 induced PFF separation in placebo formulation however homogeneity was surprisingly regained upon addition of minocycline. In one or more embodiments hydrogenated caster oil is used to prevent separation or to restore homogeneity. In one or more embodiments a tetracycline is used to prevent separation or to restore homogeneity. In one or more embodiments a paraffin is used to prevent separation or to restore homogeneity.

In one or more embodiments, there is provided a substantially surfactant free composition comprising:
a) about 60% to about 95% by weight of a hydrophobic solvent;
b) an oleaginous foamer complex comprising:
  (1) about 0.1% to about 20% by weight of a fatty alcohol; and
  (2) about 0.1% to about 20% by weight of a fatty acid and/or a wax; or
c) an active agent,
wherein the active agent is compatible with and chemically stable in the composition.

Hydrophobic Solvent

In an embodiment, the composition of the present invention comprises at least one hydrophobic organic solvent. In one or more embodiments the hydrophobic organic solvent should be compatible with the active ingredient. Oils which are incompatible are omitted. For example, minocycline compositions will be free of pomegranate seed oil. A "hydrophobic organic solvent" (also termed "hydrophobic solvent") as used herein refers to a material having solubility in distilled water at ambient temperature of less than about 1 gm per 100 mL, more preferably less than about 0.5 gm per 100 mL, and most preferably less than about 0.1 gm per 100 mL. It is liquid at ambient temperature. The identification of a "hydrophobic solvent", as used herein, is not intended to characterize the solubilization capabilities of the solvent for any specific active agent or any other component of the foamable composition. Rather, such term is provided to aid in the identification of materials suitable for use as a hydrophobic solvent in the foamable compositions described herein.

In one or more embodiments the hydrophobic solvent is present at a concentration of about 60% to about 95% or about 65% to about 90%; or about 70% to about 90% or about 75% to about 85%.

In one or more embodiments, the composition of the present invention comprises at least one hydrophobic solvent, selected from the group consisting of an oil including a mineral oil, a hydrocarbon oil, an ester oil, a liquid triglyceride oil, an oil of plant origin, an oil from, animal origin, an unsaturated or polyunsaturated oil, a diglyceride, a PPG alkyl ether and a silicone oil.

As exemplified herein, members of each of the above listed groups of hydrophobic solvents have been found to be compatible with hydrophobic tetracyclines, such as minocycline and doxycycline.

Non-limiting examples of hydrocarbon oils include mineral oil, liquid paraffin, an isoparaffin, a polyalphaolefin, a polyolefin, polyisobutylene, a synthetic isoalkane, isohexadecane and isododecane.

Non-limiting examples of ester oils include alkyl benzoate, alkyl octanoate, C12-C15 alkyl benzoate, C12-C15 alkyl octanoate, arachidyl behenate, arachidyl propionate, benzyl laurate, benzyl myristate, benzyl palmitate, bis (octyldodecyl stearoyl) dimer dilinoleate, butyl myristate, butyl stearate, cetearyl ethylhexanoate, cetearyl isononanoate, cetyl acetate, cetyl ethylhexanoate, cetyl lactate, cetyl myristate, cetyl octanoate, cetyl palmitate, cetyl ricinoleate, decyl oleate, diethyleneglycol diethylhexanoate, diethyleneglycol dioctanoate, diethyleneglycol diisononanoate, diethyleneglycol diisononanoate, diethylhexanoate, diethylhexyl adipate, diethylhexyl malate, diethylhexyl succinate, diisopropyl adipate, diisopropyl dimerate, diisopropyl sebacate, diisosteary dimer dilinoleate, diisostearyl fumerate, dioctyl malate, dioctyl sebacate, dodecyl oleate, ethylhexyl palmitate, ester derivatives of lanolic acid, ethylhexyl cocoate, ethylhexyl ethylhexanoate, ethylhexyl hydroxystarate, ethylhexyl isononanoate, ethylhexyl palmytate, ethylhexyl pelargonate, ethylhexyl stearate, hexadecyl stearate, hexyl laurate, isoamyl laurate, isocetyl isocetyl behenate, isocetyl lanolate, isocetyl palmitate, isocetyl stearate, isocetyl salicylate, isocetyl stearate, isocetyl stearoyl stearate, isocetearyl octanoate, isodecyl ethylhexanoate, isodecyl isononanoate, isodecyl oleate, isononyl isononanoate, isodecyl oleate, isohexyl decanoate, isononyl octanoate, isopropyl isostearate, isopropyl lanolate, isopropyl laurate, isopropyl myristate, isopropyl palmitate, isopropyl stearate, isostearyl behenate, isosteary citrate, isostearyl erucate, isostearyl glycolate, isostearyl isononanoate, isostearyl isostearate, isostearyl lactate, isostearyl linoleate, isostearyl linolenate, isostearyl malate, isostearyl neopentanoate, isostearyl palmitate, isosteary salicylate, isosteary tartarate, isotridecyl isononanoate, isotridecyl isononanoate, lauryl lactate, myristyl lactate, myristyl myristate, myristyl neopentanoate, myristyl propionate, octyldodecyl myristate, neopentylglycol dicaprate, octyl dodecanol, octyl stearate, octyl palmitate, octyldodecyl behenate, octyldodecyl hydroxystearate, octyldodecyl myristate, octyldodecyl stearoyl stearate, oleyl erucate, oleyl lactate, oleyl oleate, propyl myristate, propylene glycol myristyl ether acetate, propylene glycol dicaprate, propylene glycol dicaprylate, propylene glycol dicaprylate, maleated soybean oil, stearyl caprate, stearyl heptanoate, stearyl propionate, tocopheryl acetate, tocopheryl linoleate, glyceryl oleate, tridecyl ethylhexanoate, tridecyl isononanoate and triisocetyl citrate.

Non-limiting examples of liquid triglycerides and oils of plant origin include alexandria laurel tree oil, avocado oil, apricot stone oil, barley oil, borage seed oil, calendula oil, canelle nut tree oil, canola oil, caprylic/capric triglyceride castor oil, coconut oil, corn oil, cotton oil, cottonseed oil, evening primrose oil, flaxseed oil, groundnut oil, hazelnut oil, glycereth triacetate, glycerol triheptanoate, glyceryl trioctanoate, glyceryl triundecanoate, hempseed oil, jojoba oil, lucerne oil, maize germ oil, marrow oil, millet oil, neopentylglycol dicaprylate/dicaprate, olive oil, palm oil, passionflower oil, pentaerythrityl tetrastearate, poppy oil, propylene glycol ricinoleate, rapeseed oil, rye oil, safflower oil, sesame oil, shea butter, soya oil, soybean oil, sweet almond oil, sunflower oil, sysymbrium oil, syzigium aromaticum oil, tea tree oil, walnut oil, wheat germ glycerides and wheat germ oil.

Non-limiting examples of PPG alkyl ethers include PPG-2 butyl ether, PPG-4 butyl ether, PPG-5 butyl ether, PPG-9 butyl ether, PPG-12 butyl ether, PPG-14 butyl ether, PPG-15 butyl ether, PPG-15 stearyl ether, PPG-16 butyl ether, PPG-17 butyl ether, PPG-18 butyl ether, PPG-20 butyl ether, PPG-22 butyl ether, PPG-24 butyl ether, PPG-26 butyl ether, PPG-30 butyl ether, PPG-33 butyl ether, PPG-40 butyl ether, PPG-52 butyl ether, PPG-53 butyl ether, PPG-10 cetyl ether, PPG-28 cetyl ether, PPG-30 cetyl ether, PPG-50 cetyl ether, PPG-30 isocetyl ether, PPG-4 lauryl ether, PPG-7 lauryl ether, PPG-2 methyl ether, PPG-3 methyl ether, PPG-3 myristyl ether, PPG-4 myristyl ether, PPG-10 oleyl ether, PPG-20 oleyl ether, PPG-23 oleyl ether, PPG-30 oleyl ether, PPG-37 oleyl ether, PPG-40 butyl ether, PPG-50 oleyl ether and PPG-11 stearyl ether. Preferred PPG alky ethers according to the present invention include PPG-15 stearyl ether, PPG-2 butyl ether and PPG-9-13 butyl ether.

Non-limiting examples of oils from animal origin include herring oil, cod-liver oil and salmon oil.

The hydrophobic solvent may be an emollient, i.e., a hydrophobic liquid having a softening or soothing effect especially to the skin. In some embodiments the liquid oil may contain a solid or semi solid hydrophobic matter at room temperature.

Essential oil, which is usually a concentrated, hydrophobic liquid containing volatile aroma compounds from plants usually conveying characteristic fragrances. Non limiting examples include lavender, peppermint, and eucalyptus. A therapeutic oil is a hydrophobic liquid which is said to have a therapeutic effect or to have associated with it certain healing properties. Therapeutic oils contain active biologically occurring molecules and, upon topical application, exert a therapeutic effect. Non limiting examples include manuka oil, rosehip oil, which contains retinoids and is known to reduce acne and post-acne scars, and tea tree oil, which possesses anti-microbial activity including antibacterial, antifungal and antiviral properties as well as any other therapeutically beneficial oil known in the art of herbal medication. Many essential oils are considered "therapeutic oils." Other non limiting examples of essential oils are basil, camphor, cardamom, carrot, citronella, clary sage, clove, cypress, frankincense, ginger, grapefruit, hyssop, jasmine, lavender, lemon, mandarin, marjoram, myrrh, neroli, nutmeg, petitgrain, sage, tangerine, vanilla and verbena.

Some embodiments include silicone oils. Non-limiting examples of silicone oils include a cyclomethicone, dimethicone, a polyalkyl siloxane, a polyaryl siloxane, a polyalkylaryl siloxane, a polyether siloxane copolymer, a poly(dimethylsiloxane)-(diphenyl-siloxane) copolymer, a dimethyl polysiloxane, an epoxy-modified silicone oil, a fatty acid-modified silicone oil, a fluoro group-modified silicone oil, a methylphenylpolysiloxane, phenyl trimethicone and a polyether group-modified silicone oil. In some embodiments, the silicone oil is cyclomethicone, cyclotetrasiloxane, cyclohexasiloxane, phyenyltrimethicone, Dow corning 246 Fluid (d6+d5) (cyclohexasiloxane & cyclopentasiloxane), Dow Corning 244 Fluid (cyclotetrasiloxane), Cyclomethicone 5-NF (cyclopentasiloxane), stearyl dimethicone, phenyltrimethicone, cetyl dimethicone, caprylyl methicone, PEG/PPG 18/18 dimethicone, or dimethiconol.

In one or more embodiments, the hydrophobic solvent may be selected from capric/caprylic triglycerides, cyclomethicone; isopropyl myristate, isopropyl palmitate, PPG-15 stearyl ether; octyldodecanol; isohexadecanol, diisopropyl adipate; cetearyl octanoate; MCT oil; heavy mineral oil; light mineral oil; coconut oil and soybean oil.

Mixtures of two or more hydrophobic solvents in the same foamable composition are contemplated. Furthermore, in certain embodiments, the use of mixtures of two or more hydrophobic solvents is preferred.

Yet, in certain embodiments, the hydrophobic solvent is a mixture of one or more liquid hydrophobic solvents, as listed above, together with an additional hydrophobic substance, which is not liquid (such as petrolatum). In an embodiment the resultant mixture upon including propellant is liquid at ambient temperature. In certain embodiments the main hydrophobic substance in the formulation is a petrolatum, which is a semi solid, in combination with at least one liquid hydrophobic solvent. For example petrolatum may be added to provide a degree of occlusivity so that the formulation when applied to a skin surface can operate to increase skin moisture and/or reduced transdermal water loss. In certain other embodiments a liquid hydrophobic solvent is not added. Fluidity of the composition can be achieved by utilizing liquidizing solvents (e.g. C12 C15 Alkyl benzoate) and/or liquefied propellants and/or optionally liquid adjuvants. Inclusion of higher amounts of propellant was found useful in order to improve flowability of the formulation from the canister or by using propellants having a higher vapor pressure.

In one or more embodiments the hydrophobic solvent is a natural oil, extracted from plants, such as the fruit of olives or avocado or from their seeds, such as, grape seed oil or pomegranate seed oil. Non limiting examples of suitable oils, which can also have a therapeutic effect, include almond oil, avocado oil, calendula oil, coconut oil, cocoglycerides, grape seed oil, jojoba oil, peanut oil, pomegranate seed oil, soy bean oil, and wheat germ oil. In one or more embodiments the hydrophobic solvent is a hydrocarbon based oil, such as light mineral oil or heavy mineral oil. Each oil has its own unique characteristics, as will be appreciated by a man of the art. Some are readily absorbed onto the skin, whist others are heavier or greasy and are less easily absorbed. It should be kept in mind that greasiness is a subjective feeling. With this caveat in mind pomegranate and avocado are thought to be oils with a greasier feeling. On the other hand jojoba, almond, grape seed, calendula and peanut oils are not considered greasy. Somewhere in between are soybean, wheat germ and coconut oils. Some oils have a strong natural odor, such as pomegranate seed oil whilst others display a milder odor, such as soybean, wheat germ, avocado, and almond. Others display a subtle or almost non existent odor, such as, jojoba, coconut, grape seed, calendula and peanut oil. Sometimes odor is a reflection of the level of processing the oil has undergone with a lower or disappearing odor reflecting a higher level of oil refinement. In an embodiment oils are blended to facilitate good absorption with unctuous occlusive properties. In one or more embodiments fragrance can be added to mask distinctive odors of oils. In one or more embodiments the oil is a mixture of two or more oils.

Foamer Complex Components

The foamer complex comprises: a first member, comprising about 0.1% to about 20% by weight of a fatty alcohol; and a second member, comprising about 0.1% to about 20% by weight of a fatty acid; and/or a wax. In certain embodiments the amount of the first and second members respectively comprises about 0.4% to about 18% by weight. In certain embodiments the amount of the first and second members each respectively comprises about 0.6% to about 12% by weight. In certain embodiments the amount of the first and second members each respectively comprises about 0.8% to about 10% by weight. In certain embodiments the amount of the first and second members each respectively comprises about 2% to about 7% by weight. In certain other embodiments, the concentration of each member respectively can be within any one of the following ranges (i) between about 0.1% and about 1%, (ii) between about 1% and about 5%, (iii) between about 5% and about 10%, or (iv) between about 10% and about 20%. In one or more embodiments, each member is at a concentration at about 5% to about 10% by weight.

Fatty Alcohol

The foamer complex includes a fatty alcohol. The fatty alcohol which acts as a foam adjuvant is included in the foamable compositions as a main constituent, to evolve the foaming property of the composition and/or to stabilize the foam. In one or more embodiments, the fatty alcohol is selected from the group consisting of fatty alcohols having 15 or more carbons in their carbon chain, such as cetyl alcohol and stearyl alcohol (or mixtures thereof). Other examples of fatty alcohols are arachidyl alcohol (C20), behenyl alcohol (C22), tetracosanol, hexacosanol, octacosanoi, triacontanol, tetratriacontanol, 1-triacontanol (C30), as well as alcohols with longer carbon chains (up to C50). In one or more embodiments the fatty alcohol has a carbon, chain length of 14 to 22 carbons. In one or more other embodiments, the fatty alcohol is selected from the group consisting of fatty alcohols having 14 or less carbons in their carbon chain, such as lauryl alcohol and myristyl alcohol. In an embodiment the fatty alcohol is a solid at room temperature. In an embodiment where the formulation is very viscous liquid fatty acids or fatty alcohols may for example be added, for example isostearic acid.

In one or more preferred embodiments, the fatty alcohol is cetyl alcohol, stearyl alcohol, behenyl alcohol and combinations thereof. Fatty alcohols, derived from beeswax and including a mixture of alcohols, a majority of which has at least 20 carbon atoms in their carbon chain, are suitable as fatty alcohols in the context herein. In certain embodiments the amount of the fatty alcohol required to support the foam system can be approximately inversely related to the length of its carbon chains. In one or more other embodiments, the fatty alcohol is selected from the group consisting of fatty alcohols having 14 or less carbons in their carbon chain, such as myristyl alcohol. Fatty alcohols are also useful in facilitating improved spreadability and absorption of the composition.

Fatty alcohols are amphiphatic, however unlike customary surfactants, they cannot usually function as stand-alone surfactants, because of their very weak emulsifying capacity. They are occasionally used as non-ionic co-emulsifiers, i.e., and are commonly used as thickeners (*Surfactants in personal care products and decorative cosmetics* By Linda D. Rhein, Mitchell Schlossmann Anthony O'Lenick, P., Third Edition, 2006, p. 247). Fatty alcohols are generally regarded as safe and they are not considered as irritants.

An important property of the fatty alcohols used in context of the composition disclosed herein is related to their therapeutic properties per se. Long chain saturated and mono unsaturated fatty alcohols, e.g., stearyl alcohol, erucyl alcohol, arachidyl alcohol and behenyl alcohol (docosanol) have been reported to possess antiviral, antiinfective, antiproliferative and anti-inflammatory properties (see, U.S. Pat. No. 4,874,794). Longer chain fatty alcohols, e.g., tetracosanol, hexacosanol, heptacosanol, octacosanol, triacontanol, etc., are also known for their metabolism modifying properties and tissue energizing properties.

Fatty Acid

The foamer complex further includes a fatty acid. The fatty acid which acts as a foam adjuvant is included in the foamable compositions to evolve the foaming property of the composition and/or to stabilize the foam, in one or more embodiments the fatty acid can have 16 or more carbons in its carbon chain, such as hexadecanoic acid (C16) heptadecanoic acid, stearic acid (C18), arachidic acid (C20), behenic acid (C22), tetracosanoic acid (C24), hexacosanoic acid (C26), heptacosanoic acid (C27), octacosanoic acid (C28), triacontanoic acid, dotriacontanoic acid, tritriacontanoic acid, tetratriacontanoic acid and pentatriacontanoic acid, as well as fatty acids with longer carbon chains (up to C50), or mixtures thereof. In one or more other embodiments, the fatty acid is selected from the group consisting of fatty alcohols having 14 or less carbons in their carbon chain, such as dodecanoic acid myristic acid, myristoleic acid, and lauric acid.

Optionally, the carbon atom chain of the fatty acid may have at least one double bond; alternatively, the fatty acid can be a branched fatty acid. The carbon chain of the fatty acid also can be substituted with a hydroxyl group, such as 12-hydroxy stearic acid. In one or more preferred embodiments, the fatty acid is stearic acid.

Waxes

The oleaginous foamer complex may include a wax. The wax which acts as a foam adjuvant is included in the foamable compositions to evolve the foaming property of the composition and/or to stabilize the foam. Wax refers to beeswax or another substance with similar properties. The term wax refers to a class of substances with properties similar to beeswax, in respect of (i) plastic behavior at normal ambient temperatures, a melting point above approximately 45° C., (ii) a relatively low viscosity when melted (unlike many plastics); and (iii) hydrophobic nature. Suitable exemplary waxes which can be incorporated into the formulation include animal, vegetable, mineral or silicone based waxes which may be natural or synthetic such as, for example: beeswax, Chinese wax, lanolin (wool wax), shellac wax, bayberry wax, candelilla wax, carnauba wax, castor wax, esparto wax, japan wax, ouricury wax, rice bran wax, soy wax, hydrogenated oil such as hydrogenated castor oil, hydrogenated cottonseed oil, or hydrogenated jojoba oil, mink wax, motan wax, ouricury wax, ozokerite, PEG-6 beeswax, rezowax, spent grain wax, stearyl dimethicone, paraffin waxes, such as paraffin 42-44, 51-53, 58-62 wax, and the like and mixtures thereof. In certain embodiments the term wax can extend to hydrogenated oils. In one or more preferred embodiments, the wax is a beeswax or hydrogenated castor oil.

Paraffin wax is unique among other hydrocarbon chains by having a CST of about 25 (e.g., 25.5), which is about in the middle of the hydrophobic range. Thus, paraffin waxes are somewhat amphipatic which may also contribute to foam stability. Notably, in comparison to longer hydrocarbons, such as polyethylene and polypropylene, paraffin wax is much more hydrophobic, thereby decreasing the surface tension of the hydrophobic solvents in the composition and facilitating foam formation and stabilization (the CST of polypropylene 31.0 and polyethylene 33.0).

Hydrogenated castor oil consists mainly of triglycerides of hydroxystearic acid and is a solid wax.

Beeswax contains a high proportion of wax esters (35 to 80%), which are linear monoesters of straight-chain fatty alcohols with even-numbered carbon chains from C24 to C36 esterified with straight-chain fatty acids such as 16:0 and 18:0 fatty acids some with hydroxyl groups in the ω-2 and ω-3 positions. The wax esters consist of C40 to C46 molecular species. Also present are free acids (about 14%) and carbohydrates (about 12%) as well as approximately 1% free wax alcohols and stearic esters of fatty acids.

In one or more embodiments, the wax is a polyolefin such as polyethylene, polypropylene, polymethylpentene, polybutene, a polyolefin elastomer, polyisobutylene, ethylene propylene rubber, ethylene propylene diene Monomer (M-class) rubber, polyethylene terephthalate, polydicyclopentadiene, linear polyolefins, branched polyolefins, cyclic polyolefins, low density polyolefins, high density polyolefins, polyolefins with a low molecular weight, polyolefins with a high molecular weight, halogenated polyolefins and the like and mixture thereof.

In one or more embodiments, the wax is polyvinyl chloride, polyvinylidene chloride, polyvinylidene fluoride, polyvinyl fluoride, polytetrafluoro ethylene, polychlorotrifluoro ethylene, polystyrene, polybutadiene, polyisoprene, polychloroprene, polymethylpentene and the like and mixture thereof.

In an embodiment the wax is selected from the group consisting of beeswax, Chinese wax, lanolin wax, shellac wax, bayberry wax, candelilla wax, carnauba wax, castor wax, esparto wax, japan wax, ouricury wax, rice bran wax, soy wax, a hydrogenated oil, hydrogenated castor oil, hydrogenated cottonseed oil, or hydrogenated jojoba oil, mink wax, montan wax, ozokerite, PEG-6 beeswax, rezo wax, spent grain wax, stearyl dimethicone, a paraffin wax, paraffin 58-62° C. wax, paraffin 51-53° C. wax, paraffin 42-44° C. wax.

In an embodiment the wax is selected from the waxes, as described in "The Complete Technology Book on Wax and Polishes, Publisher: Asia Pacific Business Press Inc., 2006" as incorporated herein by reference.

In one or more embodiments the wax includes vegetable wax, bayberry wax, candelilla wax, carnauba wax, flower wax, sandy wax, fat wax, cotton wax, esparto wax, fir wax, flax wax, Japan wax, ouricury wax, palm waxes, cuban palm wax, rice-oil wax, sugar cane wax, ucuhuba wax, or cocoa butter.

In one or more embodiments the wax includes synthetic mineral wax, fischer-tropsch wax, duroxon wax, or polymekon wax.

In one or more embodiments the wax includes miscellaneous synthetic waxes, albacer wax, atlasene wax, BASF waxes, cardis waxes, ceramid, glyco Waxes, flexo wax, or oxazoline waxes.

Combination of a Fatty Alcohol and a Fatty Acid and/or a Wax

In Example 11, which looks at prior art formulations with a fatty alcohol, alone, a foam of good quality is not obtained. When, however, a fatty alcohol (or a mixture of fatty alcohols) is combined with a fatty acid (or a mixture of fatty acids) and/or a wax (or a mixture of waxes), they can, surprisingly, act synergistically to produce a good quality breakable foam. These successful combinations of a fatty alcohol and a fatty acid or a fatty alcohol and a wax are referred to herein as "foamer complexes".

In one or more embodiments, the foamer complex is a synergistic combination of a fatty alcohol (or a mixture of fatty alcohols) and a fatty acid (or a mixture of fatty acids).

In one or more embodiments, the foamer complex is a synergistic combination of a fatty alcohol (or a mixture of fatty alcohols) and a wax (or a mixture of waxes).

In one or more embodiments, the foamer complex is a synergistic combination of a fatty alcohol (or a mixture of fatty alcohols), a fatty acid (or a mixture of fatty acids) and a wax (or a mixture of waxes).

In one or more embodiments the range of ratio of fatty alcohol to fatty acid/wax can be about 100:1 to about 1:100; or about 90:1 to about 1:45; or about 80:1 to about 1:40; or about 70:1 to about 1:35; or about 60:1 to about 1:30; or about 50:1 to about 1:25; or about 40:1 to about 1:20; or about 30:1 to about 1:15; or about 20:1 to about 1:10; or about 15:1 to about 1:5; or about 10:1 to about 1:1; or any ranges in between such as 1:20 to 20:1, or preferably from 1:10 to 10:1, or 1:4 to 4:1, or 2:3 or 3:2.

Combination of a Fatty Alcohol and a Fatty Acid and/or Shea Butter

In one or more embodiments the foamer complex can be a fatty alcohol and shea butter, a fatty acid and shea butter or a combination of a fatty alcohol and a fatty acid and shea butter. Shea butter may, for example, be used instead of paraffin wax or instead of bees wax or instead of hydrogenated caster oil or to complement one or more of them. As can be appreciated, from Example 22, wax and/or shea butter comprising complexes can be effective with petrolatum based compositions.

In one or more embodiments oily emollients are added to provide or improve a pleasant skin feeling, and/or lubricating effect with reduced friction. In one or more embodiments volatile silicones are added to reduce greasy feeling. In one or more embodiments various waxes are added to improve rheology or stabilize foam structure.

Propellant

The composition requires the addition of a propellant in order to generate a foam.

Suitable propellants include volatile hydrocarbons such as butane, propane, isobutene or mixtures thereof. In one or more embodiments a hydrocarbon mixture AP-70 is used. In one or more other embodiments a lower pressure hydrocarbon mixture AP-46 is used. Both contain butane, propane, isobutene although in different proportions. AP-70 is composed of about 50% w/w of propane, about 20% w/w of isobutane and about 30% w/w of propane. AP-46 is composed of about 16% w/w of propane, about 82% w/w of isobutane and about 2% w/w of propane. Hydro fluorocarbon (MFC) propellants are also suitable as propellants in the context disclosed herein. Exemplary HFC propellants include 1,1,1,2 tetrafluoroethane (Dymel 134), and 1,1,1,2,3, 3,3 heptafluoropropane (Dymel 227). Dimethyl ether is also useful. In one or more embodiments use of compressed gases (e.g., air, carbon dioxide, nitrous oxide, and nitrogen) is also possible.

In one or more embodiments a combination of at least two propellants, selected from HFC, hydrocarbon propellants, dimethyl ether and compressed gases is contemplated.

Yet, in additional embodiments, the propellant is a self-foaming propellant, i.e., a volatile liquid having a boiling point of less than the temperature of the target treatment site (such as the skin). An example of a post-foaming propellant is isopentane (bp=26° C.).

Any concentration of the propellant, which affords an acceptable foam is useful in accordance with the present invention. In certain embodiments the propellant makes up between about 1% and about 30% of the foamable composition, or about 3% and 30%; or about 4% and 25%; and in certain preferred embodiments between about 5% and about 16% of the composition. In preparing the formulations the ingredients other than propellant are combined to 100% and the propellant is added thereafter so that the ratio of formulation to propellant can range from 100:1 to 100:30; 100:3 to 100:30; 100:4 to 100:25 or preferably or preferably 100:5 to 100:16. Yet, in additional embodiments, the ratio of composition other than propellant to propellant is between about 100:20 and about 100:50.

In one or more embodiments the propellant can also be used to expel formulation using a bag in can system or a can in can system as will be appreciated by someone skilled in the art. In certain embodiments the part of the propellant system is in the formulation and part separate from the formulation. In this way it is possible to reduce the amount of surfactant in the formulation but still provide good expulsion from the canister, where the foamable formulation is expelled quickly but without jetting or noise.

In one or more embodiments a foam formulation is expelled from a standard pressurized canister where the propellant is part of formulation. Formulations can be expelled or helped to be expelled by using propellant which is separate from the formulation using a bag in can or can in can system. Although, these systems can be used with compressed air the pressure may not be sufficient to expel the formulation through the device and higher pressure propellant such as AP70 should be selected. In one or more embodiments, the formulation is packaged in bag in can systems or in can in can system. In one or more embodiments, the formulation is expelled from the canister using the pressure provided by the propellant mixed with the formulation. In one or more embodiments, the formulation is expelled from the canister using the pressure provided, by the propellant stored in a compartment surrounding the formulation. According to other embodiments part of the propellant system is in the formulation and part of the propellant system is separate from the formulation, which is used to expel said formulation using a bag or can in can system. In this way it is possible to reduce the amount of propellant within the formulation and avoid unwanted gaseous effects, for example in vaginal applications, but still provide good expulsion from the canister, where the foamable formulation is expelled sufficiently quickly but without jetting or noise. So by way of example, between about 1% to 3%; or between about 2% to 4%; between about 3% to 5% propellant (ratio of formulation to propellant of 100:1 to 3; 100:2 to 4; 100:3 to 5; respectively) is part of the formulation and a further amount of propellant is separate form the formulation and helps expel the formulation. In one or more embodiments a similar amount of propellant is in the formulation and a pump or other mechanical means is used to provide the additional expulsion force.

Modulating Agent

In one or more embodiments the modulating agent is used in a waterless composition which is surfactant free. The term modulating agent is used to describe an agent which can improve the stability of or stabilize a carrier or a foamable composition and/or an active agent by modulating the effect of a substance or residue present in the carrier or composition. The substance or residue may, for example, be acidic or basic or buffer system (or combinations thereof) and potentially alter an artificial pH in a waterless or substantially non-aqueous environment, such as, by modulating the ionic or polar characteristics and any acidity or basesity balance of a waterless or substantially non-aqueous carrier, composition, foamable carrier or foamable composition or resultant foam or it may be a chelating or sequestering or complexing agent or it may be one or more metal ions which may act as a potential catalyst in a waterless or substantially non-aqueous environment or it may be an ionization agent or it may be an oxidizing agent.

In an embodiment, the modulating or additional component is a pH adjusting agent or a buffering agent and can be any of the known buffering systems used in pharmaceutical or cosmetic formulations as would be appreciated by a man of the art. It can also be an organic acid, a carboxylic acid, a fatty acid an amino acid, an aromatic acid, an alpha or beta hydroxyl acid an organic base or a nitrogen containing compound.

In one or more further embodiments the modulating agent is used to describe an agent, which is a chelating or sequestering or complexing agent that is sufficiently soluble or functional in the waterless solvent to enable it to "mop up" or "lock" metal ions such as EDTA or other such pharmaceutically or cosmetically acceptable.

Modulating agents may be added to the compositions of the subject invention, preferably from about 0.1% to about 10%, more preferably from about 1% to about 5%, of the composition. Where the active agent itself is the modulating agent alone or in combination with another modulating agent it will be added at an effective dose which may be outside these ranges. For example azaleic acid may be at about 15% of the composition. In an embodiment sufficient modulating agent is added to achieve an artificial pH in which the active agent is preferably stable. Such artificial pH may be acidic, may be basic or may be neutral Further detail regarding modulating agents is found in co-pending Published U.S. Patent Application 2008/0206159, which is hereby incorporated in its entirety by reference.

The modulating agent to the foamable composition is useful for stabilizing pharmaceutical and cosmetic active agents which are unstable in certain pH conditions. It is known, for example, that active agents, which contain ester bond in their structure tend to undergo hydrolysis of the ester bond at basic pH levels. Therefore, the addition of an agent, which avoids the formation of basic pH condition, can thus, prevent degradation of such active agents. Many steroid compounds are known to undergo rearrangement at high pH, and again, adding an acidic modulating agent helps prevent such degradation. Another example of a pH-sensitive active agent is vitamin D, which degrades at low pH levels. In such a case, the addition of a basic modulating agent, such as triethanolamine is useful to maintain acceptable stability of this active agent.

It is important to maintain skin surface pH in order to prevent susceptibility to bacterial skin infections or skin damage and disease. Thus, adding a modulating agent, which contributes to the stabilization of skin pH at the desirable level, is advantageous.

In the same fashion, adding an acidic modulating agent to a foamable composition, which is intended for vaginal application is advantageous, since better protection against vaginal infection is attained in pH lower than 4.

In one or more embodiments, the modulating agent may also be a preservative or an antioxidant or an ionization agent. Any preservative, antioxidant or ionization agents suitable for pharmaceutical or cosmetic application may be used. Non-limiting examples of antioxidants are tocopherol, tocopherol succinate, ascorbic acid (vitamin C) and its salts, propyl galate, butylated hydroxy toluene and butyl hydroxy anisol. Non-limiting examples of positive ionization agents are benzyl conium chloride, and cetyl pyridium chloride. Non-limiting examples of negative ionization agents are sodium lauryl sulphate, sodium lauryl lactylate and phospholipids. In one or more embodiments the modulating agent is a flavonoid for example quercitin and/or rutin.

A safe and effective amount of an anti-oxidant/radical scavenger may be added to the compositions of the subject invention, preferably from about 0.1% to about 10%, more preferably from about 1% to about 5%, of the composition.

Ophthalmic Excipients

In one or more embodiments the formulation may comprise excipients that are suitable for ophthalmic use. By virtue of their suitability for ophthalmic use they may in certain embodiments be applicable on other sensitive targets such as for use internal and/or external wounds or burns or in body cavities. Excipients selected as pail of a drug carrier that can be used with the active pharmaceutical ingredients are identified by compatibility studies with active ingredients to ascertain which are compatible for use with the active pharmaceutical ingredients, for example, by examining which do not react with, and/or promote break down of the active pharmaceutical ingredients. In one or more embodiments, the ophthalmic excipient includes one or more known ophthalmic excipients approved by the FDA in the US.

Oleaginous ointments are viscous preparations, which remain viscous when applied to the skin or other body surfaces; and they require extensive rubbing. Because of their viscosity, eye ointments cause blurred vision and consequent low tolerability, especially for long term treatment. Because of their high viscosity, drugs are trapped in the vehicle and cannot migrate through to their target site of action, for example, the skin or the eye.

Liquid, non viscous oleaginous medications are also disadvantageous, as they spill easily and thus, are very inconvenient to use. In eye treatment, liquid drops are difficult to apply and they require lying on the back at rest for accurate administration. Furthermore, because of their low viscosity, liquid oil vehicles cannot carry suspended drugs, which tend to precipitate and if the viscosity is not high enough, thereby impairing the uniformity of the therapeutic product.

In one or more embodiments the formulations are not highly viscous. In one or more other embodiments the formulations do not provide low viscosity. In one or more embodiments the formulations are thixotropic so that on application of shear force their viscosity decreases and they become more flowable. In one or more embodiments the formulations are foams which are breakable on shear force. In one or more embodiments the foams are based on thixotropic gel formulations. In one or more embodiments the viscosity of the formulation prior to addition of propellant is more than about 1000 cps and less than about 25,000 cps. In one or more embodiments it is more than about 200 cps and less than about 24,000 cps.

Ophthalmic Active Agents

In one or more embodiments the formulation, may comprise active agents that are suitable for ophthalmic use. By virtue of their suitability for ophthalmic use they may in certain embodiments be applicable on other sensitive targets such as for use internal and/or external wounds or burns or in body cavities. Active agents are selected and combined with proper excipients and eye irritation studies including the HET CAM test can be preformed to ascertain, those which are non irritant.

It was surprisingly found that substantially surfactant free oleaginous formulations containing 1% or 4% minocycline hydrochloride, demonstrated no signs of irritation. Thus in one or more embodiments, the non-irritant active agent includes a tetracycline. In one or more embodiments, the non-irritant active agent includes a minocyline.

Additional Components

In an embodiment, a composition disclosed herein includes one or more additional components. Such additional components include but are not limited to anti perspirants, anti-static agents, bulking agents, cleansers, colorants, skin conditioners, deodorants, diluents, dyes, fragrances, hair conditioners, herbal extracts, humectants, keratolytic agents, modulating agents, pearlescent aids, perfuming agents, pH modifying or stabilizing agents, skin penetration or permeation enhancers, softeners, solubilizers, sunscreens, sun blocking agents, sunless tanning agents, viscosity modifiers, flavanoids and vitamins. As is known to one skilled in the art, in some instances a specific additional component may have more than one activity, function or effect.

In certain embodiments, the additional component is an oil soluble preservative, or an oil soluble antioxidant, or an oil soluble radical scavenger, or an oil soluble complexing agent, or an oil soluble pigment or dye.

Definitions

All % values are provided on a weight (w/w) basis.

By the term "about" herein it is meant as indicated above and that a figure or range of figures can also vary plus or minus up to 30%. So in this embodiment if a figure of "about 1" is provided then the amount can be up to 1.3 or from 0.70. In other embodiments it can reflect a variation of plus or minus 20%. In still further embodiments it can describe a variation of plus or minus 10%. In still further embodiments it can describe a variation of plus or minus 5%. As will be appreciated by one of the art there is some reasonable flexibility in formulating compositions such that where one or more ingredients are varied successful formulations may still be made even if an amount fails slightly outside the range. Therefore, to allow for this possibility amounts are qualified by about. In one or more other embodiments the figures may be read without the prefix about.

The term "thixotropic," as used herein, means that the formulation shows a decrease in viscosity upon application of shear force. The structure of the formulation breaks down leading to a reduction in viscosity. When the formulation is standing without shear force, this decrease in viscosity is recovered over time. In one or more embodiments, the gel formulation subjected to constant shear rate shows a reduction in viscosity with time. In one or more further embodiments, after the material is allowed to rest for a period of time, the viscosity increases again The term "waterless," as used herein, means that the composition contains no, or substantially no, free or unassociated or absorbed water. Similarly, "waterless" or "substantially waterless" carriers contain at most incidental and trace amounts of water.

By the term "single phase" herein it is meant that after addition of propellant to the composition or carrier, the liquid components of the foamable composition or carrier are fully miscible, and the solid components if any, are either dissolved or suspended in the composition. By substantially a single phase is meant that the composition or carrier after addition of propellant is primarily or essentially a single phase as explained above, but may also have present a small amount of material which is capable of forming or may form a separate phase amounting to less than about 5% of the composition or carrier after the addition of propellant, preferably less than about 3%, and more preferably less than about 3%.

The term "unstable active agent" as used herein, means an active agent which is oxidized and/or degraded within less than a day, and in some cases, in less than an hour upon exposure to air, light, skin or water under ambient conditions.

The term "co-surfactant" as used herein, means a molecule which on its own is not able to form and stabilize satisfactorily an oil in water emulsion but when used in combination with a surfactant the co-surfactant has properties, which can allow it to help surfactants to create an emulsion and can boost the stabilizing power or effect of the surfactant and can include, for example, a fatty alcohol, such as cetyl alcohol or a fatty acid such as stearic acid. Cetyl alcohol is a waxy hydrophobic substance that can be emulsified with water using a surfactant. Some substances may have more than one function and for example, fatty alcohols can in some formulations act as a co-solvent. In certain circumstances a co-surfactant can itself be converted in to a surfactant or soap by, for example, adding a base, such as, triethanolamine to a fatty acid like stearic acid.

The identification of a "polyol", as used herein, is an organic substance that contains at least two hydroxy groups in its molecular structure.

In one or more embodiments, the polyol is a diol (a compound that contains two hydroxy groups in its molecular structure). Examples of diols include propylene glycol (e.g., 1,2-propylene glycol and 1,3-propylene glycol), butanediol (e.g., 1,2-butanediol, 1,3-butanediol, 2,3-butanediol and 1,4-butanediol), butanediol (e.g., 1,3-butanediol and 1,4-butenediol), butynediol, pentanediol (e.g., pentane-1,2-diol, pentane-1,3-diol, pentane-1,4-diol, pentane-1,5-diol, pentane-2,3-diol and pentane-2,4-diol), hexanediol (e.g., hexane-1,6-diol hexane-2,3-diol and hexane-2,56-diol), octanediol (e.g., 1,8-octanediol), neopentyl glycol, 2-methyl-1,3-propanediol, diethylene glycol, triethylene glycol, tetraethylene glycol, dipropylene glycol and dibutylene glycol.

In one or more embodiments, the polyol is a triol (a compound that contains three hydroxy groups in its molecular structure), such as glycerin, butane-1,2,3-triol, butane-1,2,4-triol and hexane-1,2,6-triol.

In one or more embodiments, the polyol is a saccharide. Exemplary saccharides include, but are not limited to monosaccharide, disaccharides, oligosaccharides and sugar alcohols.

A monosaccharide is a simple sugar that cannot be hydrolysed to smaller units. Empirical formula is $(CH_2O)n$ and range in size from trioses (n=3) to heptoses (n=7). Exemplary monosaccharide compounds are ribose, glucose, fructose and galactose.

Disaccharides are made up of two monosaccharides joined together, such as sucrose, maltose and lactose.

In one or more embodiments, the polyol is a sugar alcohol (also known as a polyol, polyhydric alcohol, or polyalcohol) is a hydrogenated form, of saccharide, whose carbonyl group (aldehyde or ketone, reducing sugar) has been reduced to a primary or secondary hydroxyl group. They are commonly used for replacing sucrose in foodstuffs, often in combination with high intensity artificial sweeteners to counter the low sweetness. Some exemplary sugar alcohols, which are suitable for use according to the present invention are mannitol, sorbitol, xylitol, maltitol, lactitol. (Maltitol and lactitol are not completely hydrogenated compounds—they are a monosaccharide combined with a polyhydric alcohol.) Mixtures of polyols, including (1) at least one polyol selected from a diol and a triol; and (2) a saccharide are contemplated within the scope of the present disclosure.

According to some embodiments, the composition is polyol free i.e., free of polyols. In other embodiments, the composition is substantially free and comprises less than about 5% final concentration of polyols, preferably less than 2%, more preferably less than 1%. Where a formulation includes insignificant amounts of polyols it is considered to be essentially free of them.

In an embodiment, the polyol is linked to a hydrophobic moiety. In the context of the present disclosure, a polyol linked to a hydrophobic moiety is still defined as a "polyol" as long as it still contains two or more free hydroxyl groups.

In an embodiment, the polyol is linked to a hydrophilic moiety. In the context of the present disclosure, a polyol linked to a hydrophilic moiety is still defined "polyol" as long as it still contains two or more free hydroxyl groups.

The term "water activity" as used herein, activity represents the hydroscopic nature of a substance; or the tendency of a substance that absorbs water from its surroundings. Microorganisms require water to grow and reproduce, and such water requirements are best defined in terms of water activity of the substrate. The water activity of a solution is expressed as $Aw=P/Po$, where P is the water vapor pressure of the solution and Po is the vapor pressure of pure water at the same temperature. Every microorganism has a limiting Aw, below which it will not grow; e.g., for Streptococci, *Klebsiella* spp, *Escherichia coli, Clostridium perfringens*, and *Pseudomonas* spp, the Aw value is 0.95. *Staphylococcus aureus* is most resistant and can proliferate with an Aw as low as 0.86, and fungi can survive at Aw of at least 0.7. In one or more embodiments, the concentration of the hydrophobic solvent, and/or foamer complex in the composition is selected to provide an Aw value selected from the ranges of (1) about 0.8 and about 0.9; (2) about 0.7 and about 0.8; and (3) less than about 0.7. By delivering the formulation in a pressurized package does not allow for humidity to be absorbed by the preparation, and therefore, the water free character of the composition cannot be damaged.

In an embodiment no preservative is needed because the formulation is a waterless hydrophobic solvent or oil-based formulation having an Aw (Water Activity) value of less than 0.9, less, or less than about 0.8, or less than about 0.7 or less than about 0.6 and preferably less than about 0.5 which is below the level of microbial proliferation.

In one or more embodiments, the hydrophobic carrier composition further contains an anti-infective agent, selected from the group of an antibiotic agent, an antibacterial agent, an antifungal agent, an agent that controls yeast, an antiviral agent and an antiparasitic agent. In a preferred embodiment the anti infective agent comprises a tricyclic antibiotic. Not only can combining the anti-infective effect of a hydrophobic carrier composition, with an anti-infective agent can result in a synergistic effect, and consequently higher success rate of the treatment but the combination with the foamer complex achieves a formulation in which the active pharmaceutical ingredient is chemically stable and the formulation is physically stable as demonstrated herein in the Examples. Moreover the use of hydrophobic based water free formulation can maximize the antimicrobial potential of the formulations. Storage in sealed, light and airtight canisters can assist in preserving the formulations.

The identification of a "solvent," as used herein, is not intended to characterize the solubilization capabilities of the solvent for any specific active agent or any other component of the foamable composition. Rather, such information is provided to aid in the identification of materials suitable for use as a part in the foamable carriers described herein.

Substantially Alcohol Free

Lower or short chain alcohols, having up to 5 carbon atoms in their carbon chain skeleton, such as ethanol, propanol, isopropanol, butanol, iso-butanol, t-butanol and pentanol are considered less desirable solvents or co-solvents due to their skin-irritating effect. Thus, according to some embodiments, the composition is substantially alcohol-free i.e., free of short chain alcohols. In other embodiments, the composition comprises less than about 5% final concentration of lower alcohols, preferably less than 2%, more preferably less than 1%. Where a formulation contains insignificant amounts of short chain alcohols it is considered to be essentially free of them.

Substantially Standard Surfactant Free

Surfactants have been categorized in to various sub classes depending on their ionic characteristics, namely non-ionic surfactants, anionic, cationic, zwitterionic, amphoteric and amphiphilic surfactants. The term surfactant has been often loosely used in the art to include substances which do not function effectively as stand alone surfactants to reduce surface tension between two substances or phases. Reduction of surface tension can be significant in foam technology in relation to the ability to create small stable bubbles. For example fatty alcohols, fatty acids and certain waxes are amphiphatic, are essentially hydrophobic with a minor hydrophilic region and for the purposes of forming an emulsion they are usually regarded as an oil and thus have a "required" HLB value" for the purpose of determining what standard surfactant might be appropriate to use with the oil phase. However unlike standard or customary surfactants, these substances are not effective as stand-alone surfactants in foamable emulsion compositions, because of their very weak emulsifying capacity and further due to their weak foaming capacity on their own. They are occasionally used in a supporting role as co-emulsifiers, i.e., in combination with a standard surfactant but are commonly used as thickeners and have successfully been used as foam adjuvants to assist customary surfactants to boost foam quality and stability. For clarification in the context herein whilst the term "standard surfactant" or "customary surfactant" refers herein to customary non-ionic, anionic, cationic, zwitterionic, amphoteric and amphiphilic surfactants a fatty alcohol or a fatty acid and certain waxes are not regarded as a standard surfactant. However, in contrast, an ether or an ester formed from such fatty alcohols or fatty acids can be regarded as a customary surfactant.

Generally, surfactants are known to possess irritation potential. One way that is used to try and reduce potential irritation and drying of the skin or mucosa due to surfactants and their repeated use especially when formulations are to be left on the skin, or mucosa rather than being washed off is to use essentially or primarily non ionic surfactants at preferably low concentrations below 5%. The current breakthrough of identifying formulations which produce quality breakable foam yet omitting customary surfactants from a composition may contribute to improved tolerability of such a composition and can be an important advantage. This is especially so when a formulation is to be applied to a very sensitive target site, and particularly so on a repeated basis.

Non-limiting examples of classes of customary non-ionic surfactants include: (i) polyoxyethylene sorbitan esters (polysorbates), such as polysorbate 20, polysorbate 40, polysorbate 60 and polysorbate 80; (ii) sorbitan esters, such as sorbitan monostearate sorbitan monolaurate and sorbitan monooleate; (iii) polyoxyethylene fatty acid esters, such as, PEG-8 stearate, PEG-20 stearate, PEG-40 stearate, PEG-100 stearate, PEG-8 laurate, PEG-10 laurate, PEG-12 laurate, PEG-20 laurate, PEG-8 oleate, PEG-9 oleate, PEG-10 oleate, PEG-12 oleate, PEG-15 oleate and PEG-20 oleate; (iv) PEG-fatty acid diesters, such as PEG-150 distearate; (v) polyethylene glycol (PEG) ethers of fatty alcohols, such as: (vi) glycerol esters, such as glyceryl monostearate, glyceryl monolaurate, glyceryl monopalmitate and glyceryl monooleate; (vii) PEG-fatty acid mono- and di-ester mixtures; (viii) polyethylene glycol glycerol fatty acid esters; (ix) propylene glycol fatty acid esters; (x) mono- and diglycerides: (xi) sugar esters (mono-, di- and tri-esters of sucrose with fatty acids) and (xii) polyethylene glycol alkyl phenols.

In certain embodiments, the composition is free of customary surfactants, or "surfactant-free" and in certain embodiments the foamable composition is substantially free of customary surfactants, or "substantially surfactant-free".

In the context herein, the term "substantially surfactant-free composition" relates to a composition that contains a total of less than about 0.4% of a surfactant selected from the group consisting of customary non-ionic, anionic, cationic, zwitterionic, amphoteric and ampholytic surfactants. Preferably, the composition comprises less than about 0.2% by weight of a standard surfactant and more preferably less than about 0.1%. Non-surfactant or surfactant-free compositions will comprise no or negligible levels of surface active agents.

In additional embodiments, the term "substantially surfactant-free" relates to a composition wherein the ratio between the foamer complex and the surfactant is between 10:1 or 5:1; or between 20:1 and 10:1 or between 100:1 and 20:1.

In certain embodiments, the composition is free or substantially free of an ionic surfactant. In certain embodiments, the composition is free or substantially free of a non-ionic surfactant.

Substantially Polymer-Free

By the term polymeric agent it is intended to mean a compound having multiple repeated units such as cellulose polymers, acrylic polymers, block polymers and copolymers. In one or more certain embodiments the polymeric agent has a molecular weight of in excess of a 1000 Daltons. In one or more embodiments the formulations are substantially polymer free. In one or more embodiments the formulations are substantially polymer free of a polymeric agent selected from the group consisting of a bioadhesive agent, a gelling agent, a film forming agent and a phase change agent, being locust bean gum, sodium alginate, sodium caseinate, egg albumin, gelatin agar, carrageenin gum, sodium alginate, xanthan gum, quince seed extract, tragacanth gum, guar gum, cationic guars, hydroxypropyl guar gum, starch, amine-bearing polymers such as chitosan; acidic polymers obtainable from natural sources, such as alginic acid and hyaluronic acid; chemically modified starches and the like, carboxyvinyl polymers, polyvinylpyrrolidone, polyvinyl alcohol, poly acrylic acid polymers, polymethacrylic acid polymers, polyvinyl acetate polymers, polyvinyl chloride polymers, polyvinylidene chloride polymers, semi-synthetic polymeric materials such as cellulose ethers, such as methylcellulose, hydroxypropyl cellulose, hydroxypropyl methylcellulose, hydroxyethyl cellulose, hydroxy propylmethyl cellulose, methylhydroxyethylcellulose, methylhydroxypropylcellulose, hydroxyethylcarboxymethylcellulose, carboxymethyl cellulose, carboxymethylcellulose carboxymethylhydroxyethylcellulose, and cationic celluloses, carbomer (homopolymer of acrylic acid is crosslinked with an allyl ether pentaerythritol, an allyl ether of sucrose, or an allyl ether of propylene); poloxamers (synthetic block copolymer of ethylene oxide and propylene); polyethylene glycol having molecular weight of 1000 or more (e.g., PEG 1,000, PEG 4,000, PEG 6,000 and PEG 10,000) and which could function as a hydro alcoholic foam booster. By substantially polymer free it is intended to mean less than about 5%, preferably less than about 2%. By essentially polymer free it is intended to mean less than about 1%, preferably less than about 0.5%. In further embodiments they are essentially polymer free and in still further embodiments they are free of polymeric agents.

In alternative embodiments the formulations may comprise a polymeric agent in such case the polymeric agents are oil soluble polymeric agents. Non limiting examples of oil-soluble polymeric agents are: Ethyl cellulose, alkylated guar gum, trimethylsiloxysilicate, alkyl-modified silicone, polyamide-modified silicone, homopolymers and copolymers of alkyl methacrylates, alkyl acrylates, and alkyl styrenes polyisobutene, polybutyl metacrylate, polycyclohexylstyrene.

According to one or more embodiments, the composition comprises less than about 0.1% by weight of a polymeric agent and more preferably less than about 0.05%. Polymer-free compositions will comprise no or negligible levels of polymeric agents.

In the art, the term polymeric agent can be used loosely to refer to any polymer. However, in some embodiments polymers that do not have a gel building role but may act in other ways are not excluded from the compositions. In one or more embodiments a polyether siloxane copolymer and a poly(dimethylsiloxane)-(diphenyl-siloxane) copolymer and the like, which can provide a good feeling to the composition are not excluded.

Physical Characteristics of the Foamable Composition and Foam

A foamable composition manufactured according to one or more embodiments herein is very easy to use. When applied onto the afflicted body surface of mammals, i.e., humans or animals, it is in a foam state, allowing free application without spillage. Upon further application of a mechanical force, e.g., by rubbing the composition onto the body surface, it freely spreads on the surface and is rapidly absorbed.

In one or more embodiments the foamable composition is a single phase solution. In one or more embodiments the foamable composition is substantially a single phase solution. In certain circumstances, where the active agent is insoluble and is presented as a homogenous suspension, the formulation is turbid or cloudy.

In one or more embodiments the foam composition has an acceptable shelf-life of at least one year, or at least two years at ambient temperature. A feature of a product for cosmetic or medical use is long term stability. Propellants, which are a mixture of low molecular weight-hydrocarbons, tend to impair the stability. The foamable compositions herein are surprisingly stable, even in the absence of customary surfactants. Following accelerated stability studies, they demonstrate desirable texture: they form fine bubble structures that do not break immediately upon contact with a surface, spread easily on the treated area and absorb quickly.

The composition should also be free flowing, to allow it to flow through the aperture of the container, e.g., and aerosol container, and create an acceptable foam. Compositions containing a substantial amount of semi-solid hydrophobic solvents, e.g., white petrolatum, as the main ingredients of the oil phase of the emulsion, will likely exhibit high viscosity and poor flow ability and can be inappropriate candidates for a foamable composition. Thus in one or more embodiments semi-solid hydrophobic solvents are a subsidiary component in the composition, for example being present at less than about 25%, less than about 20%, less than about 15%, less than about 10%, or less than about 5% by weight of the foamable composition. In other embodiments they can be present in higher amounts due to the solvent effect of the propellant diluting the formulation and enabling flowability or where the formulation is presented as a gel or ointment.

Foam Quality

Foam quality can be graded as follows:

Grade E (excellent): very rich and creamy in appearance, does not show any bubble structure or shows a very fine (small) bubble structure; does not rapidly become dull; upon spreading on the skin, the foam retains the creaminess property and does not appear watery.

Grade G (good): rich and creamy in appearance, very small bubble size, "dulls" more rapidly than an excellent foam, retains creaminess upon spreading on the skin, and does not become watery.

Grade FG (fairly good): a moderate amount of creaminess noticeable, bubble structure is noticeable; upon spreading on the skin the product dulls rapidly and becomes somewhat lower in apparent viscosity.

Grade F (fair): very little creaminess noticeable, larger bubble structure than a "fairly good" foam, upon spreading on the skin it becomes thin in appearance and watery.

Grade P (poor): no creaminess noticeable, large bubble structure, and when spread on the skin it becomes very thin and watery in appearance.

Grade VP (very poor): dry foam, large very dull bubbles, difficult to spread on the skin.

Topically administrable foams are typically of quality grade E or G, when released from the aerosol container. Smaller bubbles are indicative of a more stable foam, which does not collapse spontaneously immediately upon discharge from the container. The finer foam structure looks and feels smoother, thus increasing its usability and appeal.

Foam Density

Another property of the foam is specific gravity or density, as measured upon release from the aerosol can. Typically, foams have specific gravity of less than 0.50 g/mL or less than 0.12 g/mL, depending on their composition and on the propellant concentration. In one or more embodiments the foam density is about less than 0.3 g/mL.

Shakability

'Shakability' means that the composition contains some or sufficient flow to allow the composition to be mixed or remixed on shaking. That is, it has fluid or semi fluid properties. Shakability is described further in the section on Tests. In one or more certain limited embodiments the formulation is poorly shakable but is nevertheless flowable.

Breakability/Collapse Time

A further aspect of the foam is breakability. The balance between stability and breakability of the foam coming out of the container is very delicate: on one hand, the foam should preferably not be "quick breaking", i.e., it should be stable upon release from the pressurized container and not break as a result of exposure to skin temperature; and on the other hand, it should be "breakable", i.e., it should spread easily, break down and absorb into the skin or membrane upon application of mild shear force. The breakable foam is thermally stable, yet breaks under shear force. Shear-force breakability of the foam is clearly advantageous over thermally-induced breakability. Thermally sensitive foams start to collapse immediately upon exposure to skin temperature and, therefore, cannot be applied on the hand and afterwards delivered to the afflicted area.

The collapse time of foam represents its tendency to be temperature-sensitive and its ability to be at least stable in the short term so as to allow a user sufficient time to comfortably handle and apply the foam to a target, area without being rushed and/or concerned that, it may rapidly collapse, liquefy and/or disappear. Collapse time, as an indicator of thermal sensitivity, is examined by dispensing a given quantity of foam and photographing sequentially its appearance with time during incubation at 36° C. Simple collapse time can be measured by applying a foam sample on a body surface like the fingers at normal body temperature of about 37° C. (Collapse time is further described in the Examples).

Oils may cause foam to be thermolabile and "quick breaking" in particular high concentrations of silicone oils. However, in certain embodiments herein, despite the presence of high oil content, quite unexpectedly the foam is substantially thermally stable. By "substantially thermally stable" it is meant that the foam upon application, onto a warm skin or body surface at about 35-37° C. does not collapse within about 30 seconds. Thus, in one or more embodiments the simple collapse time of the foam is more than about 30 seconds or more than about one minute or more than about two minutes, or more than about three minutes. In one or more limited embodiments simple collapse time can be a little shorter than 30 seconds, but not less than about 20 seconds. In one or further or alternative embodiments the collapse time is measured by introducing a sample of foam into an incubator at 36° C. and the collapse time of the foam is more than 30 seconds or more than about one minute or more than about two minutes, or more than about two minutes.

Pharmaceutical Composition

The foamable oleaginous composition of the present invention can be used by itself as a topical treatment of a body surface, as many hydrophobic solvents such as emollients, unsaturated oils, essential oils or therapeutic oils that possess cosmetic or medical beneficial effects. Furthermore, it is an ideal vehicle for active pharmaceutical ingredients and active cosmetic ingredients. In the context active pharmaceutical ingredients and active cosmetic ingredients are collectively termed "active agent" or "active agents". The absence of surfactants in the composition is especially advantageous, since no surfactant-related adverse reactions are expected from such a composition. Some surfactants may act to facilitate gelling of the pre-foam formulation. The absence of such surfactants may avoid this undesirable phenomenon. In one or more embodiments the active agent is soluble in the composition of a phase thereof. In one or more other embodiments it is partially soluble or insoluble. When partially soluble or insoluble the active agent is presented as a suspension or it can be encapsulated in a carrier.

Suitable active agents include but are not limited to adipic acid, an acaricide, an active herbal extract, an age spot and keratose removing agent, an allergen, an alpha hydroxyl acid, an analgesic agent, an androgen, an anesthetic, an anti wrinkle agent, an antiacne agent, an antiaging agent, an antiallergic agent, an antiandrogen agent, an antiapoptotic agent, an antibacterial agent, an antibiotic, an antibiotic agent, an antiburn agent, an anticancer agent, an antidandruff agent, an antidepressant, an antidermatitis agent, an antiedemic agent, an antifungal agent, an antihelminth agent, an antihistamine, an anti-hyperkeratosis agent, an anti-infective agent, an antiinflammatory agent, an antiirritant, an antilipemic agent, an antimicrobial agent, an antimycotic agent, an antioxidant, an antiparasitic agent, an anti-photoaging agent, an anti-photodamaging agent, an antiproliferative agent, an antipruritic agent, an antipsoriatic agent, an antirosacea agent, an antiseborrheic agent, an antiseptic agent, an antiswelling agent, an antiviral agent, an anti-wart agent, an anti-wrinkle agent, an anti-yeast agent, an astringent, azelaic acid, benzoyl chloride, benzoyl peroxide, a beta-hydroxy acid, calcitriol, calcium hypochlorite, carbon, a cardiovascular agent, a chemotherapeutic agent, a corticosteroid, a dicarboxylic acid, a dihydrotestosterone inhibitor, a disinfectant, doxycycline, an estrogen, a fungicide, fumaric acid, glycolic acid, a hair growth regulator, a haptene, a herbal extract (comprising an active substance), a hormonal agent, a hormone, a hydroxy acid, an immunogenic substance, an immunomodulator, an immunoregulating agent, an immunostimulant, an immunosuppressant, an immunosuppressive agent, an insect repellent, an insecticide, iron oxide, a keratolytic agent, lactic acid, a lactam, lidocaine, a local anesthetic agent, a lubricating agent, a masking agent, a metal, a metal oxide, minocycline, a mitocide, mometasone fuorate, a neuropeptide, a non-steroidal anti-inflammatory agent, an organo-beryllium compound, an organo-metallic compound, an oxidizing agent, and organo-boron compound, a pediculicide, a peptide, a pesticide, a photodynamic therapy agent, a progesterone, a prostaglandin, a protein, a radical scavenger, a refatting agent, a retinoid, a sadative agent, a scabicide, sebacic acid, a sedative, a sedative agent, a self tanning agent, silicone oxide, silver, a silver compound, a skin protective agent, a skin whitening agent, a steroid, a steroid hormone, a steroidal anti-inflammatory agent, talc, titanium dioxide, a tellurium compound, a testosterone inhibitor, a tetracycline antibiotic, urea, a urea derivative, a vasoactive agent, a vasoconstrictor, a vasodilator, a vitamin, a vitamin A, a vitamin A derivative, a vitamin B, a vitamin B derivative, a vitamin C, a vitamin C derivative, a vitamin D, a vitamin D analog, a vitamin D derivative, a vitamin E, a vitamin E derivative, a vitamin F, a vitamin F derivative, a vitamin K, a vitamin K derivative, a wart remover, a wound healing agent, zinc oxide, zirconium oxide.

Encapsulation of an Active Agent

In one or more embodiments, the active agent is encapsulated, in particles, microparticles, nanoparticles, microcapsules, microspheres, nanocapsules, nanospheres, liposomes, niosomes, polymer matrix, silica-gel, graphite, nanocrystals or microsponges. Such particles can have various functions, such as (1) protection of the drug from degradation; (2) modification of the drug release rate from the composition; (3) control of skin penetration, profile; and (4) mitigation of adverse effects, due to the controlled release of the active agent from the encapsulation particles.

Solubility of an Active Agent

Solubility of the active agent, for example a steroid is an important factor in the development of a stable foamable composition according to the present invention.

For definition purposes, in the context of the present invention, the descriptive terminology for solubility according to the US Pharmacopoeia (USP 23, 1995, p. 10), the European Pharmacopoeia (EP, $5^{th}$ Edition (2004), page 7) and several other textbooks used in the art of pharmaceutical sciences (see for example, Martindale, The Extra Pharmacopoeia, $30^{th}$ Edition (1993), page xiv of the Preface; and Remington's Pharmaceutical Sciences, $18^{th}$ Edition (1990), page 208) is adapted:

| Descriptive Term | Parts of Solvent Required for 1 Part of Solute |
|---|---|
| Very soluble | Less than 1 |
| Freely soluble | From 1 to 10 |
| Soluble | From 10 to 30 |
| Sparingly soluble | From 30 to 100 |
| Slightly soluble | From 100 to 1,000 |
| Very slightly soluble | From 1,000 to 10,000 |
| Practically insoluble or Insoluble | 10,000 and over |

Thus, in one or more embodiments, the active agent is "soluble", "freely soluble" or "very soluble" (as defined above) in the composition. Yet, in certain cases, the active agent is "very slightly soluble", "slightly soluble" or "sparingly soluble" in the composition.

Yet, in one or more embodiments, the active agent is insoluble i.e., "requires 10,000 parts or more of a solvent to be solubilized", in the composition.

In certain embodiments it is desirable that the active agent is maximally soluble in the composition, because solubility of the active agents is expected to increase its bioavailability.

Yet, in certain preferred additional embodiments it is desirable that the active agent is insoluble or is partially soluble and all or part thereof is suspended in the composition, because, inter alia, its degradation is enhanced when it is dissolved. In such cases, the hydrophobic solvent is selected by (1) testing the solubility of said active agent in various hydrophobic solvents, followed by (2) inclusion in the composition of such solvents that do not solubilize the active agent. In one or more embodiments the active agent is presented as a suspension.

It is known that every chemical compound has different solubility in different solvents or compositions, and therefore it is not possible to provide a general list compounds that are not soluble or partially soluble or suspended in the composition. However, any active agent, as exemplified in the lists herein, is suitable as insoluble or partially soluble or suspended, if visual or microscopic observation demonstrates crystals or particles of such active agent in the oleaginous composition.

In one or more further embodiments the active agent is micronized, which can assist in delivery into the skin, mucosal membrane and body cavity surfaces and also aid homogenous distribution within the formulation. In effect, part of the active agent is presented to a target in soluble form and part is presented in insoluble form. As the soluble part is absorbed it may help to form a gradient in which insoluble agent replaces absorbed agent. In one or more embodiments insoluble agent is suspended. In one or more embodiments the suspension is homogenous. In certain embodiments the formulation is readily re-suspended and homogenous on shaking. In certain embodiments the agent is soluble.

In one or more embodiments the active agent is used to prevent a disease or disorder. In one or more embodiments the active agent is used to treat or alleviate a disease or disorder. In one or more embodiments the active agent is used to protect a target. An example of protection includes protection from radiation or the effects thereof.

Exemplary Groups of Active Agents
Antibiotics

In the context of the present disclosure, an antibiotic agent is a substance, that has the capacity to inhibit the growth of or to destroy bacteria and other microorganisms.

In one or more embodiments, the antibiotic agent is selected from the classes consisting beta-lactam antibiotics, aminoglycosides, ansa-type antibiotics, anthraquinones, antibiotic azoles, antibiotic glycopeptides, macrolides, antibiotic nucleosides, antibiotic peptides, antibiotic polyenes, antibiotic polyethers, quinoiones, antibiotic steroides, sulfonamides, tetracycline, dicarboxylic acids, antibiotic metals including antibiotic metal ions, oxidizing agents, a periodate, a hypochlorite, a permanganate, substances that release free radicals and/or active oxygen, cationic antimicrobial agents, quaternary ammonium compounds, biguanides, triguanides, bisbiguanides and analogs and polymers thereof, naturally occurring antibiotic compounds, including antibiotic plant oils and antibiotic plant extracts and any one of the following antibiotic compounds including non classified antibiotic compound analogs, derivatives, salts, ions, complexes and mixtures thereof.

Tetracyclines

According to some embodiments, the antibiotic agent is a tetracycline. The tetracyclines (also referred to herein as "tetracycline antibiotics") are a group of antibacterials, originally derived from certain *Streptomyces* spp., having the same tetracyclic nucleus, naphthacene, and similar properties. They are usually bacteriostatic but act by interfering with protein synthesis in susceptible organisms. Tetracycline antibiotics are susceptible to degradation by oxidation.

Tetracyclines include, but are not limited to, dihydrosteffimycin, demethyltetracycline, aclacinomycin, akrobomycin, baumycin, bromotetracycline, ectocyclin, chlortetracycline, clomocycline, daunorubicin, demeclocycline, doxorubicin, doxorubicin hydrochloride, doxycycline, lymecyclin, marcellomycin, meclocycline, meclocycline sulfosalicylate, methacycline, minocycline, minocycline hydrochloride, musettamycin, oxytetracycline, rhodirubin, rolitetracycline, rubomycin, serirubicin, steffimycin, tetracycline and analogs, salts and derivatives thereof.

Chlortetracycline, oxytetracycline, tetracycline, demeclocycline are all natural products that have been isolated from *Streptomyces* spp. The more recent tetracyclines, namely methacycline, doxycycline, and minocycline, are semisynthetic derivatives. Methacycline, like demeclocycline, has a longer half-life than tetracycline. Minocycline is active against some tetracycline-resistant bacteria, including strains of staphylococci. Both doxycycline and minocycline are more lipid-soluble than the other tetracyclines and they penetrate well into tissues. They are thus more suitable for incorporating into oily or emollient containing formulations. However, they have a place in the treatment of chlamydial infections, rickettsial infections such as typhus and the spotted fevers, mycoplasmal infections such as atypical pneumonia, pelvic inflammatory disease, Lyme disease, brucellosis, tularaemia, plague, cholera, periodontal disease, and acne. The tetracyclines have also been useful in the treatment of penicillin-allergic patients suffering from venereal, diseases, actinomycosis, bronchitis, and leptospirosis. Minocycline may sometimes be used in multidrug regimens for leprosy. Doxycycline may be used for the treatment and prophylaxis of malaria; it is also used in the management of anthrax.

In an embodiment the active ingredient may be any one of the following non limiting examples chlortetracycline, demeclocycline, doxycycline, lymecycline, meclocycline, methacycline, minocycline, oxytetracycline, rolitetracycline, tetracycline. In a preferred embodiment they are doxycyline or minocycline.

Tetracycline antibiotics can be incorporated into the formulations of the present invention to treat, ameliorate or prevent a multitude of disorders responsive to tetracycline antibiotics. The formulations can be applied topically to the skin or to the genitals or to mucosal, membranes and on and around the eye, sub-gingival and can be applied into a wide range of body cavities, including aural, digestive, oral, nasal, urethra, penal, endocervical, rectum, respiratory, and vaginal and tooth pocket. Non limiting examples of applications include eye infections, blepharitis, dry eye, inclusion conjunctivitis, glaucoma, inflammatory ocular conditions where bacterial infection or a risk of bacterial ocular infection exists, neuropathic atrophy (in diabetes), abrasions, injuries, wounds, burns, ulcers, pyoderma, furunculosis, granuloma inguinale, periodontitis, rosacea, post-operation infections and tissue reconstruction, trachoma, lymphogranuloma venereum, granuloma inguinale, acne, inflammation, sinusitis, neuro-protection, washing out, disinfection, and stabilization of body cavities, at on around or in the site of an operation, which for example can provide multiple therapeutic effects, such as, inhibition of post operation adhesions, anti infection, neuro-protection.

Whether delivered as a foam, gel, ointment or suspension the active pharmaceutical tetracycline can be present by weight in the range of about 0.2% to about 20%, or at about 0.2%, at about 0.3%, at about 0.4%, at about 0.5%, at about 0.6%, at about 0.7%, at about 0.8%, at about 0.9%, at about 1%, at about 1.5%, at about 2%, at about 2.5%, at about 3%, at about 3.5% at about 4%, at about 4.5%, at about 5%, at about 6%, at about 7%, at about 8%, at about 9%, at about 10%, at about 12%, or at about 14%, at about 16%, at about 18%, or at about 20%.

Tetracyclines Eye and Skin Infections

Tetracyclines have been used in ophthalmic ointments for the prevention or treatment of infections of the eye caused by s usceptible bacteria. Although minor skin infections and wounds usually heal without treatment, some minor skin wounds do not heal without therapy and it is impossible to determine at the time of injury which wounds will be self-healing. Therefore, some experts believe that, by reducing the number of superficial bacteria, topical anti-infectives are useful for preventing infection in minor skin injuries (e.g., cuts, scrapes, burns).

Tetracycline hydrochloride may be used topically in the treatment of inflammatory acne vulgaris. Tetracyclines are usually bacteriostatic in action, but may be bactericidal in high concentrations or against highly susceptible organisms.

Tetracyclines appear to inhibit, protein synthesis in susceptible organisms primarily by reversibly binding to 30S ribosomal subunits, thereby inhibiting binding of aminoacyl transfer-RNA to those ribosomes. In addition, tetracyclines appear to reversibly bind to 50S ribosomal subunits. There is preliminary evidence that tetracyclines also alter cytoplasmic membranes of susceptible organisms resulting in leakage of nucleotides and other intracellular components from the cell. At high concentrations, tetracyclines also inhibit mammalian protein synthesis.

The exact mechanisms by which tetracyclines reduce lesions of acne vulgaris have not been fully elucidated; however, the effect, appears to be partly the result of the antibacterial activity of the drugs. Following topical application to the skirt of a 0.22% solution of tetracycline hydrochloride in a vehicle containing n-decyl methyl sulfoxide (Topicycline®; no longer commercially available in the US), the drug inhibits the growth of susccptiblc organisms (principally *Propionibacterium acnes*) on the surface of the skin and reduces the concentration of free fatty acids in sebum. The reduction in free fatty acids in sebum may be an indirect result of the inhibition of lipase-producing organisms which convert triglycerides into free fatty acids or may be a direct result of interference with lipase production in these organisms. Free fatty acids are comedogenic and are believed to be a possible cause of the inflammatory lesions (e.g., papules, pustules, nodules, cysts) of acne. However, other mechanisms also appear to be involved because clinical improvement of acne vulgaris with topical tetracyclines does not necessarily correspond with a reduction in the bacterial flora of the skin or a decrease in the free fatty acid content of sebum. (Martindale Electronic Version 2007).

Tetracyclines, Solubility and Stability

Tetracyclines are known to be unstable in the presence of water, as well as numerous types of formulation excipients, such as protic solvents, various surfactants and certain oils. We surprisingly discovered that the inclusion of tetracyclines in a composition comprising a hydrophobic solvent and a foamer complex described herein results in a stable product, with extended stability of the tetracycline. In an embodiment a hydrophobic solvent is selected by (1) testing the solubility of said active agent in various hydrophobic solvents, (2) identifying those that do not solubilize the active agent followed by (3) inclusion in the composition of such solvents that do not solubilize the active agent. In certain embodiments the tetracycline is insoluble in the composition.

Doxycyline

According to some embodiments, the tetracycline is doxycycline. Doxycycline is a tetracycline antibiotic and also has anti-inflammatory and immunomodulatory effects. Doxycycline is a semisynthetic tetracycline antibiotic derived from oxytetracycline. In addition to antimicrobial activity, the drug has anti-inflammatory and immunomodulatory effects. It is available as Doxycycline calcium, doxycycline hyclate and doxycycline monohydrate. Doxycycline hyclate and doxycycline monohydrate occur as yellow, crystalline powders. The hyclate is soluble in water and slightly soluble in alcohol; the monohydrate is very slightly soluble in water and sparingly soluble in alcohol. Doxycycline calcium is formed in situ during the manufacturing process. Following reconstitution of doxycycline hyclate powder for IV administration with sterile water for injection, solutions have a pH of 1.8-3.3.

The mechanism(s) by which doxycycline reduces inflammatory lesions (papules and pustules) in patients has not been elucidated, but these effects may result at least in part from the anti-inflammatory actions of the drug; other mechanisms may be involved Doxycycline is used for the treatment of rosacea treatment or prophylaxis of anthrax (including inhalational anthrax [postexposure]), treatment of presumed or confirmed rickettsial infections, including Rocky Mountain spotted fever (RMSF), fever, ehrlichiosis, and anaplasmosis, and for the treatment of *Bartonella* infections, for the treatment of brucellosis, for the treatment of *Burkholderia* Infections, Chlamydial Infections, Lymphogranuloma venereum Psittacosis, Ehrlichiosis and Anaplasmosis, Gonorrhea and Associated Infections, Epididymitis, Proctitis, Granuloma Inguinale (Donovanosis,) Legionella Infections, Leptospirosis, Lyme Disease, Prophylaxis of Lyme Disease, Erythema Migrans, Early Neurologic Lyme Disease, Lyme Carditis, or Borrelial Lymphocytoma, Lyme Arthritis, Malaria, and prevention, Mycobacterial infections, *Mycobacterium marinum* Infections, Pelvic Inflammatory Disease, Parenteral Regimens, Plague, pleural Effusion, Rickettsial Infections, Q Fever, Syphilis, Tularemia, Treatment, Postexposure Prophylaxis.

When reconstituted and diluted with 0.9% sodium chloride or 5% dextrose, doxvcycline hyclate IV solutions containing 0.1-1 mg of doxycycline per ml are stable for 48 hours at 25° C.; when reconstituted and diluted with Ringer's, 10% invert sugar, Normosol-M® in D5W, Normosol-R® in D5W, Plasma-Lyte® 56 in 5% dextrose, or Plasma-Lyte® 148 in 5% dextrose, doxycycline hyclate IV solutions containing 0.1-1 mg/mL are stable for 12 hours at room temperature. The manufacturer states that doxycycline hyclate solutions prepared with any of these infusion solutions are stable for 72 hours at 2-8° C. when protected from direct sunlight and artificial light; however, after storage in this manner, infusion of these solutions must be completed within 12 hours Doxycycline hyclate IV solutions diluted to a concentration of 0.1-1 mg/mL with lactated Ringer's injection or 5% dextrose in lactated Ringer's injection must be infused within 6 hours to ensure stability. During infusion, all doxycycline hyclate IV solutions must be protected from direct sunlight. (Martindale 2007 Electronic Version). Thus it can be seen that Doxycycline is not stable for more than short periods of a matter of hours.

Preparations of doxycycline hyclate have an acid pH and incompatibility may reasonably be expected with alkaline preparations or with drugs unstable at low pH.

Doxycycline is more active than tetracycline against many bacterial species including *Streptococcus pyogenes*, enterococci, *Nocardia* spp., and various anaerobes. Cross-resistance is common although some tetracycline-resistant *Staphylococcus aureus* respond to doxycycline. Doxycycline is also more active against protozoa, particularly *Plasmodium* spp.

Doxycycline is a tetracycline derivative with uses similar to those of tetracycline. It may sometimes be preferred to other tetracyclines in the treatment of susceptible infections because of its fairly reliable absorption and its long half-life that permits less frequent (often once daily) dosing. It also has the advantage that it can be given (with care) to patients with renal impairment. However, relatively high doses may need to be given for urinary-tract infections because of its low renal excretion.

For relapsing fever and louse-borne typhus, for the prophylaxis of leptospirosis, for periodontiti, for Lymphatic filariasis, for Musculoskeletal and joint disorders and for the treatment of acne.

Minocycline

According to some embodiments, the tetracycline is minocycline. Minocycline hydrochloride is a semisynthetic tetracycline antibiotic derived from tetracycline. The drug is usually bacteriostatic in action; it exerts its antimicrobial activity by inhibiting protein synthesis. It is a yellow crystalline powder that is sparingly soluble in water; slightly soluble in alcohol; practically insoluble in chloroform and in ether; soluble in solutions of alkali hydroxides and carbonates. pH of a solution in water containing the equivalent of minocycline 1% is between 3.5 and 4.5. Preparations of minocycline hydrochloride have an acid pH and incompatibility may reasonably be expected with alkaline preparations or with drugs unstable at low pH.

Minocycle is highly sensitive and should be stored in airtight containers and protected from light to prevent degradation. Therefore use in foamable formulations stored in airtight sealed containers under pressure with propellant may contribute to preserving stability subject to selection of compatible canisters and accessories.

The instability of Minocycline was confirmed in a compatibility study described herein that demonstrated that different hydrophilic solvents were incompatible with minocyline. Whereas, hydrophobic emollients and waxes revealed compatibility with Minocyline, except for pomegranate seed oil.

All fatty alcohols, as well some fatty acids (such as stearic acid, oleic acid, palmitic acid) surfactants (sucrose fatty esters however not all of them dissolved in oil) and some additives (aerosil and menthol) were compatible with minocycline. Isostearic acid, ethocel and titanium dioxide polysorbates, spans, polyoxyethylene alkyl ethers (brij), PEG stearates (myrj) were not compatible.

Addition of water caused rapid degradation of minocycline and addition of antioxidants (alpha-tocopherol, BHA/BHT and propyl gallate) did not prevent such degradation. Thus compatible excipients became incompatible in the presence of water and addition of antioxidants did not remedy this result.

Surprisingly, it was found that enhanced penetration was achieved without the need of adding a hydrophilic solvent and thus degradation of minocyline could be further reduced or prevented. Minocycline was delivered intradermally at sufficient levels to treat skin infections but did not pass through the skin transdermally and therefore topical application should be free from adverse systemic effects.

UVB irradiation of the skin is known to decrease cell viability, total antioxidant capacity, while increasing the levels of inflammation (pro-inflammatory cytokines secretion) and epidermal cell apoptosis. Photosensitivity, manifested as an exaggerated sunburn reaction on areas of the body exposed to direct sunlight or ultraviolet light, has occurred with tetracyclines and Minocycline has been associated with pigmentation of the skin and other tissues.

It has surprisingly discovered that oleaginous formulations containing Minocycline had not only protective properties as known in the art but also therapeutic properties in the case of UVB-induced skin damage. Cell viability was increased and apoptosis was decreased in a dose-dependant manner when formulation was applied pre UVB irradiation. Apoptosis activation was significantly decreased when the formulation was applied post UVB irradiation of a skin organ culture. Thus, it may be able to reduce skin photodamage and photoaging, and more generally to reduce oxidative stress and inflammation in skin pathologies which are known to be accompanied by apoptotic cell death for example rosacea and impetigo. Furthermore the increase in viability of cells indicates that Minocycline has regenerative properties. Furthermore these properties and uses of minocycline may extend to other tetracycline antibiotics.

According to one or more embodiments the substantially surfactant-free oleaginous formulations comprising a tetracycline, such as, Minocycline have protective and therapeutic properties in the case of UVB-induced skin damage. According to one or more embodiments the substantially surfactant-free oleaginous formulations comprising a tetracycline, such as, Minocycline have properties selected from a list including anti-apoptotic, anti-inflammatory, anti-photodamaging and anti-photoaging. According to one or more embodiments the substantially surfactant-free oleaginous formulations comprising a tetracycline, such as, Minocycline have activity that decreases apoptosis and increases cell viability. According to one or more embodiments there are provided substantially surfactant-free oleaginous formulations comprising a tetracycline, such as, Minocycline for use to reduce oxidative stress and inflammation in skin pathologies which are known to be accompanied by apoptotic cell death for example rosacea and impetigo.

Minocycline has a spectrum of activity and mode of action similar to that of tetracycline but it is more active against many species including *Staphylococcus aureus*, streptococci, *Neisseria meningitidis*, various enterobacteria, *Acinetobacter, Bacteroides, Haemophilus, Nocardia*, and some mycobacteria, including *M. leprae*. It was found in an in-vitro study that Minocycline also inhibited the growth of *Streptococcus pyogenes, Pseudomonas aeruginosa, Staphylococcus aureus*, as well as a methicillin-resistant strain of *Staphylococcus aureus* (MRSA) and *Propionbacterium acnes*.

Partial cross-resistance exists between minocycline and other tetracyclines but some strains resistant to other drugs of the group remain sensitive to minocycline, perhaps because of better cell-wall penetration. Minocycline is a tetracycline derivative with uses similar to those of tetracycline. It is also a component of multidrug regimens for the treatment of leprosy and has been used in the prophylaxis of meningococcal infection to eliminate the carrier state, but the high incidence of vestibular disturbances means that it is not the drug of choice for the latter. It has neuroprotective properties. It is being investigated for motor neurone disease, for the management of Huntington's chorea. It is used in the treatment of rheumatoid arthritis and in the treatment of various skin disorders, including acne.

Steroids

In an embodiment, the active agent is a steroid. In certain embodiments the steroid is a corticosteroid, including but not limited to, hydrocortisone, hydroxyltriamcinolone, alpha-methyl dexamethasone, dexamethasone-phosphate, beclomethsone dipropionate, clobetasol valemate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methyl prednisolone, triamcinolone acetonide, cortisone, cortodoxone, flucetonide, fludrocortisone, difluorosone diacetate, fluradrenolone acetonide, medrysone, amcinafel, amcinafide, betamethasone and the balance of its esters, chloroprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylpropionate, hydrocortmate, mepreddisone, paramethasone, prednisolone, prednisone, beclomethasone dipropionate, triamcinolone, as well as analogs, derivatives, salts, ions and complexes thereof.

In certain embodiments, the steroid is a hormone or a vitamin, as exemplified by pregnane, cholestane, ergostane, aldosterone, androsterone, calcidiol, calciol, calcitriol, calcipotriol, clomegestone, cholesterol, corticosterone, cortisol, cortisone, dihydrotestosterone, ergosterol, estradiol, estriol, estrone, ethinylestradiol, fusidic acid, lanosterol, prednisolone, prednisone, progesterone, spironolactone, timobesone and testosterone, as well as analogs, derivatives, salts, ions and complexes thereof. For substances like calcitriol, very low amounts such as about 0.0001% to about 0.005% by weight, of foam formulation or gel or ointment or suspension, or about 0.0001%, about 0.0002%, about 0.0003%, about 0.0004%, about 0.0005%, about 0.0006%, about 0.0007%, about 0.0008%, about 0.0009%, about 0.001%, about 0.0011%, about 0.0012%, about 0.0013%, about 0.0014%, about 0.0015%, about 0.0016%, about 0.0017%, about 0.0018%, about 0.0019%, about 0.002%, about 0.003%, about 0.004%, about 0.005% by weight are effective. In some embodiments the active pharmaceutical agent, is delivered by more than one route, for example, topically and body cavity.

In an embodiment, the steroid is mometasone furoate. In certain embodiments it can be used topically to treat psoriasis and dermatitis. In certain other embodiments it can be applied in nasal administration to treat, disorders, such as, allergic rhinitis and asthma.

NSAID

In an embodiment, the active agent is a non-steroidal anti-inflammatory agent. In the context a nonsteroidal anti-inflammatory agent, (also termed herein "NSAID") is a pharmaceutically active compound, other than a corticosteroid, which affects the immune system in a fashion that results in a reduction, inhibition, prevention, amelioration or prevention of an inflammatory process and/or the symptoms of inflammation and/or the production pro-inflammatory cytokines and other pro-inflammatory mediators, thereby treating or preventing a disease that involves inflammation.

In one or more embodiments, the NSAID is an inhibitor of the cyclooxygenase (COX) enzyme. Two forms of cyclooxygenase are known today: the constitutive cyclooxygenase (COX-1); and the inducible cyclooxygenase (COX-2), which is pro-inflammatory. Thus, in one or more embodiments, the NSAID is selected from the group consisting of a COX-1 inhibitor, a COX-2 Inhibitor or a non-selective NSAID, which simultaneously inhibits both COX-1 and COX-2.

In one or more embodiments, the NSAID is salicylic acid a salicylic acid derivatives. Exemplary salicylic acid derivative include, in a non limiting fashion, aspirin, sodium salicylate, choline magnesium trislicylate, salsalate, diflunisal, salicylsalicylic acid, sulfasalazine, olsalazine, esters of salicylic acid with a carboxylic acid, esters of salicylic acid with a dicarboxylic acid, esters of salicylic acid with a fatty acid, esters of salicylic acid with a hydroxyl fatty acid, esters of salicylic acid with an essential fatty acid, esters of salicylic acid with a polycarboxylic acid, and any compound wherein salicylic acid is linked to an organic moiety through a covalent bond.

In one or more embodiments, the NSAID is para-aminophenol (e.g., acetaminophen) and salts and derivatives thereof.

In one or more embodiments, the NSAID is an indole or an indole-acetic acid derivative (e.g., indomethacin, sulindac, etodolac) and salts and derivatives thereof.

In one or more embodiments, the NSAID is an aryl acetic acids (e.g., tolmetin, diclofenac, ketorolac) and salts and derivatives thereof.

In one or more embodiments, the NSAID is an arylpropionic acid and salts and derivatives thereof. Exemplary arylpropionic acid derivative include, in a non limiting fashion, are ibuprofen, naproxen, flubiprofen, ketoprofen, fenoprofen, oxaprozin.

In one or more embodiments, the NSAID is anthranilic acids or an anthranilic acid derivative, also termed "fenamates" (e.g., mefenamic acid, meclofenamic acid) and salts and derivatives thereof.

In one or more embodiments, the NSAID is selected from the group of enolic acids, enolic acid salts, enolic acid esters, amides, anhydrides and salts and derivatives thereof. Non-limiting examples of enolic acid derivatives include oxicams (piroxicam, tenoxicam) and pyrazolidinediones (phenylbutazone, oxyphenthratrazone)

Yet, in additional embodiments, the NSAID is an alkanone (e.g., nabumetone).

Selective COX-2 inhibitors include, in an exemplary mariner diaryl-substituted furanones (e.g., Rofecoxib); diaryl-substituted pyrazoles (e.g., Celecoxib); indole acetic acids (e.g., Etodolac); and sulfonamides (e.g., Nimesulide) and salts and derivatives thereof.

Local Anesthetic Agents

In an embodiment, the active agent is a local anesthetic agent. Without limiting the scope, the anesthetic agent can be selected from the group consisting of benzocaine, lidocaine, bupivacaine, chlorprocaine, dibucaine, etidocaine, mepivacaine, tetracaine, dyclonine, hexylcaine, procaine, cocaine, ketamine, pramoxine, phenol, any pharmaceutically acceptable salts thereof and mixtures of such anesthetic agents. Any mixture of synergistically beneficial anesthetic agents is contemplated.

Keratolytically Active Agents

A keratolytic agent may be included as an active agent of a foamable composition. The term "keratolytically active agent" as used herein includes a compound that loosens and removes the stratum corneum of the skin, or alters the structure of the keratin layers of skin. Keratolytically active agents are used in the treatment of dermatological disorders that involve dry skill, hyperkeratinization (such as psoriasis), skin itching (such as xerosis), acne and rosacea.

Suitable keratolytically active agents include phenol and substituted phenolic compounds. Such compounds are known to dissolve and loosen the intracellular matrix of the hyperkeratinized tissue. As such, they are used in the treatment of dermatological disorders. Dihydroxybenzene and derivatives thereof have been recognized as potent keratolytic agents. Resorcinol (m-dihydroxybenzene) and derivatives thereof are used in anti-acne preparations. In addition to hydroquinone (p-dihydroxybenzene) having anti-pigmentation properties, hydroquinone is also known to be keratolytic. These compounds also exhibit antiseptic properties. Cresols also possess bactericidal and keratolytic properties.

Vitamin A and vitamin A derivatives, also termed herein "retinoids", such as retinoic acid, isoretinoic acid, retinol and retinal, as well as adapalene, tazarotene, isotretinoin, acitretin and additional retinoids known in the art of pharmaceuticals and cosmetics are another class of keratolytically active agents.

Another group of keratolytically active agents include alpha-hydroxy acids, such as lactic acid and glycolic acid and their respective salts and derivatives; and beta-hydroxy acids, such as salicylic acid (o-hydroxybenzoic acid) and salicylic acid salts and pharmaceutically acceptable derivatives.

Another class of keratolytically active agents includes urea and urea derivatives.

Immunomodulators

In an embodiment, the active agent is an immunomodulator. Immunomodulators are chemically or biologically-derived agents that modify the immune response or the functioning of the immune system. Immunomodulators suitable for use according to the present invention include, among other options, cyclic peptides, such as cyclosporine, tacrolimus, tresperimus, pimecrolimus, sirolimus, verolimus, laflurtimus, laquinimod and imiquimod, as well as analogs, derivatives, salts, ions and complexes thereof. Such compounds, delivered in the foam, are especially advantageous in skin disorders such as psoriasis, eczema and atopic dermatitis, where the large skin areas are to be treated.

Retinoids

In an embodiment, the active agent is a retinoid. Retinoids suitable for use according to the present invention include, among other options, retinol, retinal, retinoic acid, isotretinoin, tazarotene, adapalene, 13-cis-retinoic acid, acitretin all-trans beta carotene, alpha carotene, lycopene, 9-cis-beta-carotene, lutein and zeaxanthin, as well as any additional retinoids known in the art of pharmaceuticals and cosmetics; and analogs, derivatives, salts, ions and complexes thereof.

Anti-Acne and Anti-Rosacea Active Agents

In an embodiment, the active agent is an anti-acne or an anti-rosacea agent. The anti-acne agent can be selected from the group consisting of resorcinol, sulfur, salicylic acid and salicylates, alpha-hydroxy acids, nonsteroidal anti-inflammatory agents, benzoyl peroxide, retinoic acid, isoretinoic acid and other retinoid compounds, adapalene, tazarotene, azelaic acid and azelaic acid derivatives, antibiotic agents, such as minocycline erythromycin and clyndamyein, coal tar, zinc salts and complexes, and combinations thereof, in a therapeutically effective concentration.

Antipsoriasis Agents

In an embodiment, the active agent is an anti-psoriasis agent. Such anti-psoriasis agents can be selected, among other options, from the group of keratolytically-active agents, salicylic acid, coal tar, anthralin, corticosteroids, retinoids, photodynamic therapy agents, and vitamin D and derivatives and analogs thereof, including vitamin D3 derivatives or analogs such as calcitriol, calcipotriol.

Antiinfective Agents

In an embodiment, the active agent is an anti-infective agent. Such anti-infective agent can be selected from, the group of an antibiotic agent, an antibacterial agent, an antifungal agent, an agent that controls yeast, an antiviral agent and an antiparasitic agent. Exemplary antiinfective agents are exemplified by beta-lactam antibiotic, an aminoglycoside, an ansa-type antibiotic, an anthraquinone, an azole, metronidazole, an antibiotic glycopeptide, a macrolide, erythromycin, clindamycin, an antibiotic nucleoside, an antibiotic peptide, polymyxin B, an antibiotic polyene, an antibiotic polyether, an antibiotic quinolone, an antibiotic steroid, fucidic acid, mupirocin, chloramphenicol, a sulfonamide, tetracycline, an antibiotic metal, silver, copper, zinc, mercury, tin, lead, bismuth, cadmium, chromium, an oxidizing agent, iodine, iodate, a periodate, a hypochlorite, a permanganate, a substance that release free radicals and/or active oxygen, a cationic antimicrobial agent, a quaternary ammonium compound, a biguanide, chlorohexidine, a triguanide, a bisbiguanide, a polymeric biguanide and a naturally occurring antibiotic compound, as well as analogs, derivatives, salts, ions and complexes thereof.

The Foamable Composition Essential Ingredients as Active Agents

In certain embodiments, hydrophobic solvent possesses therapeutic properties on its own and therefore, it can be regarded as "active agent." For example, some essential oils kill microorganisms and can be effective in the treatment or prevention of conditions that involve microbial infection, such as bacterial, fungal and viral conditions. Additionally, the occlusive effect of hydrophobic solvents is useful for the treatment of conditions which involve damaged skin, such as psoriasis or atopic dermatitis. The combination of a hydrophobic solvent and a therapeutically effective fatty alcohol or fatty acid may afford a synergistic beneficial effect in conditions characterized, for example, by infection and/or inflammation.

Combination of Active Agents

Several disorders involve a combination of more than one etiological factor; and therefore, the use of more that, one active agents is advantageous. For example, psoriasis involves excessive cell proliferation and inadequate cell differentiation as well as inflammation. Atopic dermatitis involves keratinocyte growth abnormality, skin dryness and inflammation. Bacterial, fungal and viral infections involve pathogen colonization at the affected site and inflammation. Hence, in many cases, the inclusion of a combination of active agents in the foamable pharmaceutical composition can be desirable. Thus, in one or more embodiments, the foamable composition further includes at least two active agents, in a therapeutically effective concentration.

In an embodiment one of the active agents is a vitamin, a vitamin derivative or analogue thereof. In a preferred embodiment the vitamin, vitamin derivative or analogue thereof is oil soluble.

Microsponges

Microsponges (or microspheres) are rigid, porous and spongelike round microscopic particles of cross-linked polymer beads (e.g., polystyrene or copolymers thereof), each defining a substantially noncollapsible pore network. Microsponges can be loaded with an active ingredient and can provide a controlled time release of the active Ingredient to skin or to a mucosal membrane upon application of the formulation. The slow release Is intended to reduce irritation by the active agent. Microsponge® delivery technology was developed by Advanced Polymer Systems. In one or more embodiments the composition comprises one or more active agents loaded into Microsponges with a waterless carrier described herein, which may also comprise a modulating agent.

Fields of Applications

The foamable carrier of the present disclosure is suitable for treating any inflicted surface. In one or more embodiments, foamable carrier is suitable for administration to the skin, a body surface, a body cavity or mucosal surface, e.g., the cavity and/or the mucosa of the nose, mouth, eye, respiratory system, vagina, urethra or rectum and the ear canal (severally and interchangeably termed herein "target site").

The foamable carrier of the present disclosure is also suitable for preventing a disorder or disease prior to its onset. The foamable carrier comprising for example a tetracycline may be applied to a body surface or a body cavity to try and prevent apoptosis, a disorder or disease prior to onset thereof. For example, prior to an anticipated inflammatory reaction or risk thereof, or prior to an anticipated onset of apoptosis or a risk thereof, or prior to an anticipated onset of inflammatory cytokines or risk thereof prior to a medical procedure requiring intervention such as chemo therapy; radiotherapy, photodynamic therapy, laser therapy, etc. An simple example of prevention use is where the foam comprising a tetracycline (or the formulation prior to addition of propellant) is applied to the skin surface surrounding both eyes.

According to another embodiment a non-limiting list of disorders where a tetracycline antibiotic might be used to prevent a disease or disorder is provided, which includes prophylaxis of gonococcal and chlamydial ophthalmia, neonatal conjunctivitis, periodontal disease, postoperative tetracycline, prophylaxis in pregnancy termination, for prevention of skin rash/acneiform skin eruption during cancer therapy, intraoperative topical tetracycline sclerotherapy following mastectomy for prevention of postoperative mastectomy seromas etc.

By selecting a suitable active agent, or a combination of at least two active agents, the foamable composition of the present disclosure is useful in preventing or treating an animal or a human patient having any one of a variety of dermatological or mucosal diseases or disorders; in alleviating such diseases or disorders; or where such agent or agents have shown proficiency in preventative therapy in preventing such diseases or disorders, including but not limited to a bacterial infection, a benign tumor, a bullous disease, a burn, a chlamydia infection, a condition which respond to hormone therapy, a cut, a dermatitis, a dermatophyte infection, a dermatose, a disorder of a body cavity, a disorder of cornification, a disorder of the nose, a disorder of the penile urethra or ear canal, a disorder of the rectum, a disorder of the respiratory system, a disorder of the vagina, a disorder which responds to hormone replacement therapy, a disorder which, responds to transdermal nicotine administration, a disorders of hair follicles, a disorders of sebaceous glands, a disorders of sweating, a fungal infection, a gonorrhea infection, a gynecological disorders that respond to hormonal therapy, a malignant tumor, a non-dermatological disorder which responds to topical or transdermal delivery of an active agent, a parasitic infection, a pelvic inflammation, a pigmentation disorder, a scaling papular diseases, a sexual dysfunction disorder, a sexually transmitted disease, a vaginal disorder, a viral infection, a vulvar disorder, a vulvovaginal infection, a wound, a yeast infection, abscess, acne, acne conglobata, acne fulminans, acne scars, acne vulgaris, actinic keratosis, acute and chronic salpingitis, acute febrile neutrophilic dermatosis, acute lymphangitis, acute pelvic inflammatory disease, acute soft tissue injury, albinism, allergic contact dermatitis, alopecia, alopecia areata, alopecia totalis, alopecia universalis, an allergy, an anal abscess or fistula, an anal and rectal disease, an anal disorder, an anal fissure, an anal wart, an ear disorder, an hormonal disorder, an inflammatory reaction, an intra-vaginal or rectal sexually-transmitted and non-sexually-transmitted infectious disease, anal cancer, anal excoriation, anal fissures, anal itch, anal pruritus, anal soreness, anal warts, angiomas, arthritis, athlete's foot, atopic dermatitis, back pain, bacterial skin infections, bacterial vaginosis, baldness, basal cell carcinoma, benign tumors, blisters, bromhidrosis, bullous diseases, bullous pemphigoid, burn, calluses, calluses candidiasis, cancer of the cervix, cancer of the vagina, cancer of the vulva, candidal vaginitis, candidiasis, carbuncles, cellulitis, cervical cancer, cervicitis, chancroid, chemical burns, chicken pox, chloasma, cholesteatoma, cholinergic urticaria, chronic dermatitis, chronic effects of sunlight, cold sores, cold urticaria, comedones, constipation, contact dermatitis, corns, creeping eruption, Crohn's disease, cutaneous abscess, cutaneous larva migrans, cutaneous myiasis, dark spots, delusional parasitosis, Dercum disease, dermatitis, dermatitis herpetiformis, dermatofibroma, dermatological inflammation, dermatological pain, dermatophytoses, dermographism, diaper rash, drug eruptions and reactions, drug-induced hyperpigmentation, dyshidrotic eczema, dysmenorrhea, dyspareunia, dysplastic nevi, ecthyma, ectodermal dysplasia, ectopic pregnancy, eczema, endometriosis, endometritis, epidermal necrolysis, epidermoid cyst, erysipelas, erythema multiforme, erythema nodosum, erythrasma, exfoliative dermatitis, fallopian tube cancer and gestational trophoblastic disease, fecal incontinence, female orgasmic disorder, folliculitis, fungal nail infections, fungal skin infections, furuncles, gangrene, generalized exfoliative dermatitis, genital cancer, genital herpes, genital ulcer, genital warts, granuloma annulare, granuloma inguinale, gynecological neoplasms including endometrial cancer, head lice, hemorrhoids, hepatitis B, herpes, herpes simplex, hidradenitis suppurativa, hirsutism, HIV/AIDS, hives, human papillomavirus (HPV), hyperhidrosis, hyperpigmentation melasma, hypertrichosis, hypohidrosis, hypopigmentation, ichthyosis, impetigo, inflammatory acne, inflammatory reactions, ingrown nails, intertrigo, irritant contact dermatitis, ischemic necrosis, itching, jock itch, joint pain, Kaposi's sarcoma, keloid, keratinous cyst, keratoacanthoma, keratosis pilaris, lichen planus, lichen sclerosus, lichen simplex chronicus, linear immunoglobulin A disease, lipomas, localized pain in general, lymphadenitis, lymphangitis, lymphogranloma venereum, male pattern baldness, malignant melanoma, malignant tumors, mastocytosis, measles, melanoma, midcycle pain, midcycle pain due to ovulation, miliaria, mittelschmerz, moles, molluscum contagiosum, MRSA, mucopurulent cervicitis (MPC), muscle pain, necrotizing fasciitis, necrotizing myositis, necrotizing subcutaneous infection, necrotizing subcutaneous infections, nodular papulopustular acne, nongonococcal urethritis (NGU), non-inflammatory acne, nummular dermatitis, oophoritis, oral herpes, osteoarthritis, osteoarthritis, ovarian cancer, ovarian cysts and masses, paget's disease of the nipples, panniculitis, papules, parapsoriasis paronychia, parasitic infections, parasitic skin infections, paronychial infection, pediculosis, pelvic congestion syndrome, pelvic inflammatory disease, pelvic pain, pemphigus, perianal pruritus, perianal thrash, perioral dermatitis, photo-allergy, photo-damage, photo-irritation, photosensitivity, pigmentation disorders, pimples, pityriasis Lichenoides, pityriasis rosea, pityriasis rubra pilaris, poison ivy, poison oak, polyps of the colon and rectum, postinflammatory hyperpigmentation, postinflammatory hypopigmentation, post-operative or post-surgical skin conditions, premenstrual syndrome, pressure sores, pressure ulcers, pressure urticaria, pruritis, pruritus ani, pseudofolliculitis barbae, psoriasis, PUPPP, purpura, pustules, pyogenic granuloma, rash, reactions to sunlight, rectal abscess, rectal fistula, rheumatic pain, ringworm, rosacea, roseola, rubella, salpingitis, scabies, scalded skin syndrome, scaling papular diseases, scarring, scleroderma, sebaceous cyst, seborrheic dermatitis, seborrheic keratoses, seborrheic keratosis, sexual arousal disorder, shingles, skin aging, skin cancer, skin neoplasia, skin neoplasms, skin rash, skin tags, skin ulcers, sports injuries, squamous cell carcinoma, staphylococcal scalded skin syndrome, stasis dermatitis, Stevens-Johnson syndrome, sun spots, sunburn, thermal burns, tinea corporis, tinea cruris, tinea pedis, tinea versicolor, toxic epidermal necrolysis, trauma or injury to the skin, *Trichomonas vaginalis*, trichomoniasis, vaginal cancer, vaginal dryness, vaginismus, varicella, zoster virus, viral skin infections, vitamin D deficiency, vitiligo, vulvar cancer, vulvar disorders, vulvar dystrophy, vulvar intraepithelial neoplasia (VIN), vulvar pain, vulvodynia, warts, water hives, wrinkles, xerosis, yeast skin infections, zoster Likewise, the foamable composition of the present disclosure is suitable for preventing or treating a disorder of a body cavity or mucosal surface, e.g., the mucosa of the nose, mouth, eye, ear, respiratory system, vagina, urethra, or rectum. Non limiting examples of such conditions include chlamydia infection, gonorrhea infection, hepatitis B, herpes, HIV/AIDS, human papillomavirus (HPV), genital warts, bacterial vaginosis, candidiasis, chancroid, granuloma Inguinale, lymphogranloma venereum, mucopurulent cervicitis (MPC), molluscum contagiosum, nongonococcal urethritis (NGU), trichomoniasis, vulvar disorders, vulvodynia, vulvar pain, yeast infection, vulvar dystrophy, vulvar intraepithelial neoplasia (VTN), contact dermatitis, pelvic inflammation, endometritis, salpingitis, oophoritis, genital cancer, cancer of the cervix, cancer of the vulva, cancer of the vagina, vaginal dryness, dyspareunia, anal and rectal disease, anal abscess/fistula, anal cancer, anal fissure, anal warts, Crohn's disease, hemorrhoids, anal itch, pruritus ani, fecal incontinence, constipation, polyps of the colon and rectum.

In an embodiment of the present disclosure, the composition is useful for the treatment of an infection. In one or more embodiments, the composition is suitable for the treatment of an infection, selected from the group of a bacterial infection, a fungal infection, a yeast infection, a viral infection and a parasitic infection.

In an embodiment of the present disclosure, the composition is useful for the treatment of wound, ulcer and burn. This use is particularly important since the composition of the present disclosure creates a thin, semi-occlusive layer, which coats the damaged tissue, while allowing exudates to be released from the tissue.

The composition of the present disclosure is also suitable for administering a hormone to the skin or to a mucosal membrane or to a body cavity, in order to deliver the hormone into the tissue of the target organ, in any disorder that responds to treatment with a hormone.

In one embodiment the disorder is an inflammation, skin inflammation, acne, rosacea, actinic keratosis, skin cancer, a local pain, joint pain and osteoarthritis; the active agent is a nonsteroidal anti-inflammatory drug, given at a therapeutically effective concentration.

In light of the hygroscopic nature of the composition, it is further suitable for the treatment and prevention of post-surgical adhesions. Adhesions are scars that form abnormal connections between tissue surfaces. Post-surgical adhesion formation is a natural consequence of surgery, resulting when tissue repairs itself following incision, cauterization, suturing, or other means of trauma. When comprising appropriate protective agents, the foam is suitable for the treatment or prevention of post surgical adhesions. The use of foam, is particularly advantageous because foam can expand in the body cavity and penetrate into hidden areas that cannot be reached by any other alternative means of administration.

Cosmetic Use

In one or more embodiments, the composition may be used for cosmetic use. For example it may be used as part of a cosmetic formulation to prevent a cosmetic disorder or to improve the skin. Alternatively it may be used with cosmetic effect for example as a cosmetic remover. It can be dispensed in small quantities as a foam targeted to a surface and applied locally with mechanical force causing the foam to break.

Route of Administration

The formulations disclosed herein can be applied to the target site as a foam. In one or more alternative embodiments the formulations are prepared without propellant and are applied as a gel or ointment, for example, with the tetracycline as a suspension. Application can be hourly, 2 hourly, 3 hourly, four hourly, six hourly or eight hourly, twelve hourly, daily, alternate-day or intermittent, as necessary. For reasons of compliance less frequent applications, where possible are preferable such as twice-daily or daily single applications. In cases where prolonged or long term treatment is required a higher initial dose is provided followed by a gradual reduction to a lower maintenance dose, which can be increased if further outbreaks occur.

The formulations are suitable for administration directly or indirectly to an inflicted area, in need of treatment, through the following routes of administration:

1. Topical administration: for local effect, it is applied directly where its action is desired;
2. Enteral: when the desired effect is systemic (non-local), it is given via the digestive tract; and
3. Parenteral: when the desired effect is systemic, it is given by other routes than the digestive tract The following list more specifically exemplifies some routes of administration.

1. Topical

Topical administration is any form of administration that reaches a body organ topically, such as epicutaneous administration (application onto the skin), inhalation, enema, eye drops (onto the conjunctiva), ear drops, intranasal (into the nose) and vaginal.

Exemplary dosage forms that are suitable for topical administration of the stable formulations, such as tetracycline formulations include cream, gel, liniment, lotion, ointment, paste, spray, foam, mousse, lacquer (e.g., for nail treatment) and transdermal patch. Additionally, topical vaginal dosage forms may include a douche, an intrauterine device, a pessary (vaginal suppository), a vaginal ring and a vaginal tablet. Rectal dosage forms include enema and suppositories. Inhaled dosage forms include aerosol inhalers, metered dose inhalers and solutions for nebulizer. Ophthalmic dosage forms include eye drop (solution or suspension), ophthalmic gel and ophthalmic ointment. In a preferred embodiment the dosage form is a foam that is thermally stable and breakable under shear force but is not "quick breaking" which allows comfortable application and well directed administration to the target area, 2. Enteral Enteral is any form of administration that involves any part of the gastrointestinal tract by mouth (orally), as buccal or sublingual tablets, capsules, suspensions, solutions, powder or drops; by gastric feeding tube, duodenal feeding tube, or gastrostomy; and rectally, in suppository or enema form.

3. Parenteral by Injection or Infusion

Intravenous (into a vein); intraarterial (into an artery); intramuscular (into a muscle); intracardiac (into the heart); subcutaneous (under the skin); intraosseous infusion (into the bone marrow); intradermal, (into the skin itself); intrathecal (into the spinal canal); and intraperitoneal (into the peritoneum).

4. Other Parenteral

Transdermal (diffusion through the intact skin); transmucosal (diffusion through a mucous membrane), e.g. insufflation (snorting), sublingual, buccal (absorbed through cheek near gumline) and vaginal; and inhalational; epidural (synonym: peridural) (injection or infusion into the epidural space); and intravitreal.

EXAMPLES

The invention is described with reference to the following examples, in a non-limiting manner. The following examples exemplify the foamable compositions and methods described herein. The examples are for the purposes of illustration only and are not intended to be limiting. Many variations will suggest themselves and are within the full intended scope.

Example 1

General Manufacturing Procedures

The following procedures are used to produce the foam samples described in the examples below, in which only the steps relevant to each formulation are performed depending on the type and nature of ingredients used.

Step 1: Hydrophobic solvents such as mineral oils are mixed at room temperature. Others solvents such as silicones, if present, are added at room temperature under mixing until formulation homogeneity is obtained.

Step 2: The formulation is warmed to 70-80° C. and solid compounds such as fatty alcohols, fatty acids and waxes are added and mixed until complete dissolution.

Step 3: The formulation is cooled down to 30-40° C. and active agents if present, and water if present are added under mixing until formulation homogeneity is obtained.

Step 4: The formulation is packaged in aerosol canisters which are crimped with a valve, pressurized with propellant and equipped with an actuator suitable for foam dispensing. Optionally a metered dosage unit can utilized, to achieved delivery of repeatable measured doses of foam.

Materials

TABLE 1

Exemplary possible ingredients suitable for the production of foamable compositions disclosed herein. Equivalent materials from other manufacturers can also be used satisfactorily.

| Chemical Name | Function | Commercial Name | Supplier |
| --- | --- | --- | --- |
| 1,3-Butandiol | Solvent | Butylene Glycol | Sigma-Aldrich |
| Aluminum Starch Octenylsuccinate | Absorbent | Aluminum Starch Octenylsuccinate | National Starch |
| Alpha-tocopherol | Antioxidant | Alpha-tocopherol | Sigma-Aldrich |
| Beeswax white | Foam adjuvant | Beeswax white | Henry Lamotte |
| Behenyl alcohol | Foam adjuvant | Lanette 22 | Cognis |
| Benzyl alcohol | Preservative | Benzyl alcohol emprove | Merck |
| Betamethasone 21-valerate | Active agent | Betamethasone 21-valcrate | BP commission laboratory |
| BHA | Antioxidant | Butylhydroxyanisole | Merk |
| BHT | Antioxidant | Butylated Hydroxitoluene | Spectrum |
| C12-15 Alkyl Lactate | Emollient | C12-15 Alkyl Lactate | A&E Connock |
| Calcitriol | Active agent | Calcitriol | Solvay Pharmaceutical BV |
| Castor oil | Solvent | Castor oil | Fluka |
| Ceteareth-20 | Surfactant | Sympatens acs 200G | Colb |
| Cetearyl alcohol & coconut alcohol | Surfactant | Montanov S | Seppic |
| Cetearyl octanoate | Solvent | Luvitol EHO | BASF |
| Ceteth-2 | Surfactant | Lipocol C-2 | Lipo |
| Cetostearyl alcohol | Foam adjuvant | Speziol C16-C18 | Cognis |
| Cetyl alcohol | Foam adjuvant | Speziol C16 | Cognis |
| Cholesterol | Wax | Cholesterol | Spectrum |
| Cocoglycerides | Solvent | Novata A | Cognis |
| Coconut oil | Solvent | Coconut oil | Henry Lamotte |
| Cyclomethicone-5 | Solvent | ST-cyclomethicone-5 | Dow |
| Diethylene glycol monoethyl ether | Solvent | Transcutol | Gattefosse |
| Diisopropyl adipate | Solvent | Isoadipate | Symrise GmbH |
| Dimethyl Isosorbide | Solvent | Dimethyl Isosorbide | Dotticon |
| Dimethyl Sulfoxide | Solvent | Dimethyl Sulfoxide | Fluka |
| Doxycycline Hyclate | Active agent | Doxycycline Hyclate | Yangzhou |
| Ethanol Absolute | Solvent | Ethanol Absolute | J. T. Baker |
| Ethylcellulose | Polymer | EC-Ethocel 100 cP FP | Colorcon Dow |
| Gelled mineral oil | Solvent | Versagel M 750 | Penreco |
| Glycerin | Solvent | Glycerin | Cognis |
| Glyceryl monostearate | Surfactant | Cutina GMS V PH | Cognis |
| Hard Fat | Wax | Softisan 378 | Sasol |
| Heavy Mineral Oil | Solvent | Paraffin oil liquid heavy | Gadot |
| Hexylene Glycol | Solvent | Hexylene Glycol | Sigma-Aldrich |

TABLE 1-continued

Exemplary possible ingredients suitable for the production of foamable compositions disclosed herein. Equivalent materials from other manufacturers can also be used satisfactorily.

| Chemical Name | Function | Commercial Name | Supplier |
| --- | --- | --- | --- |
| Hydrogenated castor oil | Foam adjuvant | Cutina HR | Cognis |
| Isododecane | Solvent | AB117128 | ABCR GmbH & Co. KG |
| Isopropyl myristate | Solvent | Isopropyl Myristate Ph. | Cognis |
| Isostearic acid | Foam adjuvant | Isostearic acid | Stearinerie Dubois |
| Isostearyl alcohol | Solvent | Prisorine 3515 | Croda |
| Lanolin | Foam adjuvant | Lanolin | Spectrum |
| Laureth-4 | Surfactant | Dehydol LS 4 DEO N | Cognis |
| Light Mineral Oil | Solvent | Pioner 2076P | Hansen & Rosenthal |
| MCT Oil | Solvent | Captex 355 | Abitec |
| Menthol | Additive | Menthol | Premium Ingredients Int. |
| Methyl glucose sesquistearate | Surfactant | Tego Care PS | Evonik Goldeshmidt |
| Metroidazole | Active agent | Metroidazole | Galdetma |
| Minocycline HCl | Active agent | Minocycline HCl | Hovione |
| Mometasone Furoate | Active agent | Mometasone Furoate | Sicor de Mexico |
| Myristyl alcohol | Foam adjuvant | Speziol C14 | Cognis |
| Naproxen | Active agent | | |
| Octyldodecanol | Solvent | Eutanol G | Cognis |
| Oleth-20 | Surfactant | Emulgin O 0 S | Cognis |
| Oleyl alcohol | Solvent | HD Eutanol V PH | Cognis |
| Oleic acid | Solvent | Oleic acid | Spectrum |
| Palmetic acid | Foam adjuvant | Edenor C16 98-100GW | Cognis |
| Paraffin wax 42-44 | Wax | Paraffin 42-44 | Merck |
| Paraffin wax 51-53 | Wax | Paraffin 51-53 | Merck |
| Paraffin wax 58-62 | Wax | Paraffin 58-62 | Merck |
| PEG-100 Stearate | Surfactant | Myrj 59 P | Croda |
| PEG-150 distearate | Surfactant | Emulgin EO 33 | Cognis |
| PEG-40 Hydrogenated castor oil | Surfactant | Emulgin HRE 40 | Cognis |
| PEG-40 Stearate | Surfactant | Myrj 52 S | Croda |
| PEG-75 Lanolin | Surfactant | SOLULAN 75 | Lubrizol |
| Polyethylene glycol-200 | Solvent | PEG 200 | Merck |
| Polyethylene glycol-400 | Solvent | PEG 400 | Sigma-Aldrich |
| Polysorbate 20 | Surfactant | Tween 20 | Merck |
| Polysorbate 60 | Surfactant | Tween 60 | Merck |
| PPG 15 stearyl ether | Solvent | Arlamol E | Uniqema |
| PPG-20 Methyl Glucose Ether Distearate | Humectant | Glucam P20 Distearate | Lubrizol |
| PPG-20-methyl glucose ether | Humectant | Glucam P-20 | Lubrizol |
| Progesterone | Active agent | Progesterone | Changzhou jiaerke pharmaceuticals |
| Propane/Isobutane/Butane (20:78:2) | Propellant | A-46 | Aeropress |
| Propane/Isobutane/Butane (55:18:27) | Propellant | AP-70 | Aeropress |
| Propyl gallate | Antioxidant | Propyl gallate | Sigma-Aldrich |
| Propylene glycol | Solvent | Propylene glycol | Gadot |
| Silica, Surface modified | Dispersant | Aerosil R 972 PH | Evonik-Goldschmidt GmbH |
| Sorbitan monopalmitate | Surfactant | SPAN 40 | Spectrum |
| Sorbitan monostearate | Surfactant | SPAN 60 | Uniqema |
| Sorbitan monooleate | Surfactant | SPAN 80 | Spectrum |
| Sorbitan sesquistearate | Surfactant | Tego care PS | Degussa |
| Soybean oil | Solvent | Soybean oil | Spectrum |
| Steareth-2 | Surfactant | Brij 72 | Spectrum |
| Steareth-21 | Surfactant | Brij 721 | Spectrum |
| Stearic acid | Foam adjuvant | Edenol ST1M | Cognis |
| Stearyl Alcohol | Foam adjuvant | Speziol C18 | Cognis |
| Sucrose stearic acid estersD1803 | Surfactant | Surfhope SE D1803 | Mitsubishi |
| Sucrose stearic acid estersD1807 | Surfactant | Surfhope SE D1807 | Mitsubishi |
| Sucrose stearic acid estersD1811 | Surfactant | Surfhope SE D1811 | Mitsubishi |
| Sucrose stearic acid estersD1813 | Surfactant | Surfhope SE D1813 | Mitsubishi |
| Terbinafine HCl | Active agent | Terbinafine HCl | Taro |
| Titanium dioxide | — | Kemira AFDC | Kemira |
| White Petrolatum (hard) | Carrier | Vaseline codex GAL | Aiglon |
| White Petrolatum (soft) | Carrier | Sofmetic LMF | MMP |

Canisters Filling and Crimping

Each aerosol canister is filled with the pre-foam formulation ("PFF", i.e., foamable carrier) and crimped with valve using vacuum crimping machine. The process of applying a vacuum will cause most of the oxygen present to be eliminated. Addition of hydrocarbon propellant may, without being bound by any theory, further help to reduce the likelihood of any remaining oxygen reacting with the active ingredient. It may do so, without being bound by any theory, by one or more of dissolving in, to the extent present, the oil or hydrophobic phase of the formulation, by dissolving to a very limited extent in the aqueous phase, by competing with some oxygen from the formulation, by diluting out any oxygen, by a tendency of oxygen to occupy the dead space, and by oxygen occupying part of the space created by the vacuum being the unfilled volume of the canister or that remaining oxygen is rendered substantially ineffective in the formulation.

Pressurizing & Propellant Filling

Pressurizing is carried out using a hydrocarbon gas or gas mixture. Canisters are filled and then warmed for 30 seconds in a warm bath at 50° C. and well shaken immediately thereafter.

TESTS

By way of non-limiting example the objectives of hardness, collapse time and freeze-thaw cycle ("FTC") stability tests are briefly set out below as would be appreciated by a person of skill in the art.

Collapse Time

Collapse Time, which is the measure of thermal stability, is examined by dispensing a given quantity of foam and photographing sequentially its appearance with time during incubation at 36° C. The collapse time result is defined as the time when the foam height reaches 50% of its initial height or if the foam has not yet reached 50% of its initial height after say 180 seconds then the collapse time is recorded as being >180. By way of illustration one foam may remain at 100% of its initial height for three minutes, a second foam may reach 90% of its initial height after three minutes, a third foam may reach 70% of its initial height after three minutes, and a fourth foam may reach 51% of its initial height after three minutes, nevertheless in each of these four cases the collapse time is recorded as >180 seconds since for practical purposes for easy application by a patient to a target the majority of the foam remains intact for more than 180 seconds. If the foam for example reaches 50% of its original height after say 100 seconds it would be recorded as having a collapse time of 100 seconds. It is useful for evaluating foam products, which maintain structural stability at skin temperature for at least 1 minute. Foams which are structurally stable on the skin, for at least one minute are termed "short, term stable" carriers or foams.

Alternatively, a Simple Collapse Time can be assessed by placing a foam sample on the warm fingers of a volunteer and measuring the time it takes to melt on the fingers.

Density

In this procedure, the foam product is dispensed into vessels (including dishes or tubes) of a known volume and weight. Replicate measurements of the mass of foam filling the vessels are made and the density is calculated. The canister and contents are allowed to reach room temperature. Shake the canister to mix the contents and dispense and discard 5-10 mL. Then dispense foam into a pre-weighed tube, filling it until excess is extruded. Immediately remove (level off) excess foam at both ends and weigh the filled tube on the weighing balance.

Viscosity

Viscosity is measured with Brookfield LVDV-H+ PRO with spindle SC4-25 at ambient temperature and 10, 5 and 1 RPM. Viscosity is usually measured at 10 RPM. However, at about the apparent upper limit for the spindle of ~>50,000 CP, the viscosity at 1 RPM may be measured, although the figures are of a higher magnitude. Unless otherwise stated viscosity of the pre-foam formulation (PFF) is provided. It is not practical to try and measure the viscosity of the foamable formulation with regular propellants since they have to be stored in sealed pressurized canisters or bottles. In order to simulate the viscosity in the foamable formulations with propellant an equivalent weight of pentane (a low volatile hydrocarbon) is added to and mixed with the pre-foam formulation and left overnight. The viscosity is then measured as above.

FTC (Freeze Thaw Cycles)

Foam appearance under extreme conditions of repeated heating and cooling is evaluated by cycling through cooling, heating, (first cycle) cooling, heating (second cycle) etc., conditions, commencing with −10° C. (24 hours) followed by +40° C. (24 hours) and measuring the appearance following each cycle. The cycle is repeated for up to three times.

Chemical Stability

The amount of active agent present is analyzed chromatographically in foam released from various pressurized canisters. Analysis is carried out at baseline and at appropriate time intervals thereafter. The canisters are typically stored in controlled temperature incubators at one or more of 5° C., 25° C. and 40° C. At appropriate time intervals canisters are removed and the amount of active agent in the foam sample is measured.

Bubble Size

Foams are made of gas bubbles entrapped in liquid. The bubble size and distribution reflects in the visual texture and smoothness of the foam. Foam bubbles size is determined by dispensing a foam sample on a glass slide, taking a picture of the foam surface with a digital camera, equipped with a macro lens. The diameter of about 30 bubbles is measured manually relatively to calibration standard template. Statistical parameters such as mean bubble diameter, standard deviation and quartiles are then determined. Measuring diameter may also be undertaken with image analysis software. The camera used was a Nikon D40X Camera (resolution 10 MP) equipped with Sigma Macro Lens (ref: APO MACRO 150 mm F2.8 EX DCs HSM). Pictures obtained are cropped to keep a squared region of 400 pixels×400 pixels.

Shakability

Shakability represents she degree to which the user is able to feel/hear the presence of the liquid contents when the filled pressurized canister is shaken. Shaking is with normal mild force without vigorous shaking or excessive force. When the user cannot sense the motion of the contents during shaking the product may be considered to be non-shakable. This property may be of particular importance in cases where shaking is required for affecting proper dispersion of the contents.

| Table of Shakability scoring | |
|---|---|
| Good shakability (conforms to required quality specification) | 2 |
| Moderate shakability (conforms to required quality specification) | 1 |
| Not shakable (fails to meet required quality specification) but may still be flowable and allow foam formation of quality | 0 |
| Is substantially not able to pass through valve | Block |

Aging by Centrifugation:

1. Principle of test

The centrifugation used in this procedure serves as a stress condition simulating the aging of the liquid formulation under investigation. Under these conditions, the centrifugal force applied facilitates coalescence of dispersed globules or sedimentation of dispersed solids, resulting in loss of the desired properties of the formulation.

2. Procedure 2.1. Following preparation of the experimental formulation/s, allow to stand at room temperature for ≥24 h (hour).

2.2. Handle pentane in a chemical hood. Add to each experimental formulation in a 20-mL glass vial a quantity of pentane equivalent to the specified quantity of propellant for that formulation, mix and allow formulation to stand for at least 1 h and not more than 24 h.

2.3. Transfer each mixture to 1.5 ml microtubes. Tap each microtube on the table surface to remove entrapped air bubbles.

2.4. Place visually balanced microtubes in the centrifuge rotor and operate the centrifuge at say 1,000 rpm for 5 min or 10 min. The centrifuge can be a BHG HEMLE Z 231 M.

2.5. Centrifugation can also be executed at a higher rpm for a shorter period or a lower rpm for a longer period bearing in mind the G-force experienced by the formulations is many fold greater than the one G to which a formulation would be exposed to during its shelf life. Centrifugation can also be executed at a higher rpm for the same period, say 3000 or 10,000 rpm to simulate an extremely high stress level.

Penetration

Transdermal penetration of Minocycline was tested using the Franz cell in-vitro diffusion system. This system is commonly used to test the delivery of drugs through the skin from semisolid topical dosage forms. Pig skin was used according to the OECD Draft, New Guideline 428, since pig skin shows similar permeation characteristics to human skin. The following experimental parameters were employed:

1. Two formulations were tested: 244 foam, with 1% minocycline and 244 foam with 4% minocycline. The two carrier formulations were unchanged accept that the amount of mineral, oil was reduced by 3% to allow for the increase in minocycline.
2. Vertical Franz diffusion cells were used (PermeGear, 1.77 cm$^2$ area, 14 ml receptor fluid).
3. 6 cells were used to test the 4% formulation, 5 cells were used to test the 1% formulation and one cell was used as a "negative control" (without any applied sample). Approximately 500 mg of product was placed in each cell. [Note the amount per skin area was calculated to be about three times more than an amount that might be applied clinically, namely for 244 with 4% minocycline 300 mg by weight of foam product which comprises about 12 mg of minocycline.]
4. The receiving compartments were sampled at baseline and 3, 6, 9 and 24 hours following application. At the 24 hours time point the skin was processed as follows:
    Residues of materials were removed from the skin using filter paper, followed by stripping the skin once using adhesive tape "Scotch Magic® Tape", 3M.
    Sequential 19 tapes (9 and 10) were transferred into two separate vials with 3 mL extraction solution ("Stratum Corneum 1" and "Stratum Corneum 2").
    The circular skin area (1.77 cm2) was cut and transferred to a 3 mL extraction solution (Viable skin—VS samples) vial.
5. The amount of active agent present was analyzed chromatographically: About 1 g of foam or pre-foam formulation is dissolved in 25 mL while mixing. The sample solution is filtered with PTFE 0.2 μm filter. The filtrate is analyzed by UPLC using a C-18 column; elution is performed with a mobile phase containing 0.1M Ammonium oxalate:0.01M EDTA:DMF:THF, 60:18:12:8(v/v). Note DMF is dimethylformamide and THF is tetrahydrofurane. The content of MCH and of 4-Epimer is calculated using the ratio between MCH peak area response in the sample solution and the average response area of MCH peak in the working standard solution present at a similar concentration.

Residence on the Skin

The degradation of active pharmaceutical ingredient, namely, minocycline was assessed following exposure to pig skin. Formulation 232A, containing 1% minocycline was applied to freshly retrieved porcine dermatomed skin and samples of the foam were analyzed chromatographically for both minocycline and a known 4-Epi degradation product at the start and then after 1, 3 and 6 hours of exposure.

Microbiological Tests a) Microbial load: Testing was performed according to EP 2.6.12 and 2.6.13 as described in the European Pharmacopea.

b) Preservative efficacy: Testing was performed according to USP <51> and EP 5.6, 2007 5.1.3. as described in the European and U.S. Pharmacopea.

The test consists of challenging the product with specified microorganisms, storing the inoculated preparations at a prescribed temperature, removing the inoculated samples at specified intervals of time and counting the number of viable organisms in the withdrawn samples using a plate-count procedure. Formulations were challenged by introducing the following microorganisms:

*Escherichia coli* (ATCC no. 8739)
*Staphylococcus aureus* (ATCC no. 6538)
*Pseudomonas aeruginosa* (ATCC no. 9027)
*Candida albicans* (ATCC no. 10231)
*Aspergillus niger* (ATCC no. 16404)

The number of colony-forming units (cfu/g) determined at each incubation time point was compared to the number of cfu/g measured in non-inoculated control samples. In order to verify that the samples tested are free of microbial contaminants, the microbial load (base-line) in the samples was determined prior to preservative efficacy testing. Study results are expressed as the number of surviving microorganisms (cfu/g).

c) Water Activity (Aw): The test for water activity was performed on pre-foam formulation samples introduced into the measuring cell of a PAWKIT water activity meter from DECAGON.

d) In-vitro effect on microbial growth: The tested microorganism is grown on Tryptic Soy Agar Slants. After incubation, the bacteria is harvested using sterile buffer phosphate pH 7.0, to obtain a microbial count, of about $10^4$ cfu/ml. 0.2 ml of the above suspension is spread on Letheen Agar plate and put aside to dry for 20 minutes at room temperature. A sterile disc of 6 mm diameter which has been soaked in 10 μl of the tested antibacterial pre-foam-formulation (PFF) is put on the microbial film, the plate is incubated at 35° C. for 1-2 days. A control experiment is also performed where no antibacterial material is put on the sterile discs. Antimicrobial activity of the tested material inhibits growth of the microorganism around the disc, leaving a transparent zone around it. The diameter of the inhibition zone is measured in mms.

HET-CAM

The potential of compounds to cause irreversible or severe eye irritation or corrosion may be detected by observing adverse changes, which occur in the chorioallantoic membrane (CAM) of the egg after exposure to test chemicals. The methodology is described in Example 17.

Apoptosis

UVB irradiation of the skin is known inter alia to increase epidermal cell apoptosis. Specimens are treated topically then irradiated with UVB and incubated. Apoptosis activation is measured post-irradiation by measuring the extent of caspase 3 activity. The methodology is described in Example 18.

Compatibility

Active agent is incubated with various excipients at one or more temperatures for a certain fixed period or to the point where degradation was suspected. Visual inspection is a criterion for indication of compatibility. Any change of color indicates oxidation or degradation. The methodology is described in Example 19.

Color/Pigmentation

Samples are applied to fair healthy human skin to observe whether any skin pigmentation occurs. The skin is observed prior to and following application. The methodology is described in Example 20.

Section A—Carrier Compositions

Example 2

Non Surfactant Oleaginous Foam Formulations

Surface active agents are known to be useful foaming agents, and thus it is not obvious to produce good quality foams free of surfactants. As shown table 2 below, formulations 001 and 002 containing a mixture of heavy mineral oil and light mineral oil with or without cyclomethicone fail to produce foams and release only liquids from the pressurized canisters. Compounds other than customary surfactants have been identified below that are suitable for the foaming of oleaginous vehicles.

TABLE 2

Oleaginous Compositions

| | Formulations | |
|---|---|---|
| | 001 % w/w | 002 % w/w |
| Ingredients | | |
| Heavy mineral oil | 75.00 | 70.00 |
| Light mineral oil | 25.00 | 75.00 |
| Cyclomethicone | — | 5.00 |
| Total | 100.00 | 100.00 |
| Propellant A46 | 12.00 | 12.00 |
| Results | | |
| Foam quality | Poor | Poor |

Silicone oils such as cyclomethicone are included in the formulations primarily as cosmetic agent, for their contribution to skin feeling properties. Volatile cyclomethicones can help reduce the greasy skin feeling that may be present in oleaginous formulations.

Example 3

Oleaginous Formulations Containing a Fatty Acid

Two fatty acids were used in combination with heavy mineral oil, light mineral oil and cyclomethicone, and tested for their foaming properties. As described in Table 3 below, formulation 003 containing isostearic acid (a liquid fatty acid) did not give rise to foam but merely generated bubbly liquids. Formulation 004 containing stearic acid (a solid fatty acid) initially produced a fairly good quality foam, but which was not stable and collapsed after 10 seconds. It follows that that fatty acids alone are not sufficient as foaming agents in oleaginous formulations even in reasonably high amounts. Also, the average bubble size was quite large and more than double that of a quality foam.

TABLE 3

Oleaginous compositions containing a fatty acid

| | Formulations | |
|---|---|---|
| | 003 % w/w | 004 % w/w |
| Ingredients | | |
| Heavy mineral oil | 60.00 | 60.00 |
| Light mineral oil | 25.00 | 25.00 |
| Cyclomethicone | 5.00 | 5.00 |
| Stearic acid (C18) | — | 10.00 |
| Isostearic acid (C18) | 10.00 | — |
| Total | 100.00 | 100.00 |
| Propellant A46 | 12.00 | 12.00 |
| Results | | |
| Foam quality | Fair | Fairly Good |
| Collapse Time (sec) | 10 | 10 |
| Foam density (/mL) | — | 0.071 |
| Bubble size (micrometers) | — | 245 |
| PFF Viscosity (cP) | 58 | 1442 |

Example 4

Oleaginous Compositions Containing Fatty Alcohols

The influence of fatty alcohols on the foaming properties of oleaginous formulations was studied. Several fatty alcohols of different chain length were used in combination with heavy mineral oil, light mineral oil and cyclomethicone, and checked for their foaming properties. As described in Table 4 below, formulations 005, 006 and 007 respectively containing myristyl alcohol, cetyl alcohol or stearyl did not give rise to quality foams but merely generated bubbly liquids of fair quality foam that quickly collapsed. Formulation 009 which contains behenyl alcohol (a fatty alcohol having 22 carbons) produced fairly good quality foams that quickly collapsed. It follows that fatty alcohols alone are not sufficient as foaming agents in oleaginous formulations.

TABLE 4

Oleaginous compositions containing various fatty alcohols

| | Formulations | | | |
|---|---|---|---|---|
| | 005 % w/w | 006 % w/w | 007 % w/w | 009 % w/w |
| Ingredients | | | | |
| Heavy mineral oil | 60.00 | 60.00 | 60.00 | 60.00 |
| Light mineral oil | 25.00 | 25.00 | 25.00 | 25.00 |
| Cyclomethicone | 5.00 | 5.00 | 5.00 | 5.00 |
| Myristyl alcohol (C14) | 10.00 | — | — | — |
| Cetyl alcohol (C16) | — | 10.00 | — | — |
| Stearyl alcohol (C18) | — | — | 10.00 | — |
| Behenyl alcohol (C22) | — | — | — | 10.00 |
| Total | 100.00 | 100.00 | 100.00 | 100.00 |
| Propellant A46 | 12.00 | 12.00 | 12.00 | 12.00 |

TABLE 4-continued

Oleaginous compositions containing various fatty alcohols

| | Formulations | | | |
|---|---|---|---|---|
| | 005 % w/w | 006 % w/w | 007 % w/w | 009 % w/w |
| Results | | | | |
| Foam quality | Fair | Fair | Fair | Fairly Good |
| Collapse Time (sec) | 10 | 10 | 10 | 10 |
| Foam density (/mL) | — | — | — | 0.160 |
| Bubble size (micrometers) | — | — | — | 125 |
| PFF Viscosity (cP) | 206 | 938 | 585 | 3839 |

Example 5

Oleaginous Formulations Containing a Combination of Fatty Acids and Fatty Alcohols Formulations were prepared, containing a combination of fatty acids and fatty alcohols and checked for their foaming properties. As described in Table 5a below, formulations 010 (containing stearic acid and myristyl alcohol) and formulation 0.17 (containing isostearic acid and stearyl alcohol) did not give rise to quality foams but merely generated bubbly liquids.

However, very surprisingly, the combination of stearic acid with cetyl alcohol, stearyl alcohol, cetostearyl alcohol or behenyl alcohol give rise to good quality foams having a fine bubble structure as shown in formulations 011, 012, 013 and 014. Such foams can be successfully produced in the presence or in the absence of silicone oils, as shown in formulation 011 and 016, despite the defoaming effect of silicones. Moreover, formulations 012 and 014 containing a combination of stearic acid with stearyl alcohol or behenyl alcohol give rise to stable foams which did not collapse after 180 sec at 36° C. Thus, it has been discovered that a combination of fatty alcohols and fatty acids has a synergistic effect and possesses effective foaming properties in the case of oleaginous compositions to achieve a thermally stable breakable foam. Interestingly cetyl and stearyl alcohol achieved the lowest average bubble size, whilst using a combination of the two led to a substantial reduction in viscosity of the pre foam formulation.

TABLE 5a

Oleaginous compositions containing various Fatty Acids and Fatty Alcohols

| | Formulation | | | | | | | |
|---|---|---|---|---|---|---|---|---|
| Ingredients | 010 % w/w | 011 % w/w | 012 % w/w | 013 % w/w | 014 % w/w | 015 % w/w | 016 % w/w | 017 % w/w |
| Heavy mineral oil | 60.00 | 60.00 | 60.00 | 60.00 | 60.00 | 57.00 | 60.00 | 60.00 |
| Light Mineral oil | 25.00 | 25.00 | 25.00 | 25.00 | 25.00 | 25.00 | 30.00 | 25.00 |
| Cyclomethicone | 5.00 | 5.00 | 5.00 | 5.00 | 5.00 | 5.00 | — | 5.00 |
| Myristyl alcohol | 5.00 | — | — | — | — | 3.00 | — | — |
| Cetyl alcohol | — | 5.00 | — | — | — | — | — | — |
| Stearyl alcohol | — | — | 5.00 | — | — | 5.00 | 5.00 | 5.00 |
| Cetostearyl alcohol | — | — | — | 5.00 | — | — | — | — |
| Behenyl alcohol | — | — | — | — | 5.00 | — | — | — |
| Isostearic acid | — | — | — | — | — | — | — | 5.00 |
| Stearic acid | 5.00 | 5.00 | 5.00 | 5.00 | 5.00 | 5.00 | 5.00 | — |
| Total | 100.00 | 100.00 | 100.00 | 100.00 | 100.00 | 100.00 | 100.00 | 100.00 |
| Propellant A46 | 12.00 | 12.00 | 12.00 | 12.00 | 12.00 | — | 12.00 | 12.00 |
| Propellant AP-70 | — | — | — | — | — | 8.00 | — | — |
| Results | | | | | | | | |
| Foam quality | Fair | Good | Good | Good | Good | Good | Good | Fair |
| Collapse Time (sec) | 10 | 30 | >180 | 30 | >180 | >180 | >180 | 10 |
| Foam density (g/mL) | — | 0.142 | 0.157 | 0.210 | 0.139 | 0.082 | 0.100 | — |
| Bubble size (micrometers) | — | 60 | 74 | 137 | 139 | — | — | — |
| PFF Viscosity (cP) | 107 | 22763 | 23866 | 107 | 5023 | 18987 | — | — |

Formulations were prepared, containing various ratios of fatty acids to fatty alcohols and checked for their foaming properties, as described in Table 5b.

TABLE 5b

Oleaginous compositions containing various Fatty Acids and Fatty Alcohols ratios

| | Formulations | | | | |
|---|---|---|---|---|---|
| | 215 % w/w | 213 % w/w | 211 % w/w | 212 % w/w | 214 % w/w |
| Ingredients | | | | | |
| Heavy Mineral oil | 65.0 | 65.0 | 65.0 | 65.0 | 65.0 |
| Light Mineral oil | 25.0 | 25.0 | 25.0 | 25.0 | 25.0 |
| Stearyl alcohol | 1.50 | 3.33 | 5.00 | 6.66 | 8.50 |
| Stearic acid | 8.50 | 6.66 | 5.00 | 3.33 | 1.50 |
| Total | 100.0 | 100.0 | 100.0 | 100.0 | 100.0 |
| Propellant AP-70 | 10.0 | 10.0 | 10.0 | 10.0 | 10.0 |
| Results | | | | | |
| Foam Quality | Good | Good | Excellent | Good- | Fairly Good |
| Collapse Time (sec) | >180 | >180 | >180 | >180 | — |
| Ratio fatty alcohol:fatty acid | 3.17 (1:5.6) | 1:2 | 1:1 | 2:1 | (5.6:1) 17:3 |

It was observed that in oleaginous foam formulations containing fatty alcohols and fatty acids, the ratio of the concentrations of fatty alcohol to fatty acid influenced the foaming properties. Foams of good quality that did not collapse after 180 seconds at 36° C. were obtained with a ratio of fatty alcohol:fatty acid of 3:17 to 2:1. Foams of excellent quality were obtained when the ratio was 1:1. However, fairly good foams were obtained with a ratio of 5.6:1. Thus, in one or more embodiments the ratio of fatty alcohol to fatty acid is about 3:17 to about 2:1; or about 1:6 to about 16:3; or about 1:7 to about 5:1 or between any first ratio to any second ratio.

Formulations were prepared, containing various concentrations of fatty acids and fatty alcohols with a fixed ratio of fatty alcohol to fatty acid of 1:1 and checked for their foaming properties, as described in Table 5c.

TABLE 5c

Oleaginous compositions containing various Fatty Acids and Fatty Alcohols concentrations

| | Formulations | | | | |
|---|---|---|---|---|---|
| | 221 % w/w | 222 % w/w | 223 % w/w | 211 % w/w | 224 % w/w |
| Ingredients | | | | | |
| Heavy Mineral oil | 65.0 | 65.0 | 65.0 | 65.0 | 65.0 |
| Light Mineral oil | 32.5 | 30.0 | 28.0 | 25.0 | 20.0 |
| Stearyl alcohol | 1.25 | 2.50 | 3.50 | 5.00 | 7.50 |
| Stearic acid | 1.25 | 2.50 | 3.50 | 5.00 | 7.50 |
| Total | 100.0 | 100.0 | 100.0 | 100.0 | 100.0 |
| Propellant AP-70 | 10.0 | 10.0 | 10.0 | 10.0 | 10.0 |

TABLE 5c-continued

Oleaginous compositions containing various Fatty Acids and Fatty Alcohols concentrations

| | Formulations | | | | |
|---|---|---|---|---|---|
| | 221 % w/w | 222 % w/w | 223 % w/w | 211 % w/w | 224 % w/w |
| Results | | | | | |
| Foam Quality | Fair | Good | Excellent | Excellent | Block |
| Collapse Time (sec) | — | >180 | >180 | >180 | — |

It was observed that foams of good to excellent quality that did not collapse after 180 seconds at 36° C. were obtained with a fixed ratio of fatty alcohol to fatty acid of 1:1 and a total concentration of fatty alcohol together with fatty acid ranging from about 5% to about 10%. For a total concentration of fatty alcohol together with fatty acid of 15%, the PFF content was very viscous and could not be expelled through the valve. This can be overcome by including higher amounts of propellant, or propellant of higher vapor pressure or a low viscosity solvent such as alkyl benzoate.

Example 6

Oleaginous Formulations Containing Fatty Alcohols, Fatty Acids and Waxes

Formulations, containing a combination of fatty acids, fatty alcohols and waxes were prepared and checked for their foaming properties. As noted in Table 6a below, formulations 018 containing fatty alcohols and low amounts of stearic acid did not give rise to quality foams but generated fairly good quality foam that very quickly collapsed. Surprisingly, the addition of hydrogenated castor oil and beeswax (in formulation 019) both of which are solid waxes at room temperature, enhanced the foam quality and good quality foam that was stable at 36° C. was obtained. Furthermore, formulations containing waxes feel less greasy upon application on skin. Thus, it has been discovered that waxes are useful foamer ingredients instead of fatty acids in oleaginous foams free of standard surfactants, and additionally they can enhance both the skin feeling and the foam quality.

TABLE 6a

Oleaginous compositions containing waxes

| | Formulations | |
|---|---|---|
| | 018 % w/w | 019 % w/w |
| Ingredients | | |
| Heavy mineral oil | 63.00 | 59.50 |
| Light mineral oil | 25.00 | 25.00 |
| Cyclomethicone | 5.00 | 5.00 |
| Hydrogenated castor oil | — | 1.50 |
| Beeswax | — | 2.00 |
| Cetostearyl alcohol | 2.50 | 2.50 |
| Stearyl alcohol | 1.50 | 1.50 |
| Behenyl alcohol | 1.00 | 1.00 |
| Stearic acid | 2.00 | 2.00 |
| Total | 100.00 | 100.00 |
| Propellant A46 | 12.00 | 12.00 |

TABLE 6a-continued

Oleaginous compositions containing waxes

| | Formulations | |
|---|---|---|
| | 018 % w/w | 019 % w/w |
| Results | | |
| Foam quality | Fairly Good | Good |
| Collapse Time (sec) | 10 | 120 |
| Foam density (g/mL) | — | 0.207 |
| Bubble Size (micrometers) | 155 | 79 |

It is apparent that the addition of a wax to the composition improved the foam quality from fairly-good (insufficient) to good (acceptable) and collapse time from 10 (unacceptable) to 120 seconds (acceptable).

Additional formulations were prepared, containing waxes alone and in combination with a fatty acid or a fatty alcohol and checked for their foaming properties. As described in Table 6b below, formulations 021, 021b and 022 containing beeswax alone or in combination with hydrogenated castor oil did not give rise to quality foams but merely generated bubbly liquids. Formulations 020 containing hydrogenated castor oil alone generated fairly good quality foam that collapsed after 10 seconds. On the other hand the combination of beeswax, hydrogenated castor oil and fatty alcohol enhanced the foam quality and produced good quality foam that were stable at 36° C. for more than 180 seconds, as shown in formulation 023. However, formulations 024 and 024b composed of combinations of beeswax, hydrogenated castor oil and fatty acid only without fatty alcohol generated fairly good foam that quickly collapsed. This shows the importance of the presence of both fatty alcohols and waxes in oleaginous foam compositions. Additionally, wax such as hydrogenated caster oil or beeswax can not only be used in place of a fatty acid but it can be used to facilitate a lower level of fatty acid presence without compromising the foam properties.

TABLE 6b

Oleaginous compositions containing waxes

| | Formulations | | | | | | |
|---|---|---|---|---|---|---|---|
| Ingredients | 020 % w/w | 021 % w/w | 021b % w/w | 022 % w/w | 023 % w/w | 024 % w/w | 024b % w/w |
| Heavy mineral oil | 60.00 | 60.00 | 60.00 | 60.00 | 60.00 | 60.00 | 60.00 |
| Light mineral oil | 25.00 | 25.00 | 30.00 | 25.00 | 25.00 | 25.00 | 25.00 |
| Cyclomethicone | 5.00 | 5.00 | — | 5.00 | 5.00 | 5.00 | 5.00 |
| Hydrogenated castor oil | 10.00 | — | — | 5.00 | 2.50 | 2.50 | 5.00 |
| Beeswax | — | 10.00 | 10.00 | 5.00 | 2.50 | 2.50 | 2.50 |
| Stearyl alcohol | — | — | — | — | 5.00 | — | — |
| Stearic acid | — | — | — | — | — | 5.00 | 5.00 |
| Total | 100.00 | 100.00 | 100.00 | 100.00 | 100.00 | 100.00 | 100.00 |
| Propellant A46 | 12.00 | 12.00 | 12.00 | 12.00 | 12.00 | 12.00 | 12.00 |
| Results | | | | | | | |
| Foam quality | Fairly Good | Fair | Fair | Fair | Good | Fairly Good | Fairly Good |
| Collapse Time (sec) | 10 | 10 | 10 | 10 | >180 | 10 | 10 |

Formulations were prepared, containing various ratio of beeswax to hydrogenated castor oil, with a fixed concentration of fatty alcohol and checked for their foaming properties, as described in Table 6c.

TABLE 6c

Oleaginous compositions containing waxes in different ratios

| | Formulations | | | | |
|---|---|---|---|---|---|
| | 229 % w/w | 228 % w/w | 226 % w/w | 227 % w/w | 230 % w/w |
| Ingredients | | | | | |
| Heavy Mineral oil | 65.0 | 65.0 | 65.0 | 65.0 | 65.0 |
| Light Mineral oil | 25.0 | 25.0 | 25.0 | 25.0 | 25.0 |
| Stearyl alcohol | 5.00 | 5.00 | 5.00 | 5.00 | 5.00 |
| Beeswax | 0.83 | 1.67 | 2.50 | 3.33 | 4.17 |
| Hydrogenated castor oil | 4.17 | 3.33 | 2.50 | 1.67 | 0.83 |
| Total | 100.0 | 100.0 | 100.0 | 100.0 | 100.0 |
| Propellant AP-70 | 10.0 | 10.0 | 10.0 | 10.0 | 10.0 |
| Results | | | | | |
| Foam Quality | Fairly Good | Fairly Good | Good- | Good | Good |
| Collapse Time (sec) | — | — | >180 | >180 | >180 |
| Ratio Beeswax:Hydrog. Castor oil | 1:5 | 1:2 | 1:1 | 2:1 | 5:1 |

It was observed that in oleaginous foam formulations containing fatty alcohols and waxes such as beeswax and hydrogenated castor oil, the ratio of the concentrations of beeswax to hydrogenated castor oil influenced foaming properties. Foams of good quality that did not collapse after 180 seconds at 36° C. were obtained with a ratio of beeswax to hydrogenated castor oil of 1:1 or more, whereas fairly good foams were obtained when the level of the beeswax was less than 2% and the amount of hydrogenated cater oil exceeded the level of beeswax. According to one or more embodiments there is provided a composition, wherein ratio of beeswax to hydrogenated castor oil is about or at least 1:1. According to one or more other embodiments the ratio may be less than 1:1 where beeswax is more than about 2%.

Formulations were prepared, containing various ratio of fatty alcohol to wax and checked for their foaming properties, as described in Table 6d.

TABLE 6d

Oleaginous compositions containing waxes and fatty alcohols in different ratios

| Formulations Ingredients | 234 % w/w | 231 % w/w | 230 % w/w | 232 % w/w | 233 % w/w |
|---|---|---|---|---|---|
| Heavy Mineral oil | 65.0 | 65.0 | 65.0 | 65.0 | 65.0 |
| Light Mineral oil | 25.0 | 25.0 | 25.0 | 25.0 | 75.0 |
| Beeswax | 7.50 | 6.255 | 4.17 | 2.085 | 0.834 |
| Steatyl alcohol | 1.00 | 2.50 | 5.00 | 7.50 | 9.00 |
| Hydrogenated castor oil | 1.50 | 1.245 | 0.83 | 0.415 | 0.166 |
| Total | 100.0 | 100.0 | 100.0 | 100.0 | 100.0 |
| Propellant AP-70 | 10.0 | 10.0 | 10.0 | 10.0 | 10.0 |
| Results | | | | | |
| Foam Quality | Fair | Good | Good | Good— | Fair |
| Foam Collapse Time | — | >180 | >180 | >180 | — |
| Ratio Fatty alcohol:Wax | 1:9 | 2:3 | 1:1 | 3:2 | 9:1 |

In the above experiment the ratio of beeswax to hydrogenated caster oil was maintained at 5:1, whilst the amount of fatty alcohol was progressively increased. It was observed that in oleaginous foam formulations containing fatty alcohols and waxes, the ratio of the concentrations of fatty alcohol to wax (beeswax plus hydrogenated caster oil) influenced foaming properties. Foams of good quality that did not collapse after 180 seconds at 36° C. were obtained with a ratio of fatty alcohol to wax of 2:3 to 3:2 or more, whereas only fair foams were obtained with a ratio of 1:9 or 9:1. So in one or more embodiments the ratio of fatty alcohol to wax (total) is between about 2:3 to about 3:2; or between about 1:2 to about 2:1 or between about 1:3 to about 3:1; or between about 4:1 to about 1:4 or between any first ratio to any second ratio.

Example 7

Oleaginous Formulations Containing Various Hydrophobic Solvents

Formulations were prepared, containing various hydrophobic solvents and checked for their foaming properties. As described in Table 7 below, formulations containing substantial amounts of MCT oil (capric/caprylic triglycerides), octyldodecanol, coconut oil, PPG-15 stearyl ether and soybean oil provided good quality foams that were stable at 36° C., as shown in formulation 025 and 026.

TABLE 7

Oleaginous compositions containing various oils

| Formulations Ingredients | 025 % w/w | 026 % w/w |
|---|---|---|
| Light Mineral oil | — | 6.65 |
| Cyclometicone | 5.00 | 5.00 |
| MCT oil | 50.00 | — |
| Octyldodecanol | 12.00 | — |
| Coconut oil | — | 25.00 |
| PPG-15 stearyl ether | 15.00 | — |
| Soybean oil | — | 50.00 |
| Lanolin | — | 2.00 |
| Hydrogenated castor oil | 2.00 | 2.00 |
| Beeswax | 2.50 | 2.00 |
| Cetostearyl alcohol | 2.50 | 2.50 |
| Stearyl alcohol | 5.00 | 1.50 |
| Behenyl alcohol | 1.00 | 1.10 |
| Aerosil (SiO2) | — | 0.25 |
| Stearic acid | 5.00 | 2.00 |
| Total | 100.00 | 100.00 |
| Propellant A46 | 12.00 | 12.00 |
| Results | | |
| Foam quality | Good | Good |
| Collapse Time (sec) | 150 | 150 |
| Foam density (g/mL) | 0.293 | 0.167 |

Example 8

Foamable Oil Combinations with Fatty Acid, Fatty Alcohol and Wax

Part A—Without Water

Foam formulations were prepared containing high amounts of oils, in combination with fatty alcohols, fatty acids and waxes, according to the general manufacturing procedure described in Example 1. As described in Table 8a, quality breakable foams were obtained in compositions containing different oils. The pre-foam formulations were viscous semi-solid primarily due to the addition of waxes and/or foam adjuvants. Upon addition of propellant, the formulations were shakable, indicating that the formulation within the aerosol canister is liquid.

TABLE 8a

Foamable Oil Combinations with Fatty acid, Fatty alcohol and Wax

| Formulations | A6 | A7 | A8 | A9 | A10 |
|---|---|---|---|---|---|
| Avocado oil | 20.00 | 20.00 | — | — | — |
| Jojoba oil | — | — | 20.00 | 30.00 | 20.00 |
| Coconut oil | 20.00 | 20.00 | 20.00 | — | — |
| Mineral oil, light | 20.00 | — | 20.00 | 16.00 | 7.00 |
| Grapeseed oil | 20.00 | 20.00 | 20.00 | 30.00 | 30.00 |
| Calendula oil | — | 10.00 | 5.00 | — | — |
| Pomegrante Seed oil | — | 10.00 | — | — | — |
| Peanut oil | — | — | — | — | 20.00 |
| Cocoglyceride | 3.00 | 3.00 | — | — | — |
| Beeswax | 3.00 | 3.00 | 3.00 | 3.00 | 3.00 |
| Stearic acid | 2.00 | 2.00 | 2.00 | 2.00 | 2.00 |
| Cetyl alcohol | 3.00 | 3.00 | 3.00 | 4.00 | 4.00 |

TABLE 8a-continued

Foamable Oil Combinations with Fatty acid, Fatty alcohol and Wax

| Formulations | A6 | A7 | A8 | A9 | A10 |
|---|---|---|---|---|---|
| Shea butter | 2.00 | 3.00 | — | — | — |
| Behenyl alcohol | 1.00 | 1.00 | 1.00 | 2.00 | 2.00 |
| Paraffin wax | 6.00 | 5.00 | 6.00 | 13.00 | 12.00 |
| Total | 100 | 100 | 100 | 100 | |
| Propellant A70 | 10.00 | 10.00 | 10.00 | 10.00 | 10.00 |
| Results | | | | | |
| Foam Quality | Excellent | Excellent | Good | Excellent | Excellent |

Part B—with Low Water (10% or 20%)

Foam formulations were prepared containing high amounts of oils, low amounts of water, in combination with fatty alcohols, fatty acids and waxes, according to the general manufacturing procedure described in Example 1. As described in Table 8b, quality breakable foams were obtained in different compositions containing oils and low amounts of water, with or without fragrance. The pre-foam formulations were viscous semi-solid primarily due to the addition of waxes and/or foam adjuvants. Upon addition of propellant, the formulations were shakable, indicating that the formulation within the aerosol canister is liquid.

TABLE 8b

Foamable Oil Combinations with Water, Fatty acid, Fatty alcohol and Wax

| Formulations | A11 | A12 | A13 |
|---|---|---|---|
| Water | 10.00 | 10.00 | 20.00 |
| Avocado oil | 20.00 | 19.75 | 15.00 |
| Coconut oil | 20.00 | 20.00 | 20.00 |
| Grapeseed oil | 20.00 | 20.00 | 20.00 |
| Calendula oil | 5.00 | 5.00 | 2.50 |
| Pomegrante Seed oil | 5.00 | 5.00 | 2.50 |
| Cocoglyceride | 3.00 | 3.00 | 3.00 |
| Beeswax | 3.00 | 3.00 | 3.00 |
| Stearic acid | 2.00 | 2.00 | 2.00 |
| Cetyl alcohol | 3.00 | 3.00 | 3.00 |
| Shea butter | 3.00 | 3.00 | 3.00 |
| Behenyl alcohol | 1.00 | 1.00 | 1.00 |
| Paraffin wax | 5.00 | 5.00 | 5.00 |
| Fragrance (FC10618) | — | 0.25 | — |
| Total | 100 | 100 | 100 |
| Propellant A70 | 10.00 | 10.00 | 10.00 |
| Results | | | |
| Foam Quality | Excellent | Excellent | Excellent |
| Foam Density (g/mL) | 0.240 | — | 0.224 |
| Collapse time at 36° C. (sec) | >180 | — | >180 |
| Centrifugation at 1000 rpm | 20% creaming 5% separation | — | 20% creaming 5% separation |

Surprisingly, and despite the absence of surfactants, water-in-oil emulsion formulations were prepared containing high amounts of oils and low amounts of water, in combination with fatty alcohols, fatty acids and waxes, which produced quality breakable foams.

In one or more embodiments, there is provided, a foamable formulation comprising high amounts of hydrophobic solvents, low amounts of water, fatty alcohols, fatty acids and waxes, wherein the formulation generates quality breakable foam which does not collapse for more than 180 seconds at 36° C. In one or more embodiments, the amount of water is lower than about 20%. In one or more embodiments, the amount of water is lower than about 10%. In one or more embodiments, the amount of water is lower than about 5%. In one or more embodiments, the amount of water is lower than about 2%. In one or more embodiments, the oleaginous formulation is essentially free of water.

Example 9

Petrolatum Based Foamable Compositions

Foam formulations were prepared containing high amounts of Petrolatum, in combination with liquid oils, fatty alcohols and waxes, according to the general manufacturing procedure described in Example 1. As described in Table 9a, quality breakable foams were obtained in different compositions containing Petrolatum. The pre-foam formulations were viscous semi-solid. Upon addition of propellant, the formulations were shakable, indicating that the formulation within the aerosol canister is liquid.

TABLE 9a

Oleaginous Formulations containing Petrolatum

| Formulations | A1 | A2 | A3 | A8 |
|---|---|---|---|---|
| White petrolatum | 70.00 | 50.00 | 50.00 | 91.00 |
| Grape seed oil | — | 15.00 | — | — |
| Jojoba oil | 15.00 | 15.00 | 15.00 | — |
| Mineral oil | 5.00 | 9.00 | 10.00 | — |
| Wheat germ oil | — | — | 15.00 | — |
| Paraffin wax 51-53 | — | 2.00 | 5.00 | — |
| Beeswax | 1.00 | 1.00 | — | 1.00 |
| Cetostearyl alcohol | 4.00 | 4.00 | 4.00 | 4.00 |
| Hydrogenated castor oil | 3.00 | 2.00 | — | 3.00 |
| Cyclomethicone 5-NF | 1.00 | 1.00 | — | — |
| Behenyl alcohol | 1.00 | 1.00 | 1.00 | 1.00 |
| Total | 100 | 100 | 100 | 100 |
| Propellant A70 | 10.00 | 10.00 | 10.00 | 10.00 |
| Results | | | | |
| Foam Quality | Excellent | Excellent | Excellent | Excellent |
| Foam Density (g/mL) | 0.159 | 0.154 | 0.175 | 0.226 |
| Collapse time at 36° C. (sec) | >180 | >180 | >180 | >180 |
| Mean Bubble size (micrometers) | — | — | 150 | — |

In one or more embodiments, there is provided a foamable formulation comprising Petrolatum, optionally a liquid oil, a fatty alcohol and a wax, wherein the formulation generates quality breakable foam.

Foam formulations were also prepared without waxes, containing high amounts of Petrolatum, in combination with liquid oils and fatty alcohols, according to the general manufacturing procedure described in Example 1. As described in Table 9b, quality breakable foams were obtained in different compositions containing Petrolatum without waxes. The pre-foam formulations were viscous semi-solid. Upon addition of propellant, the formulations were shakable, indicating that the formulation within the aerosol canister is liquid.

TABLE 9b

Oleaginous Formulations containing Petrolatum

| Formulations | A4 | A5 | A6 | A7 |
|---|---|---|---|---|
| White petrolatum | 50.00 | 70.00 | 70.00 | 75.00 |
| Wheat germ oil | — | 10.00 | — | — |
| Jojoba oil | — | 5.00 | — | — |

TABLE 9b-continued

Oleaginous Formulations containing Petrolatum

| Formulations | A4 | A5 | A6 | A7 |
|---|---|---|---|---|
| Avocado oil | 15.00 | — | — | — |
| Coconut oil | 15.00 | — | — | — |
| Mineral oil | 10.00 | 3.00 | 20.00 | 20.00 |
| Shea butter | 5.00 | 5.00 | 5.00 | — |
| Cetostearyl alcohol | 4.00 | 4.00 | 4.00 | 4.00 |
| Cyclomethicone 5-NF | — | 2.00 | — | — |
| Behenyl alcohol | 1.00 | 1.00 | 1.00 | 1.00 |
| Total | 100 | 100 | 100 | 100 |
| Propellant 70 | 10.00 | 10.00 | 10.00 | 10.00 |
| Results |  |  |  |  |
| Foam Quality | Good | Excellent | Excellent | Excellent |
| Foam Density (g/mL) | 0.200 | 0.197 | 0.140 | 0.175 |
| Collapse time at 36° C. (sec) | 175 | >180 | >180 | >180 |

In one or more embodiments, there is provided a foamable formulation comprising Petrolatum, and a fatty alcohol with optionally shea butter, wherein the formulation generates quality breakable foam. In one or more embodiments, there is provided a foamable formulation comprising Petrolatum, optionally a liquid oil, and a fatty alcohol with optionally shea butter, wherein the formulation generates quality breakable foam.

Example 10

Oleaginous Compositions Containing Waxes

The influence of waxes on the foaming properties of oleaginous formulations was examined. The wax studied is Paraffin 51-53, which is a paraffin wax a mixture of solid saturated hydrocarbons having a melting point between 51° C. and 53° C. As observed in Table 10 below, formulations C001 and C002 respectively containing 10% stearyl alcohol and up to 2.5% Paraffin 51-53 did not give rise to high quality foams but merely generated fairly good quality foam that quickly collapsed. Surprisingly, formulations C003 to C007, containing 5% or more Paraffin 51-53 alone or in combination with stearyl alcohol generated quality foams that did not quickly collapse at 36° C. Increasing the amount of wax resulted in improved collapse times. Unexpectedly, paraffin 51-53 was able to produce a high quality foam with a collapse time in excess of 3 minutes in the absence of a fatty alcohol. Thus, in one or more embodiments the foamer complex can be a paraffin wax alone or in combination with a foam adjuvant. Moreover, formulation C007 is an example of a surfactant free, hydroxyl free, acid free, water free formulation essentially free of polyols and alcohols.

Therefore, it has been discovered that quality oleaginous foams can be produced without surfactant and even without fatty alcohols, where the foaming agent is a wax such as Paraffin 51-53.

Manufacturing Procedure: Heavy mineral oil is heated to 60-70° C., waxes and fatty alcohols if present are added under mixing until complete melting. The formulation is cooled down to room temperature, packaging in canisters which are crimped with a valve, pressurized with propellant and equipped with an actuator.

TABLE 10

Oleaginous compositions containing waxes

| | Formulations | | | | | | |
|---|---|---|---|---|---|---|---|
| | C001 | C002 | C003 | C004 | C005 | C006 | C007 |
| Heavy Mineral oil | 89.00 | 87.50 | 85.00 | 89.00 | 87.50 | 85.00 | 85.00 |
| Stearyl alcohol | 10.00 | 10.00 | 10.00 | 1.00 | 2.50 | 5.00 | — |
| Paraffin 51-53 | 1.00 | 2.50 | 5.00 | 10.00 | 10.00 | 10.00 | 15.00 |
| Total | 100 | 100 | 100 | 100 | 100 | 100 | 100 |
| Propellant AP-70 | 8.00 | 8.00 | 8.00 | 8.00 | 8.00 | 8.00 | 8.00 |
| Results |  |  |  |  |  |  |  |
| Foam Quality | Fairly Good | Fairly Good | Good | Excellent | Excellent | Excellent | Excellent |
| Collapse Time | — | — | 95 | >180 | >180 | >180 | >180 |

Example 11

Comparative Example

Two foam formulations of the present disclosure (Formulations 012 and 019) were compared with a foam formulation from patent U.S. Pat. No. 3,419,658, Example 4 which contains high viscosity mineral oil, cetyl alcohol, stearyl alcohol and isobutane. All the foam samples were tested for bubble size. As described in Table 11a, the results from Example 4 of U.S. Pat. No. 3,419,658, show a very large bubble size of 420 micrometers which indicates a poor foam quality. It is known in the art that large foam bubbles are prone to coalescence and lead to a poor foam stability. Moreover, application onto the skin is made difficult, since the foam sample from the prior art rapidly turned into a poorly absorbed runny liquid upon rubbing. Therefore, the combination and concentration of fatty alcohols described in the prior art fails to create quality foams suitable for topical application.

On the other hand, the formulations of the present disclosure provide a very small mean bubble size (74 micrometers for formulation 012 and 79 micrometers for formulation 019), which indicates a good foam quality and an extended physical stability. Foams with small bubble size also have improved organoleptic properties, which is of importance in order to ensure a better patient compliance and a better skin feeling. These foam formulations provide an easy application onto the skin, good skin absorption and do not turn into runny liquids upon rubbing. It has been thus discovered that the combination of fatty alcohol, with fatty acids and/or waxes has a clear advantages over the prior art and provides foam of improved quality, usability and stability.

TABLE 11a

Comparative example

| Ingredient | Formulation 012 % w/w | Formulation 019 % w/w | Sample according to U.S. 3,419,658, Example 4 % w/w |
|---|---|---|---|
| Heavy mineral oil | 60.00 | 59.50 | 79.00 |
| Light mineral oil | 25.00 | 25.00 | — |
| Cyclomethicone | 5.00 | 5.00 | — |
| Cetyl alcohol | — | — | 3.00 |
| Stearyl alcohol | 5.00 | 1.50 | 3.00 |
| Behenyl alcohol | — | 1.00 | — |
| Cetostearyl alcohol | — | 2.50 | — |
| Stearic acid | 5.00 | 2.00 | — |
| Hydrogenated castor oil | — | 1.50 | — |
| Beeswax | — | 2.00 | — |
| Propellant Isobutane | — | — | 15.00 |
| Total | 100.00 | 100.00 | 100.00 |
| Propellant A46 | 12.00 | 12.00 | — |
| Results | | | |
| Bubble Size (micrometers) | 74 | 79 | 420 |
| Ease of application on skin | Good | Good | Poor |
| Skin Feeling | Good | Good | Poor |

Two foam formulations of the present disclosure (Formulations 012 and 019) were also compared with placebo samples of formulations from Example 3 and Example 4 of U.S. Pat. No. 6,140,355, which contains high viscosity mineral oil, cetostearyl alcohol and hydrocarbon propellants. As noted in Table 11b, placebo samples from Example 3 and Example 4 of U.S. Pat. No. 6,140,355, are merely delivered as a bubbly liquids that collapse on release showing that the combination of fatty alcohols described in the prior art fails to create quality foams suitable for topical application.

On the other hand, the formulation of the present disclosure provides a foam of good quality with an extended physical stability. It has thus been discovered that the combination of fatty alcohol with fatty acids and/or waxes has a clear advantage over the prior art and provides foam of improved quality and stability.

TABLE 11b

Comparative example

| Ingredient | Formulation 012 % w/w | Placebo of a sample according to U.S. 6,140,355, Example 3 % w/w | Placebo of a sample according to U.S. 6,140,355, Example 4 % w/w |
|---|---|---|---|
| Heavy mineral oil | 60.00 | 96.00 | 96.00 |
| Light mineral oil | 25.00 | — | — |
| Cyclomethicone | 5.00 | — | — |
| Stearyl alcohol | 5.00 | — | — |
| Cetostearyl alcohol | — | 4.00 | 4.00 |
| Stearic acid | 5.00 | — | — |
| Total | 100.00 | 100.00 | 100.00 |
| Propellant A46 | 12.00 | — | — |
| Mixture of n-butatne/propane/isobutane 55:25:20 (Purifair ® 3.2) | — | 3.75 | 80.00 |
| Results | | | |
| Foam Quality | Good | Poor | Poor |
| Collapse Time | >180 | 0 | 0 |

Section B—Compositions with Tetracyclines

Example 12

Minocycline Oleaginous Formulations with Different Hydrophobic Solvents

Minocycline foam formulations were prepared containing soybean oil, octyldodecanol, Medium Chain Triglycerides (MCT) oil and coconut oil, which are other examples of hydrophobic solvents. Parameters such as foam quality, collapse time and density were evaluated. As described in Table 12, foams of good quality which did not collapse at 36° C. were obtained in different compositions containing these hydrophobic solvents. Coconut oil, which on its own is a semi solid paste like oil, was used in combination with liquid soybean oil.

TABLE 12

Formulation containing different hydrophobic solvents

| | Formulations | | | | | | | | | | |
|---|---|---|---|---|---|---|---|---|---|---|---|
| | 199 | 216 | 232A | 235 | 238 | 244B (1%) | 244A (4%) | 245 | 248 | 251 | 252 |
| Heavy mineral oil | 55.89 | 58.82 | — | — | 58.14 | — | — | — | — | — | — |
| Light Mineral oil | 25.00 | 25.00 | 25.00 | — | 25.00 | 4.44 | 1.44 | 4.44 | 3.04 | 4.44 | 5.54 |
| Cyclomethicone | 5.00 | 5.00 | 5.00 | 5.00 | 5.00 | 5.00 | 5.00 | 5.00 | 5.00 | 5.00 | 5.00 |
| MCT oil | — | — | — | 48.89 | — | — | — | — | — | — | — |
| Octyldodecanol | — | — | — | 12.00 | — | — | — | — | — | — | — |
| Coconut oil | — | — | 25.00 | — | — | 23.60 | 23.60 | 23.60 | 25.00 | 21.60 | 25.00 |
| PPG 15 stearyl ether | — | — | — | 15.00 | — | — | — | — | — | — | — |
| Soybean oil | — | — | 28.39 | — | — | 50.00 | 50.00 | 50.00 | 50.00 | 50.00 | 50.00 |
| Lanolin | — | — | — | — | — | — | — | — | — | 2.0 | 2.00 |

TABLE 12-continued

Formulation containing different hydrophobic solvents

| | Formulations | | | | | | | | | | |
|---|---|---|---|---|---|---|---|---|---|---|---|
| | 199 | 216 | 232A | 235 | 238 | 244B (1%) | 244A (4%) | 245 | 248 | 251 | 252 |
| Hydrogenated castor oil | — | 1.50 | 2.00 | 2.00 | 1.50 | 2.00 | 2.00 | 2.00 | 2.00 | 2.00 | 2.00 |
| Beeswax | | 1.87 | 2.50 | 2.50 | 2.00 | 2.00 | 2.00 | 2.00 | 2.00 | 2.00 | 2.00 |
| Cholesterol | — | — | — | — | — | — | — | — | 2.50 | — | — |
| Myristyl alcohol | 3.00 | — | — | — | — | 2.50 | 2.50 | 2.50 | — | 2.50 | — |
| Cetostearyl alcohol | — | 2.50 | — | 2.50 | 2.50 | 3.50 | 3.50 | 1.50 | 1.50 | 3.50 | 2.50 |
| Stearyl alcohol | 5.00 | 1.50 | 5.00 | 5.00 | 1.50 | 1.50 | 1.50 | 3.50 | 3.50 | 1.50 | 1.50 |
| Behenyl alcohol | — | 0.70 | 1.00 | 1.00 | 1.00 | 1.10 | 1.10 | 1.10 | 1.10 | 1.10 | 1.10 |
| Aerosil (SiO2) | — | — | — | — | 0.25 | 0.25 | 0.25 | 0.25 | 0.25 | 0.25 | 0.25 |
| Stearic acid | 5.00 | 2.00 | 5.00 | 5.00 | 2.00 | 3.00 | 3.00 | 3.00 | 3.00 | 3.00 | 2.00 |
| Minocycline HCl | 1.11 | 1.11 | 1.11 | 1.11 | 1.11 | 1.11 | 4.11 | 1.11 | 1.11 | 1.11 | 1.11 |
| Total | 100 | 100 | 100 | 100 | 100 | 100 | 100 | 100 | 100 | 100 | 100 |
| Propellant A46 | — | 12.00 | — | 12.00 | — | 12.00 | 12.00 | 12.00 | 12.00 | 12.00 | 12.00 |
| Propellant A70 | 8.00 | — | 8.00 | — | 8.00 | — | — | — | — | — | — |
| Results | | | | | | | | | | | |
| Foam Quality | G | E | E | G | E | E | G | E | E | G | G |
| Collapse Time at 36° C. (sec) | >180 | 160 | >180 | 150 | >180 | >180 | 110 | 140 | >180 | >180 | >180 |
| Foam Density (g/mL) | 0.082 | 0.225 | 0.149 | 0.293 | 0.237 | 0.284 | 0.193 | 0.295 | 0.211 | 0.223 | 0.167 |

Comments: All the foams were of high, quality and had a collapse time at 36° C. in excess of 100 seconds, a foam density of less than 0.3 g/ml and the formulations were able to withstand 4 Freeze and Thaw Cycles (FTC) and still generate foam of high quality with a collapse time at 36° C. in excess of 100 seconds. The pre-foam-formulation in the above formulations, before the addition of propellant, are semi-solid gel-like homogeneous compositions where no separation or sedimentation of the ingredients is observed.

Example 13

Stability of a Tetracycline Antibiotic in Oleaginous Formulations

Tetracycline antibiotics are known to be very unstable active agents that are degraded by a wide range of commonly used pharmaceutical excipients. For example, it has been found that minocycline is degraded in a few days by different hydrophilic solvents (such as water, glycerin, sodium PCA, propylene glycol and polyethylene glycols), by water dispersed polymers (such, as xanthan gum, poloxamers, carbomers, methocel, sodium CMC) and by surfactants (such as polysorbates, sorbitan esters, polyoxyalkyl esters and also lanolin-based surfactants). Thus, the achievement of a long term stable foamable formulation of tetracycline antibiotics described herein, was a major challenge and required both extensive research and creativity.

The following example illustrates the physical stability of foams and the chemical stability of minocycline HCl ("MCH") in oleaginous formulations, namely 238, 244B and 252 as described in Tables 13a, 13b(i), 13b(ii) and 1.3c below. In an accelerated stability study, samples were stored at 40° C., and the concentrations of minocycline HCl were determined by UPLC. The stability test results following 2 months, 3 months and 6 months of storage are shown in Tables 13b(i) and 13b(ii).

TABLE 13a

Composition of foam formulation incubated at 40° C.

| Formulations Ingredients | 238 % w/w | 244B % w/w | 252 % w/w |
|---|---|---|---|
| Heavy mineral oil | 58.14 | — | — |
| Light mineral oil | 25.00 | 4.44 | 5.54 |
| Cyclomethicone | 5.00 | 5.00 | 5.00 |
| Coconut oil | — | 23.60 | 25.00 |
| Soybean oil | — | 50.00 | 50.00 |
| Lanolin | — | — | 2.00 |
| Hydrogenated castor oil | 1.50 | 2.00 | 2.00 |
| Beeswax | 2.00 | 2.00 | 2.00 |
| Cetostearyl alcohol | 2.50 | 3.50 | 2.50 |
| Stearyl alcohol | 1.50 | 1.50 | 1.50 |
| Behenyl alcohol | 1.00 | 1.10 | 1.10 |
| Myristyl alcohol | — | 2.50 | — |
| Aerosil (SiO2) | 0.25 | 0.25 | 0.25 |
| Stearic acid | 2.00 | 3.00 | 2.00 |
| Minocycline HCl | 1.11 | 1.11 | 1.11 |
| Total | 100.00 | 100.00 | 100.00 |
| Propellant A46 | — | 12.00 | 12.00 |
| Propellant AP-70 | 8.00 | — | — |
| Results | | | |
| Foam quality | Excellent | Excellent | Excellent |
| Collapse Time (sec) | >180 | >180 | >180 |
| Foam density (g/mL) | 0.237 | 0.284 | 0.167 |

TABLE 13b(i)

Chemical Stability results of foam compositions containing minocycline HCl

| | | Minocycline content (% of label claim) | | |
|---|---|---|---|---|
| Formulation | T0 | after 2 months at 40° C. | after 3 months at 40° C. | after 6 months at 40° C. |
| 238 | 98.6 | 95.7 | 96.0 | 92.9 |
| 244B | 98.7 | 97.1 | 93.8 | 90.3 |
| 252 | 99.0 | 96.5 | 102.3 | NM |

NM = not measured

TABLE 13b(ii)

Physical Stability results of foam compositions containing minocycline HCl

| Formulation | Test | at T0 | after 2 months at 40° C. | after 3 months at 40° C. | after 6 months at 40° C. |
|---|---|---|---|---|---|
| 238 | Foam Quality | Excellent | Good | Good | Good |
|  | Collapse Time (sec) | >180 | >180 | 160 | NM |
|  | Foam Density (g/mL) | 0.237 | 0.259 | 0.289 | 0.263 |
| 244B | Foam Quality | Excellent | Good | Good | Good |
|  | Collapse Time (sec) | >180 | >180 | >180 | NM |
|  | Foam Density (g/mL) | 0.284 | 0.256 | NM | 0.232 |
| 252 | Foam Quality | Good | Fairly Good | Fairly Good | NM |
|  | Collapse Time (sec) | 150 | 150 | NM | NM |
|  | Foam Density (g/mL) | 0.167 | 0.126 | 0.142 | NM |

NM = not measured

Very surprisingly, and despite the known instability of tetracycline antibiotics, the accelerated stability results of formulations 238 and 244B after 2 months, 3 months and 6 months at 40° C. showed minimal degradation of the active agent in the formulations. The formulations disclosed herein thus show an extended accelerated stability for the tetracycline antibiotic active agent and an outstanding physical stability.

Regarding formulation 252, the Table indicates that foam quality decreases with time under accelerated stability storage at 40° C. Without being bound to any theory, and by comparing the ingredients present in formulations 244B and 252 and results with other formulations, it may be assumed that the decrease in foam quality is likely due to the presence of significant amounts of lanolin which may have some form of incompatibility with one or more components of the formulation. So in certain embodiments the formulations may be essentially free of lanolin, for example, where long term physical stability is required. It may be, however, that in certain other embodiments lanolin can be successfully included either in lower amounts, or by combination of lanolin with additional ingredients (such as surfactants, polymers, etc) and the formula can be physically stable in the short, medium or long term.

These results further illustrate the difficulty, complexity and unexpected and non obvious achievement of discovering surfactant free and water free formulations containing sensitive active agents that are chemically stable and are also physically stable over short term, medium term and/or long term periods. Testing and identifying single substances that are compatible chemically with the active agent is not sufficient. Combining multiple substances, which on their own are compatible can lead to collective incompatibility The discovery and knowledge of substances are chemically compatible does not presume physical stability of the composition or vice-versa. Running a compatibility study between individual formulation components and the active agents does not ensure nor achieve physical stability. Discovering combinations of ingredients that can lead to a physically stable formulation in the absence of surfactant, is itself unexpected. Further, adding propellant can destabilize the formulation as can expelling the formulation from a pressurized canister and ultimately achieving a quality foam that is stable but breakable on application of modest shear force is far from straightforward.

It has further been discovered that the propellant has a positive influence on the homogeneity of the formulation. After 2 months of storage at 40° C., several aliquots of foam formulations 238 as well as pre-foam formulation (liquid preparation without the addition of the propellant) were tested for minocycline content in order to determine to what extent the active agent is homogeneously dispersed. In the pre-foam formulation, high differences were found in the minocycline content, showing that the active agent is not homogeneously dispersed. Surprisingly, the foam formulations containing propellant demonstrated, an increase in the minocycline content homogeneity, which is of high importance in pharmaceutical applications in order to ensure a reproducible and accurate dose delivery. Without being bound to any theory, it can be assumed that inter alia the propellant acts as a solvent to the hydrophobic carrier and also as a dispersing agent, by reducing the formulation viscosity within the canister.

In another experiment, a PFF sample of formulation 244 1% was stored during 6 months at 40° C. and tested for API content uniformity. It was found that minocycline was homogeneously dispersed into the pre-foam-formulation even after prolonged incubation at 40° C. In one or more embodiments, there is provided a formulation wherein the active ingredient is homogeneously dispersed in the pre-foam-formulation and remains homogeneously dispersed after 2, 3 and/or 6 months of incubation at 40° C.

An ex-vivo study of the skin stability of a minocycline oleaginous foam formulation according to the present disclosure was performed in comparison with a reference minocycline gel, which comprised, amongst other components, water, ethanol, and propylene glycol. Gel and foam samples were applied on pig ear skins, incubated for 6 hours at 35° C. and the skin concentrations of minocycline HCl and its 4-epi degradant were determined by liquid chromatography.

As shown in Table 13c below, a rapid degradation of minocycline was observed after 6 h on skin treated with the reference silicone based gel. The minocycline content decreased by 34% and its 4-epi degradant content reached 19.4% showing that the gel reference product fails to deliver the all the antibiotic amount to the skin in its active form.

In the case of the foam formulation, very surprisingly, and despite the known instability of minocycline, the skin stability results after 6 h showed a very minimal degradation of the active agent: with the content of 4-epi degradant only reached 3.3% and no detectable decrease was observed in the amount of minocycline. Therefore, the foam formulation has an active protective effect on the tetracycline antibiotic upon contact with the skin, and prevents its degradation on the target site of treatment over several hours.

TABLE 13c

Skins stability results of foam and gel compositions containing minocycline HCl

|  | Reference Silicone Gel | Oleaginous Foam Formulation |
|---|---|---|
| Initial minocycline skin concentration | 96.90 | 92.20 |
| Initial 4-epi degradant skin concentration | 2.60 | 0.80 |
| Minocycline skin concentration after 6 h at 35° C. | 64.00 | 93.70 |
| 4-epi degradant skin concentration after 6 h at 35° C. | 19.40 | 3.30 |

Example 14

Optimization of Minocycline Oleaginous Formulations

Part A—Wax Effect on Formulation Homogeneity

Formulations were prepared, containing various concentrations of waxes and checked for their pre-formulation homogeneity, as described in Table 14a.

TABLE 14a

Influence of waxes on formulation homogeneity

| Ingredients | Formulation 244 % w/w | 282 % w/w | 283 % w/w | 287 % w/w | 288 % w/w | 276 % w/w |
|---|---|---|---|---|---|---|
| Light Mineral oil | 4.44 | 5.04 | 5.04 | 4.04 | 2.04 | 4.44 |
| Cyclomethicone | 5 | 5 | 5 | 5 | 5 | 5 |
| Coconut oil | 23.6 | 25 | 25 | 25 | 25 | 23.6 |
| Soybean | 50 | 50 | 50 | 50 | 50 | 50 |
| Hydrogenated castor oil | 2 | — | 2 | 1 | 2 | — |
| Beeswax | 2 | 2 | — | 2 | 3 | — |
| Paraffin 51-53 | — | — | — | — | — | 6.5 |
| Myristyl alcohol | 2.5 | 2.5 | 2.5 | 2.5 | 2.5 | — |
| Cetostearyl alcohol | 3.5 | 3.5 | 3.5 | 3.5 | 3.5 | 3.5 |
| Stearyl alcohol | 1.5 | 1.5 | 1.5 | 1.5 | 1.5 | 1.5 |
| Behenyl alcohol | 1.1 | 1.1 | 1.1 | 1.1 | 1.1 | 1.1 |
| Aerosil (SiO2) | 0.25 | 0.25 | 0.25 | 0.25 | 0.25 | 0.25 |
| Stearic acid | 3 | 3 | 3 | 3 | 3 | 3 |
| Minocycline HCl | 1.11 | 1.11 | 1.11 | 1.11 | 1.11 | 1.11 |
| Total | 100.0 | 100.0 | 100.0 | 100.0 | 100.0 | 100.0 |
| AP-70 | 12.0 | 12.0 | 12.0 | 12.0 | 12.0 | 10.0 |
| Results | | | | | | |
| PFF separation with MCH | No | No | No | Yes | Yes | No |
| PFF separation placebo | No | Yes | No | N/A | N/A | Yes |
| Ratio Fatty alcohol to fatty acid | 2.86:1 | 2.86:1 | 2.86:1 | 2.86:1 | 2.86:1 | 2:1 |
| Ratio Fatty alcohol plus fatty acid to wax (total) | 2.9:1 | 5.8:1 | 5.8:1 | 3.86:1 | 2.32:1 | 1.4:1 |
| Foam Quality | Good | Good | Good (slight collapse) | Good | N/A | Good |

It was observed that in the presence of hydrogenated castor oil, no to minor PFF separation was observed (see formulation 244 with beeswax and formulation 283 without beeswax). It was also observed that removal of hydrogenated castor oil resulted in PFF separation in placebo formulation, but the PFF surprisingly regained its homogeneity upon addition of minocycline (see formulation 282). It was observed that an increase in beeswax concentration resulted PFF separation (see formulation 288), and that a decrease in hydrogenated castor oil concentration resulted in PFF separation (see formulation 287). In general, it appears that stability in the above formulations is a more complex issue than simply being a function of the acid/alcohol to wax ratio and that whilst no separation was seen at the higher ratio of fatty alcohols and acids to waxes of about 6:1 and also at the lower ratio of about 7:5 some separation was seen in some inbetween ratios. Moreover the effect seems unrelated to the fatty alcohol:fatty-acid ratio which is constant with one exception.

It was observed that in the presence of Paraffin wax 51-53, PFF separation occurred in placebo formulation but the PFF regained its homogeneity upon addition of minocycline (see formulation MCH276). The homogeneity of the placebo formulation may be improved by the use of higher concentrations of paraffin wax or by the combination with another wax such as beeswax or hydrogenated castor oil. In one or more embodiments hydrogenated caster oil is used to prevent separation or to restore homogeneity. In one or more embodiments a tetracycline is used to prevent separation or to restore homogeneity. In one or more embodiments a paraffin wax is used to prevent separation or to restore homogeneity.

Part B—Propellant Effect

Formulation 244 was prepared, containing various types and concentrations of propellant and checked for foam properties, as described in Table 14b.

TABLE 14b

Influence of propellant on foam properties of formulation MCH244

| Propellant type | Propellant % w/w | Foam Quality Upright canister | Inverted canister | Shakability |
|---|---|---|---|---|
| AP-70 | 8 | Good | Good with minor collapse | 2 |
|  | 10 | Good | Good | 2 |
|  | 12 | Good | Good | 2 |
|  | 14 | Good | Good | 2 |
|  | 16 | Good | Good | 2 |
| A-46 | 8 | Good with minor collapse | Good with minor collapse | 2 |
|  | 10 | Good | N/A | 2 |
|  | 12 | Good | Good with minor collapse | 2 |
|  | 16 | Good with minor collapse | Good with minor collapse | 2 |
| Tetrafluoro-ethane (Dymel 134a) | 8 | Excellent | Excellent | 1 |
|  | 12 | Excellent | Excellent | 2 |
|  | 16 | Excellent (stiff) | Excellent (stiff) | 2 |

It was observed that replacing AP-46 with propellant AP-70 resulted in improved foam quality. Furthermore, the use of higher concentrations of AP-70 also improved foam quality. It was noticed that the use of Tetrafluoroethane also improved foam quality but however slightly reduced shakability. Higher levels of propellant resulted in a stiffness being observed in the foam.

Part C—Fatty Alcohol to Fatty Acid Ratio Effect

Formulations were prepared, containing various fatty alcohol to fatty acid ratios and a constant level of wax and were checked for their foaming properties and pre-foam formulation homogeneity, as described in Table 14c.

TABLE 14c

Influence of fatty alcohol to fatty acid ratio on foam properties and formulation homogeneity

| Formulations Ingredients | MCH244 % w/w | MCH289 % w/w | MCH277 % w/w | MCH280 % w/w |
|---|---|---|---|---|
| Light Mineral Oil | 4.44 | 3.44 | 4.44 | 4.44 |
| Cyclomethicone | 5 | 5 | 5 | 5 |
| Coconut Oil | 23.6 | 23.6 | 23.6 | 23.6 |
| Soybean | 50 | 50 | 50 | 50 |
| Hydrogenated Castor Oil | 2 | 2 | 2 | 2 |
| Beeswax | 2 | 2 | 2 | 2 |
| Myristyl Alcohol | 2.5 | 2.5 | 2.5 | 2.5 |
| Cetostearyl Alcohol | 3.5 | 3.5 | 3.5 | 3.5 |
| Stearyl Alcohol | 1.5 | 2.5 | 3 | 4.5 |
| Stearic Acid | 3 | 3 | 1.5 | — |
| Behenyl Alcohol | 1.1 | 1.1 | 1.1 | 1.1 |
| Aerosil (Silicon dioxide) | 0.25 | 0.25 | 0.25 | 0.25 |
| Minocycline HCl | 1.11 | 1.11 | 1.11 | 1.11 |
| Total | 100 | 100 | 100 | 100 |
| Propellant AP-70 | 12 | 12 | 12 | 12 |
| Results | | | | |
| PFF separation with HCl | No | N/A | No | No |
| PFF separation placebo | No | N/A | No | No |
| Shakability | 2 | 2 | 2 | 1 |
| Foam quality | Good | Good (stiff) | Good (slightly collapses) | Good (close to Fairly Good) |
| Ratio Fatty alcohol to fatty acid | 0.5:1 | 0.83:1 | 1:0.5 | ∞ |
| Ratio Fatty alcohol plus fatty acid to wax (total) | 2.9:1 | 3.15:1 | 2.9:1 | 2.9:1 |

All the foams were of quality the foam quality appears slightly improved as the ratio of fatty alcohol to acid decreased. Lowest shakability results were seen when the fatty acid was omitted. None of the formulations displayed separation and they were all homogenous. Moreover the effect seems unrelated to the fatty alcohol:fatty acid ratio which is constant with one exception.

Example 15

Skin Penetration and Skin Residence Studies

Part A—Skin Penetration

As can be seen from the results in Table 15A below, minocycline is delivered intradermally at sufficient levels to treat skin infections but does not pass through the skin transdermally and therefore topical application should be free from adverse systemic effects.

TABLE 15A

In Vitro Skin Delivery: formulation 244 with 1% and 4% minocycline

| | μg Minocycline (Mean) | |
|---|---|---|
| | 244 foam 1% (n = 5) | 244 foam 4% (n = 6) |
| Stratum Corneum 1 | 11.45 | 46.91 |
| Stratum Corneum 2 | 1.62 | 12.43 |
| Total Stratum Corneum | 13.07 | 59.34 |
| Viable Skin | 1.03 | 2.68 |
| Total Intradermal Delivery | 14.10 | 62.02 |
| Receiving Compartment | 0.00 | 0.00 |

The following conclusions can be drawn:

1. Transdermal delivery: Following 24 hours of exposure, the amount which was found in the receptor cells was below the limit of quantification (LOQ) of the analytical method (LOQ=2 μg/mL).
2. Intra-dermal delivery (delivery into the skin): The total mean amount of Minocycline in the skin following 24 hours of exposure was 14 μg for the 1% formulation and 62 μg for the 4% formulation. The weight of skin at the delivery area is about 100 mg, which implies that the concentration of Minocycline in the skin following 24 hours of exposure is about 140 μg/gr of skin for the 1% formulation and about 620 μg/gr for the 4% formulation. According to the literature, the minimum inhibitory concentration (MIC) for Minocycline is less than 4 μg/mL, and therefore, it can be concluded that the concentrations found in the skin are sufficient to treat bacterial skin infections.

Part B—Skin Residence

The objective of this study is to assess the degradation of Minocycline following exposure to skin. Formulation MCH232A, containing 1% Minocycline was applied to freshly retrieved pig's ear skin and samples were analyzed during 6 hours of exposure. As presented in Table 15B, the product remained stable during the exposure and only minor amounts converted into the 4-epi degradation product.

TABLE 15B

Skin Residence

| | Time | | | | | | | |
|---|---|---|---|---|---|---|---|---|
| | T0 | | 1 Hour | | 3 Hours | | 6 Hours | |
| Substance | | | | | | | | |
| | MCH | 4-Epi | MCH | 4-Epi | MCH | 4-Epi | MCH | 4-Epi |
| % of Applied Dose | 92.20% | 0.8% | 96.9% | 1.20% | 87.8% | 2.40% | 93.7% | 3.20% |

Example 16

Microbial Properties of Oleaginous Minocycline Compositions

Part A—Microbial Load

Formulation 2.52 was examined for microbial load following 3 months storage at 25° C., as a representative formulation. As shown in Table 16A, the test revealed an absence of microorganisms in the formulation.

TABLE 16A

Microbial Count and Detection of Specific Microorganisms in Formulation MCH252 Following Storage for 3 Months at 25° C.

| Formulation | Total aerobic microbial count (cfu/g) | Total combined yeast & mold count (cfu/g) | E. coli, presence | Pseudomonas aureus, presence | Salmonella, presence | Staphylococcus aureus, presence (coagulase test) |
|---|---|---|---|---|---|---|
| Sample 1 | <10 | <10 | negative | negative | negative | negative |
| Sample 2 | <10 | <10 | negative | negative | negative | negative |

Part B—Antimicrobial Effectiveness

As seen in Table 16B, results for formulation 238, as a representative example, were found to be in agreement with USP acceptance criteria for incubation times at 2 weeks. The number of colonies counted in samples following incubation period of 2 weeks (14 days) was found below 10 cfu/g, indicating approximately a 5-log reduction from the initial microbial inoculated level for *E. coli, S. aureus*, and *P. aeruginosa*. After an incubation period of 14 days, a 2-log reduction from the initial challenge level was found with *C. albicans* and less than a 1-log reduction was found with *A. niger*.

TABLE 16B

Antimicrobial effectiveness in non aqueous Formulation 238

| Test organisms | Before inoculation, cfu/g | Initial challenge level, cfu/g | No. of surviving microorganisms, cfu/g | | |
|---|---|---|---|---|---|
| | | | 1 day | 1 week | 2 weeks |
| E. coli | <10 | $6.1 \times 10^5$ | <10 | <10 | <10 |
| *Staphylococcus aureus* | <10 | $4.3 \times 10^5$ | <10 | <10 | <10 |
| *Pseudomonas aeruginosa* | <10 | $2.8 \times 10^5$ | <10 | <10 | <10 |
| Candida albicans | <10 | $2.1 \times 10^5$ | $7.5 \times 10^4$ | $4.7 \times 10^4$ | $3.6 \times 10^3$ |
| Aspergillus niger | <10 | $5.9 \times 10^5$ | $3.4 \times 10^4$ | $7.5 \times 10^4$ | $2.3 \times 10^5$ |
| Unininoculated control formulation 232A | | — | <10 | <10 | <10 |

It should be noted that antimicrobial effectiveness herein was challenged in non aqueous media.

Part C—In-Vitro Effect of 244 1% on Microbial Growth

An in-vitro study showed that formulation 244 with 1% minocycline inhibited the growth of *Streptococcus pyogenes, Pseudomonas aeruginosa, Staphylococcus aureus*, as well as a methicillin-resistant strain of *Staphylococcus aureus* (MRSA) and *Propionbacterium acnes*, as shown in Table 16C.

TABLE 16C

In Vitro Antibacterial Effect: Comparison between 10 μl of 244 2%, Fucidin Ointment 2% and Placebo-Diameter of inhibition (mm).

|  | 244 1% Inhibition Diameter | 244 Placebo Inhibition Diameter | Fucidin Inhibition Diameter |
|---|---|---|---|
| *Staphylococcus aureus* 6538 | >40, >40, >40 mm | 13, 21, 20 mm | >40, >40, >40 mm |
| *Pseudomonas aeruginosa* 9027 | 40, 40, 40 mm | 0, 0, 0 mm | 11, 12, 16 mm |
| *Staphylococcus aureus* MRSA 43300 | >40, >40, >40 mm | 17, 18, 20 mm | 40, 40, 38 mm |
| *Streptococcus pyogenes* 19615 | 38, 43, 40 mm | 12, 15, 11 mm | 10, 12, 22 mm |
| Propionbacterium acnes | 32, 30, 35 mm | NA | NA |

0 = Ineffective;
>30 = Very Effective

Part D—Water Activity (Aw)

The water activity measured on formulation 232A was 0.47, which prevents the growth of bacteria, fungi and yeast. Based on this information and above test results, it appears that the waterless surfactant free formulations herein will not support bacterial growth.

Example 17

Eye Irritation Study—HET CAM

The potential of compounds to cause irreversible or severe eye irritation or corrosion may be detected by observing adverse changes, which occur in the chorioallantoic membrane (CAM) of the egg after exposure to test chemicals. Fertilized hen's eggs are rotated in an incubator for 9 days, after which any defective eggs are discarded. The shell around the air cell is removed and the inner membranes are extracted to reveal the chorionallantoic membrane. Test chemicals are added to the membrane and left in contact for up to 5 minutes. The membrane is examined for vascular damage and the time taken for injury to occur is recorded. Irritancy is scored according to the speed at which damage occurs. To validate the HET-CAM data, Positive & Negative Controls and Vehicle Control (if applicable), are tested in parallel to the Test Item. For each Test Item, Positive and Negative Controls, mean scores of replicate eggs is determined. Irritation Score (IS) is interpreted as follows:

| Irritation Score | Irritation Classification |
|---|---|
| 0-0.9 | Non-Irritant |
| 1-4.9 | Slight Irritant |
| 5-8.9 | Moderate Irritant |
| 9-21 | Severe Irritant |

As can be seen in Table 17 using the in vitro irritation HET-CAM, formulations 244 placebo, with 1% minocycline hydrochloride and with 4% minocycline hydrochloride, demonstrated no signs of irritation.

TABLE 17

Eye irritation HET CAM studies

| Treatment | Irritation Score | Classification |
|---|---|---|
| Negative Control (Saline 0.9%) | 0 | Non irritant |
| Positive Control (NaOH 4 mg/ml) | 17.09 | Severe |
| 244-1% MCH | 0 | Non irritant |
| 244-4% MCH | 0 | Non irritant |
| 244-Placebo | 0 | Non irritant |

Example 18

Anti-Inflammatory Effects of Oleaginous Minocycline Compositions

UVB irradiation of the skin is known to decrease cell viability, total antioxidant capacity, while increasing the levels of inflammation (pro-inflammatory cytokines secretion) and epidermal cell apoptosis.

Pre-Treatment with Formulation 244

Specimens of human skin in organ culture were treated topically with formulation_244 for 24 hours, then irradiated with UVB (400 mJ/cm2) and incubated for additional 72 hours. Apoptosis activation was measured 24 h post-irradiation by measuring the extent of caspase 3 activity in epidermal sheets.

Table 18a and Table 18b demonstrate the effect of formulation 244 with 1% and 4% minocycline on epidermal cell apoptosis and viability following UVB irradiation of the skin organ culture. As shown in Table 18a, apoptosis activation was significantly decreased by formulation 244 in a dose-dependant manner. Cell viability, as measured by the MTT assay 72 hours after irradiation was increased, as shown in Table 18b. One set of mediators implicated in apoptosis belong to the asparate-specific cysteinyl proteases or caspases. A member of this family, caspase-3 has been identified as being a key mediator of apoptosis of mammalian cells.

TABLE 18a

Effect of Formulation 244 on apoptosis activation in skin organ culture after UVB irradiation

| | Caspase 3 activity (slope/min) | |
|---|---|---|
| | Non-irradiated | Irradiated |
| Carrier | 24 | 177 |
| 244-1% MCH | 4 | 100 |
| 244-4% MCH | 3 | 69 |

TABLE 18b

Effect of Formulation 244 on skin organ culture viability

| | Viability (RFU 540/590 nm) | |
|---|---|---|
| | Non-irradiated | Irradiated |
| Carrier | 6971.25 | 6207.5 |
| 244-1% MCH | 7615.25 | 8862.25 |
| 244-4% MCH | 8155.5 | 9015.5 |

Comments: It was observed that in the case of cells in contact with a placebo formulation, irradiation causes a decrease in cell viability. On the other hand, in cells in contact with a formulation containing minocycline, higher cell viability was observed both before and after irradiation compared to the placebo, which is a sign of cell regeneration. Therefore, the present formulation comprising minocycline is able to prevent cell death in the case of irradiation and can even stimulate or cause cell regeneration.

Treatment with Formulation 244 After UV Damage Induction

Specimens of human skin in organ culture were irradiated with UVB (400 mJ/cm2) and incubated for additional 72 hours. Formulation 244 4% was then applied to the skin and apoptosis activation was measured 24 h post-treatment by measuring the extent of caspase 3 activity in epidermal sheets.

As shown in Table 18c, Formulation 244 4% treatment resulted in about 60% decrease in epidermal cell apoptosis.

TABLE 18c

Therapeutic effect of Formulation 244 (application post irradiation)

| | Caspase 3 activity (slope/min) |
|---|---|
| Control | 118 |
| 244-4% MCH | 46 |

These results demonstrate that formulation 244 containing minocycline has protective and/or therapeutic properties in the case of UVB-induced skin damage. It may therefore be able to reduce skin photo damage and photoaging, and more generally to reduce oxidative stress and Inflammation in skin pathologies which are known to be accompanied by apoptotic cell death.

Example 19

Compatibility Study

Procedure: Minocycline hydrochloride ("MCH") was incubated as a suspension with various excipients at 25° C. and 40° C. for maximum of sixty days or to the point where degradation was suspected. The ratio between MCH and the tested excipient is detailed below. Visual inspection was the major criterion for indication of compatibility. The color of intact MCH suspension is pale yellow; and any change of color (e.g., to dark orange, red, green, brown and black) indicates oxidation or degradation.

Hydrophilic solvents were tested for compatibility with MCH at a ratio of MCH:excipient of 1:250. Dimethyl Isosorbide, Glycerin, Ethanol, Propylene glycol, Butylene Glycol, PEG 200, Hexylene Glycol, PEG 400, Dimethyl Sulfoxide and Diethylene glycol monoethyl ether were found to be incompatible with MCH.

Oily emollients and waxes were tested for compatibility with MCH at a ratio of MCH:excipient of 1:250 for Oily emollients and 1:50 for waxes. Hydrogenated castor oil, Castor oil, Cocoglycerides, Disopropyl adipate, Mineral oil light, Coconut oil, Beeswax, MCT oil, Cyclomethicone, Isododecane, Cetearyl octanoate, Gelled mineral oil, Isopropyl myristate, PPG 15 stearyl ether, Mineral oil heavy, Octyl dodecanol, White Petrolatum, Petrolatum (Sofmetic), Paraffin 51-53, Paraffin 51-53, Paraffin 58-62, Calendula oil, Shea butter, Grape seed oil, Almond oil, Jojoba oil, Avocado oil, Peanut oil, Wheat germ oil and Hard Fat were found to be compatible with MCH. Pomegranate seed oil was found to be incompatible with MCH.

The compatibility of MCH with hydrophobic surfactant was tested following solubilization of the surfactant in mineral oil (mineral oil was previously shown to be compatible with MCH). Surfactants were tested for compatibility with MCH at a ratio of MCH:excipient of 1:50. PEG 150 distearate, Laureth 4, PEG 40 hydrogenated castor oil, PEG 75 lanolin, Glucam P20 distearate, PEG100 stearate, Glyceryl monostearate, PEG 40 stearate, Montanov S (Cocoyl Alcohol (and) C12-20 Alkyl Glucoside)), Alkyl lactate, Benton gel, SPAN 60, Sorbitan sesquistearate, SPAN 40, SPAN 80, Tween 20, Ceteth 2, Sucrose stearic acid esters D1813, Ceteareth 20, Steareth 2/Steareth 21, Methyl glucose sesquistearate, Oleth 20, PPG 20 methyl glucose ether, Tween 60 were found to be incompatible with MCH. Sucrose stearic acid esters D1803, Sucrose stearic acid esters D1807 and Sucrose stearic acid esters D1811 were found to be compatible with MCH; however, not all of them dissolved in oil (e.g. 1811, 1813).

Foam adjuvants were tested for compatibility with MCH at a ratio of MCH:excipient of 1:50. Isostearyl alcohol, Behenyl alcohol, Stearyl alcohol, Cetyl alcohol, Oleyl alcohol, Myristyl alcohol, Cetostearyl alcohol, Palmitic acid, Stearic acid and Oleic acid were found to be compatible with MCH. Isostearic acid was not compatible with MCH.

Additives were tested for compatibility with MCH at a ratio of MCH:excipient of 1:50. Aerosil and Menthol were found to be compatible with MCH. Titanium dioxide and Ethocel were not compatible with MCH.

Additives were tested for compatibility with MCH. Minimal quantities of water (100 μL) were added to MCH, suspended in excipients that had demonstrated compatibility to examine whether water can enhance oxidation/degradation in the absence or presence of antioxidant. In parallel, antioxidants were added to the MCH suspensions comprising water. Antioxidants were also added to excipients which were found to be non compatible with MCH. Addition of water caused prompt degradation of MCH. Addition of the antioxidants alpha-tocopherol, BHA/BHT and propyl gallate did not prevent MCH degradation. Compatible excipients became incompatible in the presence of water. Addition of antioxidants did not alter this result.

Example 20

Color and Pigmentation Study

Part A—Color Change

Samples of formulations 238 and 216 with 1% minocycline were incubated during 3 months at 25° C., 30° C. and 40° C. Following this period the foam product was actuated and the change in color was observed. Minimal to no change was observed following 3 months storage at all three temperatures.

Part B—Pigmentation

A large amount of MCH 244 4% was actuated on human skin to observe whether any skin pigmentation occurs. Minimal to no skin pigmentation following rubbing the foam onto the skin was noticed, when observed after about 30 seconds.

Example 21

Oleaginous "Oil-Gel" Compositions Stability

Formulations 244A and 244B were prepared without the addition of propellant, packaged in a tube and tested for stability during 8 days. The tubes were opened each day and exposed to air and moisture to mimic typical patient use. On days 0, 3, 5, and 8 an aliquot was removed and analyzed. Results are presented in Table 21 and demonstrate that MCH in these formulations was stable when tube was exposed to air and moisture on a daily basis. On visual inspection no color change was observed during the eight day period. The contents of the tube were also observed after a month and no visual difference was noted. The formulations presented as homogeneous oil-gels. These gels are semi-solid at rest and liquefy upon application of shear forces. The agents are uniformly distributed throughout the carrier. Upon slight rubbing, both formulations readily liquefy in order to ensure an easy application and an optimal spreading of the composition. So not only are these formulations capable of generating a high quality foam that is stable and breakable on application of shear force but can also be used as a gel or ointment and whether applied as a foam or a gel or ointment it is easy to spread, readily absorbable, relatively non greasy and non-sticky and can be used for the treatment of a great number of diseases and syndromes affecting skin, mucosal membranes, eye and body cavities.

TABLE 21

| Batch/Sample name | MCH % | | | | 4-Epi MCH % | | | |
|---|---|---|---|---|---|---|---|---|
| | T = 0 | 3 d | 5 d | 8 d | T = 0 | 3 d | 5 d | 8 d |
| MCH 244A | 99.38 | 100.13 | 100.6 | 100.8 | 1.65 | 1.7 | 1.6 | 1.6 |
| MCH 244B | 99.00 | 99.70 | 100.4 | NM | 1.5 | 1.6 | 1.6 | NM |

NM = Not measured

Example 22

Oleaginous Eye Compositions

Minocycline oleaginous compositions suitable for ophthalmic use were prepared using ingredients allowed in pharmaceutical eye formulation according to the FDA Inactive Ingredients Guide.

Manufacturing Procedure: Heat Petrolatum and light mineral oil to 50-60° C. and add Cetyl alcohol. Mix until complete melting. Cool down to 35-40° C., add minocycline, mix until formulation homogeneity is obtained and cool down to room temperature.

TABLE 22

| Ophtalmic oleaginous compositions containing minocycline | | |
|---|---|---|
| Formulations Ingredients | O-001 % w/w | O-002 % w/w |
| White Petrolatum (hard) | 50.00 | 25.00 |
| Light mineral oil | 48.40 | 73.40 |
| Cetyl alcohol | 0.50 | 0.50 |
| Minocycime HCl | 1.11 | 1.11 |
| Total | 100 | 100 |

Formulations O-001 and O-002 gave homogeneous oil-gels suitable for use in ophthalmic preparations. The two formulations differ in their texture, formulation O-002 being more liquid due to the inclusion of high amounts of liquid oils. Upon slight rubbing, both formulations readily liquefy in order to ensure an easy application onto the eye and an optimal spreading of the composition. For application as a foam, a wax or shea butter or a hydrogenation caster oil may be usefully added together with a propellant. Shea butter can be obtained in several different formats: Liquid, semi solid or butter like consistency. In the presence of another hydrophobic solvent good shakability of a foamable formulation with petrolatum can be obtained even with semi shea butter of solid or butter like consistency. In one or more embodiments, the foamer complex can be a fatty alcohol and shea butter. In one or more embodiments, the foamer complex can be a fatty acid and shea butter. In one or more embodiments, the foamer complex can be a hydrogenated caster oil and shea butter. In one or more embodiments, the foamer complex can be a wax, such as beeswax or paraffin wax and shea butter.

Section C—Compositions with Active Ingredients

Example 23

Oleaginous Formulations Containing Different Active Ingredients

Several active ingredients (API) were added to formulation 012 in order to assess the compatibility between the oleaginous foam vehicle and various APIs. Parameters such as foam quality, and collapse time were evaluated as described in Table 23a and 23b below.

TABLE 23a

Oleaginous compositions containing different active ingredients

| Ingredient | 012A % w/w | 012B % w/w | 012C % w/w | 012D % w/w | 012E % w/w | 012F % w/w | 012G % w/w |
|---|---|---|---|---|---|---|---|
| Heavy mineral oil | 60.00 | 60.00 | 60.00 | 60.00 | 60.00 | 60.00 | 60.00 |
| Light mineral oil | 25.00 | 25.00 | 25.00 | 25.00 | 25.00 | 25.00 | 25.00 |
| Cyclomethicone | 5.00 | 5.00 | 5.00 | 5.00 | 5.00 | 5.00 | 5.00 |
| Stearyl alcohol | 5.00 | 5.00 | 5.00 | 5.00 | 5.00 | 5.00 | 5.00 |
| Stearic acid | 5.00 | 5.00 | 5.00 | 5.00 | 5.00 | 5.00 | 5.00 |
| Total | 100 | 100 | 100 | 100 | 100 | 100 | 100 |
| Doxycycline Hyelate | 1.00 | — | — | — | — | — | — |
| Betamethasone Valerate | — | 0.12 | — | — | — | — | — |
| Progesterone | — | — | 0.05 | — | — | — | — |
| Terbinafine | — | — | — | 1.00 | — | — | — |
| Metronidazole | — | — | — | — | 1.00 | — | — |
| Calcitriol | — | — | — | — | — | 0.05 | — |
| Naproxen | — | — | — | — | — | — | 5.00 |
| Propellant A46 | 12.00 | 12.00 | 12.00 | 12.00 | 12.00 | 12.00 | 12.00 |
| Results |  |  |  |  |  |  |  |
| Foam Quality | Good | Good | Good | Good | Good | Good | Good |
| Collapse Time (sec) | >180 | >180 | >180 | >180 | >180 | >180 | >180 |

TABLE 23b

Oleaginous compositions containing calcipotriol

| Ingredient | 012H % w/w |
|---|---|
| Hard Fat (Softisan 378) | 18.00 |
| Hydrogenated castor oil | 2.00 |
| Aluminum Starch Octenylsuccinate | 1.00 |
| Capric Caprylic Triglycerides | 20.00 |
| Heavy mineral oil | 39.99 |
| Paraffin wax 58-62 | 10.00 |
| Stearyl alcohol | 2.00 |
| Cetyl alcohol | 3.00 |
| Cetostearyl alcohol | 4.00 |
| Calcipotriol | 0.01 |
| Total | 100.00 |
| Propellant AP-70 | 8.00 |
| Results |  |
| Foam Quality | Excellent |
| Collapse Time (sec) | >180 |

Formulations containing Doxycycline Hyclate, Betamethasone Valerate, Progesterone, Terbinafine, Metronidazole, Calcitriol, Calcipotriol and Naproxen gave rise to breakable foams of good quality which were stable at 36° C. during more than 3 minutes.

Example 24

Oleaginous Formulations Containing Calcitriol and Stability

Example 24A

Surfactant Free Formulations

Foam formulations containing calcitriol as an active ingredient were prepared. Parameters such as foam quality, collapse time and density were evaluated. As described in Table 24A, foams of good to excellent quality which did not collapse at 36° C. for at least more than two minutes were obtained in different compositions containing these hydrophobic solvents.

Manufacturing procedure: Hydrophobic solvents are mixed together and heated to 70-80° C., fatty alcohols are added and mixed until complete melting. The mixture is cooled to 40-45° C. Calcitriol is added and mixed until dissolved and until a uniform preparation is obtained. The mixture is cooled to 15-20° C. using an ice bath while mixing. The preparation is filled into canisters which are crimped with a suitable valve, pressurized with propellant and equipped with an actuator.

TABLE 24A

Formulations without surfactant containing calcitriol

| Formulation | C016 | C017 | C16B | C16C |
|---|---|---|---|---|
| Calcitriol | 0.0015 | 0.0015 | 0.0015 | 0.0015 |
| Behenyl alcohol | 1.00 | 1.00 | 1.00 | 1.00 |
| Benzyl alcohol | — | 1.00 | — | — |
| Butylated hydroxytoluene | 0.04 | 0.04 | 0.04 | 0.04 |
| Capric/Caprylic triglycerides | 5.9585 | 5.9585 | 5.9585 | 11.9585 |
| Cetostearyl alcohol | 4.00 | 4.00 | 4.00 | 4.00 |
| Cetyl alcohol | 3.00 | 3.00 | 3.00 | 3.00 |
| Heavy Mineral oil | 50.00 | 40.00 | 50.00 | 47.00 |
| Light Mineral oil | 25.00 | 25.00 | — | 23.00 |
| Myristyl alcohol | 2.00 | 2.00 | 2.00 | 2.00 |
| Paraffin 51-53 | 6.00 | 6.00 | 6.00 | 5.50 |
| Soybean oil | — | — | 25.50 | — |

TABLE 24A-continued

Formulations without surfactant containing calcitriol

| Formulation | C016 | C017 | C16B | C16C |
|---|---|---|---|---|
| Stearyl alcohol | 3.00 | 3.00 | 2.50 | 2.50 |
| Water, purified | — | 9.00 | — | — |
| Total | 100 | 100 | 100 | 100 |
| Propellant AP-70 | 10.00 | 8.00 | 8.00 | 8.00 |
| Results | | | | |
| Foam Quality | E | E | E | E |
| Collapse Time at 36° C. (sec) | >180 | >180 | >180 | 155 |
| Foam Density (g/mL) | 0.223 | 0.216 | 0.228 | 0.205 |

Example 24B

Stability of a Vitamin D Derivative in Oleaginous Formulations

The following example illustrates the physical and chemical stability of foams and the chemical stability of Calcitriol in an oleaginous formulation, namely C016 as described in Example 16A. In an accelerated stability study, samples were stored at 40° C., and the concentration of Calcitriol was determined by UPLC. The physical and chemical stability test results following 4 weeks, 8 weeks and 12 weeks of storage are shown in Table 24b(i) and 24b(ii).

TABLE 24b(i)

Chemical Stability results of foam composition C016 containing Calcitriol

| Test | T0 | after 4 weeks at 40° C. | after 8 weeks at 40° C. | after 12 weeks at 40° C. |
|---|---|---|---|---|
| Calcitriol content (% of label claim) | 100.2 | 98.6 | 99.3 | 101.8 |

TABLE 24b(ii)

Physical Stability results of foam composition C016 containing Calcitriol

| Test | T0 | after 4 weeks at 40° C. | after 8 weeks at 40° C. | after 12 weeks at 40° C. |
|---|---|---|---|---|
| Foam Quality | Excellent | Excellent | Excellent | Excellent |
| Collapse Time (sec) | >180 | >180 | >180 | >180 |

Example 25

Stability of a Corticosteroid in Oleaginous Formulations

The following example illustrates the physical and chemical stability of foams and the chemical stability of Mometasone Furoate in an oleaginous formulation M03 as described in Table 25(i). In an accelerated stability study, samples were stored at 40° C., and the concentration of Mometasone Furoate was determined by UPLC. The stability test results following 4 weeks, 8 weeks and 12 weeks of storage are shown in Table 25(ii) and 25(iii).

TABLE 25(i)

Formulations without surfactant containing Mometasone Furoate

| Formulation | M03 |
|---|---|
| Light mineral oil | 75.00 |
| Heavy mineral oil | 59.15 |
| Cyclomethicone | 5.00 |
| Behenyl alcohol | 1.00 |
| Cetostearyl alcohol | 7.50 |
| Stearyl alcohol | 1.50 |
| Hydrogenated castor oil | 1.50 |
| Beeswax | 2.00 |
| Acrosil | 0.25 |
| Stearic acid | 2.00 |
| Mometasone furoate | 0.10 |
| Total | 100 |
| Propellant AP-70 | 10.00 |
| Results | |
| Foam Quality | E |
| Collapse Time at 36° C. (sec) | >180 |
| Foam Density (g/mL) | 0.181 |

TABLE 25(ii)

Chemical Stability results of foam composition M03 containing Mometasone Furoate

| Test | T0 | after 4 weeks at 40° C. | after 8 weeks at 40° C. | after 12 weeks at 40° C. |
|---|---|---|---|---|
| Mometasone Furoate content (% of label claim) | 101.0 | 97.9 | 93.5 | 94.6 |

TABLE 25(iii)

Physical Stability results of foam composition M03 containing Mometasone Furoate

| Test | T0 | after 4 weeks at 40° C. | after 8 weeks at 40° C. | after 12 weeks at 40° C. |
|---|---|---|---|---|
| Foam Quality | E,xcellent | Excellent | Excellent | Excellent |
| Collapse Time (sec) | >180 | 180 | 155 | >180 |

What is claimed is:

1. A method of treating rosacea, consisting of administering a surfactant free foam composition, obtained from a foamable composition dispensed from a container, to a subject in need thereof, wherein the foamable composition consists of:

i) a carrier consisting of:
   a) about 60% to about 95% by weight of the carrier of a hydrophobic solvent;
   b) about 0.1% to about 20% by weight of the carrier of at least one fatty alcohol, wherein the fatty alcohol has a carbon chain length of 14 to 22 carbons;
   c) about 0.1% to about 20% by weight of the carrier of at least one fatty acid, at least one wax, at least one shea butter, or mixtures of two or more thereof, wherein the fatty acid has a carbon chain length of 12 to 28 carbons, and the wax is selected from the group consisting of a beeswax, a hydrogenated castor oil, a paraffin wax, a wax that is solid at room temperature, and a mixture of any two or more thereof; and
   d) one active agent, wherein the one active agent is minocycline or a salt thereof; and
ii) a liquefied or compressed gas propellant;
wherein the foamable composition comprises 15% or less of petrolatum by weight of the carrier;
wherein the foamable composition is essentially waterless;
wherein the foamable composition is free of polymeric agent;
wherein, upon dispensing, the foamable composition forms a foam; and
wherein the subject in need thereof has rosacea.

2. The method of claim 1, wherein the fatty alcohol is selected from the group consisting of stearyl alcohol, cetyl alcohol, behenyl alcohol, myristyl alcohol, and a mixture of any two or more thereof; and
   wherein the hydrophobic solvent is selected from the group consisting of: an avocado oil, a calendula oil, cocoglycerides, a coconut oil, a cyclomethicone, a grape seed oil, a heavy mineral oil, a jojoba oil, a light mineral oil, medium chain triglyceride (MCT) oil, octyldodecanol, a peanut oil, a PPG-15 stearyl ether, a soybean oil, a wheat germ oil, and a mixture of any two or more thereof.

3. The method of claim 1, wherein the hydrophobic solvent is selected from the group consisting of an avocado oil, a calendula oil, cocoglycerides, a coconut oil, a cyclomethicone, a grape seed oil, a heavy mineral oil, a jojoba oil, a light mineral oil, medium chain triglyceride (MCT) oil, octyldodecanol, a peanut oil, a PPG-15 stearyl ether, a soybean oil, a wheat germ oil, and a mixture of any two or more thereof.

4. The method of claim 1, wherein the fatty acid comprises stearic acid.

5. The method of claim 1, wherein the foamable composition comprises at least one fatty alcohol and at least one wax, or at least one fatty alcohol and at least one fatty acid, or at least one fatty alcohol, at least one fatty acid, and at least one wax.

6. The method of claim 1, wherein the wax comprises a combination of a beeswax and a hydrogenated castor oil, wherein the ratio of beeswax to hydrogenated castor oil is between about 1:1 and about 5:1.

7. The method of claim 1, wherein the ratio of fatty alcohol to wax is between about 4:1 and about 1:4.

8. The method of claim 1, wherein the foamable composition is free of short chain alcohols.

9. The method of claim 1, wherein the hydrophobic solvent is a liquid oil.

10. The method of claim 1, wherein the foamable composition comprises about 10% or less of petrolatum by weight of the carrier.

11. The method of claim 1, wherein the foamable composition comprises a fatty acid and a fatty alcohol at a ratio of between about 1:10 and about 10:1.

12. The method of claim 1, wherein the fatty alcohol comprises stearyl alcohol, cetyl alcohol, or both.

13. The method of claim 1, wherein the fatty alcohol comprises one or more of stearyl alcohol, cetyl alcohol, behenyl alcohol, or myristyl alcohol.

14. The method of claim 1, wherein the minocycline antibiotic is present at about 0.5% to about 6% by weight of the carrier.

15. The method of claim 1, wherein the hydrophobic solvent is selected from the group consisting of an alexandria laurel tree oil, an almond oil, an essential oil, an unsaturated or polyunsaturated oil, an apricot stone oil, an avocado oil, a barley oil, a basil oil, a borage seed oil, a calendula oil, a camphor oil, a canelle nut tree oil, a canola oil, a cardamom oil, a carrot oil, a castor oil, a citronella oil, a clary sage oil, a clove oil, a coconut oil, a cod-liver oil, a corn oil, a cotton oil, a cottonseed oil, a cypress oil, an epoxy-modified silicone oil, an ester oil, an evening primrose oil, a fatty acid-modified silicone oil, a flaxseed oil, a fluoro group-modified silicone oil, a frankincense oil, a ginger oil, a grape seed oil, a grapefruit oil, a groundnut oil, a hazelnut oil, a heavy mineral oil, a hempseed oil, a herring oil, hydrocarbon oils, a hyssop oil, a jasmine oil, a jojoba oil, a lavender oil, a lemon oil, a light mineral oil, a lucerne oil, a maize germ oil, a maleated soybean oil, a mandarin oil, a manuka oil, a marjoram oil, a marrow oil, medium chain triglyceride (MCT) oil, a millet oil, a mineral oil, a myrrh oil, a neroli oil, a nutmeg oil, oils from animal origin, oils of plant origin, an olive oil, a palm oil, a passionflower oil, a peanut oil, a petitgrain oil, a polyether group-modified silicone oil, a poppy oil, a rapeseed oil, a rosehip oil, a rye oil, a safflower oil, a sage oil, a salmon oil, a sesame oil, a silicone oil, a soya oil, a soybean oil, a sunflower oil, a sweet almond oil, a sysymbrium oil, a syzigium *aromaticum* oil, a tangerine oil, a tea tree oil, unsaturated or polyunsaturated oils, a vanilla oil, a *verbena* oil, a walnut oil, a wheat germ oil, and a mixture of any two or more thereof.

16. The method of claim 1, wherein the hydrophobic solvent comprises
   (i) a diglyceride, capric/caprylic triglycerides, glycereth triacetate, glycerol triheptanoate, glyceryl oleate, glyceryl trioctanoate, liquid triglycerides, or a wheat germ glyceride;
   (ii) a PPG alkyl ether, a PPG-10 cetyl ether, a PPG-10 oleyl ether, a PPG-11 stearyl ether, a PPG-12 butyl ether, a PPG-14 butyl ether, a PPG-15 butyl ether, a PPG-15 stearyl ether, a PPG-16 butyl ether, a PPG-17 butyl ether, a PPG-18 butyl ether, a PPG-2 butyl ether, a PPG-2 methyl ether, a PPG-20 butyl ether, a PPG-20 oleyl ether, a PPG-22 butyl ether, a PPG-23 oleyl ether, a PPG-24 butyl ether, a PPG-26 butyl ether, a PPG-28 cetyl ether, a PPG-3 methyl ether, a PPG-3 myristyl ether, a PPG-30 butyl ether, a PPG-30 cetyl ether, a PPG-30 isocetyl ether, a PPG-30 oleyl ether, a PPG-33 butyl ether, a PPG-37 oleyl ether, a PPG-4 butyl ether, a PPG-4 lauryl ether, a PPG-4 myristyl ether, a PPG-40 butyl ether, a PPG-5 butyl ether, a PPG-50 cetyl ether, a PPG-50 oleyl ether, a PPG-52 butyl ether, a PPG-53 butyl ether, a PPG-7 lauryl ether, a PPG-9 butyl ether, or a PPG-9-13 butyl ether;
   (iii) benzyl laurate, benzyl myristate, benzyl palmitate, bis dimer dilinoleate, butyl myristate, butyl stearate, propyl myristate, propylene glycol dicaprate, propylene glycol dicaprylate, propylene glycol myristyl ether acetate, propylene glycol ricinoleate, stearyl caprate, stearyl propionate, tocopheryl acetate, tocopheryl linoleate, triisocetyl citrate, decyl oleate, diethylhexyl adipate, diethylhexyl malate, diethylhexyl succinate, diisopropyl adipate, diisopropyl dimerate, diisopropyl sebacate, diisosteary dimer dilinoleate, diisostearyl fumerate, dioctyl malate, dioctyl sebacate, disopropyl adipate, dodecyl oleate, ester derivatives of lanolic acid, ethylhexyl hydroxystearate, ethylhexyl palmitate, ethylhexyl pelargonate, ethylhexyl stearate, hexyl laurate, isoamyl laurate, isocetyl behenate, isocetyl lanolate, isocetyl palmitate, isocetyl salicylate, isocetyl stearate, isocetyl stearoyl stearate, isodecyl oleate, isododecane, isohexadecane, isohexadecanol, isopropyl isostearate, isopropyl lanolate, isopropyl laurate, isopropyl myristate, isopropyl palmitate, isopropyl stearate, isosteary citrate, isosteary salicylate, isosteary tartarate, isostearyl behenate, isostearyl erucate, isostearyl glycolate, isostearyl isostearate, isostearyl lactate, isostearyl linoleate, isostearyl linolenate, isostearyl malate, isostearyl palmitate, lauryl lactate, myristyl lactate, myristyl myristate, myristyl propionate, neopentylglycol dicaprate, neopentylglycol dicaprylate/dicaprate, octyl palm itate, octyl stearate, octyldodecyl behenate, octyldodecyl hydroxystearate, octyldodecyl myristate, octyldodecyl stearoyl stearate, oleyl erucate, oleyl lactate, oleyl oleate, or pentaerythrityl tetrastearate;

(iv) alkyl benzoate, alkyl octanoate, C12-C15 alkyl benzoate, C12-C15 alkyl octanoate, stearyl heptanoate, tridecyl ethyl hexanoate, tridecyl isononanoate, a cetearyl ethyl hexanoate, cetearyl isononanoate, cetearyl octanoate, cetyl ethyl hexanoate, cetyl octanoate, diethyleneglycol diethylhexanoate, diethyleneglycol diisononanoate, diethyleneglycol dioctanoate, diethylhexanoate, ethylhexyl cocoate, ethylhexyl ethyl hexanoate, ethylhexyl isononanoate, isocetearyl octanoate, isodecyl ethylhexanoate, isodecyl isononanoate, isohexyl decanoate, isononyl isononanoate, isononyl octanoate, isostearyl isononanoate, isostearyl neopentanoate, isotridecyl isononanoate, or myristyl neopentanoate;

(v) a caprylyl methicone, cetyl dimethicone, stearyl dimethicone, a cyclohexasiloxane, a cyclomethicone, cyclopentasiloxane, a cyclotetrasiloxane, dimethicone, dimethyl polysiloxane, methylphenylpolysiloxane, PEG/PPG 18/18 dimethicone, phenyl trimethicone, a polydiphenyl-siloxane copolymer, a polyalkyl siloxane, a polyalkylaryl siloxane, a polyaryl siloxane, or a polyether siloxane copolymer;

(vi) an acetylated lanolin alcohol, a liquid paraffin, octyldodecanol, a polyalphaolefin, a polyisobutylene, a polyolefin, or a synthetic isoalkane; or (vii) a mixture of any two or more thereof.

17. The method of claim 1, wherein the foamable composition is administered at least once daily.

18. The method of claim 1, wherein the foamable composition is administered at least once daily and the minocycline is present at about 3% by weight of the carrier.

19. The method of claim 1, wherein the foamable composition is administered at least once daily and the minocycline is present at about 1.5% by weight of the carrier.

20. The method of claim 1, wherein the foamable composition comprises at least one fatty alcohol, at least one fatty acid, and at least one wax.

21. The method of claim 1, wherein the ratio of fatty alcohol to fatty acid is about 1:7 to about 16:3.

22. The method of claim 1, wherein the ratio of fatty alcohol to fatty acid is about 3:17 to about 2:1.

23. The method of claim 1, wherein the foamable composition is free of petrolatum.

24. The method of claim 1, wherein the salt of minocycline is minocycline hydrochloride.

* * * * *